(12) United States Patent
Qiao et al.

(10) Patent No.: US 7,205,318 B2
(45) Date of Patent: Apr. 17, 2007

(54) LACTAM-CONTAINING CYCLIC DIAMINES AND DERIVATIVES AS A FACTOR XA INHIBITORS

(75) Inventors: Jennifer X. Qiao, Princeton, NJ (US); Tammy C. Wang, Lawrenceville, NJ (US); Gren Z. Wang, West Chester, PA (US); Timur Gungor, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 332 days.

(21) Appl. No.: 10/801,469

(22) Filed: Mar. 16, 2004

(65) Prior Publication Data

US 2004/0204454 A1 Oct. 14, 2004

Related U.S. Application Data

(60) Provisional application No. 60/508,232, filed on Oct. 2, 2003, provisional application No. 60/455,733, filed on Mar. 18, 2003.

(51) Int. Cl.
*A61K 31/445* (2006.01)
*C07D 453/02* (2006.01)

(52) U.S. Cl. ............... 514/326; 514/340; 514/422; 548/527; 548/518; 546/135; 546/207; 546/268.4

(58) Field of Classification Search ............... 548/527, 548/518; 546/135, 207, 268.4; 514/326, 514/340, 422
See application file for complete search history.

(56) References Cited

U.S. PATENT DOCUMENTS

| 6,951,872 | B2 * | 10/2005 | Jacobson et al. | 514/319 |
| 6,967,208 | B2 * | 11/2005 | Pinto et al. | 514/303 |
| 6,989,391 | B2 * | 1/2006 | Pinto et al. | 514/303 |
| 2003/0191115 | A1 | 10/2003 | Pinto et al. | |
| 2005/0119266 | A1 * | 6/2005 | Shi et al. | 514/248 |
| 2005/0267097 | A1 * | 12/2005 | Pinto et al. | 514/211.03 |

FOREIGN PATENT DOCUMENTS

| WO | WO 99/32477 | 7/1999 |
| WO | WO 01/74774 | 10/2001 |
| WO | WO 03/00657 | 1/2003 |
| WO | WO 03/00680 | 1/2003 |
| WO | WO 03/045912 | 6/2003 |

\* cited by examiner

*Primary Examiner*—Joseph K. McKane
*Assistant Examiner*—Robert Shiao
(74) *Attorney, Agent, or Firm*—Jing G. Sun; David H. Vance

(57) ABSTRACT

The present application describes lactam-containing cyclic diamines and derivatives thereof of Formula I:

$$P_4\text{-}M\text{-}M_4I$$

or pharmaceutically acceptable salt forms thereof, wherein M is a non-aromatic carbocycle or heterocycle. Compounds of the present invention are useful as inhibitors of trypsin-like serine proteases, specifically factor Xa.

19 Claims, No Drawings

LACTAM-CONTAINING CYCLIC DIAMINES AND DERIVATIVES AS A FACTOR XA INHIBITORS

CROSS-REFERENCE TO RELATED APPLICATIONS

The present application claims the priority benefits of U.S. Provisional Application No. 60/455,733, filed Mar. 18, 2003, and U.S. Provisional Application No. 60/508,232, filed Oct. 2, 2003, which are expressly incorporated fully herein by reference.

FIELD OF THE INVENTION

This invention relates generally to lactam-containing cyclic diamines and derivatives thereof which are inhibitors of trypsin-like serine protease enzymes, especially factor Xa, pharmaceutical compositions containing the same, and methods of using the same as anticoagulant agents for treatment of thromboembolic disorders.

BACKGROUND OF THE INVENTION

WO01/074774, WO03/00657, and WO03/00680 describe Factor Xa inhibitors of the following formula (wherein $Q^3$ completes a ring and $T^0$ is C(O) in 074774):

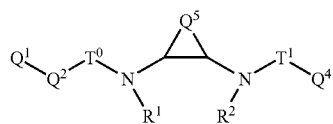

Compounds shown in WO01/074774, WO03/00657, and WO03/00680 are not considered to be part of the present invention.

WO03/045912 describes Factor Xa inhibitors of the following formula (wherein $W^1$ completes a ring):

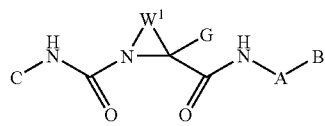

Compounds shown in WO03/045912 are not considered to be part of the present invention.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors. In addition, it is also desirable to find new compounds with improved pharmacological characteristics compared with known factor Xa inhibitors. For example, it is preferred to find new compounds with improved factor Xa inhibitory activity and selectivity for factor Xa versus other serine proteases (i.e., trypsin). It is also desirable and preferable to find compounds with advantageous and improved characteristics in one or more of the following categories, but are not limited to: (a) pharmaceutical properties (e.g., solubility, permeability, and amenability to sustained release formulations); (b) dosage requirements (e.g., lower dosages and/or once-daily dosing); (c) factors which decrease blood concentration peak-to-trough characteristics (e.g., clearance and/or volume of distribution); (d) factors that increase the concentration of active drug at the receptor (e.g., protein binding and volume of distribution); (e) factors that decrease the liability for clinical drug-drug interactions (e.g., cytochrome P450 enzyme inhibition or induction); (f) factors that decrease the potential for adverse side-effects (e.g., pharmacological selectivity beyond serine proteases, potential chemical or metabolic reactivity, and limited CNS penetration); and, (g) factors that improve manufacturing costs or feasibility (e.g., difficulty of synthesis, number of chiral centers, chemical stability, and ease of handling).

SUMMARY OF THE INVENTION

Accordingly, the present invention provides novel lactam-containing cyclic diamines and derivatives thereof that are useful as factor Xa inhibitors or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating thromboembolic disorders comprising administering to a mammal in need of such treatment a therapeutically effective amount of at least one of the compounds of the present invention or a pharmaceutically acceptable salt or prodrug form thereof.

The present invention provides a novel method of treating a patient in need of thromboembolic disorder treatment, comprising: administering a compound of the present invention or a pharmaceutically acceptable salt form thereof in an amount effective to treat a thromboembolic disorder.

The present invention provides a novel method, comprising: administering a compound of the present invention or a pharmaceutically acceptable salt form thereof in an amount effective to treat a thromboembolic disorder.

The present invention provides novel lactam-containing compounds and derivatives thereof for use in therapy.

The present invention provides the use of novel lactam-containing compounds for the manufacture of a medicament for the treatment of a thromboembolic disorder.

These and other objects, which will become apparent during the following detailed description, have been achieved by the inventors' discovery that lactam-containing cyclic diamines and derivatives thereof as defined below, or pharmaceutically acceptable salt or prodrug forms thereof, are effective factor Xa inhibitors.

DETAILED DESCRIPTION OF PREFERRED EMBODIMENTS
In a first embodiment, the present invention provides a novel compound selected from:
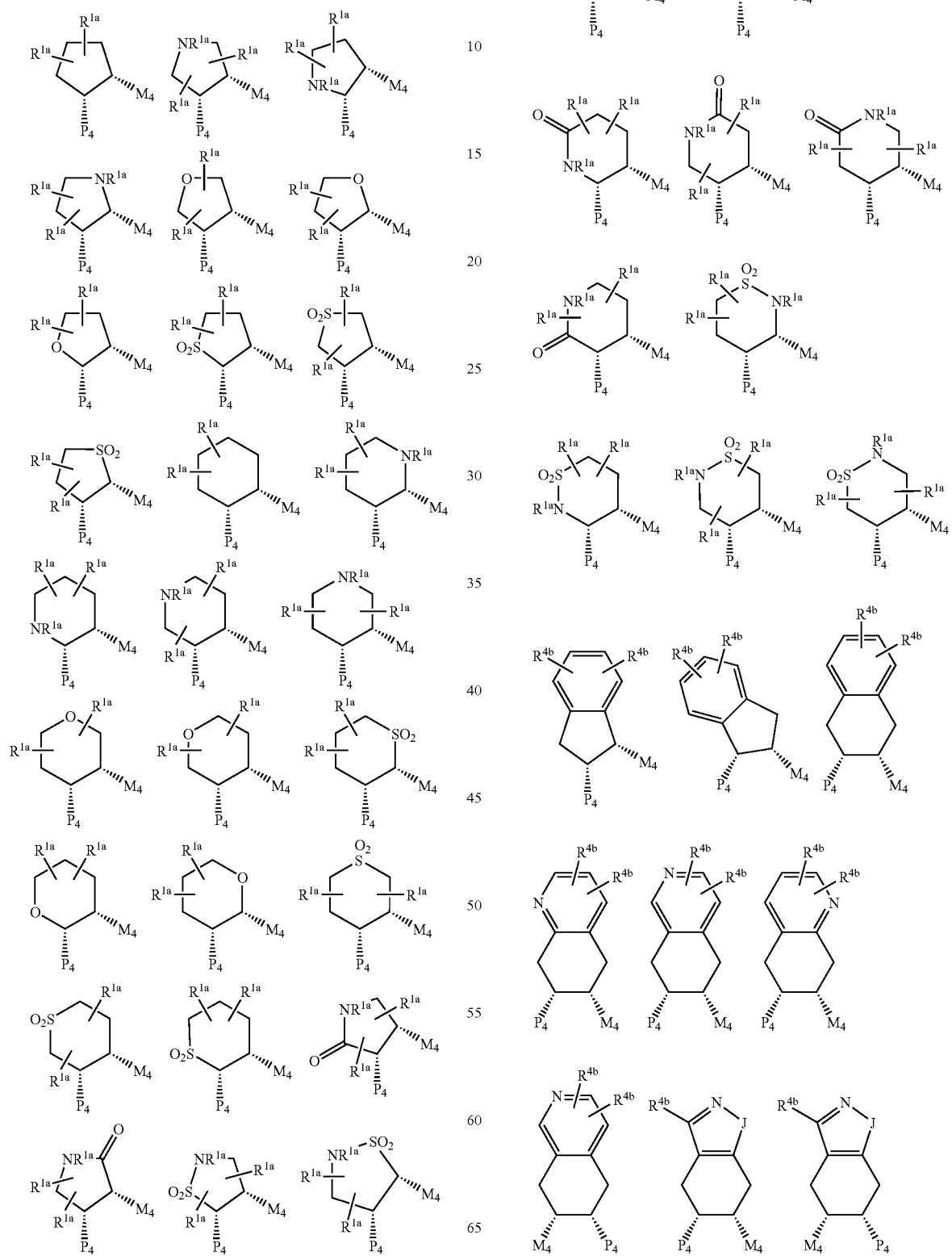

-continued
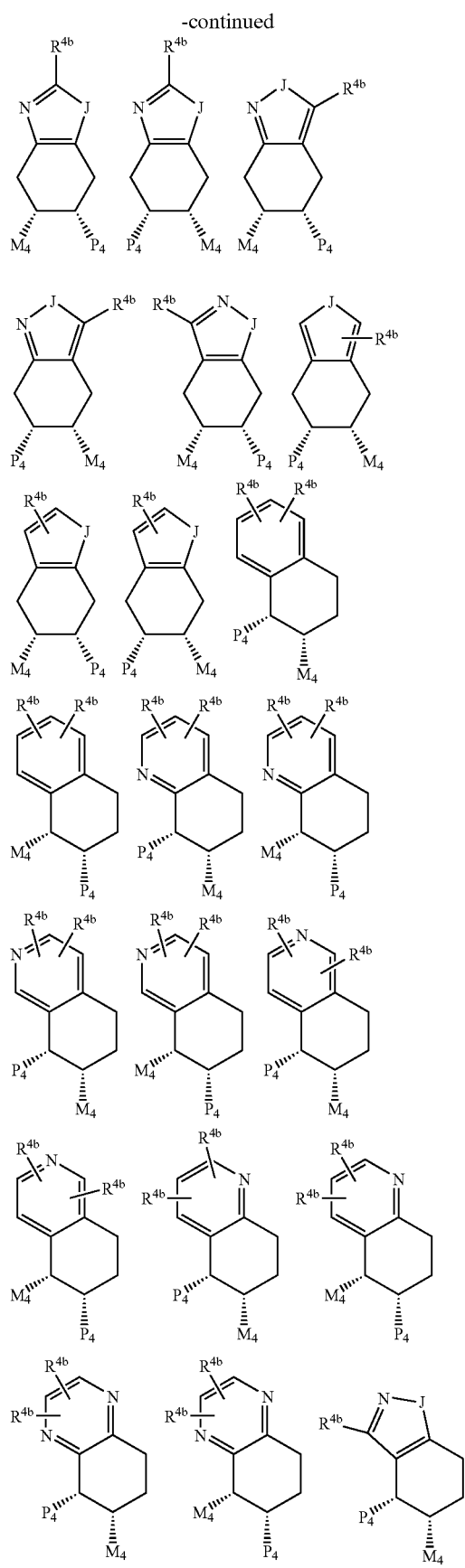
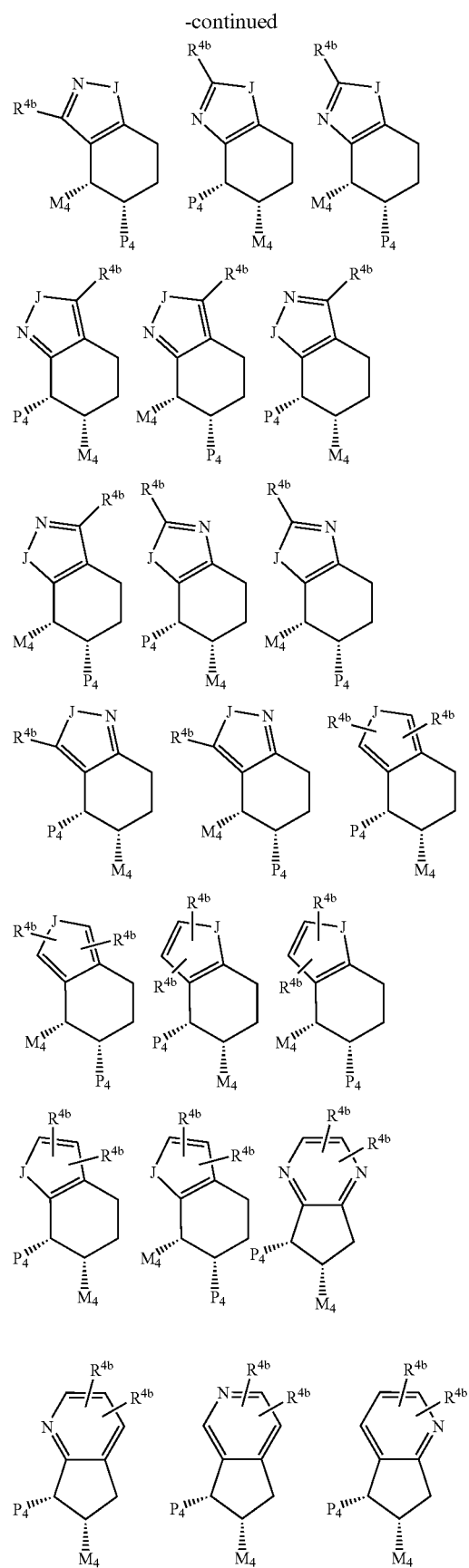

-continued
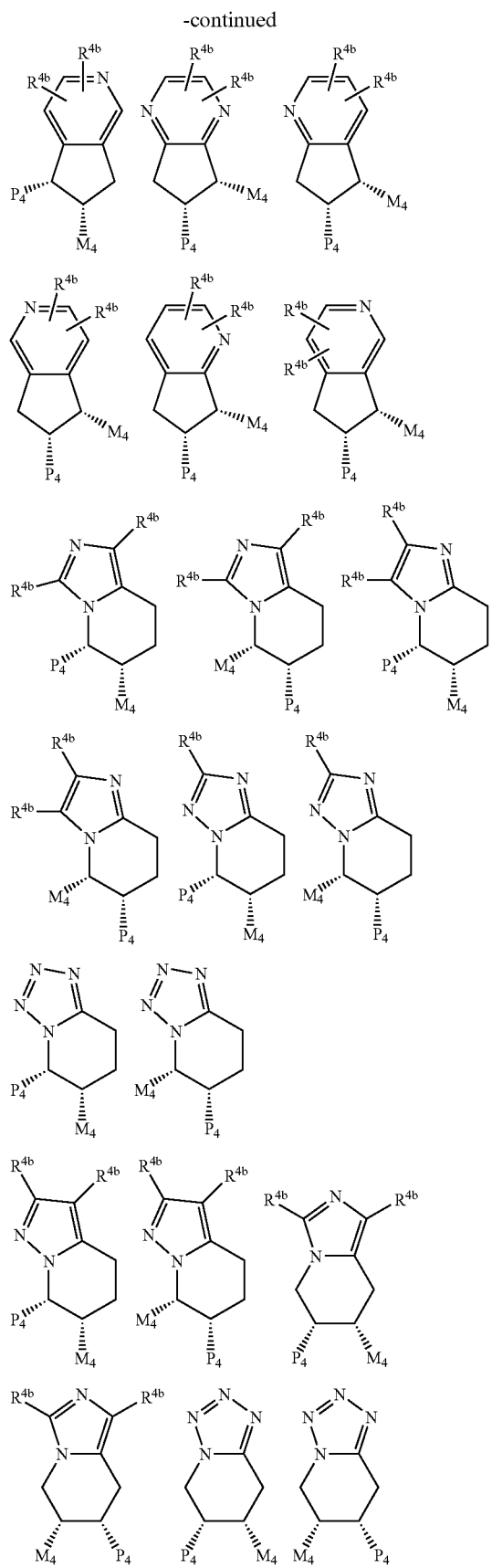
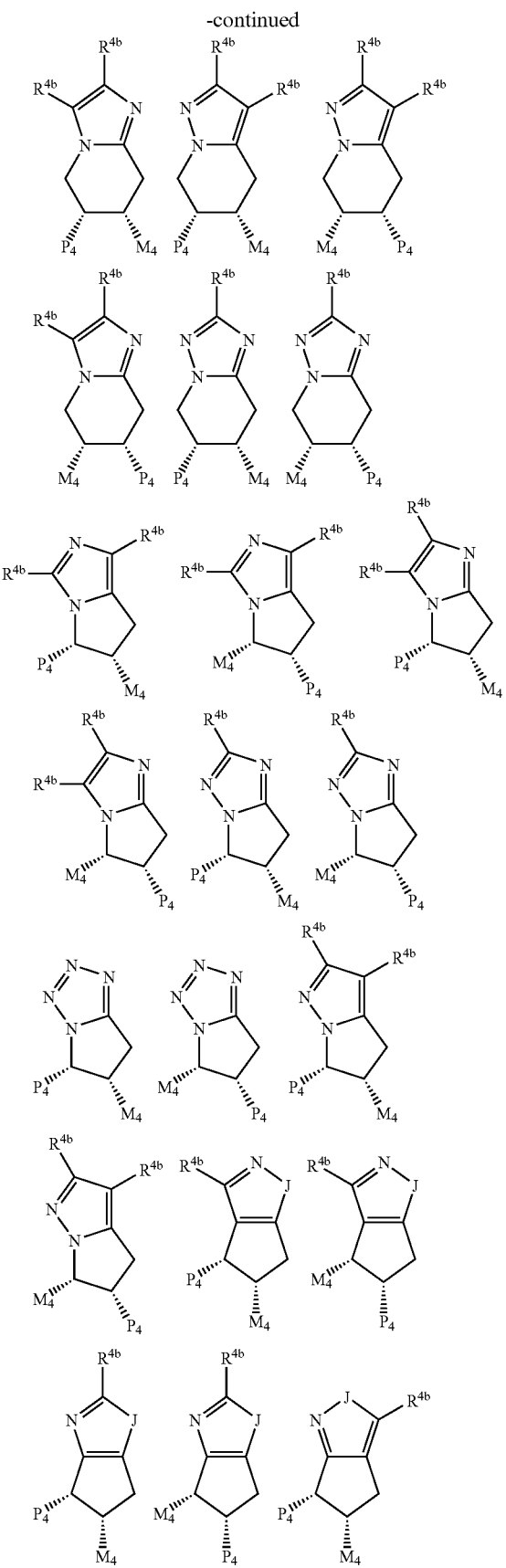

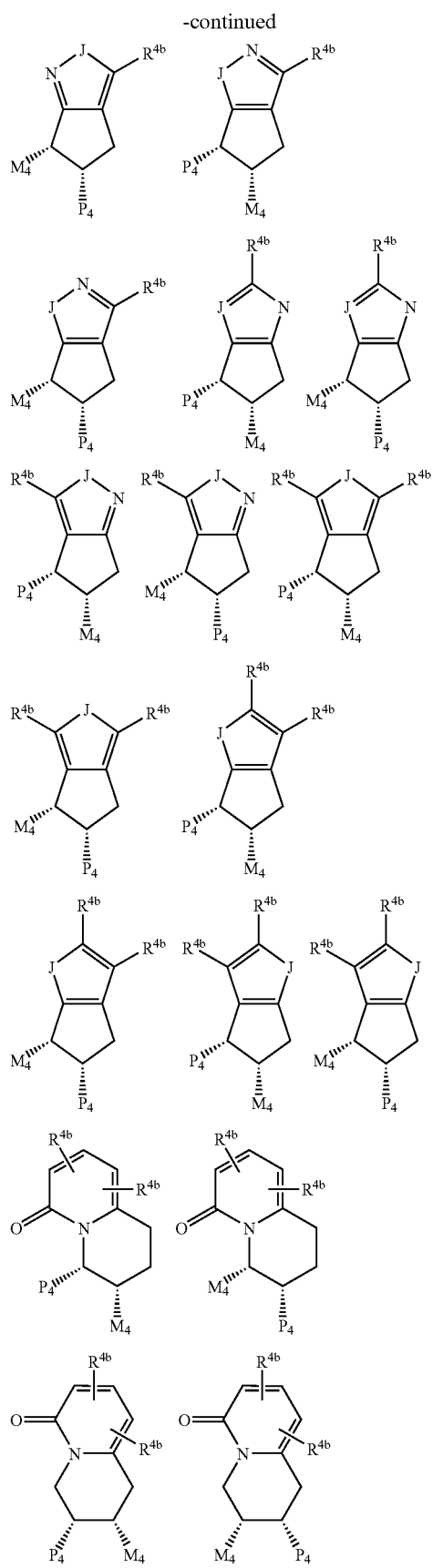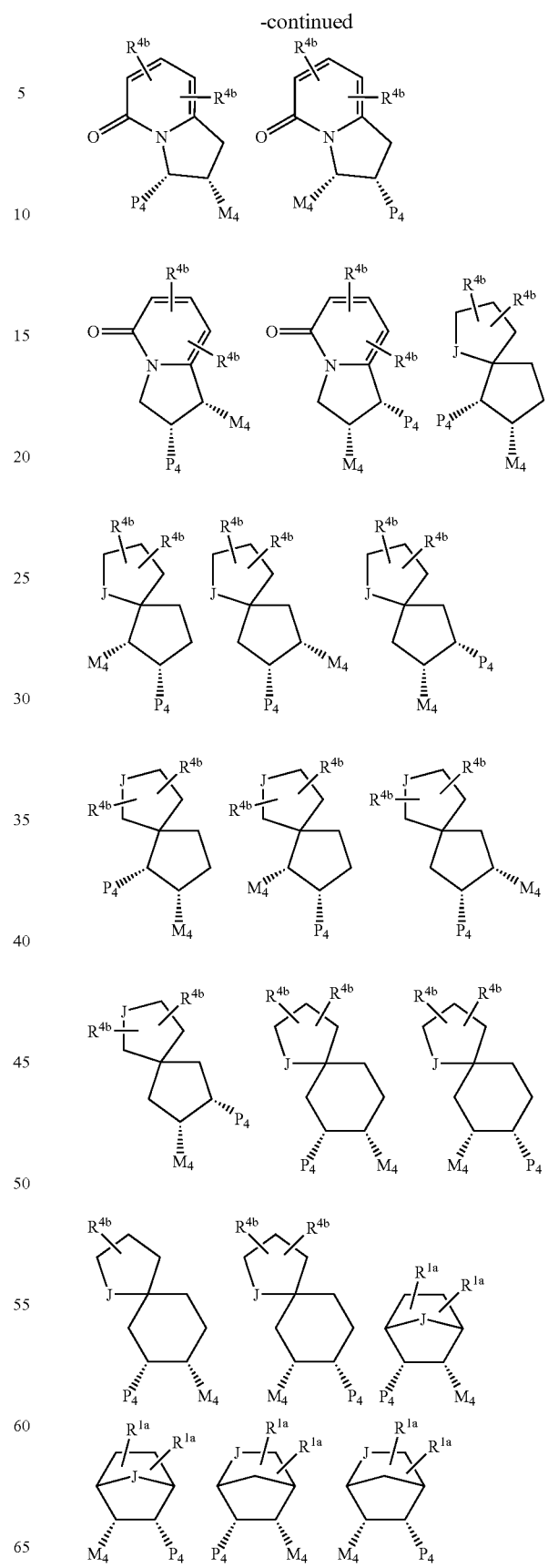

-continued
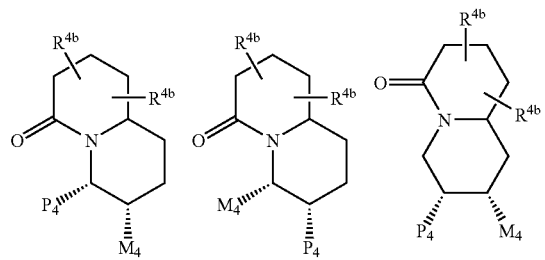
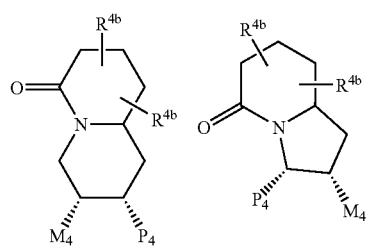
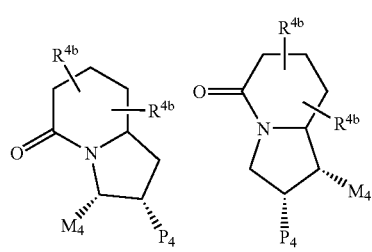
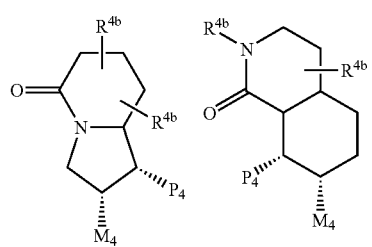
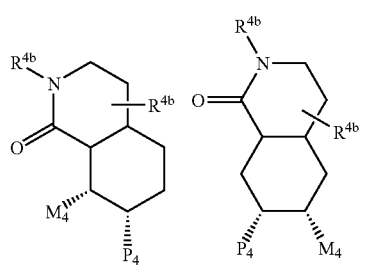
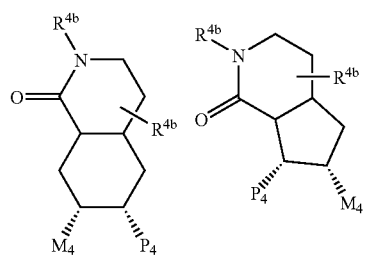
-continued
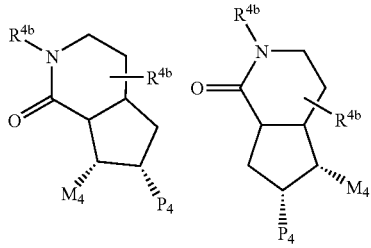
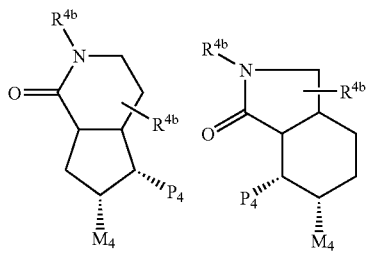
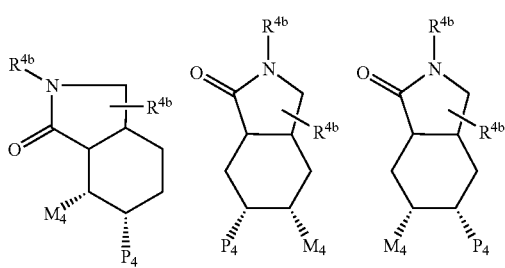
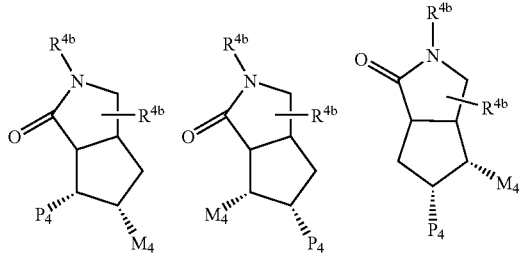
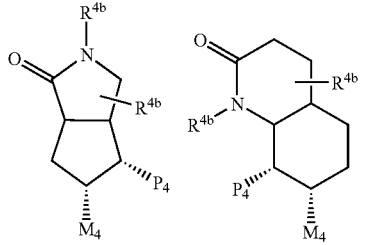
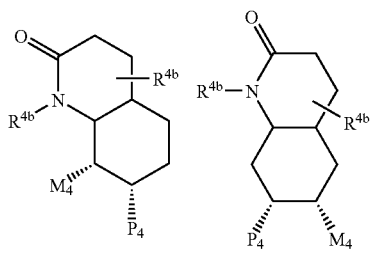

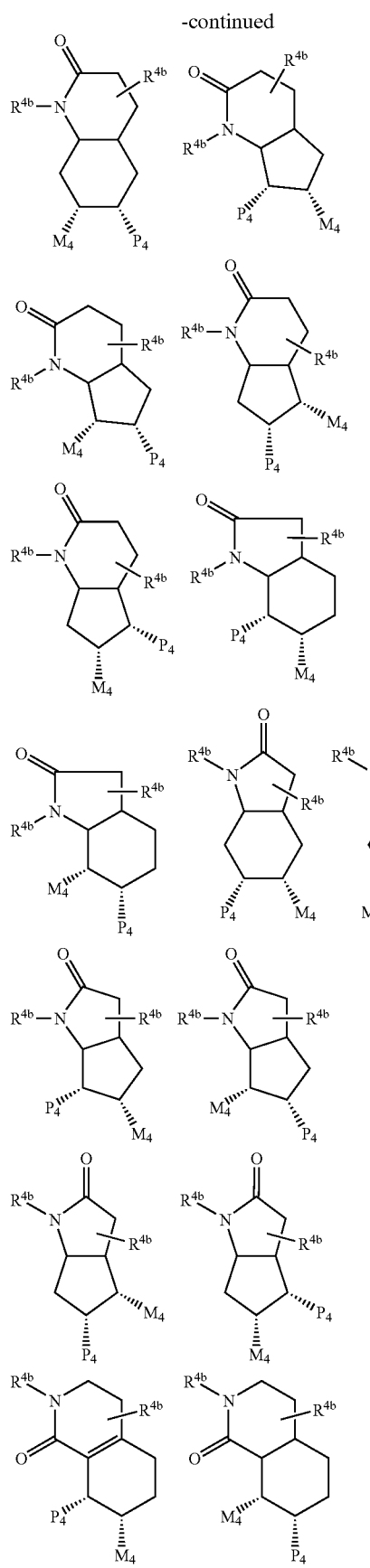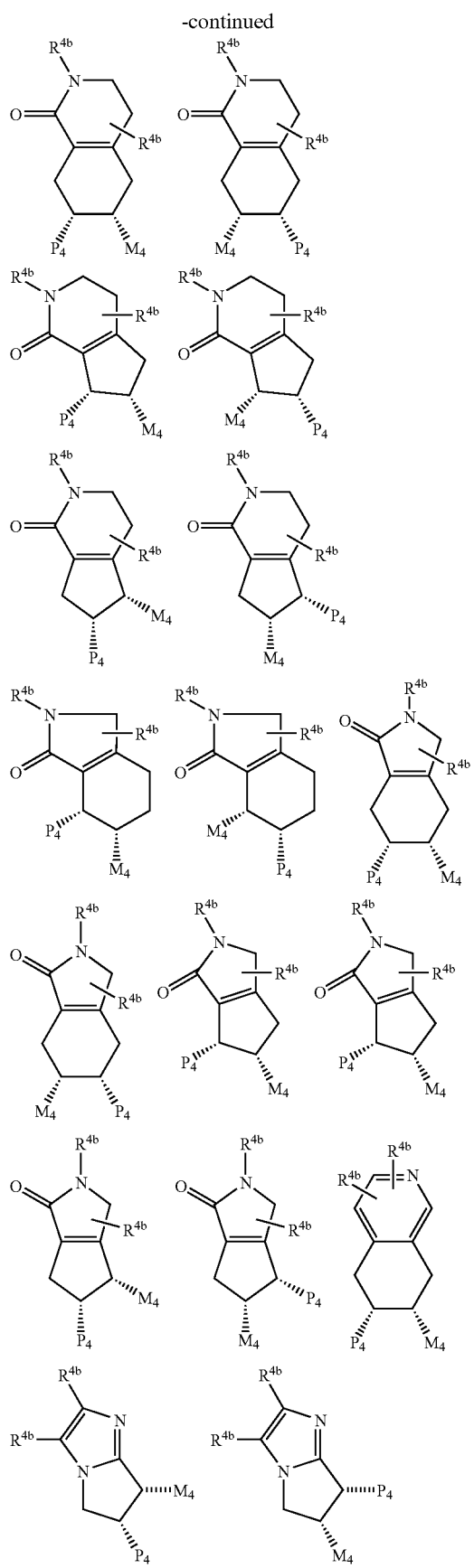

-continued

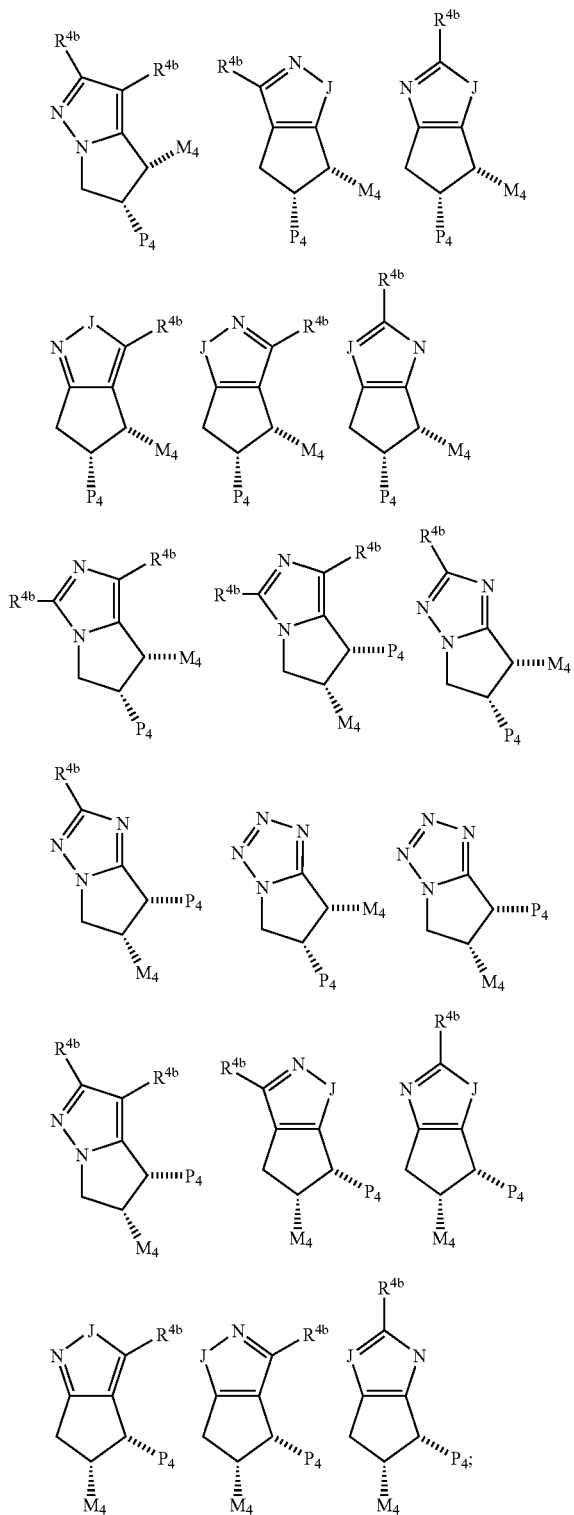

or a stereoisomer or pharmaceutically acceptable salt thereof, wherein:

J is selected from O, S, S(O)$_2$, CR$^{1a}$, and NR$^{1a}$;

one of P$_4$ and M$_4$ is -Z-A-B and the other -G$_1$-G;

G is a group of formula IIa or IIb:

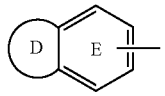

IIa

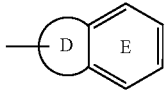

IIb ring D, including the two atoms of Ring E to which it is attached, is a 5–6 membered ring consisting of carbon atoms and 0–2 heteroatoms selected from the group consisting of N, O, and S(O)$_p$;

ring D is substituted with 0–2 R and there are 0–3 ring double bonds;

E is selected from phenyl, pyridyl, pyrimidyl, pyrazinyl, and pyridazinyl, and is substituted with 1–3 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1–3 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1 R and with a 5–6 membered heterocycle consisting of: carbon atoms and 1–4 heteroatoms selected from the group consisting of N, O, and S(O)$_p$, wherein the 5–6 membered heterocycle is substituted with 0–2 carbonyls and 1–3 R and there are 0–3 ring double bonds;

R is selected from H, C$_{1-4}$ alkyl, F, Cl, Br, I, OH, OCH$_3$, OCH$_2$CH$_3$, OCH(CH$_3$)$_2$, OCH$_2$CH$_2$CH$_3$, —CN, NH$_2$, NH(C$_{1-3}$ alkyl), N(C$_{1-3}$ alkyl)$_2$, C(=NH)NH$_2$, CH$_2$NH$_2$, CH$_2$NH(C$_{1-3}$ alkyl), CH$_2$N(C$_{1-3}$ alkyl)$_2$, CH$_2$CH$_2$NH$_2$, CH$_2$CH$_2$NH(C$_{1-3}$ alkyl), CH$_2$CH$_2$N(C$_{1-3}$ alkyl)$_2$, C(=NR$^8$)NR$^7$R$^9$, NHC(=NR$^8$)NR$^7$R$^9$, ONHC(=NR$^8$)NR$^7$R$^9$, NR$^8$CH(=NR$^7$), (CR$^8$R$^9$)$_r$C(O)H, (CR$^8$R$^9$)$_r$C(O)R$^{2c}$, (CR$^8$R$^9$)$_r$NR$^7$R$^8$, (CR$^8$R$^9$)$_r$C(O)NR$^7$R$^8$, (CR$^8$R$^9$)$_r$NR$^7$C(O) R$^7$, (CR$^8$R$^9$)$_r$OR$^3$, (CR$^8$R$^9$)$_r$S(O)$_p$NR$^7$R$^8$, (CR$^8$R$^9$)$_r$NR$^7$S (O)$_p$R$^7$, (CR$^8$R$^9$)$_r$SR$^3$, (CR$^8$R$^9$)$_r$S(O)R$^3$, (CR$^8$R$^9$)$_r$S(O)$_2$R$^3$, and OCF$_3$, provided that S(O)$_p$R$^7$ and S(O)$_2$R$^3$ form other than S(O)$_2$H or S(O)H;

alternatively, when 2 R groups are attached to adjacent atoms, they combine to form methylenedioxy or ethylenedioxy;

A is selected from C$_{3-10}$ carbocycle substituted with 0–2 R$^4$, and 5–12 membered heterocycle consisting of: carbon atoms and 1–4 heteroatoms selected from the group consisting of N, O, and S(O)$_p$ and substituted with 0–2 R$^4$;

B is

Provided that Z and B are Attached to Different atoms on A and that the A-Z-N moiety forms other than a N-N-N group;

Q$_1$ is selected from C=O and SO$_2$;

ring Q is a 4–7 membered monocyclic or tricyclic ring consisting of, in addition to the N-Q$_1$ group shown, carbon atoms and 0–2 heteroatoms selected from NR$^{4c}$, O, and S(O)$_p$, wherein: 0–2 double bonds are present within the ring and the ring is substituted with 0–2 R$^{4a}$;

alternatively, ring Q is a 4–7 membered ring to which another ring is fused, wherein: the 4–7 membered ring consists of, in addition to the N-Q$_1$ group shown, carbon atoms and 0–2 heteroatoms selected from NR$^{4c}$, O, and S(O)$_p$ and 0–1 double bonds are present within the ring; the fusion ring is phenyl or a 5–6 membered heteroaromatic consisting of carbon atoms and 1–2 heteroatoms selected from NR$^{4c}$, O, and S(O)$_p$;

ring Q, which includes the 4–7 membered ring and the fusion ring, is substituted with 0–3 R$^{4a}$;

X is absent or is selected from (CR$^2$R$^2$a)$_{1-4}$, C(O), C(O)CR$^2$R$^{2a}$, CR$^2$R$^{2a}$C(O), S(O)$_2$, S(O)$_2$CR$^2$R$^{2a}$, CR$^2$R$^{2a}$S(O)$_2$, NR$^2$S(O)$_2$, NR$^2$CR$^2$R$^{2a}$, and OCR$^2$R$^{2a}$, wherein the left side of X is attached to ring A;

G$_1$ is selected from (CR$^3$R$^{3a}$)$_{1-5}$, (CR$^3$R$^{3a}$)$_{0-2}$CR$^3$=CR$^3$(CR$^3$R$^{3a}$)$_{0-2}$, (CR$^3$R$^{3a}$)$_{0-2}$C≡C(CR$^3$R$^{3a}$)$_{0-2}$, (CR$^3$R$^{3a}$)$_u$C(O)(CR$^3$R$^{3a}$)$_w$, (CR$^3$R$^{3a}$)$_u$C(O)O(CR$^3$R$^{3a}$)$_w$, (CR$^3$R$^{3a}$)$_u$OC(O)(CR$^3$R$^{3a}$)$_w$, (CR$^3$R$^{3a}$)$_u$O(CR$^3$R$^{3a}$)$_w$, (CR$^3$R$^{3a}$)$_u$NR$^{3b}$(CR$^3$R$^{3a}$)$_w$, (CR$^3$R$^{3a}$)$_u$NR$^{3e}$(CR$^3$R$^{3a}$)$_w$, (CR$^3$R$^{3a}$)$_u$C(O)NR$^{3b}$(CR$^3$R$^{3a}$)$_w$, (CR$^3$R$^{3a}$)$_u$NR$^{3b}$C(O)(CR$^3$R$^{3a}$)$_w$, (CR$^3$R$^{3a}$)$_u$OC(O)NR$^{3b}$(CR$^3$R$^{3a}$)$_w$, (CR$^3$R$^{3a}$)$_u$NR$^{3b}$C(O)O(CR$^3$R$^{3a}$)$_w$, (CR$^3$R$^{3a}$)$_u$NR$^{3b}$C(O)NR$^{3b}$(CR$^3$R$^{3a}$)$_w$, (CR$^3$R$^{3a}$)$_u$NR$^{3b}$C(S)NR$^{3b}$(CR$^3$R$^{3a}$)$_w$, (CR$^3$R$^{3a}$)$_u$S(CR$^3$R$^{3a}$)$_w$, (CR$^3$R$^{3a}$)$_u$S(O)(CR$^3$R$^{3a}$)$_w$, (CR$^3$R$^{3a}$)$_u$S(O)$_2$(CR$^3$R$^{3a}$)$_w$, (CR$^3$R$^{3a}$)$_u$S(O)NR$^{3b}$(CR$^3$R$^{3a}$)$_w$, (CR$^3$R$^{3a}$)$_u$NR$^{3b}$S(O)$_2$(CR$^3$R$^{3a}$)$_w$, (CR$^3$R$^{3a}$)$_u$S(O)$_2$NR$^{3b}$(CR$^3$R$^{3a}$)$_w$, (CR$^3$R$^{3a}$)$_u$NR$^{3b}$S(O)$_2$NR$^{3b}$(CR$^3$R$^{3a}$)$_w$, (CR$^3$R$^{3a}$)$_u$C(O)(CR$^3$R$^{3a}$)$_u$C(O)(CR$^3$R$^{3a}$)$_w$, (CR$^3$R$^{3a}$)$_u$NR$^{3b}$(CR$^3$R$^{3a}$)$_u$C(O)NR$^{3b}$(CR$^3$R$^{3a}$)$_w$, (CR$^3$R$^{3a}$)$_u$NR$^{3b}$C(O)(CR$^3$R$^{3a}$)$_u$C(O)(CR$^3$R$^{3a}$)$_w$, (CR$^3$R$^{3a}$)$_u$C(O)(CR$^3$R$^{3a}$)$_u$C(O)NR$^{3b}$(CR$^3$R$^{3a}$)$_w$, (CR$^3$R$^{3a}$)$_u$NR$^{3b}$C(O)(CR$^3$R$^{3a}$)$_u$C(O)NR$^{3b}$(CR$^3$R$^{3a}$)$_w$, (CR$^3$R$^{3a}$)$_u$S(O)$_2$NR$^{3b}$C(O)(CR$^3$R$^{3a}$)$_w$, (CR$^3$R$^{3a}$)$_u$C(O)NR$^{3b}$S(O)$_2$(CR$^3$R$^{3a}$)$_w$, (CR$^3$R$^{3a}$)$_u$S(O)$_2$NR$^{3b}$C(O)NR$^{3b}$(CR$^3$R$^{3a}$)$_w$, (CR$^3$R$^{3a}$)$_u$NR$^{3b}$C(O)(CR$^3$R$^{3a}$)$_u$C(S)NR$^{3b}$(CR$^3$R$^{3a}$)$_w$, and (CR$^3$R$^{3a}$)$_u$NR$^{3b}$C(S)(CR$^3$R$^{3a}$)$_u$C(O)NR$^{3b}$(CR$^3$R$^{3a}$)$_w$, wherein u+w or u+u+w total 0, 1, 2, 3, or 4, and the right side of G$_1$ is attached to ring G, provided that G$_1$ does not form an N—S, NCH$_2$N, NCH$_2$O, or NCH$_2$S bond with either group to which it is attached;

Z is selected from (CR$^3$R$^{3a}$)$_{1-5}$, (CR$^3$R$^{3a}$)$_{0-2}$CR$^3$=CR$^3$(CR$^3$R$^{3a}$)$_{0-2}$, (CR$^3$R$^{3a}$)$_{0-2}$C≡C(CR$^3$R$^{3a}$)$_{0-2}$, (CR$^3$R$^{3a}$)$_u$C(O)(CR$^3$R$^{3a}$)$_w$, (CR$^3$R$^{3a}$)$_u$C(O)O(CR$^3$R$^{3a}$)$_w$, (CR$^3$R$^{3a}$)$_u$OC(O)(CR$^3$R$^{3a}$)$_w$, (CR$^3$R$^{3a}$)$_u$O(CR$^3$R$^{3a}$)$_w$, (CR$^3$R$^{3a}$)$_u$NR$^{3b}$(CR$^3$R$^{3a}$)$_w$, (CR$^3$R$^{3a}$)$_u$NR$^{3e}$(CR$^3$R$^{3a}$)$_w$, (CR$^3$R$^{3a}$)$_u$C(O)NR$^{3b}$(CR$^3$R$^{3a}$)$_w$, (CR$^3$R$^{3a}$)$_u$NR$^{3b}$C(O)(CR$^3$R$^{3a}$)$_w$, (CR$^3$R$^{3a}$)$_u$OC(O)NR$^{3b}$(CR$^3$R$^{3a}$)$_w$, (CR$^3$R$^{3a}$)$_u$NR$^{3b}$C(O)O(CR$^3$R$^{3a}$)$_w$, (CR$^3$R$^{3a}$)$_u$NR$^{3b}$C(O)NR$^{3b}$(CR$^3$R$^{3a}$)$_w$, (CR$^3$R$^{3a}$)$_u$NR$^{3b}$C(S)NR$^{3b}$(CR$^3$R$^{3a}$)$_w$, (CR$^3$R$^{3a}$)$_u$S(CR$^3$R$^{3a}$)$_w$, (CR$^3$R$^{3a}$)$_u$S(O)(CR$^3$R$^{3a}$)$_w$, (CR$^3$R$^{3a}$)$_u$S(O)$_2$(CR$^3$R$^{3a}$)$_w$, (CR$^3$R$^{3a}$)$_u$S(O)NR$^{3b}$(CR$^3$R$^{3a}$)$_w$, (CR$^3$R$^{3a}$)$_u$NR$^{3b}$S(O)$_2$(CR$^3$R$^{3a}$)$_w$, (CR$^3$R$^{3a}$)$_u$S(O)$_2$NR$^{3b}$(CR$^3$R$^{3a}$)$_w$, (CR$^3$R$^{3a}$)$_u$NR$^{3b}$S(O)$_2$NR$^{3b}$(CR$^3$R$^{3a}$)$_w$, (CR$^3$R$^{3a}$)$_u$C(O)(CR$^3$R$^{3a}$)$_w$, (CR$^3$R$^{3a}$)$_u$C(O)(CR$^3$R$^{3a}$)$_u$C(O)(CR$^3$R$^{3a}$)$_w$, (CR$^3$R$^{3a}$)$_u$NR$^{3b}$(CR$^3$R$^{3a}$)$_u$C(O)(CR$^3$R$^{3a}$)$_w$, (CR$^3$R$^{3a}$)$_u$NR$^{3b}$C(O)(CR$^3$R$^{3a}$)$_u$C(O)(CR$^3$R$^{3a}$)$_w$, (CR$^3$R$^{3a}$)$_u$C(O)(CR$^3$R$^{3a}$)$_u$C(O)NR$^{3b}$(CR$^3$R$^{3a}$)$_w$, (CR$^3$R$^{3a}$)$_u$NR$^{3b}$C(O)(CR$^3$R$^{3a}$)$_u$C(O)NR$^{3b}$(CR$^3$R$^{3a}$)$_w$, (CR$^3$R$^{3a}$)$_u$S(O)$_2$NR$^{3b}$C(O)(CR$^3$R$^{3a}$)$_w$, (CR$^3$R$^{3a}$)$_u$C(O)NR$^{3b}$S(O)$_2$(CR$^3$R$^{3a}$)$_w$, (CR$^3$R$^{3a}$)$_u$S(O)$_2$NR$^{3b}$C(O)NR$^{3b}$(CR$^3$R$^{3a}$)$_w$, (CR$^3$R$^{3a}$)$_u$NR$^{3b}$C(O)(CR$^3$R$^{3a}$)$_u$C(S)NR$^{3b}$(CR$^3$R$^{3a}$)$_w$, and (CR$^3$R$^{3a}$)$_u$NR$^{3b}$C(S)(CR$^3$R$^{3a}$)$_u$C(O)NR$^{3b}$(CR$^3$R$^{3a}$)$_w$, wherein u+w or u+u+w total 0, 1, 2, 3, or 4, and the right side of Z is attached to ring A, provided that Z does not form an N—S, NCH$_2$N, NCH$_2$O, or NCH$_2$S bond with either group to which it is attached;

R$^{1a}$, at each occurrence, is selected from H, —(CR$^3$R$^{3a}$)$_r$—R$^{1b}$, —(CR$^3$R$^{3a}$)$_r$—CR$^3$R$^{1b}$R$^{1b}$, —(CR$^3$R$^{3a}$)$_r$—O—(CR$^3$R$^{3a}$)$_r$—R$^{1b}$, —C$_{2-6}$ alkenylene-R$^{1b}$, —C$_{2-6}$ alkynylene-R$^{1b}$, —(CR$^3$R$^{3a}$)$_r$—C(=NR$^{1b}$)NR$^3$R$^{1b}$, NR$^3$CR$^3$R$^{3a}$R$^{1c}$, OCR$^3$R$^{3a}$R$^{1c}$, SCR$^3$R$^{3a}$R$^{1c}$, NR$^3$(CR$^3$R$^{3a}$)$_2$(CR$^3$R$^{3a}$)$_t$R$^{1b}$, C(O)NR$^2$(CR$^3$R$^{3a}$)$_2$(CR$^3$R$^{3a}$)$_t$R$^{1b}$,CO$_2$(CR$^3$R$^{3a}$)$_2$(CR$^3$R$^{3a}$)$_t$R$^{1b}$, CO$_2$(CR$^3$R$^{3a}$)$_2$(CR$^3$R$^{3a}$)$_t$R$^{1b}$, S(CR$^3$R$^{3a}$)$_2$(CR$^3$R$^{3a}$)$_t$R$^{1b}$, S(O)$_p$(CR$^3$R$^{3a}$)$_r$R$^{1d}$, O(CR$^3$R$^{3a}$)$_r$R$^{1d}$, NR$^3$(CR$^3$R$^{3a}$)$_r$R$^{1d}$, OC(O)NR$^3$(CR$^3$R$^{3a}$)$_r$R$^{1d}$, NR$^3$C(O)NR$^3$(CR$^3$R$^{3a}$)$_r$R$^{1d}$, NR$^3$C(O)O(CR$^3$R$^{3a}$)$_r$R$^{1d}$, and NR$^3$C(O)(CR$^3$R$^{3a}$)$_r$R$^{1d}$, provided that R$^{1a}$ forms other than an N-halo, N—S, O—O, or N—CN bond;

alternatively, when two R$^{1a}$ groups are attached to adjacent atoms, together with the atoms to which they are attached they form a 5–7 membered ring consisting of: carbon atoms and 0–2 heteroatoms selected from the group consisting of N, O, and S(O)$_p$, this ring being substituted with 0–2 R$^{4b}$ and having 0–3 ring double bonds;

R$^{1b}$ is selected from H, C$_{1-3}$ alkyl, F, Cl, Br, I, —CN, —NO$_2$, —CHO, (CF$_2$)$_r$CF$_3$, (CR$^3$R$^{3a}$)$_r$OR$^2$, NR$^2$R$^{2a}$, C(O)R$^{2b}$, CO$_2$R$^{2b}$, OC(O)R$^2$, (CF$_2$)$_r$CO$_2$R$^{2a}$, S(O)$_p$R$^{2b}$, NR$^2$(CH$_2$)$_r$OR$^2$, C(=NR$^{2c}$)NR$^2$R$^{2a}$, NR$^2$C(O)R$^{2b}$, NR$^2$C(O)NHR$^2$, NR$^2$C(O)$_2$R$^{2a}$, OC(O)NR$^2$R$^{2a}$, C(O)NR$^2$R$^{2a}$, C(O)NR$^2$R$^{2b}$, C(S)NR$^2$R$^{2a}$, C(O)NR$^2$(CH$_2$)$_r$OR$^2$, SO$_2$NR$^2$R$^{2a}$, NR$^2$SO$_2$R$^2$, C(O)NR$^2$SO$_2$R$^2$, C$_{3-6}$ carbocycle substituted with 0–2 R$^{4b}$, and 5–10 membered heterocycle consisting of carbon atoms and from 1–4 heteroatoms selected from the group consisting of N, O, and S(O)$_p$, and substituted with 0–2 R$^{4b}$, provided that R$^{1b}$ forms other than an O—O, N-halo, N—S, or N—CN bond;

R$^{1c}$ is selected from H, CH(CH$_2$OR$^2$)$_2$, C(O)R$^{2c}$, C(O)NR$^2$R$^{2a}$, S(O)R$^2$, S(O)$_2$R$^2$, and SO$_2$NR$^2$R$^{2a}$;

R$^{1d}$ is selected from C$_{3-6}$ carbocycle substituted with 0–2 R$^{4b}$ and 5–10 membered heterocycle consisting of carbon atoms and from 1–4 heteroatoms selected from the group consisting of N, O, and S(O)$_p$, and substituted with 0–2 R$^{4b}$, provided that R$^{1d}$ forms other than an N—S bond;

R$^2$, at each occurrence, is selected from H, CF$_3$, C$_{1-6}$ alkyl, —(CH$_2$)$_r$—C$_{3-10}$ carbocycle substituted with 0–2 R$^{4b}$, and —(CH$_2$)$_{r-5-10}$ membered heterocycle consisting of: carbon atoms and 1–4 heteroatoms selected from the group consisting of N, O, and S(O)$_p$, and substituted with 0–2 R$^{4b}$;

R$^{2a}$, at each occurrence, is selected from H, CF$_3$, C$_{1-6}$ alkyl, —(CH$_2$)$_r$—C$_{3-10}$ carbocycle substituted with 0–2 R$^{4b}$, and —(CH$_2$)$_{r-5-10}$ membered heterocycle consisting of: carbon atoms and 1–4 heteroatoms selected from the group consisting of N, O, and S(O)$_p$, and substituted with 0–2 R$^{4b}$;

alternatively, NR$^2$R$^{2a}$ forms a 4, 5, or 6 membered saturated, partially saturated, or unsaturated ring substituted with 0–2 R$^{4b}$ and consisting of: carbon atoms, the nitrogen atom to which R$^2$ and R$^{2a}$ are attached, and 0–1 additional heteroatoms selected from the group consisting of N, O, and S(O)$_p$;

R$^{2b}$, at each occurrence, is selected from CF$_3$, C$_{1-4}$ alkoxy substituted with 0–2 R$^{4b}$, C$_{1-6}$ alkyl substituted with 0–3 R$^{4b}$, —(CH$_2$)$_r$—C$_{3-13}$ carbocycle substituted with 0–2 R$^{4b}$, and —(CH$_2$)$_{r-5-10}$ membered heterocycle consisting of: carbon atoms and 1–4 heteroatoms selected from the group consisting of N, O, and S(O)$_p$, and substituted with 0–2 R$^{4b}$;

R$^{2c}$, at each occurrence, is selected from CF$_3$, OH, C$_{1-4}$ alkoxy, C$_{1-6}$ alkyl, —(CH$_2$)$_r$—C$_{3-10}$ carbocycle substituted with 0–2 R$^{4b}$, and —(CH$_2$)$_r$-5–10 membered heterocycle containing from 1–4 heteroatoms selected from the group consisting of N, O, and S(O)$_p$, and substituted with 0–2 R$^{4b}$;

R$^3$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl, and phenyl;

$R^{3a}$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl, and phenyl;

alternatively, NR$^3$R$^{3a}$ forms a 5 or 6 membered saturated, partially unsaturated, or unsaturated ring consisting of: carbon atoms, the nitrogen atom to which R$^3$ and R$^{3a}$ are attached, and 0–1 additional heteroatoms selected from the group consisting of N, O, and S(O)$_p$;

$R^{3b}$, at each occurrence, is selected from H, C$_{1-6}$ alkyl substituted with 0–2 R$^{1a}$, C$_{2-6}$ alkenyl substituted with 0–2 R$^{1a}$, C$_{2-6}$ alkynyl substituted with 0–2 R$^{1a}$, —(C$_{0-4}$ alkyl)-5–10 membered carbocycle substituted with 0–3 R$^{1a}$, and —(C$_{0-4}$ alkyl)-5–10 membered heterocycle substituted with 0–3 R$^{1a}$ and consisting of: carbon atoms and 1–4 heteroatoms selected from the group consisting of N, O, and S(O)$_p$;

$R^{3c}$, at each occurrence, is selected from CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl, and phenyl;

$R^{3d}$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C$_{1-4}$ alkyl-phenyl, and C(=O)R$^{3c}$;

$R^{3e}$, at each occurrence, is selected from H, SO$_2$NHR$^3$, SO$_2$NR$^3$R$^3$, C(O)R$^3$, C(O)NHR$^3$, C(O)OR$^{3f}$, S(O)R$^{3f}$, S(O)$_2$R$^{3f}$, C$_{1-6}$ alkyl substituted with 0–2 R$^{1a}$, C$_{2-6}$ alkenyl substituted with 0–2 R$^{1a}$, C$_{2-6}$ alkynyl substituted with 0–2 R$^{1a}$, —(C$_{0-4}$ alkyl)-5–10 membered carbocycle substituted with 0–3 R$^{1a}$, and —(C$_{0-4}$ alkyl)-5–10 membered heterocycle substituted with 0–3 R$^{1a}$ and consisting of: carbon atoms and 1–4 heteroatoms selected from the group consisting of N, O, and S(O)$_p$;

$R^{3f}$, at each occurrence, is selected from: C$_{1-6}$ alkyl substituted with 0–2 R$^{1a}$, C$_{2-6}$ alkenyl substituted with 0–2 R$^{1a}$, C$_{2-6}$ alkynyl substituted with 0–2 R$^{1a}$, —(C$_{0-4}$ alkyl)-5–10 membered carbocycle substituted with 0–3 R$^{1a}$, and —(C$_{0-4}$ alkyl)-5–10 membered heterocycle substituted with 0–3 R$^{1a}$ and consisting of: carbon atoms and 1–4 heteroatoms selected from the group consisting of N, O, and S(O)$_p$;

$R^4$, at each occurrence, is selected from H, =O, (CR$^3$R$^{3a}$)$_r$OR$^2$, F, Cl, Br, I, C$_{1-4}$ alkyl, (CR$^3$R$^{3a}$)$_r$CN, (CR$^3$R$^{3a}$)$_r$NO$_2$, (CR$^3$R$^{3a}$)$_r$NR$^2$R$^{2a}$, (CR$^3$R$^{3a}$)$_r$C(O)R$^{2c}$, (CR$^3$R$^{3a}$)$_r$NR$^2$C(O)R$^{2b}$, (CR$^3$R$^{3a}$)$_r$C(O)NR$^2$R$^{2a}$, (CR$^3$R$^{3a}$)$_r$NR$^2$C(O)NR$^2$R$^{2a}$, (CR$^3$R$^{3a}$)$_r$C(=NR$^2$)NR$^2$R$^{2a}$, (CR$^3$R$^{3a}$)$_r$C(=NS(O)$_2$R$^5$)NR$^2$R$^{2a}$, (CR$^3$R$^{3a}$)$_r$NHC(=NR$^2$)NR$^2$R$^{2a}$, (CR$^3$R$^{3a}$)$_r$C(O)NHC(=NR$^2$)NR$^2$R$^{2a}$, (CR$^3$R$^{3a}$)$_r$SO$_2$NR$^2$R$^{2a}$, (CR$^3$R$^{3a}$)$_r$NR$^2$SO$_2$NR$^2$R$^{2a}$, (CR$^3$R$^{3a}$)$_r$NR$^2$SO$_2$—C$_{1-4}$ alkyl, (CR$^3$R$^{3a}$)$_r$NR$^2$SO$_2$R$^5$, (CR$^3$R$^{3a}$)$_r$S(O)$_p$R$^{5a}$, (CR$^3$R$^{3a}$)$_r$(CF$_2$)$_r$CF$_3$, NHCH$_2$R$^{1c}$, OCH$_2$R$^{1c}$, SCH$_2$R$^{1c}$, NH(CH$_2$)$_2$(CH$_2$)$_r$R$^{1b}$, O(CH$_2$)$_2$(CH$_2$)$_r$R$^{1b}$, S(CH$_2$)$_2$(CH$_2$)$_r$R$^{1b}$, (CR$^3$R$^{3a}$)$_r$-5–6 membered carbocycle substituted with 0–1 R$^5$, and a (CR$^3$R$^{3a}$)$_r$-5–6 membered heterocycle consisting of: carbon atoms and 1–4 heteroatoms selected from the group consisting of N, O, and S(O)$_p$ and substituted with 0–1 R$^5$;

$R^{4a}$, at each occurrence, is selected from H, =O, (CR$^3$R$^{3a}$)$_r$OR$^2$, (CR$^3$R$^{3a}$)$_r$F, (CR$^3$R$^{3a}$)$_r$Br, (CR$^3$R$^{3a}$)$_r$Cl, C$_{1-4}$ alkyl, (CR$^3$R$^{3a}$)$_r$CN, (CR$^3$R$^{3a}$)$_r$NO$_2$, (CR$^3$R$^{3a}$)$_r$NR$^2$R$^{2a}$, (CR$^3$R$^{3a}$)$_r$C(O)R$^{2c}$, (CR$^3$R$^{3a}$)$_r$NR$^2$C(O)R$^{2b}$, (CR$^3$R$^{3a}$)$_r$C(O)NR$^2$R$^{2a}$, (CR$^3$R$^{3a}$)$_r$N=CHOR$^3$, (CR$^3$R$^{3a}$)$_r$C(O)NH(CH$_2$)$_2$NR$^2$R$^{2a}$, (CR$^3$R$^{3a}$)$_r$NR$^2$C(O)NR$^2$R$^{2a}$, (CR$^3$R$^{3a}$)$_r$C(=NR$^2$)NR$^2$R$^{2a}$, (CR$^3$R$^{3a}$)$_r$NHC(=NR$^2$)NR$^2$R$^{2a}$, (CR$^3$R$^{3a}$)$_r$SO$_2$NR$^2$R$^{2a}$, (CR$^3$R$^{3a}$)$_r$NR$^2$SO$_2$NR$^2$R$^{2a}$, (CR$_3$R$^{3a}$)$_r$C(O)NHSO$_2$—C$_{1-4}$ alkyl, (CR$^3$R$^{3a}$)$_r$NR$^2$SO$_2$R$^5$, (CR$^3$R$^{3a}$)$_r$S(O)$_p$R$^{5a}$, (CR$^3$R$^{3a}$)$_r$(CF$_2$)$_r$CF$_3$, (CR$^3$R$^{3a}$)$_r$-5–6 membered carbocycle substituted with 0–1 R$^5$, and a (CR$^3$R$^{3a}$)$_r$-5–6 membered heterocycle consisting of: carbon atoms and 1–4 heteroatoms selected from the group consisting of N, O, and S(O)$_p$, and substituted with 0–1 R$^5$;

$R^{4b}$, at each occurrence, is selected from H, =O, (CH$_2$)$_r$OR$^3$, (CH$_2$)$_r$F, (CH$_2$)$_r$Cl, (CH$_2$)$_r$Br, (CH$_2$)$_r$I, C$_{1-4}$ alkyl, (CH$_2$)$_r$CN, (CH$_2$)$_r$NO$_2$, (CH$_2$)$_r$NR$^3$R$^{3a}$, (CH$_2$)$_r$C(O)R$^3$, (CH$_2$)$_r$C(O)OR$^{3c}$, (CH$_2$)$_r$NR$^3$C(O)R$^{3a}$, (CH$_2$)$_r$—C(O)NR$^3$R$^{3a}$, (CH$_2$)$_r$NR$^3$C(O)NR$^3$R$^{3a}$, (CH$_2$)$_r$—C(=NR$^3$)NR$^3$R$^{3a}$, (CH$_2$)$_r$NR$^3$C(=NR$^3$)NR$^3$R$^{3a}$, (CH$_2$)$_r$SO$_2$NR$^3$R$^{3a}$, (CH$_2$)$_r$NR$^3$SO$_2$NR$^3$R$^{3a}$, (CH$_2$)$_r$NR$^3$SO$_2$—C$_{1-4}$ alkyl, (CH$_2$)$_r$ NR$^3$SO$_2$CF$_3$, (CH$_2$)$_r$NR$^3$SO$_2$-phenyl, (CH$_2$)$_r$S(O)$_p$CF$_3$, (CH$_2$)$_r$S(O)$_p$—C$_{1-4}$ alkyl, (CH$_2$)$_r$S(O)$_p$-phenyl, and (CH$_2$)$_r$(CF$_2$)$_r$CF$_3$;

$R^{4c}$, at each occurrence, is selected from H, C$_{1-4}$ alkyl, (CR$^3$R$^{3a}$)$_{r1}$OR$^2$, (CR$^3$R$^{3a}$)$_{r1}$F, (CR$^3$R$^{3a}$)$_{r1}$Br, (CR$^3$R$^{3a}$)$_{r1}$Cl, (CR$^3$R$^{3a}$)$_{r1}$CN, (CR$^3$R$^{3a}$)$_{r1}$NO$_2$, (CR$^3$R$^{3a}$)$_{r1}$NR$^2$R$^{2a}$, (CR$^3$R$^{3a}$)$_{r1}$C(O)R$^{2c}$, (CR$^3$R$^{3a}$)$_{r1}$NR$^2$C(O)R$^{2b}$, (CR$^3$R$^{3a}$)$_r$C(O)NR$^2$R$^{2a}$, (CR$^3$R$^{3a}$)$_{r1}$N=CHOR$^3$, (CR$^3$R$^{3a}$)$_r$C(O)NH(CH$_2$)$_2$NR$^2$R$^{2a}$, (CR$^3$R$^{3a}$)$_{r1}$NR$^2$C(O)NR$^2$R$^{2a}$, (CR$^3$R$^{3a}$)$_{r1}$C(=NR$^2$)NR$^2$R$^{2a}$, (CR$^3$R$^{3a}$)$_{r1}$NHC(=NR$^2$)NR$^2$R$^{2a}$, (CR$^3$R$^{3a}$)$_{r1}$SO$_2$NR$^2$R$^{2a}$, (CR$^3$R$^{3a}$)$_{r1}$NR$^2$SO$_2$NR$^2$R$^{2a}$, (CR$^3$R$^{3a}$)$_{r1}$NR$^2$SO$_2$—C$_{1-4}$ alkyl, (CR$_3$R$^{3a}$)$_r$C(O)NHSO$_2$—C$_{1-4}$ alkyl, (CR$^3$R$^{3a}$)$_{r1}$NR$^2$SO$_2$R$^5$, (CR$^3$R$^{3a}$)$_r$S(O)$_p$R$^{5a}$, (CR$^3$R$^{3a}$)$_r$(CF$_2$)$_r$CF$_3$, (CR$^3$R$^{3a}$)$_r$-5–6 membered carbocycle substituted with 0–1 R$^5$, and a (CR$^3$R$^{3a}$)$_r$-5–6 membered heterocycle consisting of: carbon atoms and 1–4 heteroatoms selected from the group consisting of N, O, and S(O)$_p$, and substituted with 0–1 R$^5$;

$R^5$, at each occurrence, is selected from H, C$_{1-6}$ alkyl, =O, (CH$_2$)$_r$OR$^3$, F, Cl, Br, I, —CN, NO$_2$, (CH$_2$)$_r$NR$^3$R$^{3a}$, (CH$_2$)$_r$C(O)R$^3$, (CH$_2$)$_r$C(O)OR$^{3c}$, (CH$_2$)$_r$NR$^3$C(O)R$^{3a}$, (CH$_2$)$_r$C(O)NR$^3$R$^{3a}$, (CH$_2$)$_r$NR$^3$C(O)NR$^3$R$^{3a}$, (CH$_2$)$_r$CH(=NOR$^{3d}$), (CH$_2$)$_r$C(=NR$^3$)NR$^3$R$^{3a}$, (CH$_2$)$_r$NR$^3$C(=NR$^3$)NR$^3$R$^{3a}$, (CH$_2$)$_r$SO$_2$NR$^3$R$^{3a}$, (CH$_2$)$_r$NR$^3$SO$_2$NR$^3$R$^{3a}$, (CH$_2$)$_r$NR$^3$SO$_2$—C$_{1-4}$ alkyl, (CH$_2$)$_r$NR$^3$SO$_2$CF$_3$, (CH$_2$)$_r$NR$^3$SO$_2$-phenyl, (CH$_2$)$_r$S(O)$_p$CF$_3$, (CH$_2$)$_r$S(O)$_p$—C$_{1-4}$ alkyl, (CH$_2$)$_r$S(O)$_p$-phenyl, (CF$_2$)$_r$CF$_3$, phenyl substituted with 0–2 R$^6$, naphthyl substituted with 0–2 R$^6$, and benzyl substituted with 0–2 R$^6$;

$R^{5a}$, at each occurrence, is selected from C$_{1-6}$ alkyl, (CH$_2$)$_r$OR$^3$, (CH$_2$)$_r$NR$^3$R$^{3a}$, (CH$_2$)$_r$C(O)R$^3$, (CH$_2$)$_r$C(O)OR$^{3c}$, (CH$_2$)$_r$NR$^3$C(O)R$^{3a}$, (CH$_2$)$_r$C(O)NR$^3$R$^{3a}$, (CF$_2$)$_r$CF$_3$, phenyl substituted with 0–2 R$^6$, naphthyl substituted with 0–2 R$^6$, and benzyl substituted with 0–2 R$^6$, provided that R$^{5a}$ does not form a S—N or S(O)$_p$—C(O) bond;

$R^6$, at each occurrence, is selected from H, OH, (CH$_2$)$_r$OR$^2$, Cl, F, Br, I, C$_{1-4}$ alkyl, —CN, NO$_2$, (CH$_2$)$_r$NR$^2$R$^{2a}$, (CH$_2$)$_r$C(O)R$^{2b}$, NR$^2$C(O)R$^{2b}$, NR$^2$C(O)NR$^2$R$^{2a}$, C(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl;

$R^7$, at each occurrence, is selected from H, OH, C$_{1-6}$ alkyl, C$_{1-6}$ alkyl-C(O)—, C$_{1-6}$ alkyl-O—, (CH$_2$)$_n$-phenyl, C$_{1-4}$ alkyl-OC(O)—, C$_{6-10}$ aryl-O—, C$_{6-10}$ aryl-OC(O)—, C$_{6-10}$ aryl-CH$_2$C(O)—, C$_{1-4}$ alkyl-C(O)O—C$_{1-4}$ alkyl-OC(O)—, C$_{6-10}$ aryl-C(O)O—C$_{1-4}$ alkyl-OC(O)—, C$_{1-6}$ alkyl-NH$_2$—C(O)—, phenyl-NH$_2$—C(O)—, and phenyl-C$_{1-4}$ alkyl-C(O)—;

$R^8$, at each occurrence, is selected from H, C$_{1-6}$ alkyl, and (CH$_2$)$_n$-phenyl;

alternatively, NR$^7$R$^8$ forms a 5–10 membered heterocyclic ring consisting of carbon atoms and 0–2 additional heteroatoms selected from the group consisting of N, O, and S(O)$_p$;

$R^9$, at each occurrence, is selected from H, C$_{1-6}$ alkyl, and (CH$_2$)$_n$-phenyl;

n, at each occurrence, is selected from 0, 1, 2, and 3;

p, at each occurrence, is selected from 0, 1, and 2;

r, at each occurrence, is selected from 0, 1, 2, 3, 4, 5, and 6;

r1, at each occurrence, is selected from 1, 2, 3, 4, 5, and 6; and t, at each occurrence, is selected from 0, 1, 2, and 3.

In a second embodiment, the present invention provides a novel compound, wherein:

G is selected from the group: 2-aminomethyl-4-chloro-phenyl; 2-aminosulfonyl-4-chloro-phenyl; 2-amido-4-chloro-phenyl; 4-chloro-2-methylsulfonyl-phenyl; 2-aminosulfonyl-4-fluoro-phenyl; 2-amido-4-fluoro-phenyl; 4-fluoro-2-methylsulfonyl-phenyl; 2-aminomethyl-4-bromo-phenyl; 2-aminosulfonyl-4-bromo-phenyl; 2-amido-4-bromo-phenyl; 4-bromo-2-methylsulfonyl-phenyl; 2-aminomethyl-4-methyl-phenyl; 2-aminosulfonyl-4-methyl-phenyl; 2-amido-4-methyl-phenyl; 2-methylsulfonyl-4-methyl-phenyl; 4-fluoro-pyrid-2-yl; 4-bromo-pyrid-2-yl; 4-methyl-pyrid-2-yl; 5-fluoro-thien-2-yl; 5-bromo-thien-2-yl; 5-methyl-thien-2-yl; 2-amido-4-methoxy-phenyl; 2-amido-phenyl; 2-aminomethyl-3-fluoro-phenyl; 2-aminomethyl-4-fluoro-phenyl; 2-aminomethyl-4-methoxy-phenyl; 2-aminomethyl-5-fluoro-phenyl; 2-aminomethyl-5-methoxy-phenyl; 2-aminomethyl-6-fluoro-phenyl; 2-aminomethyl-phenyl; 2-amino-pyrid-4-yl; 2-aminosulfonyl-4-methoxy-phenyl; 2-aminosulfonyl-phenyl; 2-methylsulfonyl-phenyl; 3-(N,N-dimethylamino)-4-chloro-phenyl; 3-(N,N-dimethylamino)-phenyl; 3-(N-methylamino)-4-chloro-phenyl; 3-(N-methylamino)-phenyl; 3-amido-phenyl; 3-amino-4-chloro-phenyl; 3-aminomethyl-phenyl; 3-amino-phenyl; 3-chloro-phenyl; 4-(N,N-dimethylamino)-5-chloro-thien-2-yl; 4-(N-methylamino)-5-chloro-thien-2-yl; 4-amino-5-chloro-thien-2-yl; 4-chloro-phenyl; 4-methoxy-2-methylsulfonyl-phenyl; 4-methoxy-phenyl; 2-methoxy-pyrid-5-yl; 5-(N,N-dimethylamino)-4-chloro-thien-2-yl; 5-(N-methylamino)-4-chloro-thien-2-yl; 5-amino-4-chloro-thien-2-yl; 5-chloro-pyrid-2-yl; 5-chloro-thien-2-yl; 6-amino-5-chloro-pyrid-2-yl; 6-amino-pyrid-2-yl; 2-cyano-4-chloro-phenyl; 2-methoxy-4-chloro-phenyl; 2-fluoro-4-chloro-phenyl; phenyl; 4-ethyl-phenyl; 3-chloro-4-methyl-phenyl; 4-fluoro-phenyl; 3-fluoro-4-chloro-phenyl; 3-methyl-4-chloro-phenyl; 3-fluoro-4-methyl-phenyl; 3,4-dimethyl-phenyl; 3-chloro-4-fluoro-phenyl; 3-methyl-4-fluoro-phenyl; 4-methylsulfanyl-phenyl; 2-chlorothiazol-5-yl; 5-chlorothiazol-2-yl;

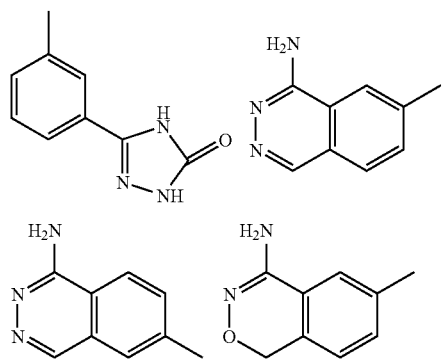

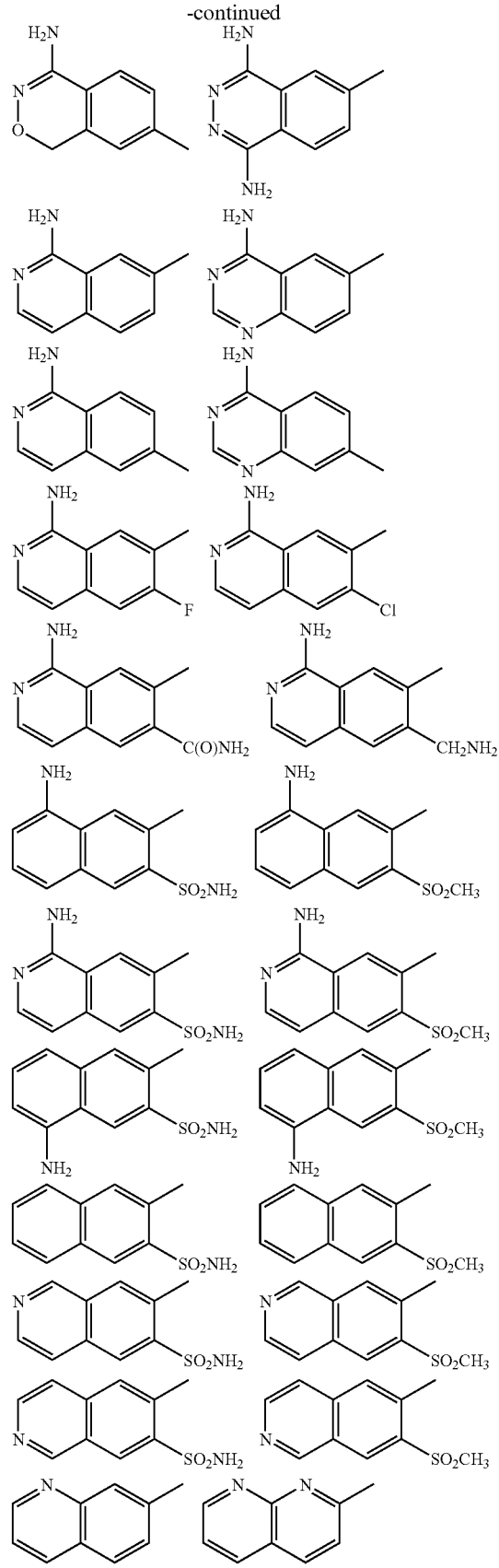

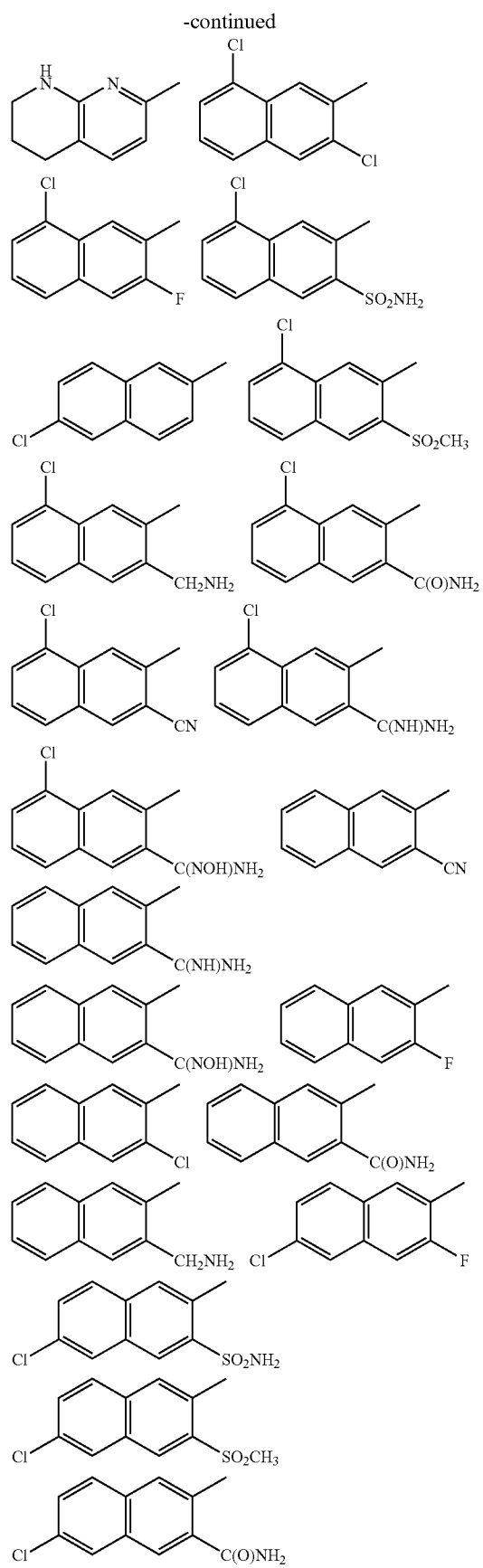
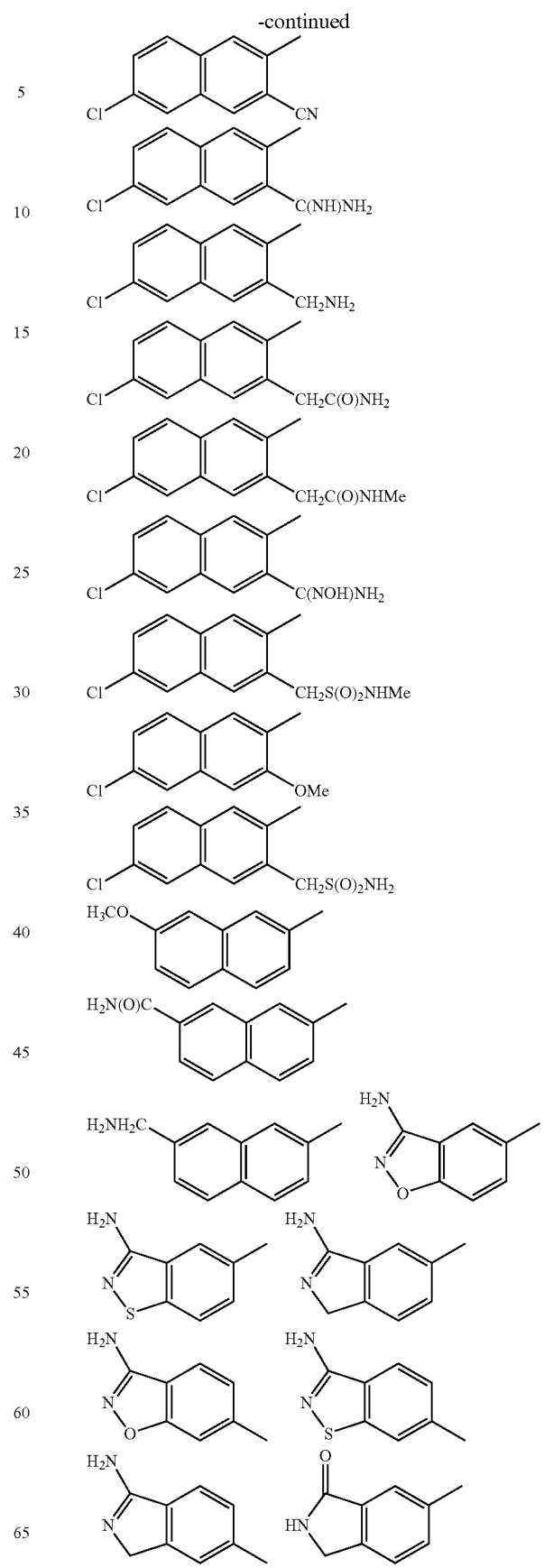

-continued
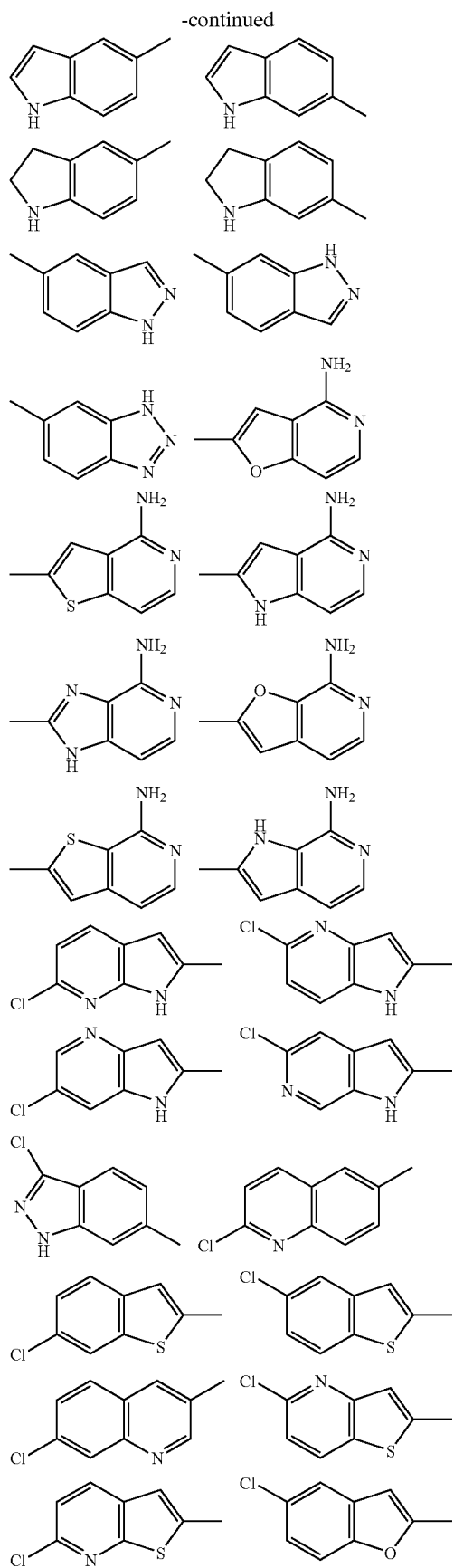
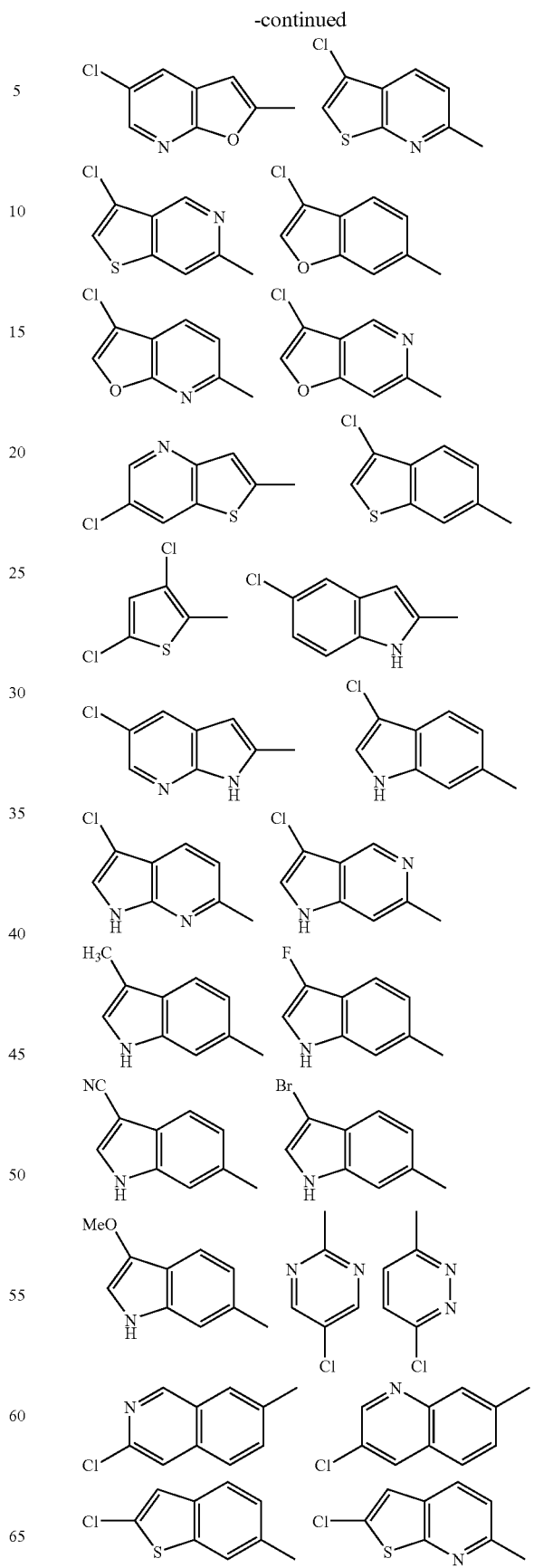

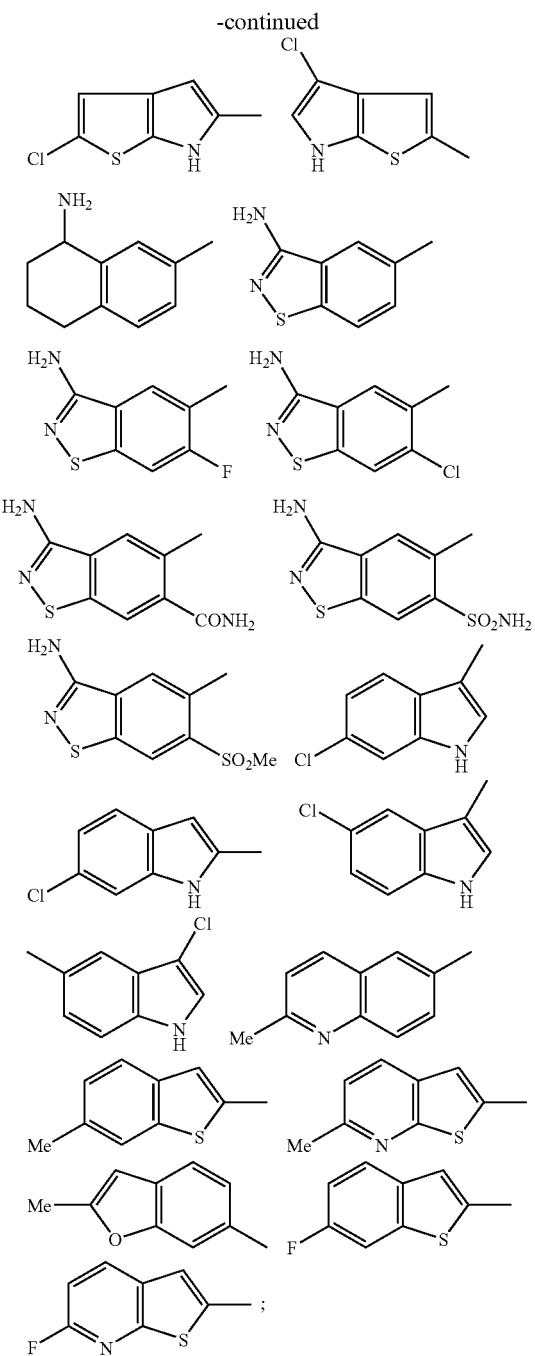

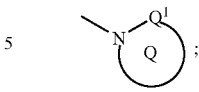

A is selected from one of the following carbocyclic and heterocyclic groups which are substituted with 0–2 $R^4$; cyclohexyl, phenyl, piperidinyl, piperazinyl, pyridyl, pyrimidyl, furanyl, morpholinyl, thienyl, pyrrolyl, pyrrolidinyl, oxazolyl, isoxazolyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolinyl, indolyl, benzimidazolyl, benzoxazolyl, benzthiazolyl, indazolyl, benzisoxazolyl, benzisothiazolyl, and isoindazolyl;

B is provided that Z and B are attached to different atoms on A;
$Q_1$ is selected from C=O and $SO_2$;
ring Q is a 5–7 membered monocyclic or tricyclic ring consisting of, in addition to the N-$Q_1$ group shown, carbon atoms and 0–1 heteroatoms selected from $NR^{4c}$, O, and $S(O)_p$, wherein: 0–2 double bonds are present within the ring and the ring is substituted with 0–2 $R^{4a}$;

alternatively, ring Q is a 5–7 membered ring to which another ring is fused, wherein: the 5–7 membered ring consists of, in addition to the N-$Q_1$ group shown, carbon atoms and 0–1 heteroatoms selected from $NR^{4c}$, O, and $S(O)_p$ and 0–1 double bonds are present within the ring; the fusion ring is phenyl;

ring Q, which includes the 5–7 membered ring and the fusion ring, is substituted with 0–2 $R^{4a}$;

$G_1$ is selected from $(CR^3R^{3a})_{1-3}$, $CR^3$=$CR^3$, $(CR^3R^{3a})_u$ $C(O)(CR^3R^{3a})_w$, $(CR^3R^{3a})_uO(CR^3R^{3a})_w$, $(CR^3R^{3a})_uNR^{3b}$ $(CR^3R^{3a})_w$, $(CR^3R^{3a})_uC(O)NR^{3b}(CR^3R^{3a})_w$, $(CR^3R^{3a})_u$ $NR^{3b}C(O)(CR^3R^{3a})_w$, $(CR^3R^{3a})_uS(CR^3R^{3a})_w$, $(CR^3R^{3a})_uS$ $(O)(CR^3R^{3a})_w$, $(CR^3R^{3a})_uS(O)_2(CR^3R^{3a})_w$, $(CR^3R^{3a})_uS(O)$ $NR^{3b}(CR^3R^{3a})_w$, $(CR^3R^{3a})_uNR^{3b}S(O)_2(CR^3R^{3a})_w$, $(CR^3R^{3a})_uS(O)_2NR^{3b}(CR^3R^{3a})_w$, $(CR^3R^{3a})_uC(O)NR^{3b}S$ $(O)_2 (CR^3R^{3a})_w$, $(CR^3R^{3a})_uNR^{3b}C(O)(CR^3R^{3a})_uC(O)NR^{3b}$ $(CR^3R^{3a})_w$, $(CR^3R^{3a})_uNR^{3b}(CR^3R^{3a})_uC(O)NR^{3b}(CR^3 R^{3a})_w$, $(CR^3R^{3a})_uNR^{3b}C(O)(CR^3R^{3a})_uC(S)NR^{3b}(CR^3 R^{3a})_w$, and $(CR^3R^{3a})_uNR^{3b}C(S)(CR^3R^{3a})_uC(O)NR^{3b}$ $(CR^3R^{3a})_w$, wherein u+w or u+u+w total 0, 1, or 2 and the right side of $G_1$ is attached to ring G, provided that $G_1$ does not form a N—S, $NCH_2N$, $NCH_2O$, or $NCH_2S$ bond with either group to which it is attached;

Z is selected from $(CR^3R^{3a})_{1-3}$, $(CR^3R^{3a})_uC(O)(CR^3 R^{3a})_w$, $(CR^3R^{3a})_uO(CR^3R^{3a})_w$, $(CR^3R^{3a})_uNR^{3b}(CR^3R^{3a})_w$, $(CR^3R^{3a})_uC(O)NR^{3b}(CR^3R^{3a})_w$, $(CR^3R^{3a})_uNR^{3b}C(O)$ $(CR^3R^{3a})_w$, $(CR^3R^{3a})_uNR^{3b}C(O)(CR^3R^{3a})_uC(O)NR^{3b}$ $(CR^3R^{3a})_w$, $(CR^3R^{3a})_uS(CR^3R^{3a})_w$, $(CR^3R^{3a})_uS(O)$ $(CR^3R^{3a})_w$, $(CR^3R^{3a})_uS(O)_2(CR^3R^{3a})_w$, $(CR^3R^{3a})_uS(O)$ $NR^{3b}(CR^3R^{3a})_w$, $(CR^3R^{3a})_uNR^{3b}S(O)_2(CR^3R^{3a})_w$, $(CR^3R^{3a})_uS(O)_2NR^{3b}(CR^3R^{3a})_w$, and $(CR^3R^{3a})_uC(O)$ $NR^{3b}S(O)_2(CR^3R^{3a})_w$, wherein u+w or u+u+w total 0, 1, or 2 and the right side of Z is attached to A, provided that $G_1$ does not form a N—S, $NCH_2N$, $NCH_2O$, or $NCH_2S$ bond with either group to which it is attached;

$R^{1a}$ is selected from H, —$(CH_2)_r$—$R^{1b}$, $(CH(CH_3))_r$— $R^{1b}$, —$(C(CH_3)_2)_r$—$R^{1b}$, $NHCH_2R^{1c}$, $OCH_2R^{1c}$, $SCH_2R^{1c}$, $NH(CH_2)_2(CH_2)_rR^1b$, and $O(CH_2)_2(CH_2)_rR^{1b}$, provided that $R^{1a}$ forms other than an N-halo, N—S, or N—CN bond;

alternatively, when two $R^{1a}$ groups are attached to adjacent atoms, together with the atoms to which they are attached they form a 5–7 membered ring consisting of: carbon atoms and 0–2 heteroatoms selected from the group consisting of N, O, and $S(O)_p$, this ring being substituted with 0–2 $R^{4b}$ and having 0–3 ring double bonds;

$R^{1b}$ is selected from H, $CH_3$, $CH_2CH_3$, $CH_2CH_2CH_3$, $CH(CH_3)_2$, F, Cl, Br, I, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_pR^{2b}$, $NR^2$ $(CH_2)_rOR^2$, $NR^2C(O)R^{2b}$, $NR^2C(O)NHR^2$, $NR^2C(O)_2R^{2a}$, $OC(O)NR^2R^{2a}$, $C(O)NR^2R^{2a}$, $C(O)NR^2R^{2b}$, $C(S)NR^2R^{2a}$, $C(O)NR^2(CH_2)_rOR^2$, $SO_2NR^2R^{2a}$, $NR^2SO_2R^2$, $C_{3-6}$ carbocycle substituted with 0–2 $R^{4b}$, and 5–6 membered heterocycle consisting of carbon atoms and from 1–4 heteroatoms selected from the group consisting of N, O, and $S(O)_p$, and substituted with 0–2 $R^{4b}$, provided that $R^{1b}$ forms other than an O—O, N-halo, N—S, or N—CN bond;

$R^{1c}$ is selected from H, $CH(CH_2OR^2)_2$, $C(O)R^{2c}$, $C(O)NR^2R^{2a}$, $S(O)R^2$, $S(O)_2R^2$, and $SO_2NR^2R^{2a}$;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, a —$CH_2$—$C_{5-6}$ carbocyclicgroup substituted with 0–2 $R^{4b}$, and 5–6 membered heterocycle consisting of: carbon atoms and 1–4 heteroatoms selected from the group consisting of N, O, and $S(O)_p$, and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{3-6}$ carbocycle substituted with 0–2 $R^{4b}$, and 5–6 membered heterocycle consisting of: carbon atoms and 1–4 heteroatoms selected from the group consisting of N, O, and $S(O)_p$, and substituted with 0–2 $R^{4b}$;

alternatively, $NR^2R^{2a}$ forms a 4, 5, or 6 membered saturated, partially saturated, or unsaturated ring substituted with 0–2 $R^{4b}$ and consisting of: carbon atoms, the nitrogen atom to which $R^2$ and $R^{2a}$ are attached, and 0–1 additional heteroatoms selected from the group consisting of N, O, and $S(O)_p$;

$R^{2b}$, at each occurrence, is selected from $CF_3$, $C_{1-4}$ alkoxy, $C_{1-5}$ alkyl substituted with 0–3 $R^{4b}$, benzyl substituted with 0–2 $R^{4b}$, $C_{3-6}$ carbocycle substituted with 0–2 $R^{4b}$, and 5–6 membered heterocycle consisting of: carbon atoms and 1–4 heteroatoms selected from the group consisting of N, O, and $S(O)_p$, and substituted with 0–2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle containing from 1–4 heteroatoms selected from the group consisting of N, O, and $S(O)_p$, and substituted with 0–2 $R^{4b}$;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

alternatively, $NR^3R^{3a}$ forms a 5 or 6 membered saturated, partially unsaturated, or unsaturated ring consisting of: carbon atoms and the nitrogen atom to which $R^3$ and $R^{3a}$ are attached;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and $C(=O)R^{3c}$;

$R^4$, at each occurrence, is selected from H, =O, $OR^2$, $CH_2OR^2$, $(CH_2)_2OR^2$, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $S(O)_pR^{5a}$, $CF_3$, $CF_2CF_3$, 5–6 membered carbocycle substituted with 0–1 $R^5$, and a 5–6 membered heterocycle consisting of: carbon atoms and 1–4 heteroatoms selected from the group consisting of N, O, and $S(O)_p$, and substituted with 0–1 $R^5$;

$R^{4a}$, at each occurrence, is selected from H, =O, $OR^2$, $CH_2OR^2$, F, $CH_2F$, Br, $CH_2Br$, Cl, $CH_2Cl$, $C_{1-4}$ alkyl, —CN, —$CH_2CN$, $NO_2$, $CH_2NO_2$, $NR^2R^{2a}$, $CH_2NR^2R^{2a}$, $C(O)R^{2c}$, $CH_2C(O)R^{2c}$, $NR^2C(O)R^{2b}$, $(CH_2)_rC(O)NR^2R^{2a}$, $NR^2C(O)NR^2R^{2a}$, $(CH_2)_rSO_2NR^2R^{2a}$, $NR^2SO_2NR^2R^{2a}$, $NR^2SO_2$—$C_{1-4}$ alkyl, $NR^2SO_2R^5$, $(CH_2)_rS(O)_pR^{5a}$, $CH_2CF_3$, $CF_3$, $CH_2$-5–6 membered carbocycle substituted with 0–1 $R^5$, 5–6 membered carbocycle substituted with 0–1 $R^5$, and a $CH_2$-5–6 membered heterocycle consisting of: carbon atoms and 1–4 heteroatoms selected from the group consisting of N, O, and $S(O)_p$, and substituted with 0–1 $R^5$, and 5–6 membered heterocycle consisting of: carbon atoms and 1–4 heteroatoms selected from the group consisting of N, O, and $S(O)_p$, and substituted with 0–1 $R^5$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $NR^3C(O)NR^3R^{3a}$, $CH_2NR^3C(O)NR^3R^{3a}$, $C(=NR^3)NR^3R^{3a}$, $CH_2C(=NR^3)NR^3R^{3a}$, $NR^3C(=NR^3)NR^3R^{3a}$, $CH_2NR^3C(=NR^3)NR^3R^{3a}$, $SO_2NR^3R^{3a}$, $CH_2SO_2NR^3R^{3a}$, $NR^3SO_2NR^3R^{3a}$, $CH_2NR^3SO_2NR^3R^{3a}$, $NR^3SO_2$—$C_{1-4}$ alkyl, $CH_2NR^3SO_2$—$C_{1-4}$ alkyl, $NR^3SO_2CF_3$, $CH_2NR^3SO_2CF_3$, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$—phenyl, $CH_2S(O)_p$-phenyl, $CF_3$, and $CH_2CF_3$;

$R^{4c}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $CH_2OR^2$, $CH_2F$, $CH_2Br$, $CH_2Cl$, $CH_2CN$, $CH_2NO_2$, $CH_2NR^2R^{2a}$, $C(O)R^{2c}$, $CH_2C(O)R^{2c}$, $CH_2NR^2C(O)R^{2b}$, $C(O)NR^2R^{2a}$, $CH_2C(O)NR^2R^{2a}$, $CH_2NR^2C(O)NR^2R^{2a}$, $SO_2NR^2R^{2a}$, $CH_2SO_2NR^2R^{2a}$, $CH_2NR^2SO_2NR^2R^{2a}$, $CH_2NR^2SO_2$—$C_{1-4}$ alkyl, $C(O)NHSO_2$—$C_{1-4}$ alkyl, $CH_2C(O)NHSO_2$—$C_{1-4}$ alkyl, $CH_2NR^2SO_2R^5$, $S(O)_pR^{5a}$, $CH_2S(O)_pR^{5a}$, $CF_3$, $CH_2CF_3$, 5–6 membered carbocycle substituted with 0–1 $R^5$, $CH_2$-5–6 membered carbocycle substituted with 0–1 $R^5$, 5–6 membered heterocycle consisting of: carbon atoms and 1–4 heteroatoms selected from the group consisting of N, O, and $S(O)_p$, and substituted with 0–1 $R^5$, and a $CH_2$-5–6 membered heterocycle consisting of: carbon atoms and 1–4 heteroatoms selected from the group consisting of N, O, and $S(O)_p$, and substituted with 0–1 $R^5$;

$R^5$, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR_3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$;

$R^{5a}$, at each occurrence, is selected from $C_{1-6}$ alkyl, $OR^3$, $CH_2OR^3$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $CF_3$, $CF_2CF_3$, phenyl substituted with 0–2 $R^6$, naphthyl substituted with 0–2 $R^6$, and benzyl substituted with 0–2 $R^6$, provided that $R^{5a}$ does not form a S—N or $S(O)_p$—C(O) bond; and $R^6$, at each occurrence, is selected from H, OH, $OR^2$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl.

In a third embodiment, the present invention provides a novel compound, wherein:

G is selected from: phenyl; 4-ethyl-phenyl; 2-aminomethyl-4-chloro-phenyl; 2-aminosulfonyl-4-chloro-phenyl; 2-amido-4-chloro-phenyl; 4-chloro-2-methylsulfonyl-phenyl; 2-aminosulfonyl-4-fluoro-phenyl; 2-amido-4-fluoro-phenyl; 4-fluoro-2-methylsulfonyl-phenyl; 2-aminomethyl-4-bromo-phenyl; 2-aminosulfonyl-4-bromo-phenyl; 2-amido-4-bromo-phenyl; 4-bromo-2-methylsulfonyl-phenyl; 2-aminomethyl-4-methyl-phenyl; 2-aminosulfonyl-4-methyl-phenyl; 2-amido-4-methyl-phenyl; 2-methylsulfonyl-4-methyl-phenyl; 4-fluoro-pyrid-2-yl; 4-bromo-pyrid-2-yl; 4-methyl-pyrid-2-yl; 5-fluoro-thien-2-yl; 5-bromo-thien-2-yl; 5-methyl-thien-2-yl; 2-amido-4-methoxy-phenyl; 2-amido-phenyl; 2-aminomethyl-3-fluoro-phenyl; 2-aminomethyl-4-fluoro-phenyl; 2-aminomethyl-5-fluoro-phenyl; 2-aminomethyl-6-fluoro-phenyl; 2-aminomethyl-phenyl; 2-amino-pyrid-4-yl; 2-aminosulfonyl-4-methoxy-phenyl; 2-aminosulfonyl-phenyl; 3-amido-phenyl; 3-amino-4-chloro-phenyl; 3-aminomethyl-phenyl; 3-chloro-phenyl; 4-chloro-phenyl; 4-methoxy-phenyl; 2-methoxy-pyrid-5-yl; 5-chloro-pyrid-2-yl; 5-chloro-thien-2-yl; 6-amino-5-chloro-pyrid-2-yl; 6-amino-pyrid-2-yl; 2-cyano-4-chloro-phenyl; 2-methoxy-4-chloro-phenyl; 2-fluoro-4-chloro-phenyl; 3-chloro-4-methyl-phenyl; 4-fluoro-phenyl; 3-fluoro-4-chloro-phenyl; 3-methyl-4-chloro-phenyl; 3-fluoro-4-methyl-phenyl; 3,4-dimethyl-phenyl; 3-chloro-4-fluoro-phenyl; 3-methyl-4-fluoro-phenyl; 4-methylsulfanyl-phenyl; 2-chlorothiazol-5-yl; 5-chlorothiazol-2-yl;

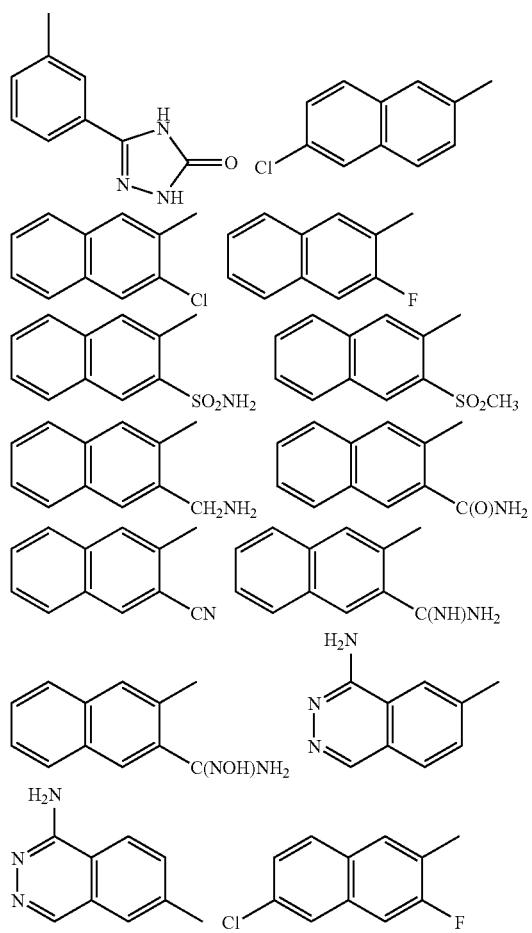

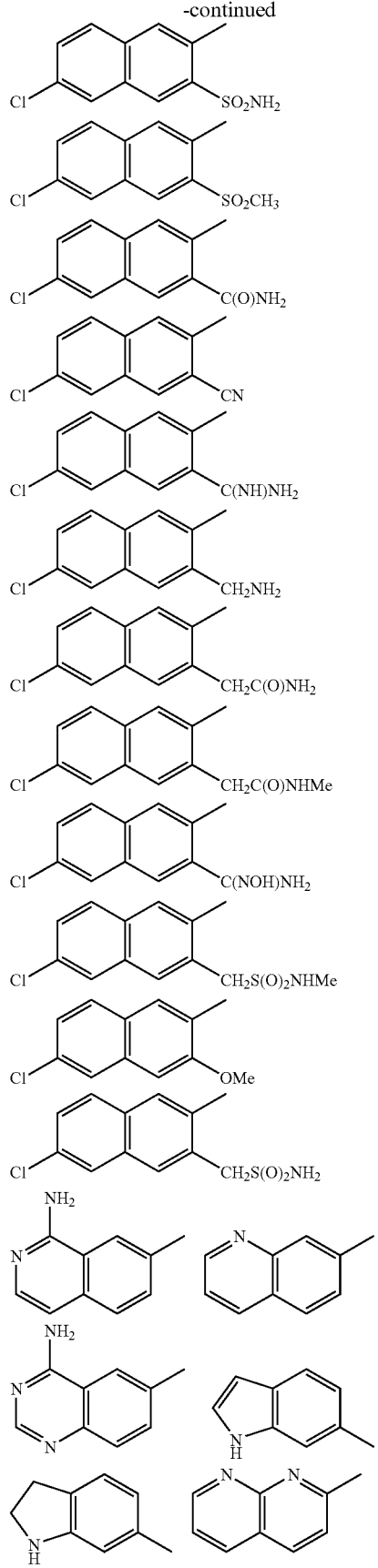

-continued
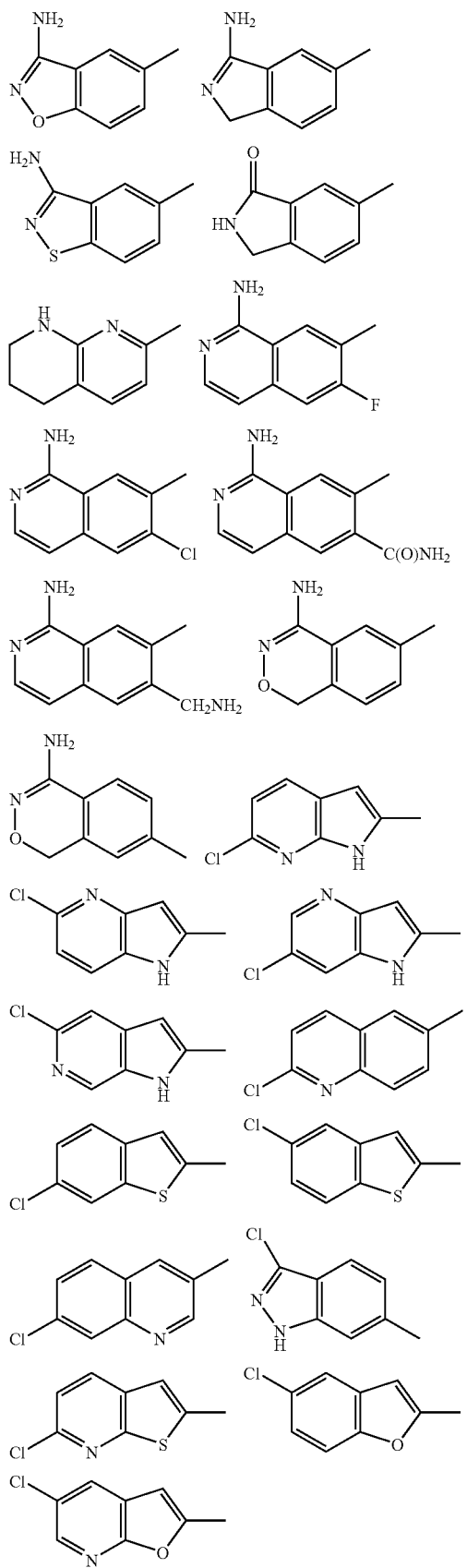
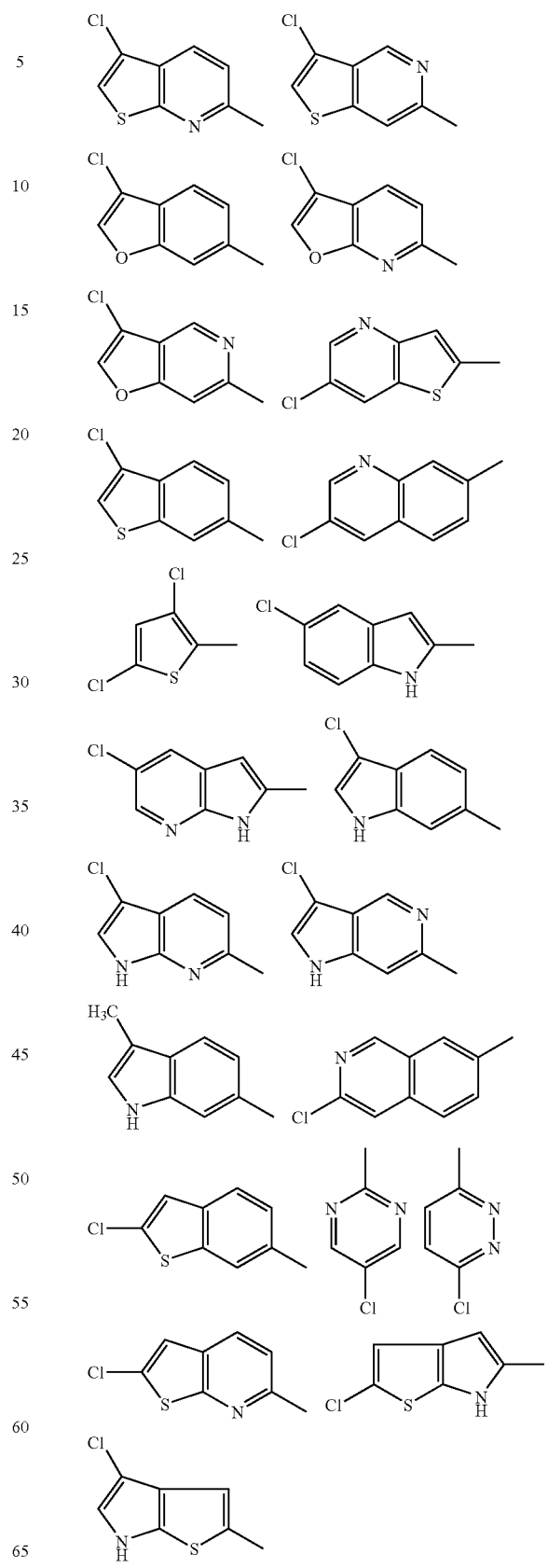

-continued
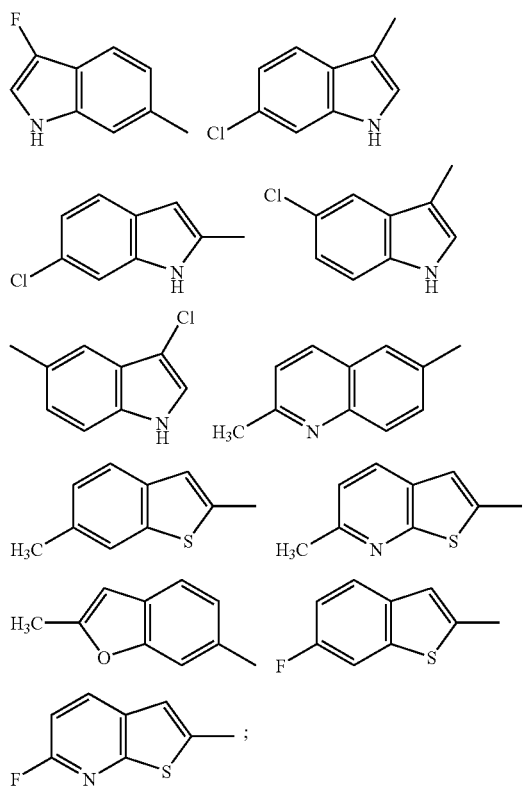
A is selected from the group: cyclohexyl, piperidinyl, indolinyl, phenyl, 2-pyridyl, 3-pyridyl, 2-pyrimidyl, 2-chloro-phenyl, 3-chloro-phenyl, 2-fluoro-phenyl, 3-fluoro-phenyl, 2-methylphenyl, 3-methylphenyl, 2-aminophenyl, 3-aminophenyl, 2-methoxyphenyl, and 3-methoxyphenyl;
B is attached to a different atom on A than M, is substituted with 0–2 $R^{4a}$, and is selected from the group:
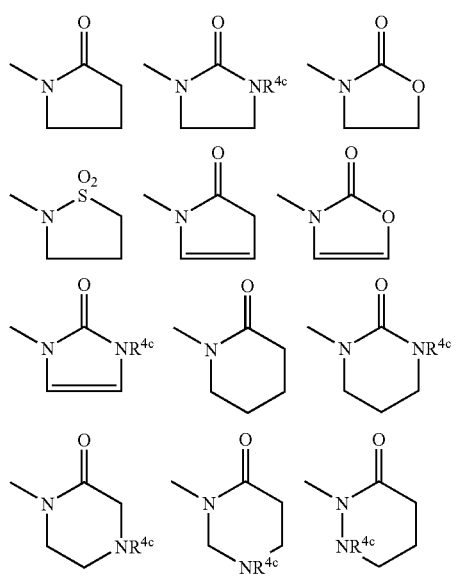
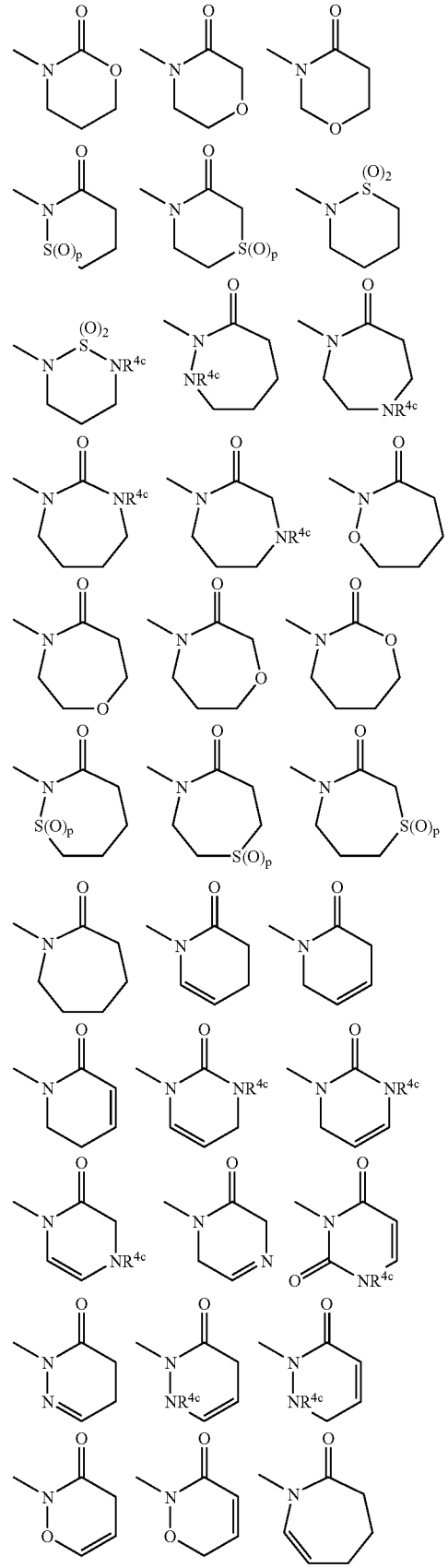

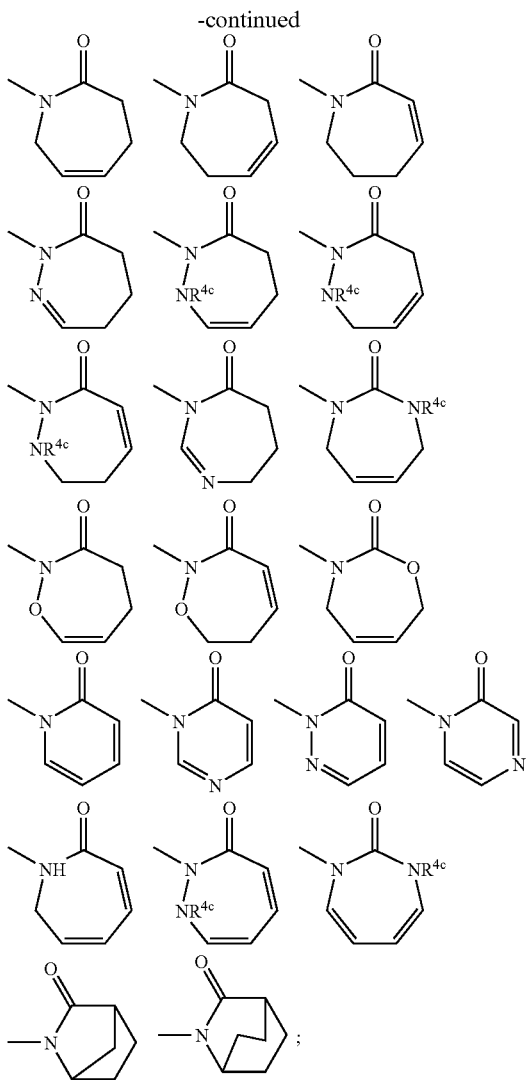

G₁ is selected from CH₂, CH₂CH₂, CH=CH, CH₂O, OCH₂, C(O), NH, CH₂NH, NHCH₂, CH₂C(O), C(O)CH₂, C(O)NH, NHC(O), NHC(O)NH, NHC(O)CH₂C(O)NH, C(O)NHS(O)₂, CH₂S, SCH₂, CH₂S(O), S(O)₂, CH₂S(O)₂, S(O)₂(CH₂), SO₂NH, NHSO₂, NHCH₂C(O)NH, NHC(O)C (O)NH, NHC(O)C(S)NH, and NHC(S)C(O)NH and the right side of G₁ is attached to ring G, provided that Z does not form a N—S, NCH₂N, NCH₂O, or NCH₂S bond with either group to which it is attached;

Z is selected from CH₂, CH₂CH₂, CH₂O, OCH₂, C(O), NH, CH₂NH, NHCH₂, CH₂C(O), C(O)CH₂, C(O)NH, NHC (O), NHC(O)NH, NHC(O)CH₂C(O)NH, C(O)NHS(O)₂, CH₂S, SCH₂, CH₂S(O), S(O)₂, CH₂S(O)₂, S(O)₂(CH₂), SO₂NH, and NHSO₂ and the right side of Z is attached to A, provided that Z does not form a N—S, NCH₂N, NCH₂O, or NCH₂S bond with either group to which it is attached;

R$^{1a}$ is selected from H, R$^{1b}$, CH(CH₃)R$^{1b}$, C(CH₃)₂R$^{1b}$, CH₂R$^{1b}$, and CH₂CH₂R$^{1b}$, provided that R$^{1a}$ forms other than an N-halo, N—S, or N—CN bond;

alternatively, when two R$^{1a}$ groups are attached to adjacent atoms, together with the atoms to which they are attached they form a 5–6 membered ring consisting of: carbon atoms and 0–2 heteroatoms selected from the group consisting of N, O, and S(O)$_p$, this ring being substituted with 0–2 R$^{4b}$ and having 0–3 ring double bonds;

R$^{1b}$ is selected from H, CH₃, CH₂CH₃, F, Cl, Br, —CN, —CHO, CF₃, OR², NR²R$^{2a}$, C(O)R$^{2b}$, CO₂R$^{2b}$, OC(O)R², CO₂R$^{2a}$, S(O)$_p$R$^{2b}$, NR²(CH₂)$_r$OR², NR²C(O)R$^{2b}$, C(O) NR²R$^{2a}$, C(O)NR²R$^{2b}$, C(S)NR²R$^{2a}$, SO₂NR²R$^{2a}$, NR²SO₂R², C$_{3-5}$ cycloalkyl substituted with 0–2 R$^{4b}$, phenyl substituted with 0–2 R$^{4b}$, and 5–6 membered aromatic heterocycle consisting of carbon atoms and from 1–4 heteroatoms selected from the group consisting of N, O, and S(O)$_p$, and substituted with 0–2 R$^{4b}$, provided that R$^{1b}$ forms other than an O—O, N-halo, N—S, or N—CN bond;

R², at each occurrence, is selected from H, CF₃, CH₃, CH₂CH₃, CH₂CH₂CH₃, CH(CH₃)₂, phenyl substituted with 0–2 R$^{4b}$, a benzyl substituted with 0–2 R$^{4b}$, and 5–6 membered aromatic heterocycle consisting of: carbon atoms and 1–4 heteroatoms selected from the group consisting of N, O, and S(O)$_p$, and substituted with 0–2 R$^{4b}$;

R$^{2a}$, at each occurrence, is selected from H, CF₃, CH₃, CH₂CH₃, CH₂CH₂CH₃, CH(CH₃)₂, C(CH₃)₃, C$_{3-5}$ cycloalkyl substituted with 0–1 R$^{4b}$, benzyl substituted with 0–2 R$^{4b}$, phenyl substituted with 0–2 R$^{4b}$, and 5–6 membered aromatic heterocycle consisting of: carbon atoms and 1–4 heteroatoms selected from the group consisting of N, O, and S(O)$_p$, and substituted with 0–2 R$^{4b}$;

alternatively, NR²R$^{2a}$ forms a 4, 5, or 6 membered saturated, partially saturated, or unsaturated ring substituted with 0–2 R$^{4b}$ and consisting of: carbon atoms, the nitrogen atom to which R² and R$^{2a}$ are attached, and 0–1 additional heteroatoms selected from the group consisting of N, O, and S(O)$_p$;

R$^{2b}$, at each occurrence, is selected from CF₃, C$_{1-4}$ alkoxy, C$_{1-5}$ alkyl substituted with 0–3 R$^{4b}$, C$_{3-5}$ cycloalkyl substituted with 0–2 R$^{4b}$, benzyl substituted with 0–2 R$^{4b}$, phenyl substituted with 0–2 R$^{4b}$, and 5–6 membered heterocycle consisting of: carbon atoms and 1–4 heteroatoms selected from the group consisting of N, O, and S(O)$_p$, and substituted with 0–2 R$^{4b}$;

R$^{2c}$, at each occurrence, is selected from CF₃, OH, OCH₃, OCH₂CH₃, OCH₂CH₂CH₃, OCH(CH₃)₂, CH₃, CH₂CH₃, CH₂CH₂CH₃, CH(CH₃)₂, benzyl substituted with 0–2 R$^{4b}$, phenyl substituted with 0–2 R$^{4b}$, and 5–6 membered aromatic heterocycle containing from 1–4 heteroatoms selected from the group consisting of N, O, and S(O)$_p$, and substituted with 0–2 R$^{4b}$;

R$^{4a}$, at each occurrence, is selected from H, =O, CH₂OR², OR², F, Br, Cl, CH₃, CH₂CH₃, CH₂CH₂CH₃, CH(CH₃)₂, CH₂CH₂CH₂CH₃, CH₂CH(CH₃)₂, CH(CH₃) CH₂CH₃, C(CH₃)₃, —CN, NO₂, NR²R$^{2a}$, CH₂NR²R$^{2a}$, C(O)R$^{2c}$, NR²C(O)R$^{2b}$, C(O)NR²R$^{2a}$, NR²C(O)NR²R$^{2a}$, SO₂NR²R$^{2a}$, and —CF₃;

R$^{4b}$, at each occurrence, is selected from H, =O, OR³, CH₂OR³, F, Cl, CH₃, CH₂CH₃, CH₂CH₂CH₃, CH(CH₃)₂, —CN, NO₂, NR³R$^{3a}$, CH₂NR³R$^{3a}$, C(O)R³, CH₂C(O)R³, C(O)OR$^{3c}$, CH₂C(O)OR$^{3c}$, NR³C(O)R$^{3a}$, CH₂NR³C(O) R$^{3a}$, C(O)NR³R$^{3a}$, CH₂C(O)NR³R$^{3a}$, SO₂NR³R$^{3a}$, CH₂SO₂NR³R$^{3a}$, NR³SO₂—C$_{1-4}$ alkyl, CH₂NR³SO₂—C$_{1-4}$ alkyl, NR³SO₂-phenyl, CH₂NR³SO₂-phenyl, S(O)$_p$CF₃, CH₂S(O)$_p$CF₃, S(O)$_p$—C$_{1-4}$ alkyl, CH₂S(O)$_p$—C$_{1-4}$ alkyl, S(O)$_p$-phenyl, CH₂S(O)$_p$-phenyl, and CF₃;

R$^{4c}$, at each occurrence, is selected from H, CH₃, CH₂CH₃, CH₂CH₂CH₃, CH(CH₃)₂, CH₂CH₂CH₂CH₃, CH₂CH(CH₃)₂, CH(CH₃)CH₂CH₃, C(CH₃)₃, CH₂OR², CH₂F, CH₂Br, CH₂Cl, CH₂CN, CH₂NO₂, CH₂NR²R$^{2a}$, C(O)R$^{2c}$, CH₂C(O)R$^{2c}$, CH₂NR²C(O)R$^{2b}$, C(O)NR²R$^{2a}$, CH₂C(O)NR²R$^{2a}$, SO₂NR²R$^{2a}$, CH₂SO₂NR²R$^{2a}$, S(O)$_p$R$^{5a}$, CH$_2$S(O)$_p$R$^{5a}$, CF$_3$, phenyl substituted with 0–1 R$^5$, and benzyl substituted with 0–1 R$^5$;

R$^5$, at each occurrence, is selected from H, =O, CH$_3$, CH$_2$CH$_3$, CH$_2$CH$_2$CH$_3$, CH(CH$_3$)$_2$, OR$^3$, CH$_2$OR$^3$, F, Cl, —CN, NO$_2$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl, NR$^3$SO$_2$CF$_3$, NR$^3$SO$_2$-phenyl, S(O)$_p$CF$_3$, S(O)$_p$—C$_{1-4}$ alkyl, S(O)$_p$-phenyl, CF$_3$, phenyl substituted with 0–2 R$^6$, naphthyl substituted with 0–2 R$^6$, and benzyl substituted with 0–2 R$^6$;

R$^{5a}$, at each occurrence, is selected from CH$_3$, CH$_2$CH$_3$, CH$_2$CH$_2$CH$_3$, CH(CH$_3$)$_2$, OR$^3$, NR$^3$R$^{3a}$, C(O)R$^3$, NR$^3$C(O)R$^{3a}$, C(O)NR$^3$R$^{3a}$, CF$_3$, phenyl substituted with 0–2 R$^6$, naphthyl substituted with 0–2 R$^6$, and benzyl substituted with 0–2 R$^6$, provided that R$^{5a}$ does not form a S—N or S(O)$_p$—C(O) bond; and R$^6$, at each occurrence, is selected from H, OH, OR$^2$, F, Cl, CH$_3$, CH$_2$CH$_3$, CH$_2$CH$_2$CH$_3$, CH(CH$_3$)$_2$, —CN, NO$_2$, NR$^2$R$^{2a}$, CH$_2$NR$^2$R$^{2a}$, C(O)R$^{2b}$, CH$_2$C(O)R$^{2b}$, NR$^2$C(O)R$^{2b}$, SO$_2$NR$^2$R$^{2a}$, and NR$^2$SO$_2$C$_{1-4}$ alkyl.

In a fourth embodiment, the present invention provides a novel compound, wherein the compound is selected from:

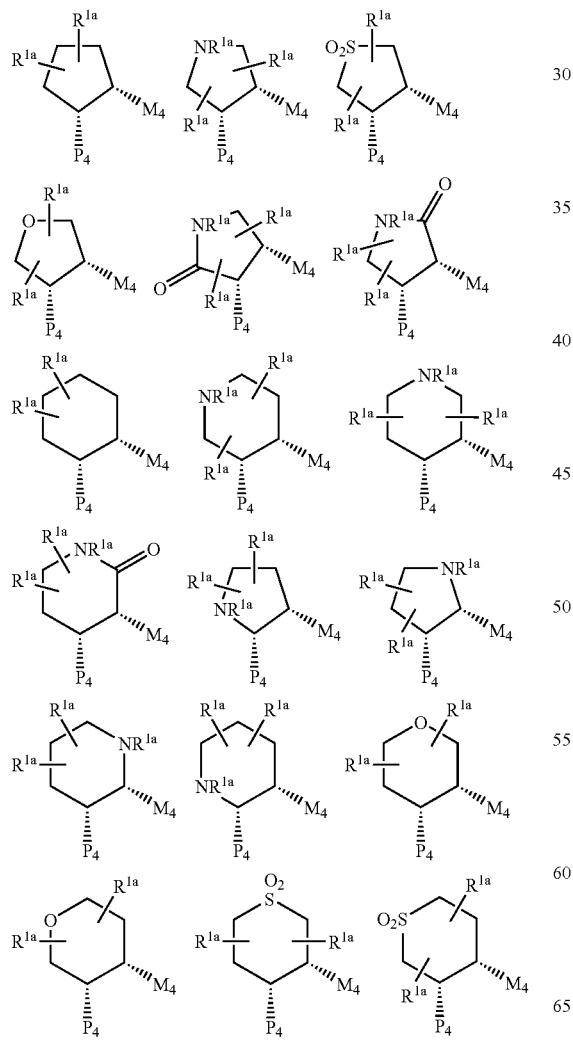
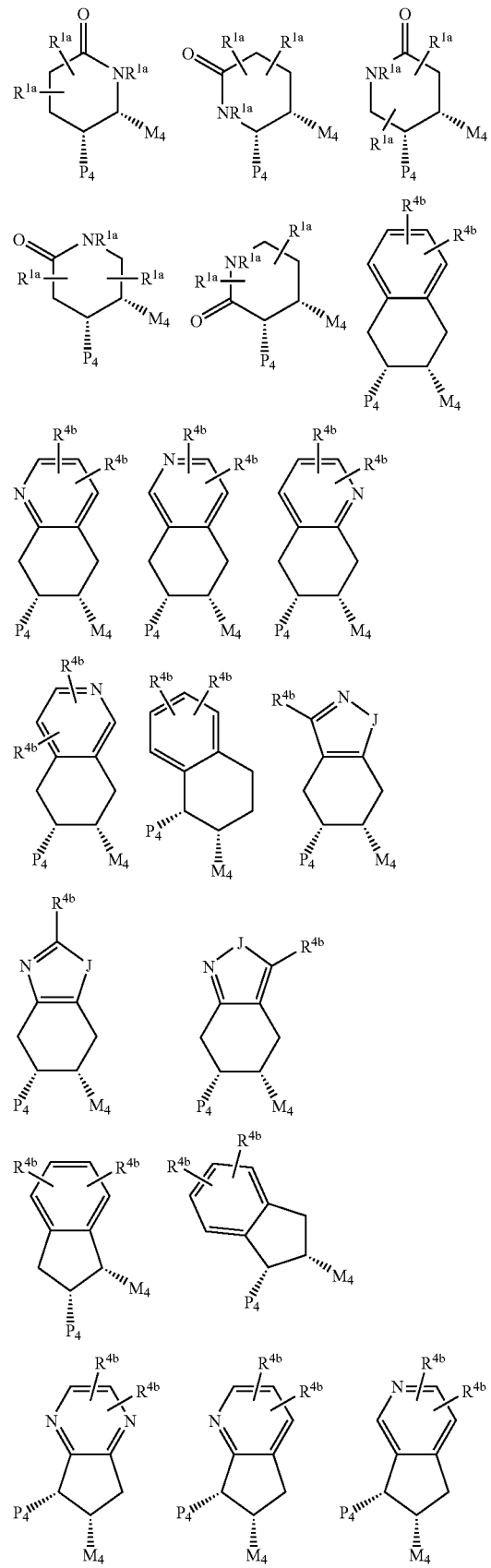

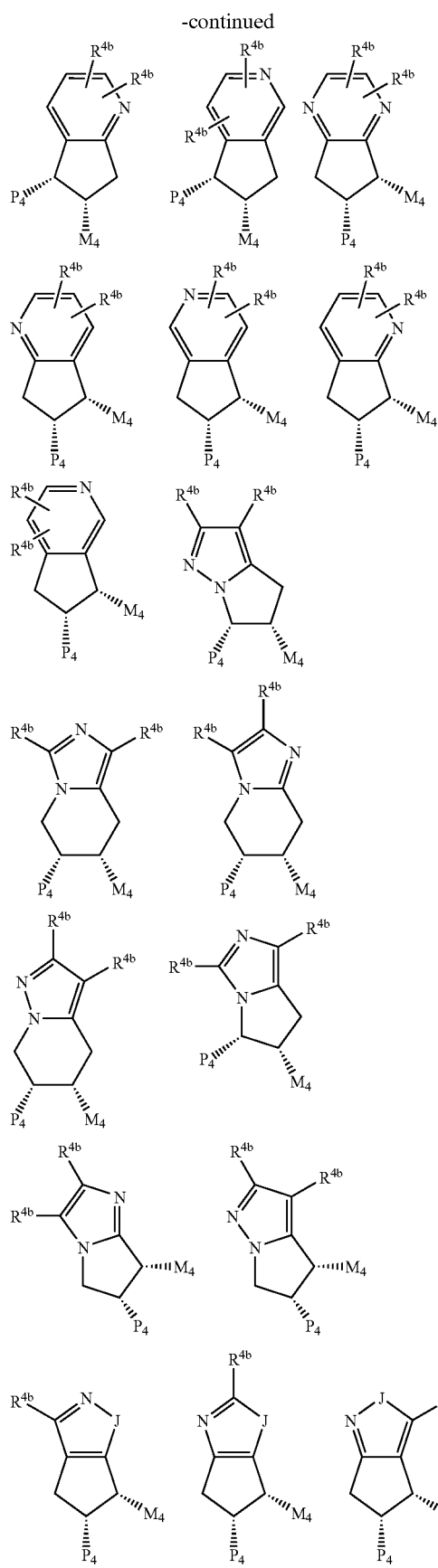
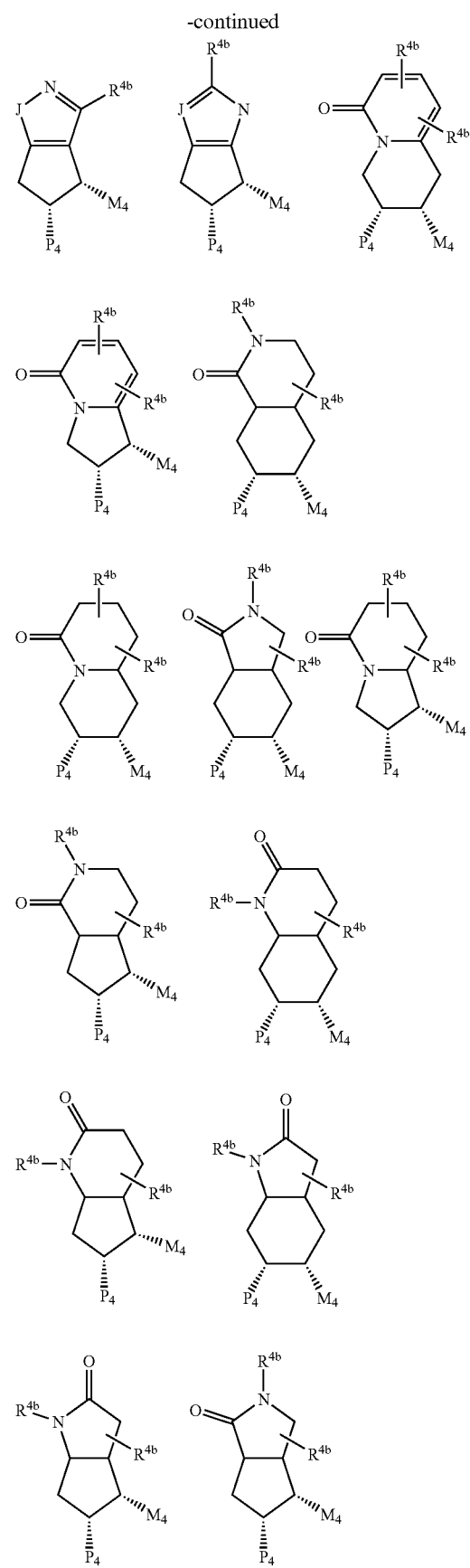

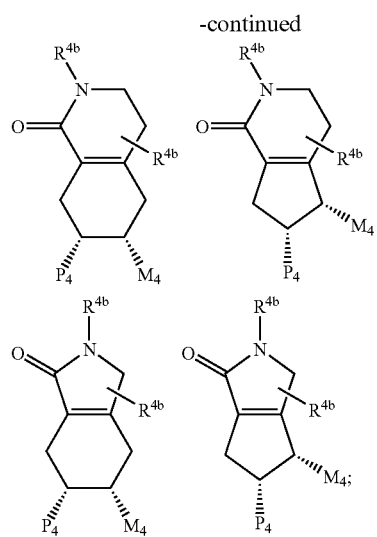
J is selected from O, S, NH, and $NR^{1a}$;
G is selected from:
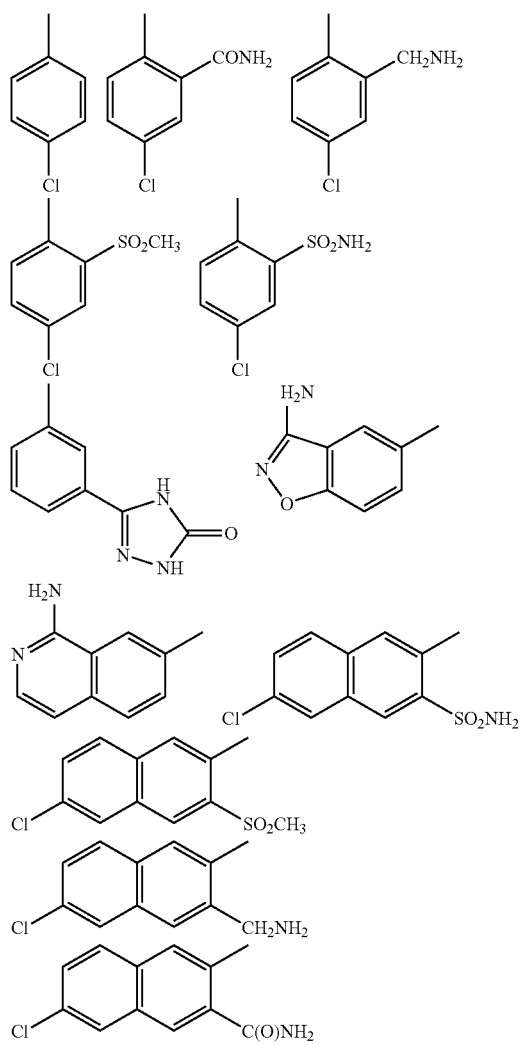
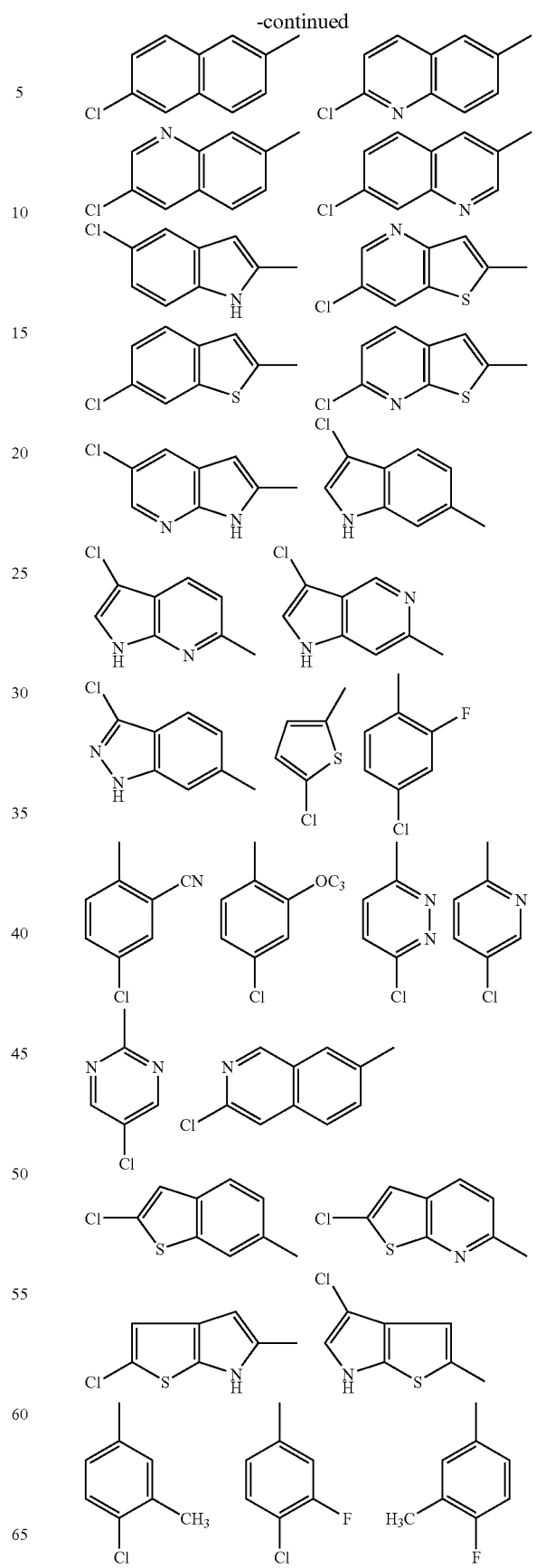

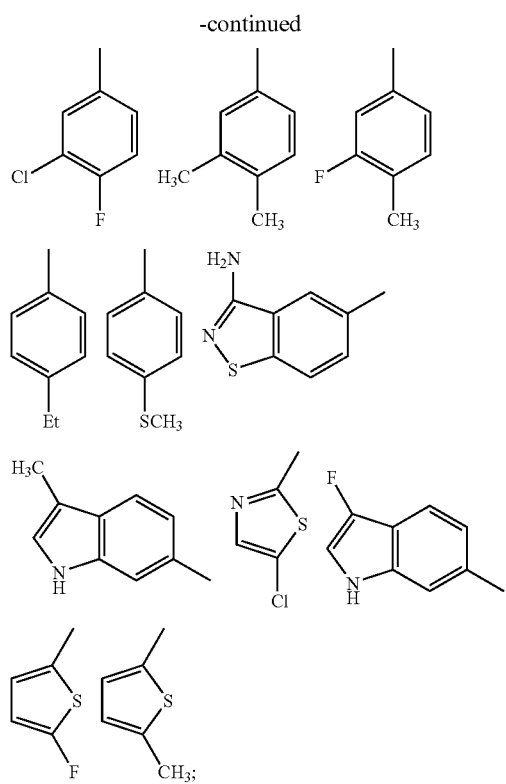
A-B is selected from:
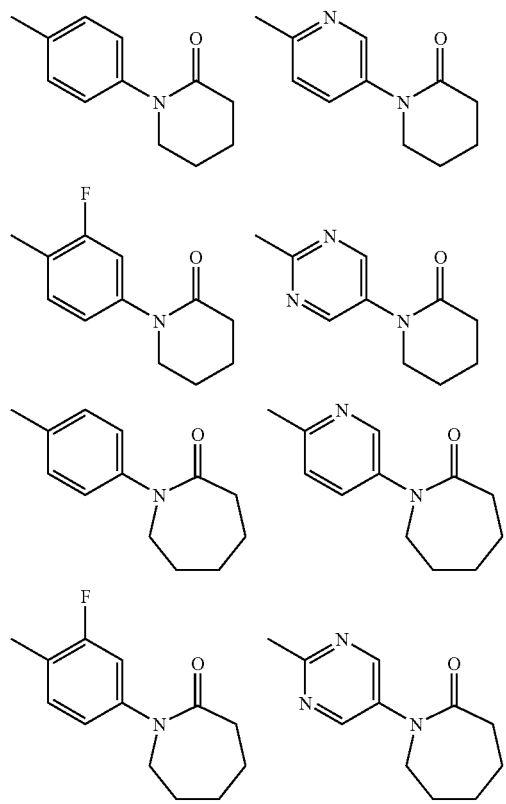
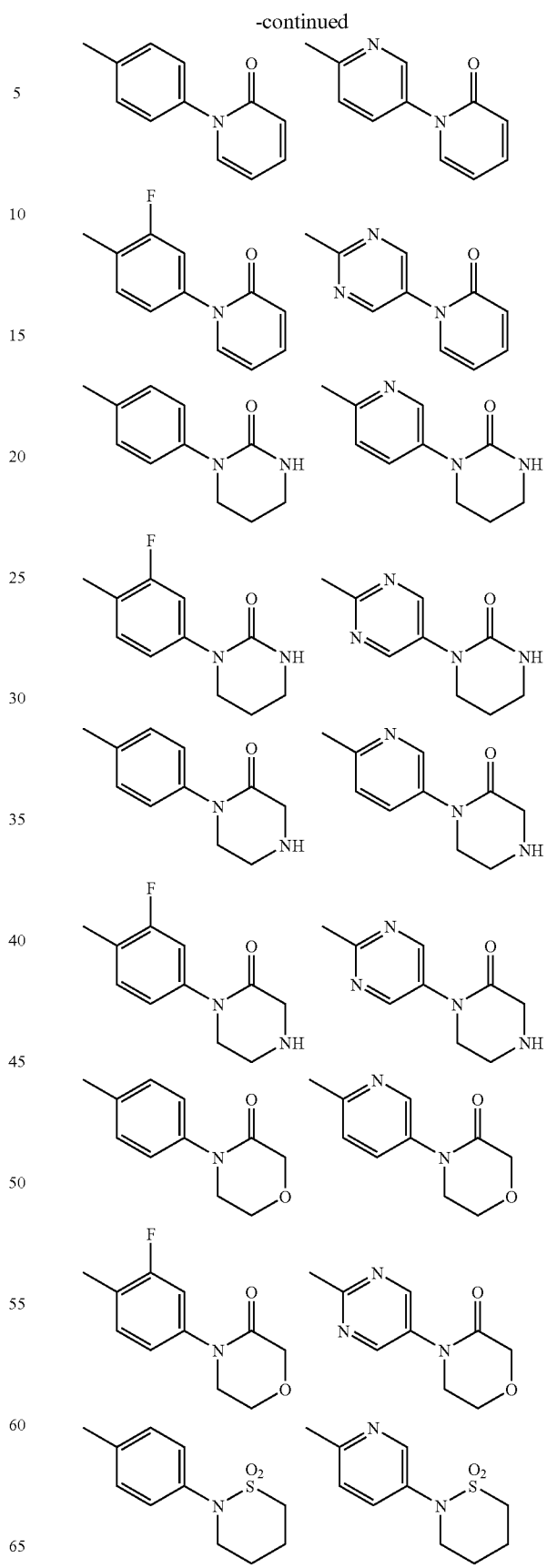

-continued
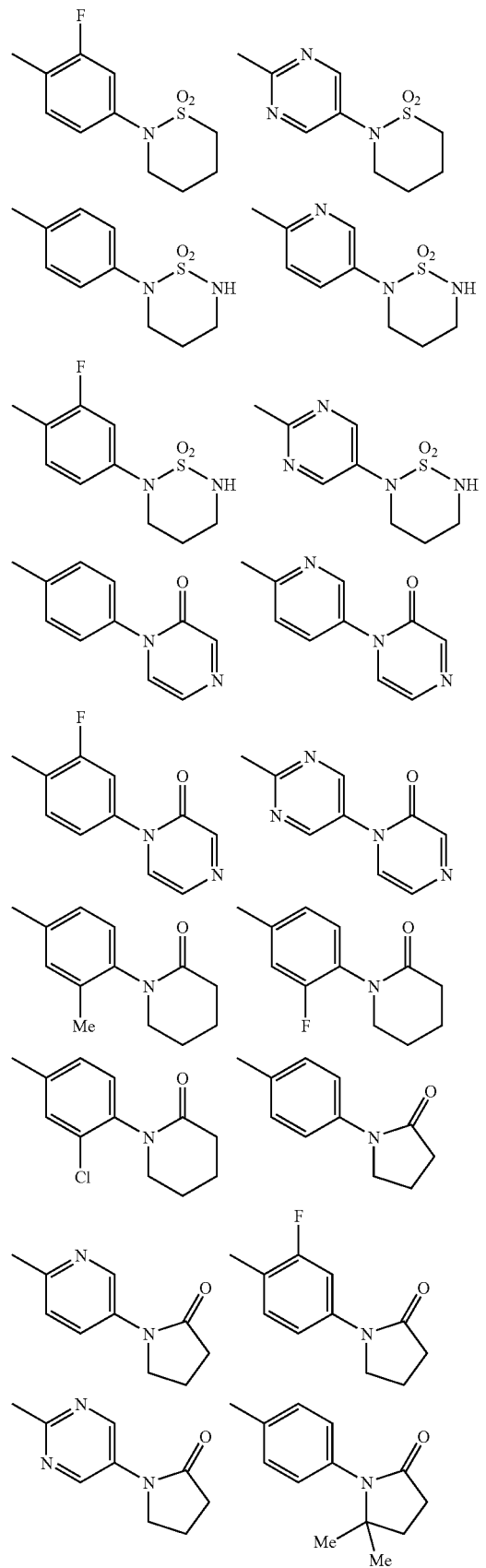
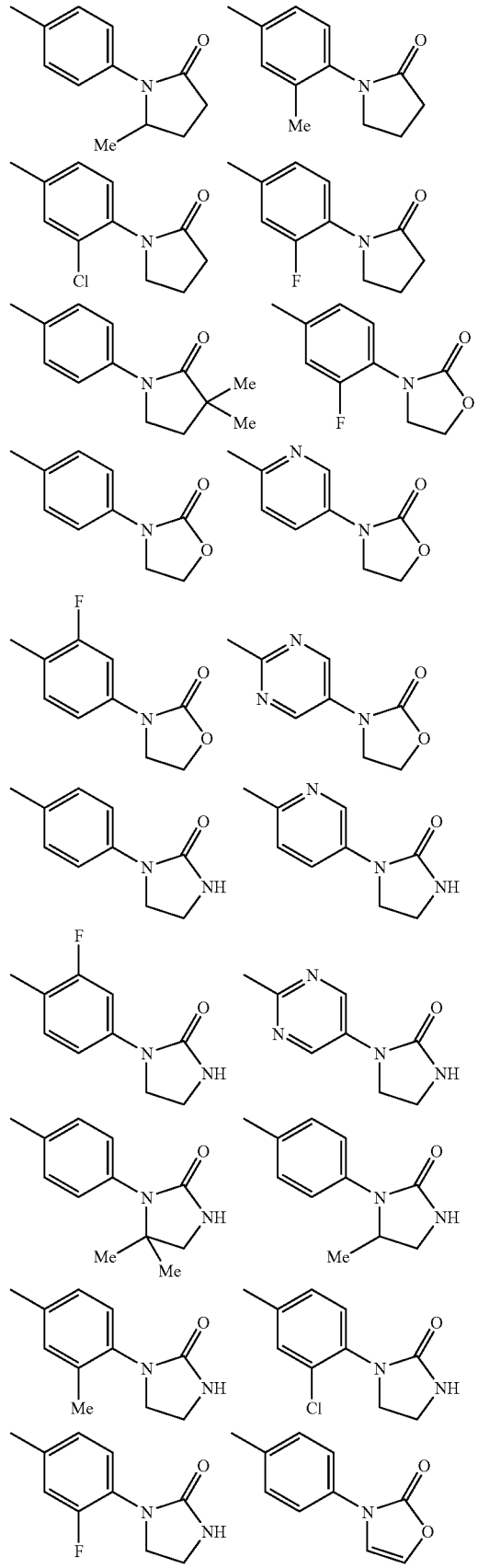

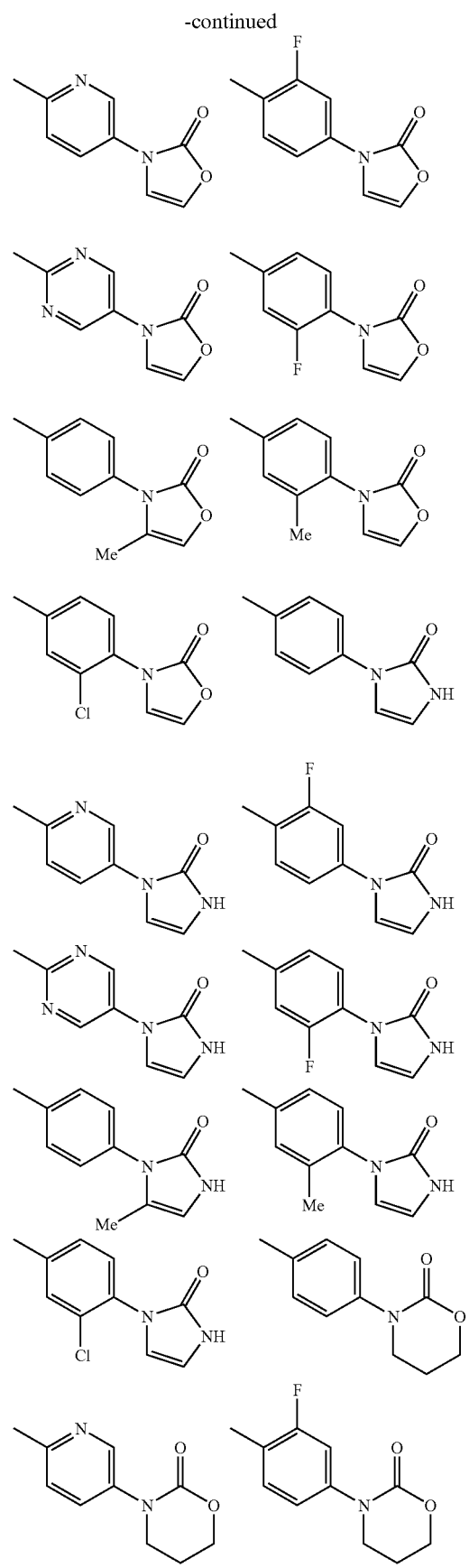
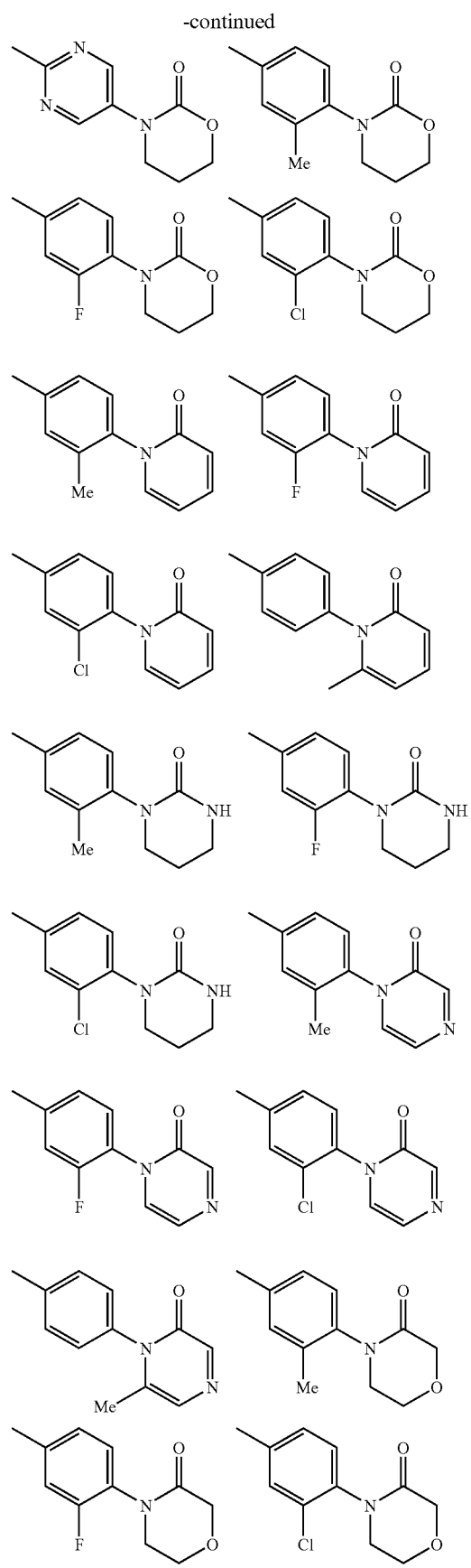

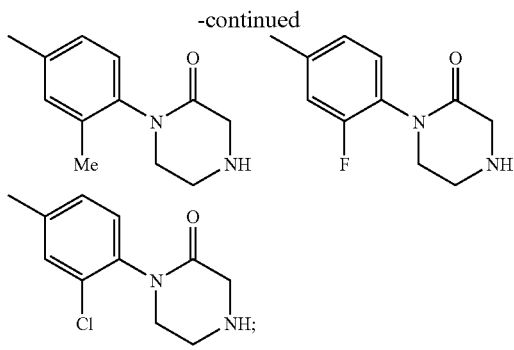

G₁ is selected from CH=CH, CH₂C(O), C(O)CH₂, NH, C(O)NH, NHC(O), CH₂S, SCH₂, CH₂S(O), CH₂SO₂, SO₂NH, NHSO₂ NHCH₂C(O)NH, NHC(O)C(O)NH, NHC(O)C(S)NH, and NHC(S)C(O)NH and the right side of $G_1$ is attached to ring G, provided that Z does not form a N—S, NCH₂N, NCH₂O, or NCH₂S bond with either group to which it is attached;

Z is selected from CH₂C(O), C(O)CH₂, NH, C(O)NH, NHC(O), CH₂S, SCH₂, CH₂S(O), CH₂SO₂, SO₂NH, and NHSO₂ and the right side of Z is attached to A, provided that Z does not form a N—S, NCH₂N, NCH₂O, or NCH₂S bond with either group to which it is attached;

$R^{1a}$ is selected from H, $R^{1b}$, C(CH₃)₂$R^{1b}$, CH₂$R^{1b}$, and CH₂CH₂$R^{1b}$, provided that $R^{1a}$ forms other than an N-halo, N—S, or N—CN bond;

$R^{1b}$ is selected from CH₃, CH₂CH₃, F, Cl, Br, —CN, CF₃, OR², NR²R²ᵃ, C(O)R²ᵇ, CO₂R²ᵇ, CO₂R²ᵃ, S(O)$_p$R²ᵇ, C(O)NR²R²ᵃ, C(O)NR²R²ᵇ, C(S)NR²R²ᵃ; SO₂NR²R²ᵃ, NR²SO₂R², cyclopropyl substituted with 0–2 $R^{4b}$, and 5–6 membered aromatic heterocycle consisting of carbon atoms and from 1–4 heteroatoms selected from the group consisting of N, O, and S(O)$_p$, and substituted with 0–2 $R^{4b}$, provided that $R^{1b}$ forms other than an O—O, N-halo, N—S, or N—CN bond;

R², at each occurrence, is selected from H, CH₃, CH₂CH₃, CH₂CH₂CH₃, CH(CH₃)₂, phenyl substituted with 0–1 $R^{4b}$, benzyl substituted with 0–1 $R^{4b}$, and 5–6 membered aromatic heterocycle consisting of: carbon atoms and 1–4 heteroatoms selected from the group consisting of N, O, and S(O)$_p$, and substituted with 0–1 $R^{4b}$;

$R^{2a}$, at each occurrence, is selected from H, CH₃, CH₂CH₃, CH₂CH₂CH₃, CH(CH₃)₂, C(CH₃)₃, cyclopropyl, benzyl substituted with 0–1 $R^{4b}$, phenyl substituted with 0–1 $R^{4b}$, and 5–6 membered aromatic heterocycle consisting of: carbon atoms and 1–4 heteroatoms selected from the group consisting of N, O, and S(O)$_p$, and substituted with 0–1 $R^{4b}$;

alternatively, NR²R²ᵃ forms a 4, 5, or 6 membered saturated, partially saturated, or unsaturated ring substituted with 0–1 $R^{4b}$ and consisting of: carbon atoms, the nitrogen atom to which R² and R²ᵃ are attached, and 0–1 additional heteroatoms selected from the group consisting of N, O, and S(O)$_p$;

$R^{2b}$, at each occurrence, is selected from CF₃, OH, OCH₃, OCH₂CH₃, OCH₂CH₂CH₃, OCH(CH₃)₂, C₁₋₅ alkyl substituted with 0–3 $R^{4b}$, C₃₋₅ cycloalkyl substituted with 0–1 $R^{4b}$, benzyl substituted with 0–1 $R^{4b}$, phenyl substituted with 0–1 $R^{4b}$, and 5–6 membered heterocycle consisting of: carbon atoms and 1–4 heteroatoms selected from the group consisting of N, O, and S(O)$_p$, and substituted with 0–1 $R^{4b}$; and $R^{4b}$, at each occurrence, is selected from H, =O, OR³, CH₂OR³, F, Cl, CH₃, CH₂CH₃, CH₂CH₂CH₃, CH(CH₃)₂, —CN, NO₂, NR³R³ᵃ, CH₂NR³R³ᵃ, C(O)R³, C(O)OR³ᶜ, NR³C(O)R³ᵃ, C(O)NR³R³ᵃ, SO₂NR³R³ᵃ, NR³SO₂—C₁₋₄ alkyl, NR³SO₂-phenyl, S(O)$_p$—C₁₋₄ alkyl, S(O)$_p$-phenyl, and CF₃.

In a fifth embodiment, the present invention provides a novel compound, wherein the compound is selcted from:

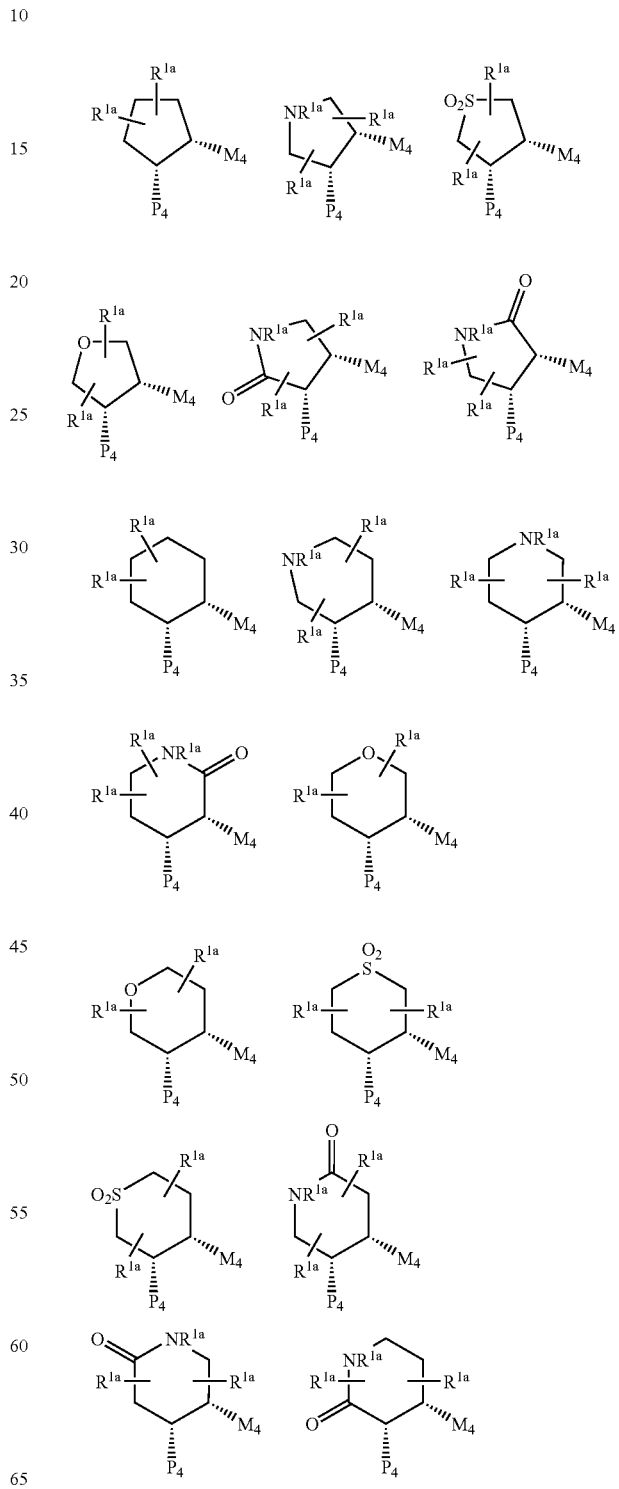

-continued
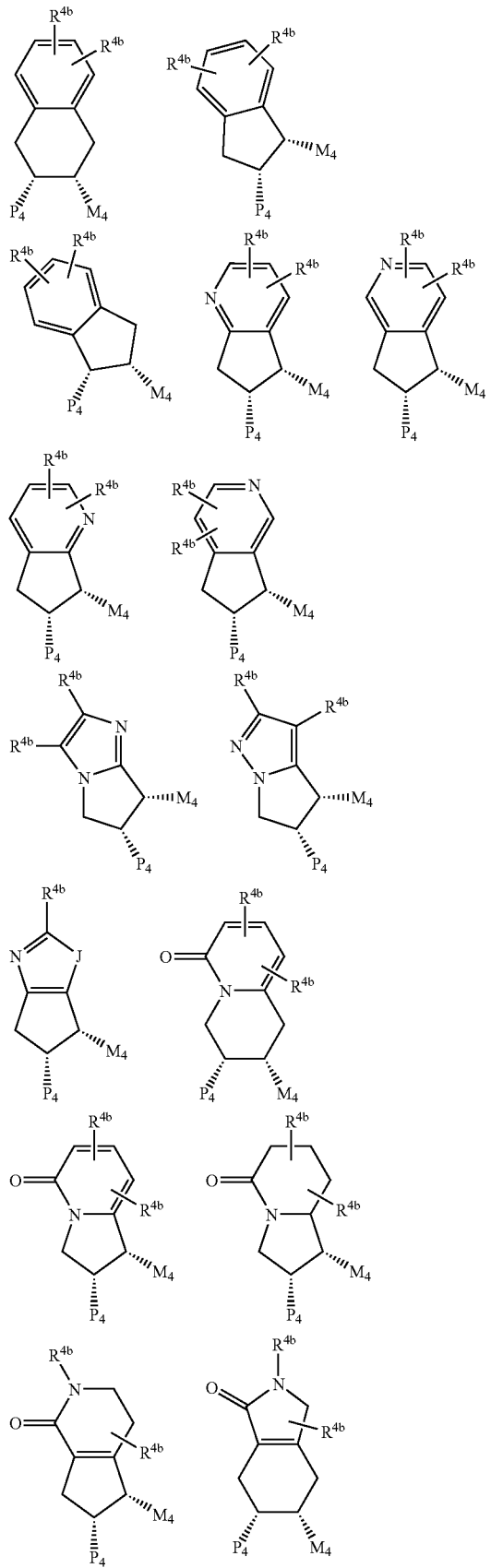
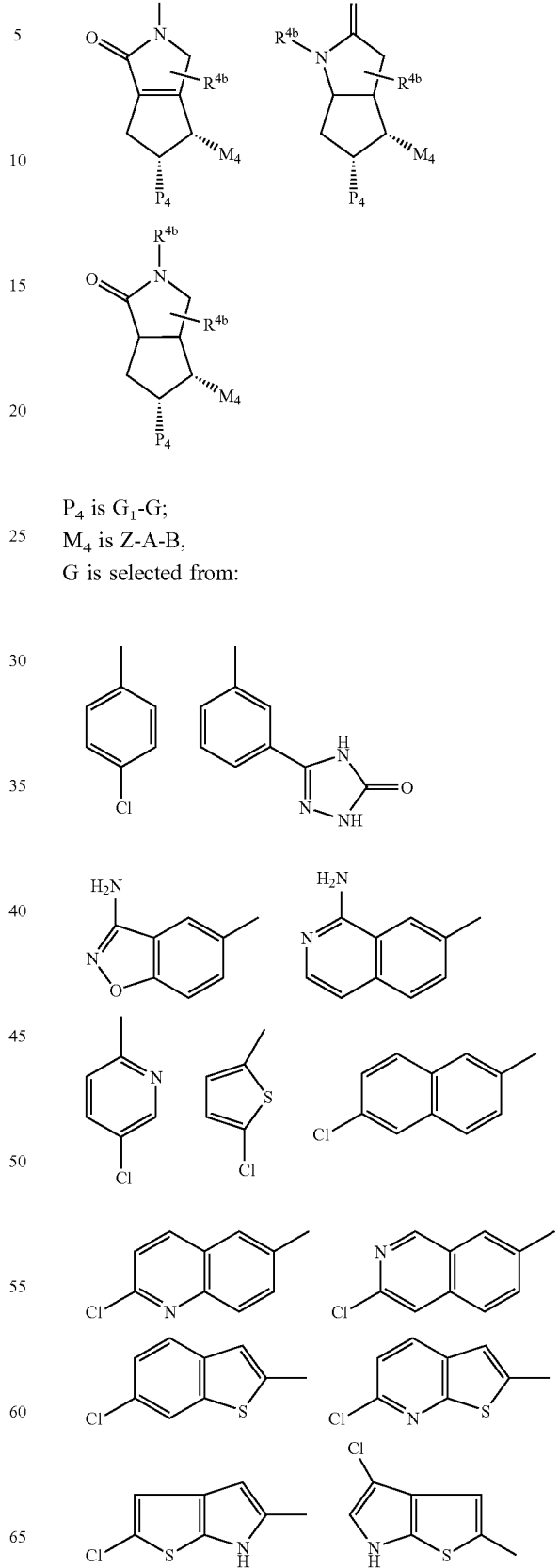
P$_4$ is G$_1$-G;
M$_4$ is Z-A-B,
G is selected from:

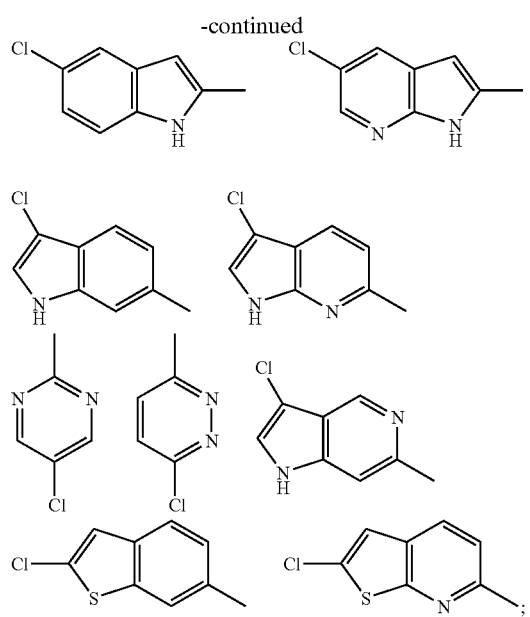
G$_1$ is NHCO or NHCOCONH;
alternatively, G-G$_1$— is selected from:
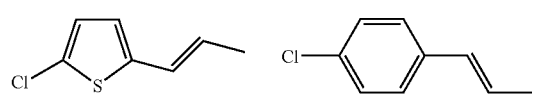
Z is NHCO or CONH;
A-B is selected from:
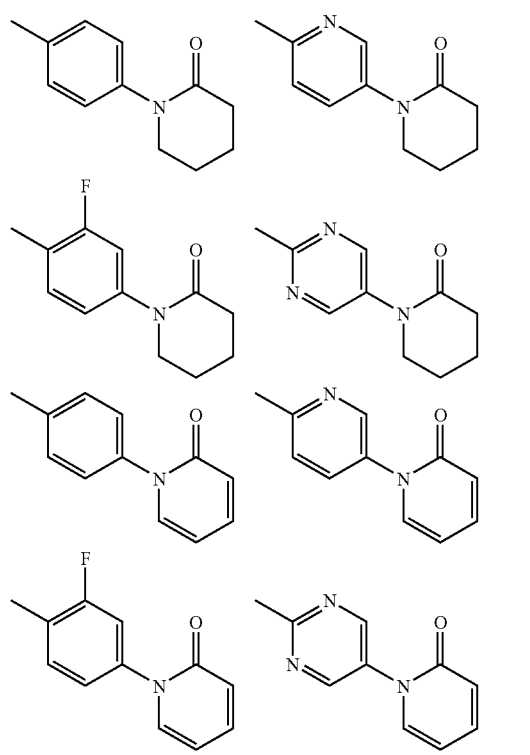
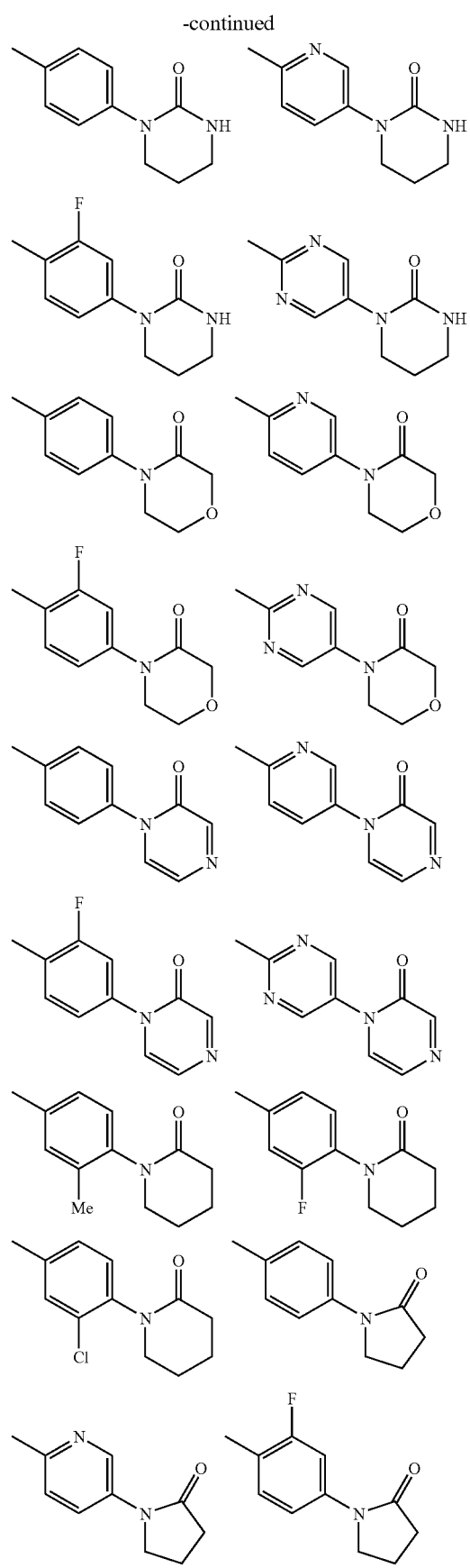

-continued

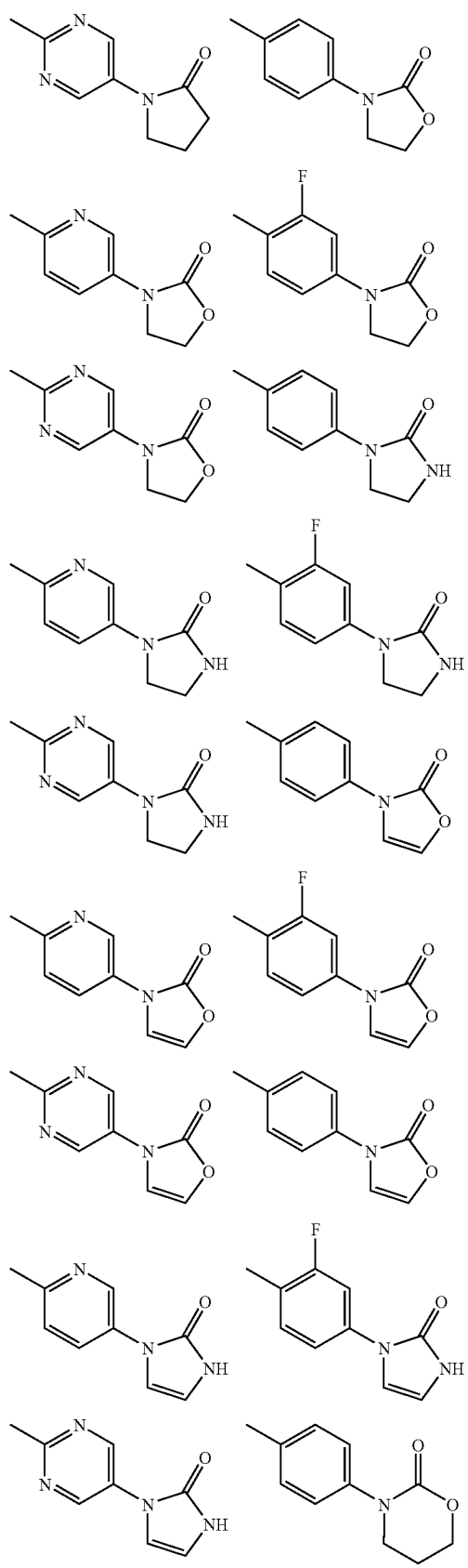

-continued

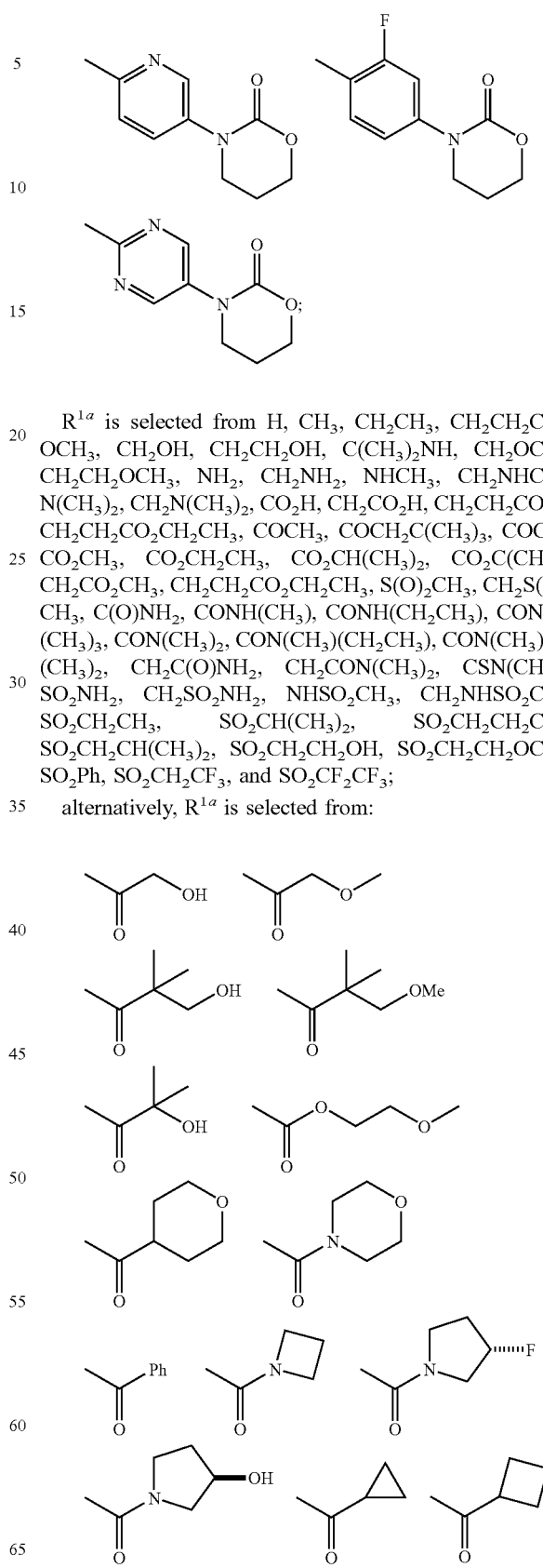

$R^{1a}$ is selected from H, CH$_3$, CH$_2$CH$_3$, CH$_2$CH$_2$CH$_3$, OCH$_3$, CH$_2$OH, CH$_2$CH$_2$OH, C(CH$_3$)$_2$NH, CH$_2$OCH$_3$, CH$_2$CH$_2$OCH$_3$, NH$_2$, CH$_2$NH$_2$, NHCH$_3$, CH$_2$NHCH$_3$, N(CH$_3$)$_2$, CH$_2$N(CH$_3$)$_2$, CO$_2$H, CH$_2$CO$_2$H, CH$_2$CH$_2$CO$_2$H, CH$_2$CH$_2$CO$_2$CH$_2$CH$_3$, COCH$_3$, COCH$_2$C(CH$_3$)$_3$, COCF$_3$, CO$_2$CH$_3$, CO$_2$CH$_2$CH$_3$, CO$_2$CH(CH$_3$)$_2$, CO$_2$C(CH$_3$)$_3$, CH$_2$CO$_2$CH$_3$, CH$_2$CH$_2$CO$_2$CH$_2$CH$_3$, S(O)$_2$CH$_3$, CH$_2$S(O)$_2$CH$_3$, C(O)NH$_2$, CONH(CH$_3$), CONH(CH$_2$CH$_3$), CONHC(CH$_3$)$_3$, CON(CH$_3$)$_2$, CON(CH$_3$)(CH$_2$CH$_3$), CON(CH$_3$)CH(CH$_3$)$_2$, CH$_2$C(O)NH$_2$, CH$_2$CON(CH$_3$)$_2$, CSN(CH$_3$)$_2$, SO$_2$NH$_2$, CH$_2$SO$_2$NH$_2$, NHSO$_2$CH$_3$, CH$_2$NHSO$_2$CH$_3$, SO$_2$CH$_2$CH$_3$, SO$_2$CH(CH$_3$)$_2$, SO$_2$CH$_2$CH$_2$CH$_3$, SO$_2$CH$_2$CH(CH$_3$)$_2$, SO$_2$CH$_2$CH$_2$OH, SO$_2$CH$_2$CH$_2$OCH$_3$, SO$_2$Ph, SO$_2$CH$_2$CF$_3$, and SO$_2$CF$_2$CF$_3$;

alternatively, $R^{1a}$ is selected from:

-continued
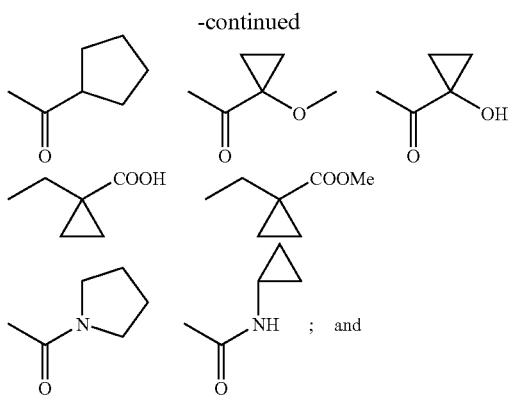
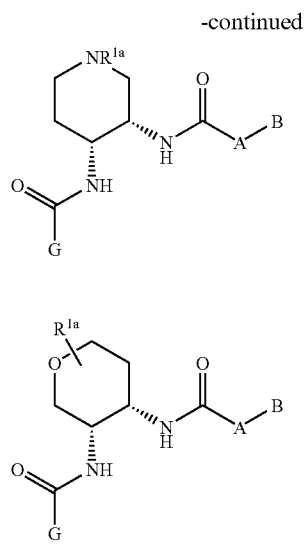
$R^{4b}$, at each occurrence, is selected from H, =O, $OR^3$, $CH_2OR^3$, F, Cl, $CH_3$, $CH_2CH_3$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$-phenyl, $S(O)_2CH_3$, $S(O)_2$-phenyl, and $CF_3$.
In a sixth embodiment, the present invention provides a novel compound, wherein the compound is selected from:
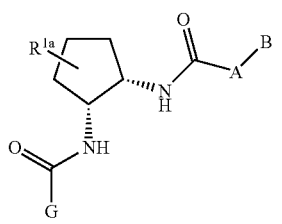
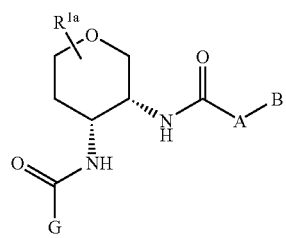
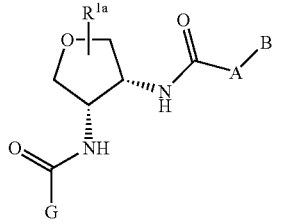
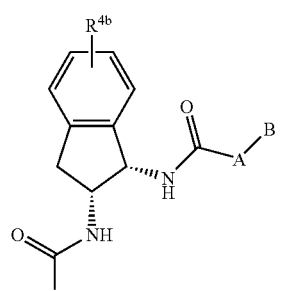
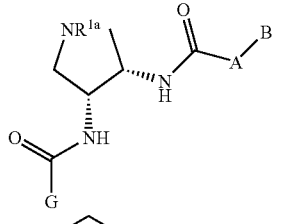
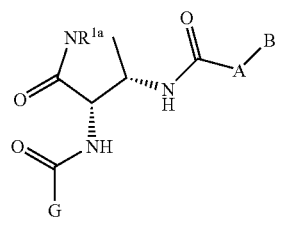
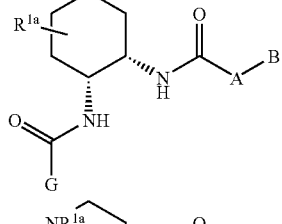
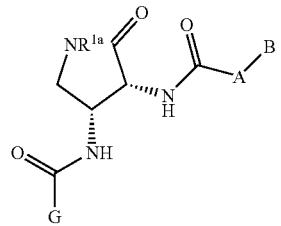

-continued

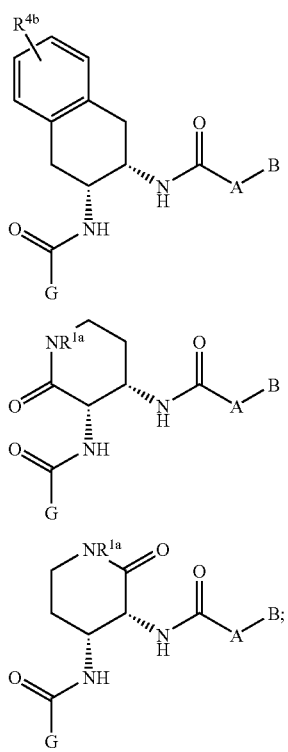

A-B is selected from:

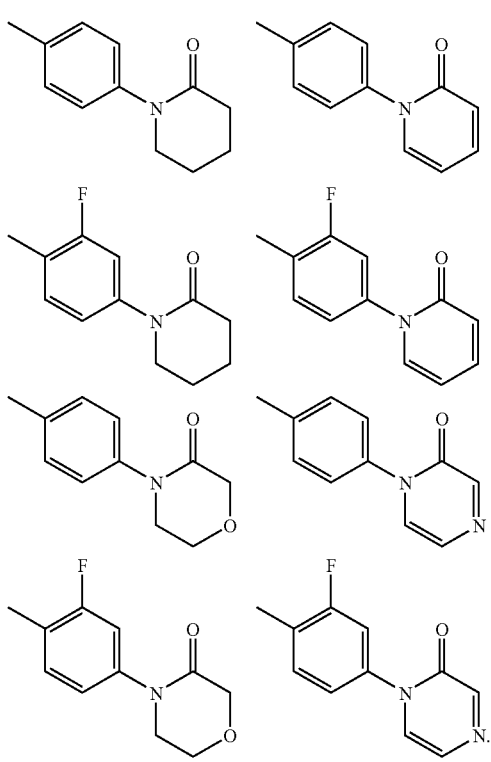

In a seventh embodiment, the present invention provides a novel compound, wherein the compound is selected from:

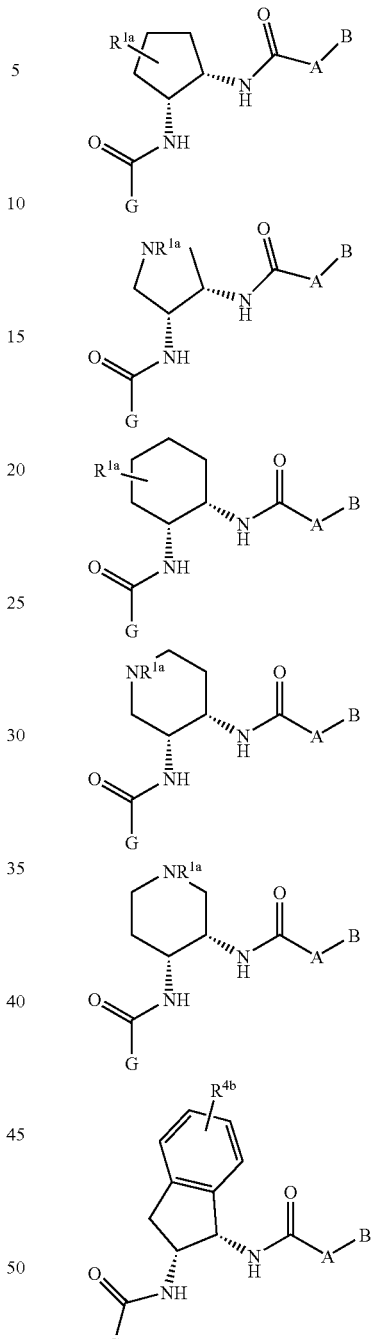

In an eighth embodiment, the present invention provides a novel compound selected from Examples 1–127 or a pharmaceutically acceptable salt thereof.

In a ninth embodiment, the present invention provides a novel compound selected from Examples 128–429 of Table 1.

In another embodiment, the present invention provides a novel pharmaceutical composition, comprising: a pharmaceutically acceptable carrier and a therapeutically effective amount of a compound of the present invention or a pharmaceutically acceptable salt form thereof.

In another embodiment, the present invention provides a novel method for treating a thromboembolic disorder, comprising: administering to a patient in need thereof a therapeutically effective amount of a compound of the present invention or a pharmaceutically acceptable salt form thereof.

In another preferred embodiment, the present invention provides a novel method, wherein the thromboembolic disorder is selected from the group consisting of arterial cardiovascular thromboembolic disorders, venous cardiovascular thromboembolic disorders, and thromboembolic disorders in the chambers of the heart.

In another preferred embodiment, the present invention provides a novel method, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another embodiment, the present invention provides a novel method of treating a patient in need of thromboembolic disorder treatment, comprising: administering a compound of the present invention or a pharmaceutically acceptable salt form thereof in an amount effective to treat a thromboembolic disorder In another embodiment, the present invention provides a novel method, comprising: administering a compound of the present invention or a pharmaceutically acceptable salt form thereof in an amount effective to treat a thromboembolic disorder.

In another embodiment, the present invention provides a novel method for treating a thromboembolic disorder, comprising: administering to a patient in need thereof a therapeutically effective amount of a first and second therapeutic agent, wherein the first therapeutic agent is compound of the present invention or a pharmaceutically acceptable salt thereof and the second therapeutic agent is at least one agent selected from a second factor Xa inhibitor, an anti-coagulant agent, an anti-platelet agent, a thrombin inhibiting agent, a thrombolytic agent, and a fibrinolytic agent.

In another preferred embodiment, the present invention provides a novel method, wherein the second therapeutic agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In another preferred embodiment, the present invention provides a novel method, wherein the second therapeutic agent is at least one anti-platelet agent.

In another preferred embodiment, the present invention provides a novel method, wherein the anti-platelet agent is aspirin and clopidogrel.

In another preferred embodiment, the present invention provides a novel method, wherein the anti-platelet agent is clopidogrel.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt form thereof; and,
(c) a package insert stating that the pharmaceutical composition can be used for the treatment of a thromboembolic disorder.

In another preferred embodiment, the present invention provides a novel article of manufacture, further comprising:
(d) a second container;

wherein components (a) and (b) are located within the second container and component (c) is located within or outside of the second container.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt form thereof; and,
(c) a package insert stating that the pharmaceutical composition can be used in combination with a second therapeutic agent to treat a thromboembolic disorder.

In another preferred embodiment, the present invention provides a novel article of manufacture, further comprising:
(d) a second container;

wherein components (a) and (b) are located within the second container and component (c) is located within or outside of the second container.

In another embodiment, the present invention provides novel compounds as described above for use in therapy.

In another embodiment, the present invention provides the use of novel compounds as described above for the manufacture of a medicament for the treatment of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N). The present invention, in general, does not cover groups such as N-halo, S(O)H, and $SO_2H$.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

As used herein, "alkyl" is intended to include both branched and straight-chain saturated aliphatic hydrocarbon groups having the specified number of carbon atoms. $C_{1-6}$ alkyl, is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example—$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-6}$ alkoxy, is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl is intended to include $C_3$, $C_4$, $C_5$, $C_6$, and $C_7$ cycloalkyl groups. Alkenyl" is intended to include hydrocarbon chains of either straight or branched configuration and one or more unsaturated carbon-carbon bonds that may occur in any stable point along the chain, such as ethenyl and propenyl. $C_{2-6}$ alkenyl is intended to include $C_2$, $C_3$, $C_4$, $C_5$, and $C_6$ alkenyl groups. "Alkynyl" is intended to include hydrocarbon chains of either straight or branched configuration and one or more triple carbon-carbon bonds that may occur in any stable point along the chain, such as ethynyl and propynyl. $C_{2-6}$ Alkynyl is intended to include $C_2$, $C_3$, $C_4$, $C_5$, and $C_6$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, or unsaturated (aromatic). Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2]bicyclooctane). A bridged ring occurs when one or more carbon atoms link two non-adjacent carbon atoms. Preferred bridges are one or two carbon atoms. It is noted that a bridge always converts a monocyclic ring into a trycyclic ring. When a ring is bridged, the substituents recited for the ring may also be present on the bridge.

As used herein, the term "heterocycle" or "heterocyclic group" is intended to mean a stable 3, 4, 5, 6, or 7-membered monocyclic or 7, 8, 9, 10, 11, or 12-membered bicyclic or tricyclic heterocyclic ring which is saturated, partially unsaturated or unsaturated (aromatic), and which consists of carbon atoms and 1, 2, 3, 4, or 5 ring heteroatoms independently selected from the group consisting of N, O and S. Heterocycle includes any bicyclic group in which one heterocyclic ring is fused to a second ring, which may be carbocyclic (e.g. benzo fusion) or heterocyclic. When a heterocycle is referred to as an "aromatic heterocycle" or "heteroaryl," this means that a fully unsaturated, i.e., aromatic, ring is present in the heterocycle. An aromatic heterocycle only requires one ring to be aromatic, if more than one ring is present. The aromatic portion of the aromatic heterocycle can be a carbocycle or heterocycle. The nitrogen and sulfur heteroatoms in the heterocycle may optionally be oxidized (i.e., N→O and S(O)p). The nitrogen atom may be unsubstituted (i.e., N or NH) or substituted (i.e., NR wherein R is a substituent) and may optionally be quaternized. The heterocyclic ring may be attached to its pendant group at any heteroatom or carbon atom that results in a stable structure. The heterocyclic rings described herein may be substituted on a carbon or on a nitrogen atom, if the resulting compound is stable. It is preferred that when the total number of S and O atoms in the heterocycle exceeds 1, then these heteroatoms are not adjacent to one another. It is preferred that the total number of S and O atoms in the heterocycle is not more than 1. It is to be noted that total number of S and O atoms in the aromatic heterocycle is not more than 1. Bridged and spiro rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a trycyclic ring. When a ring is bridged, the substituents recited for the ring may also be present on the bridge. Spiro rings are formed when to or more atoms (i.e., C, O, N, or S) of a chain are attached to the same carbon atom of a heterocycle (or carbocycle if fused to a heterocycle). When a spiro ring is present, the substituents recited for the ring may also be present on the spiro.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p 1445, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor Xa. "Therapeutically effective amount" is also intended to include an amount of the combination of compounds claimed that is effective to inhibit factor Xa. The combination of compounds is preferably a synergistic combination. Synergy, as described, for example, by Chou and Talalay, *Adv. Enzyme Regul.* 1984, 22:27–55, occurs when the effect (in this case, inhibition of factor Xa) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

Synthesis

All references cited herein are hereby incorporated in their entirety herein by reference.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require ajudgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference. The compounds of the present invention as represented as Formula I in Scheme 1 can be prepared as outlined in Schemes 2–20 and via standard methods known to those skilled in the art. M in Formula I corresponds to the central ring of the present compounds.

Scheme 1

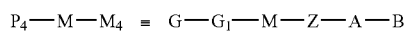

Formula I

The A-B group for compounds of the present invention can be obtained via the Ullman reaction or Buchwald modified Ullman reaction (*J. Am. Chem. Soc.* 2001, 123, 7727) using CuI and 1,2-cyclohexyldiamine or 1,10-phenanthroline as the catalyst as outlined in Scheme 2.

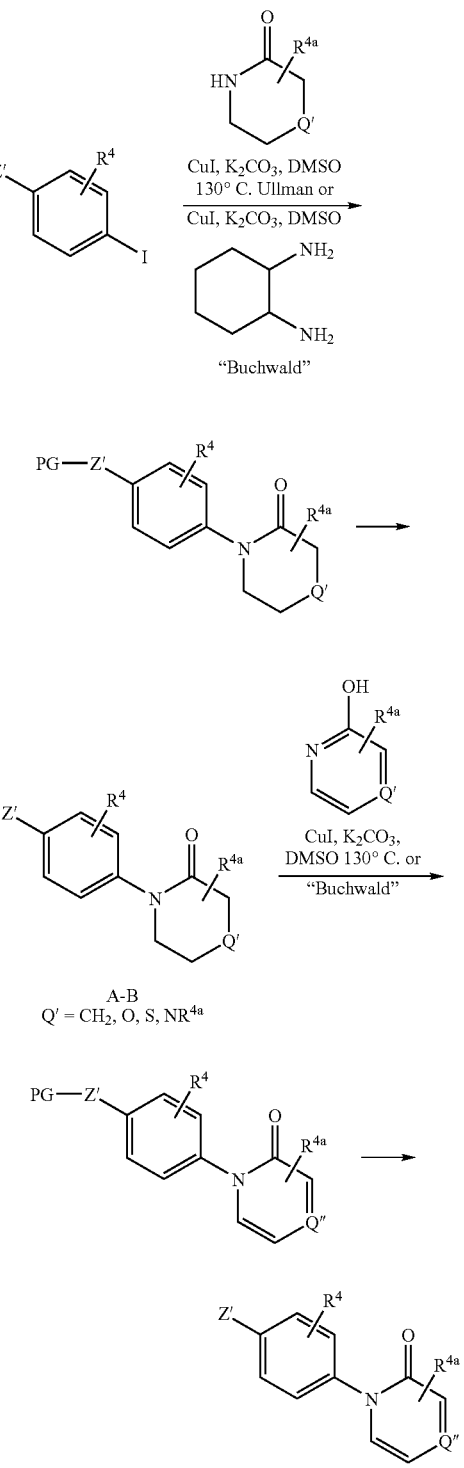

A-B groups wherein the B group contains an oxidizable group can be obtained by oxidation, e.g., S to SO and SO$_2$. The Ullman coupling methodology can also be applied to prepare the cyclic urea or cyclic carbamate analogs shown in Scheme 3.

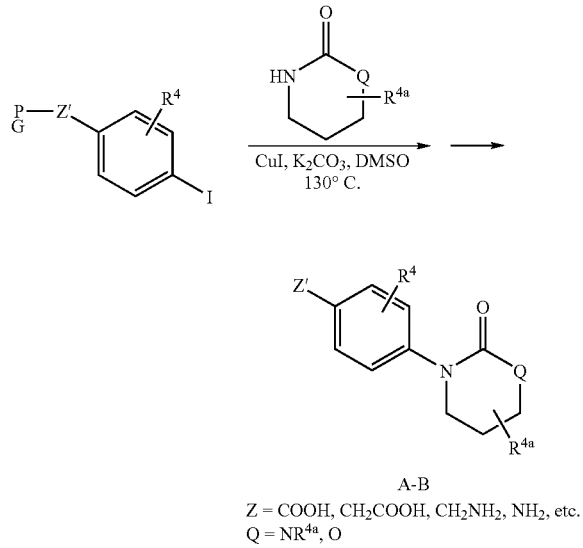

The A-B group can also be prepared via aromatic nucleophile displacement of substituted halo-nitrobenzenes followed by reduction and other transformations as shown in Scheme 4.

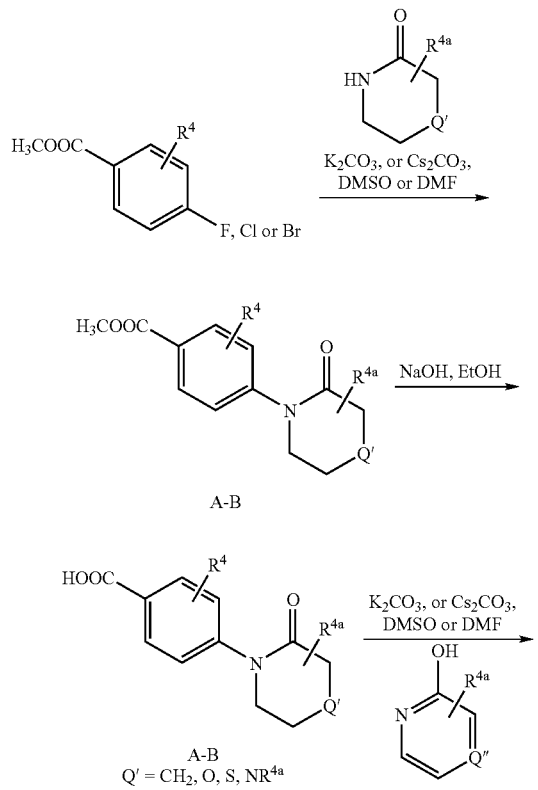

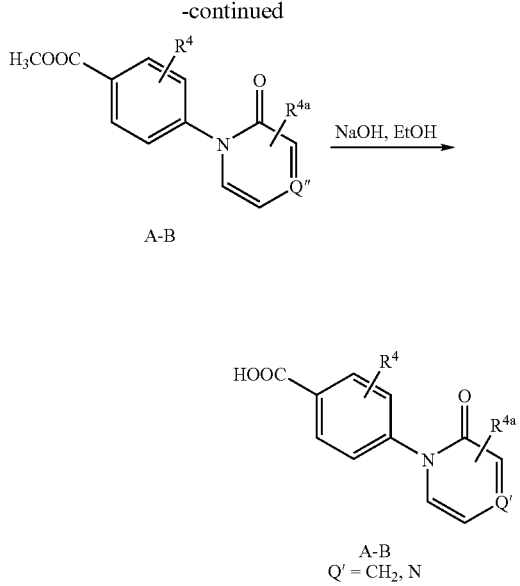

A-B groups can also be prepared via aromatic nucleophilic substitution of fluoronitrobenzenes with the 5–7 membered bases followed by α-carbon oxidation with KMnO$_4$ as shown in Scheme 5.

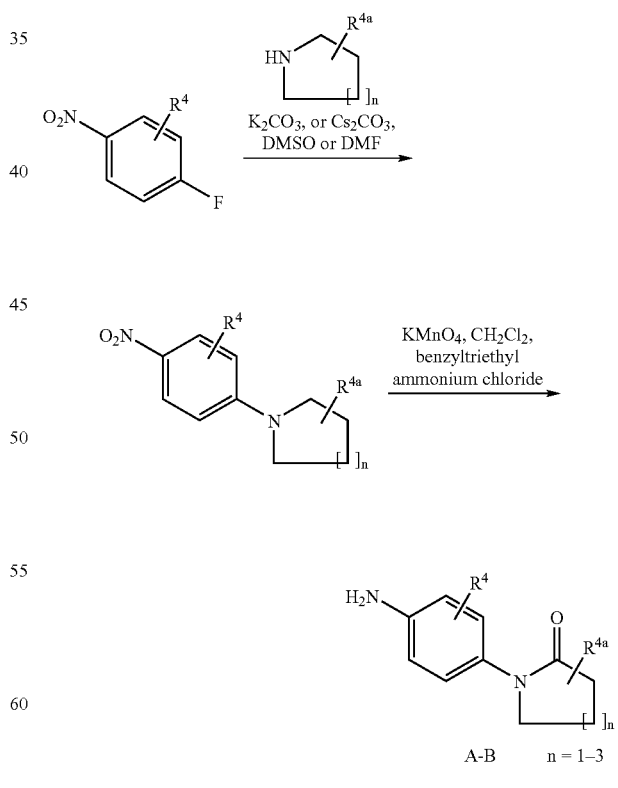

Lactam, cyclic sulfonamide, cyclic urea, and cyclic carbamate A-B analogs can also be prepared via the method outlined in Scheme 6.

Scheme 6
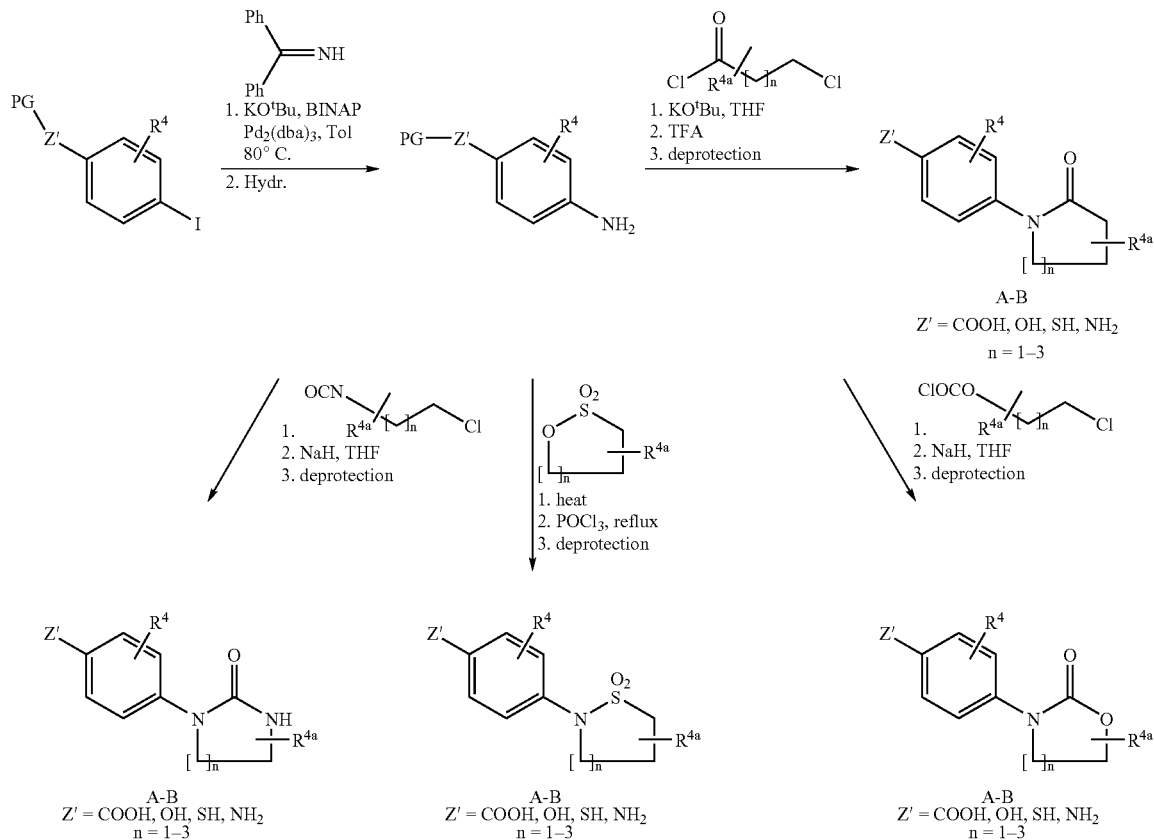
The piperidone A-B groups shown above can also be further elaborated to afford other compounds of the present invention by numerous methods known to those skilled in the art (e.g., see scheme 7).
Scheme 7
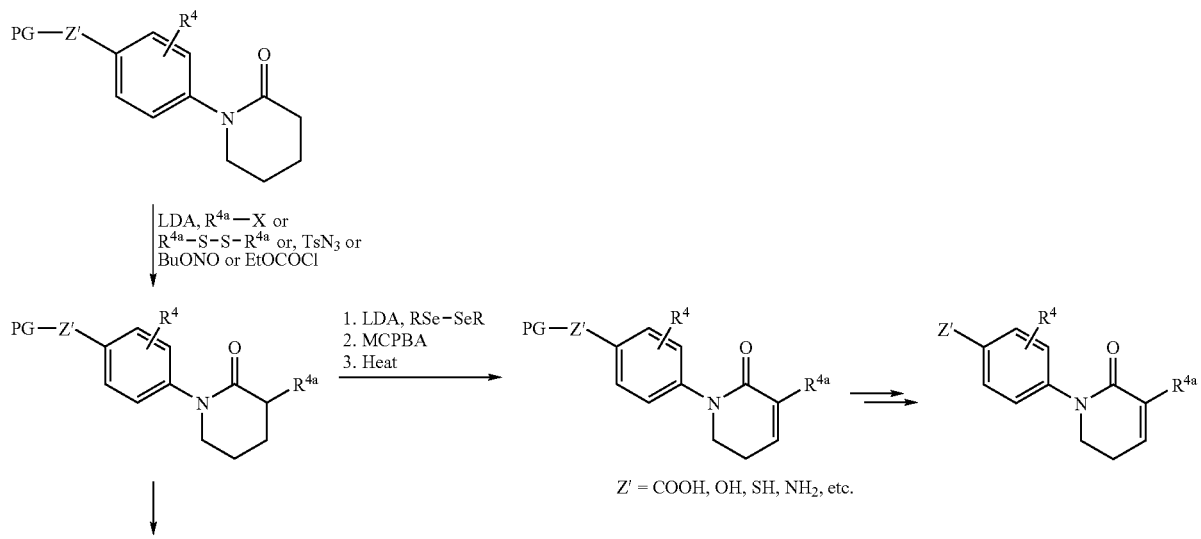

-continued

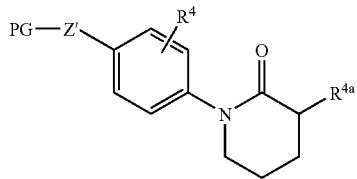

Additional A-B intermediates can be synthesized by chemical manipulation of the amino functionality of the compounds described above (see Scheme 8).

Ortho-substituted pyridyl and pyrimidyl A-B analogs (see structures below) can also be prepared using routes similar to those of Schemes 2–9.

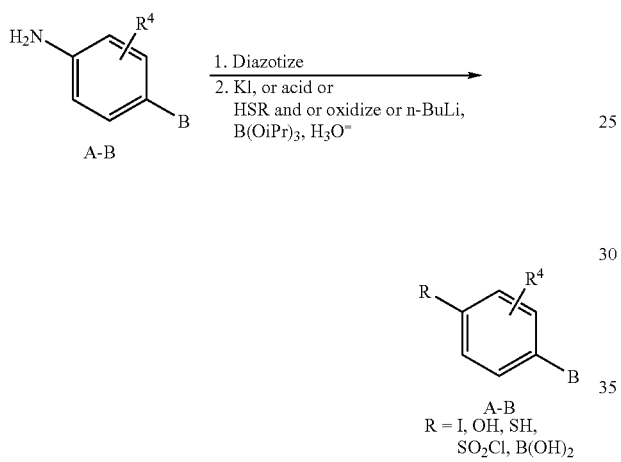

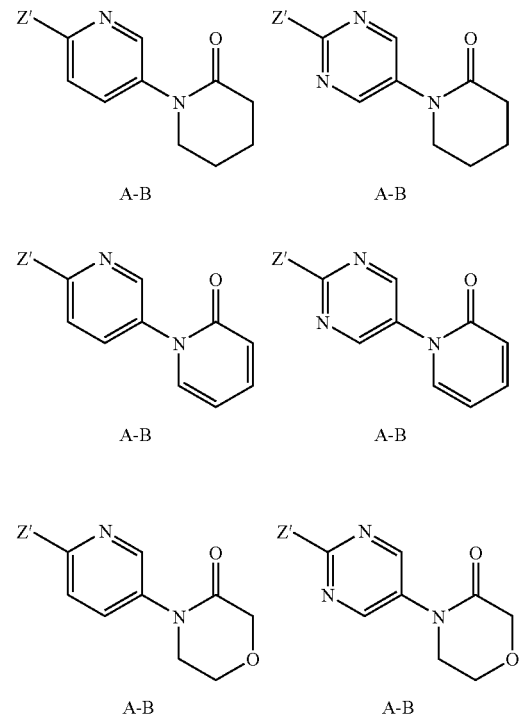

Other possible A-B groups can be synthesized from the carboxylic ester intermediates that can be homologated via the Arndt Eistert methodology to afford other A-B intermediates (see Scheme 9). Alternatively, the ester functionality can be reduced to the alcohol that in turn can be converted to a variety of A-B groups by procedures known to those skilled in the art.

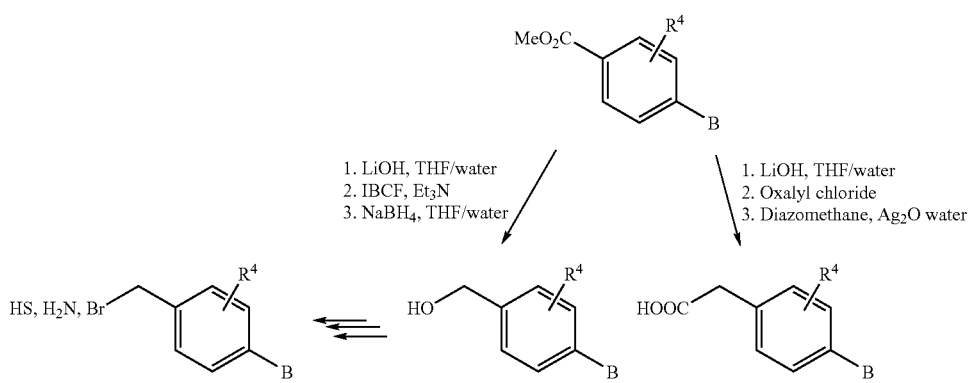

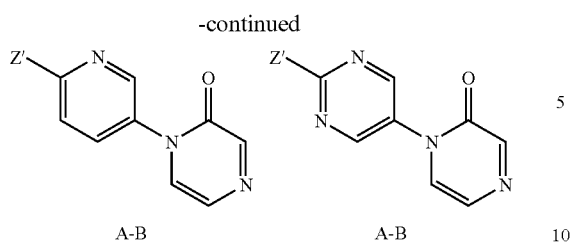

The non-aromatic intermediates in Scheme 10 can be synthesized via procedures known to those skilled in the art. These intermediates can than be further manipulated to incorporate substituent $R^{4a}$ via procedures previously described.

Scheme 10

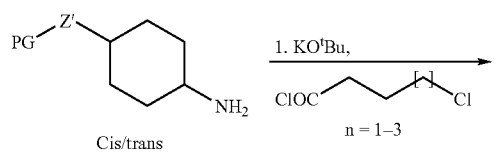

Alternative non-aromatic intermediates can be synthesized via procedures known to those skilled in the art, e.g., see scheme 11. These intermediates can also be further manipulated to incorporate substituent $R^{4a}$ via procedures described previously. Further modifications of the ester functionality can be done via procedures described above.

Scheme 11

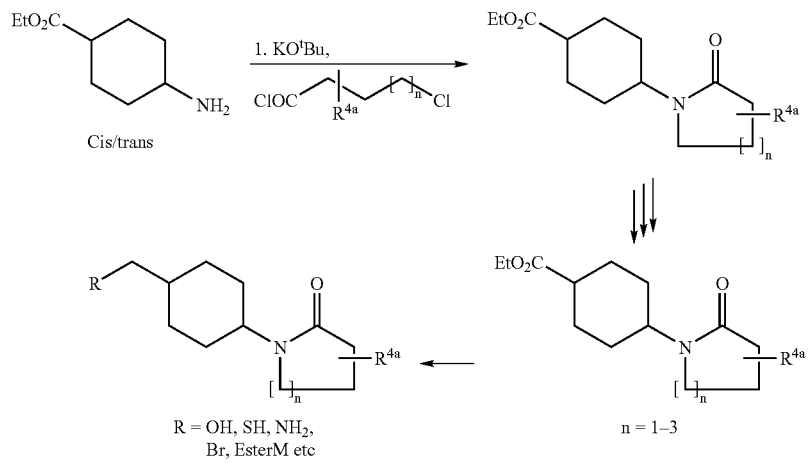

A-B groups wherein A is indoline can be prepared as shown in Scheme 12. This type of intermediate can then be attached to the remainder of the desired compound as described previously. Alternatively, the indoline can be attached to the other half of the desired compound prior to formation of the lactam ring.

Scheme 12

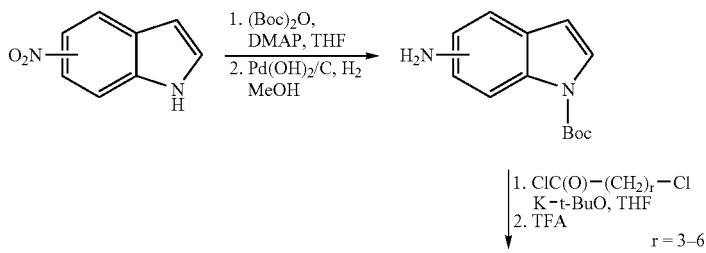

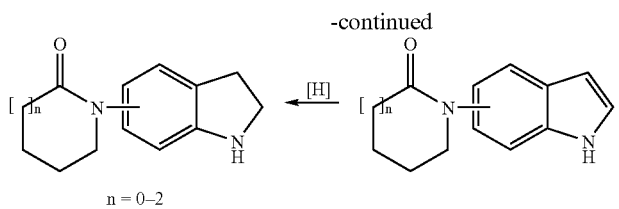

n = 0–2

Schemes 2–12 describe how to make the A-B moieties of the present invention. The functionalized G moiety of the present invention can be prepared using methods known to those of ordinary skill in the art. All of the following patents and publications are incorporated herein by reference. For compounds wherein G is a ring substituted with a basic moiety, one of ordinary skill in the art can look to U.S. Pat. No. 5,939,418, 5,925,635, 6,057,342, 6,187,797, 6,020,357, 6,060,491, 6,191,159, 6,339,099, 6,271,237 6,399,644, 6,407,256, 6,413,980, WO02/00651, WO02/102380, WO02/094197, US 2003/78,255, and US 2003/18,023 for starting materials. For compounds wherein G is a ring substituted with a non-basic group, one of ordinary skill in the art can look to U.S. Pat. No. 5,998,424, 6,413,980, 6,399,644, 6,407,256, WO02/00651, WO02/102380, WO02/094197, US 2003/78,255, and US 2003/18,023 for starting materials. For compounds wherein G is a bicyclic moiety, one of ordinary skill in the art can look to U.S. Pat. No. 6,339,099 6,369,227, 6,413,980, WO02/00651, WO02/102380, WO02/094197, US 2003/78,255, and US 2003/18, 023 for starting materials. For compounds wherein A is an indoline or similar bicycle, one of ordinary skill in the art can look to U.S. Pat. No. 6,429,205 for starting materials and intermediates to which the present B group can be coupled or from which the present A-B groups can be formed.

Schemes 13–20 depict several examples for coupling the above A-B intermediates to prepare compounds of the present invention.

Compounds of the present invention wherein ring M is a non-aromatic carbocycle or heterocycle can be prepared by using the methods described previously and known to those skilled in the art. Scheme 13 illustrates some of the monocyclic/heterocyclic M intermediates that can be used to prepared compounds of the present invention ($R^z$ is the point of attachemtn of Z-A-B and can be a protectiong group; a group modifiable to Z or A-Z; or Z, A-Z, or A; $R^g$ is the point of attachment for $G_1$-G and can be a protecting group, a group modifiable to $G_1$, or $G_1$-G). These intermediates can be prepared using methods known to those of ordinary skill in the art.

All of the following patents and publications are incorporated herein by reference. For compounds wherein ring M is a 5-, or 6-membered ring, one of ordinary skill in the art can look to WO00/47207; WO98/16497; WO94/20062; WO01/28987; WO00/69855; WO02/60859; GB2210039; EP237829; Bioorganic & Medicinal Chemistry Letters 1998, 8(5), 525–528; Tetrahedron 1997, 53(4), 1417–1438; Journal of Heterocyclic Chemistry 1988, 25(3), 1035–6; and, Tetrahedron: Asymmetry 1997, 8(11), 1861–1867, for starting materials and intermediates to which the present B and/or A-B groups can be coupled.

Scheme 13

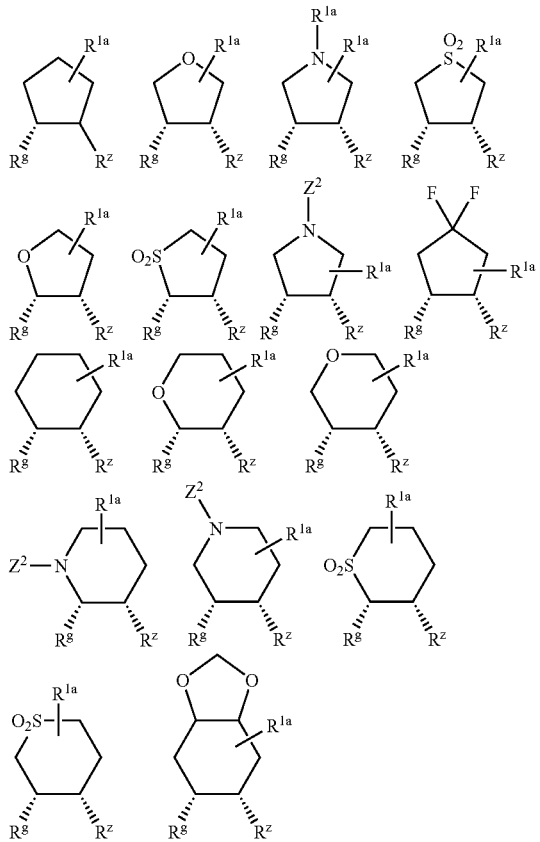

Scheme 14 describes general methods of converting the M rings shown in Scheme 13 to compounds of the present invention wherein linker $G_1$ can be —NHCO—, —NHCO-CONH—, —NHCOC(S)NH—, —NHC(S)CONH—, or —CONH—, and linker Z can be —NHCO— or —CONH—. As one of ordinary skill in the art would recognize, this method would be applicable to other non-aromatic rings not shown. The properly protected, enantiomerically pure cyclic amino acid cores can be obtained via Davies' protocol (J. Chem. Soc. Perkin Trans I, 1994, 1411) or via the reduction of enamines described by Cimarelli, C. et al (J. Org. Chem. 1996, 61, 5557). The corresponding diamino compounds can be obtained via saponification of the ester of the cyclic amino acids followed by Curtius rearrangement. On the other hand, the cyclic diamines can be prepared via literature methods. (See, for example, Tetrahedron: Assymmetry, 1997, 8, 1861 or Tetrahedron Lett. 1998, 39, 6921).

Scheme 14
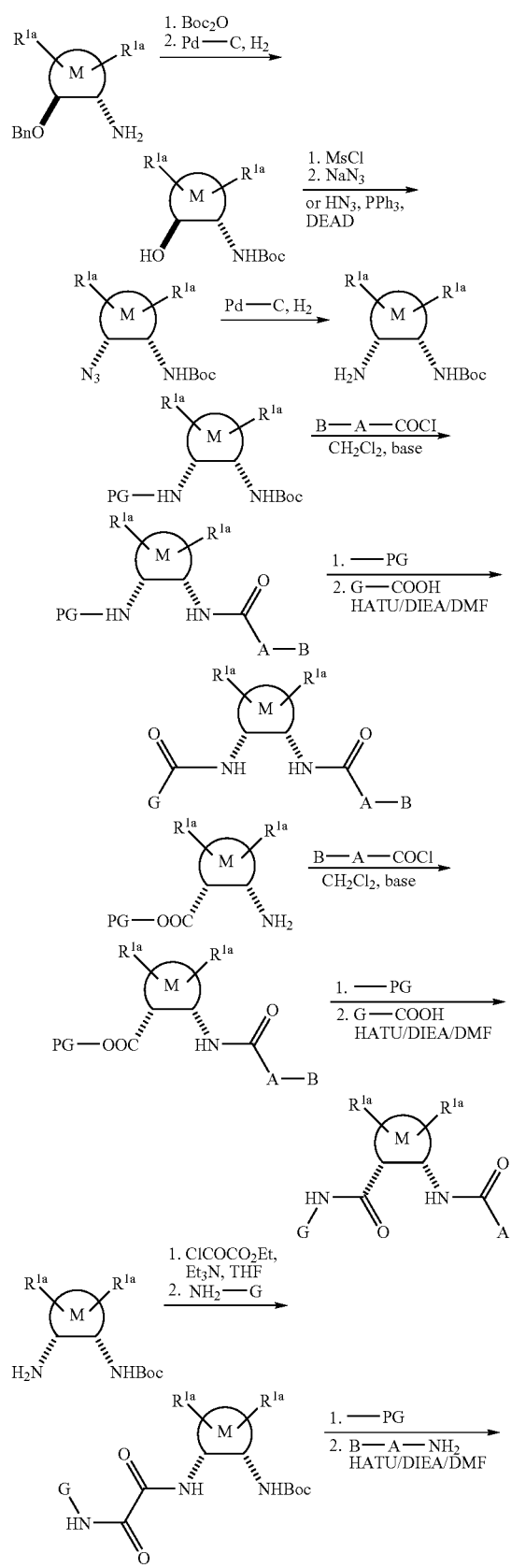
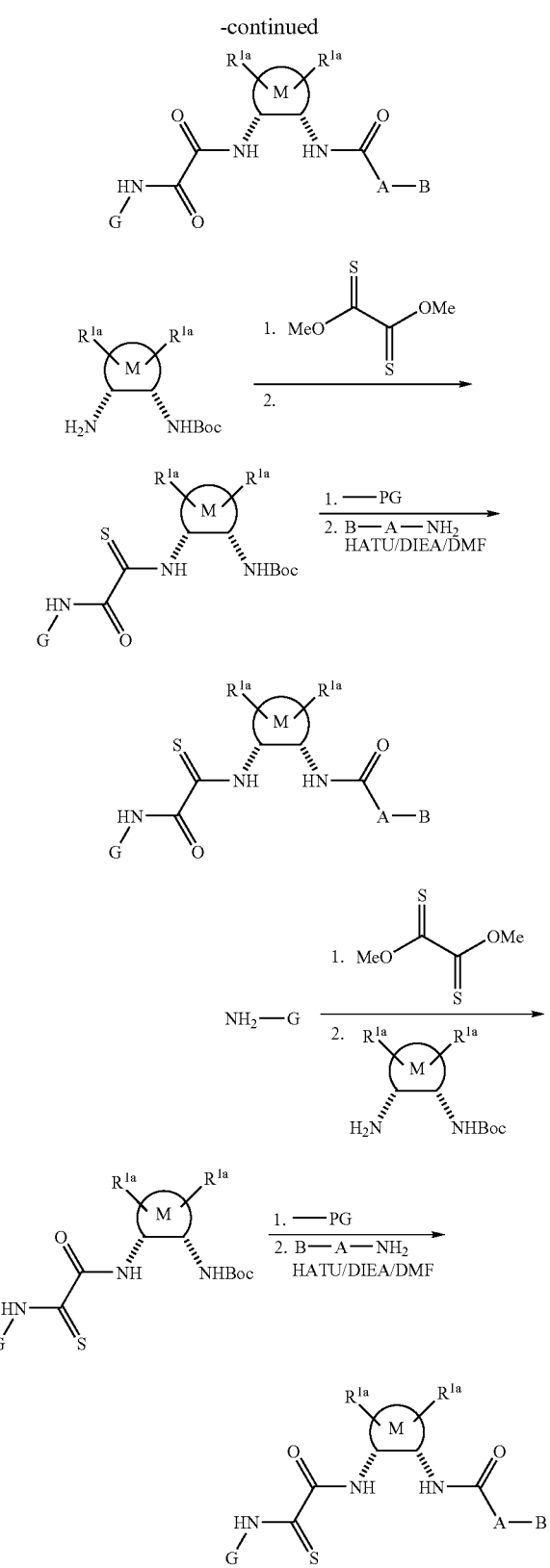
A series of compounds of the present invention wherein $G_1$ is 1,1-dioxo-sulfonylmethyl group are prepared following the sequence outlined in Scheme 15.

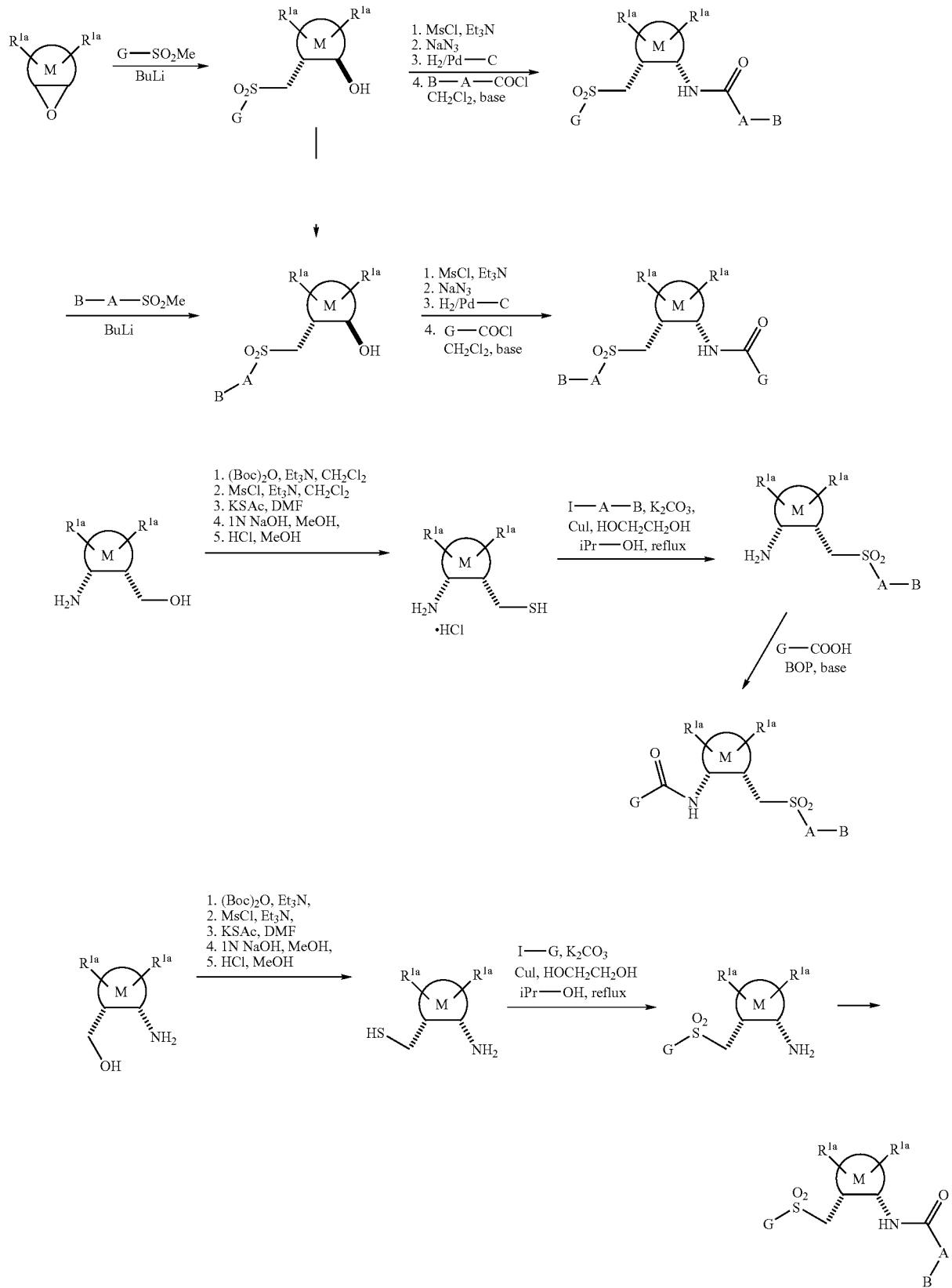
Scheme 15

Scheme 16 illustrates numerous bicyclic M intermediates that can be used to prepare compounds of the present invention. These intermediates can be prepared using methods known to those of ordinary skill in the art and using similar methods described previously.
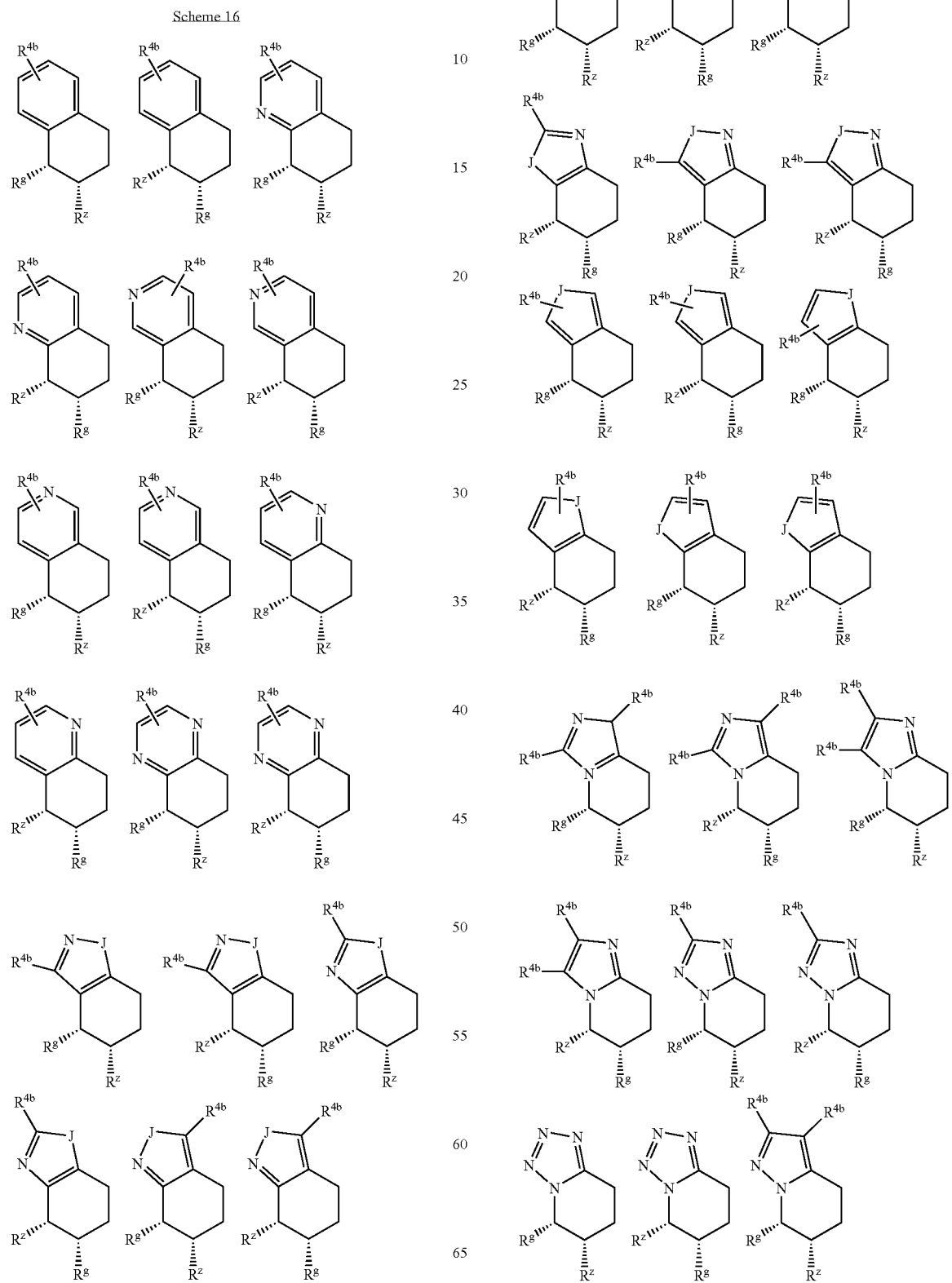

-continued
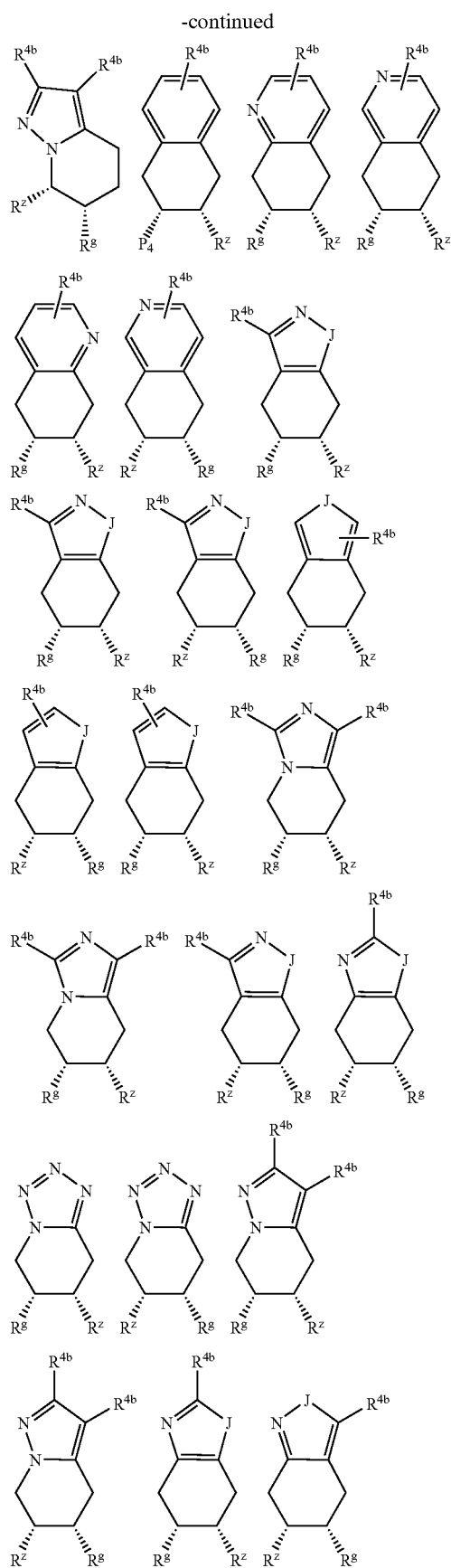
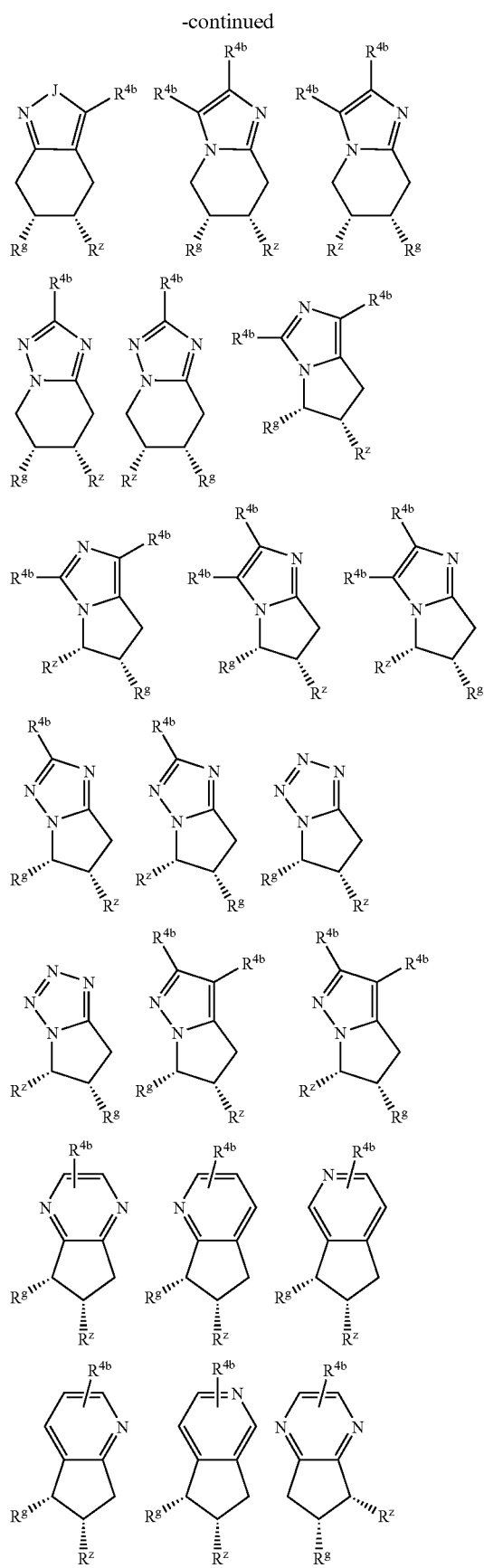

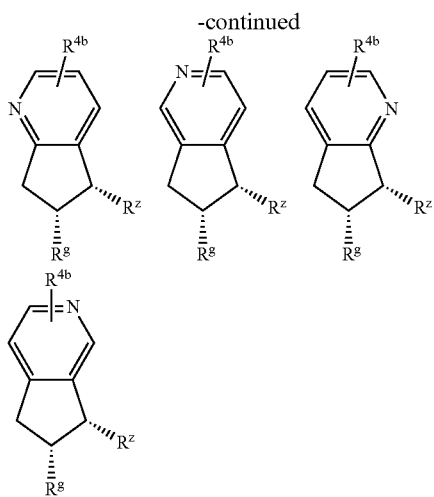

Scheme 17 illustrates the synthesis of benzofused M intermediates of the present invention. The α- or β-amino acid derivatives 1 can undergo Friedel-Crafts reaction followed by reduction to afford the fused ring intermediates 2. Replacement of the OH group with NH₂ group as described previously to afford 3, followed by standard coupling reactions can provide the compounds of the present invention. On the other hand, oxime formation of the ketone intermediate 4 followed by reduction with NaBH₄ can provide the amino alcohol intermediate 5, which can also be obtained via epoxidation of the olefin 6 and then nucleophilic displacement. Protection of the amino group in 5 followed by azide displacement of the mesylate and then reduction of the azide group can give the Boc protected diamino compound 7. Functional groups U and V can be acid chloride, carboxylic acid, or sulfonyl chloride, etc in formula U-G₁-G and V-A-B. The compounds of the present invention can be obtained from 7 using methods known to those of ordinary skill in the art and using similar methods described previously.

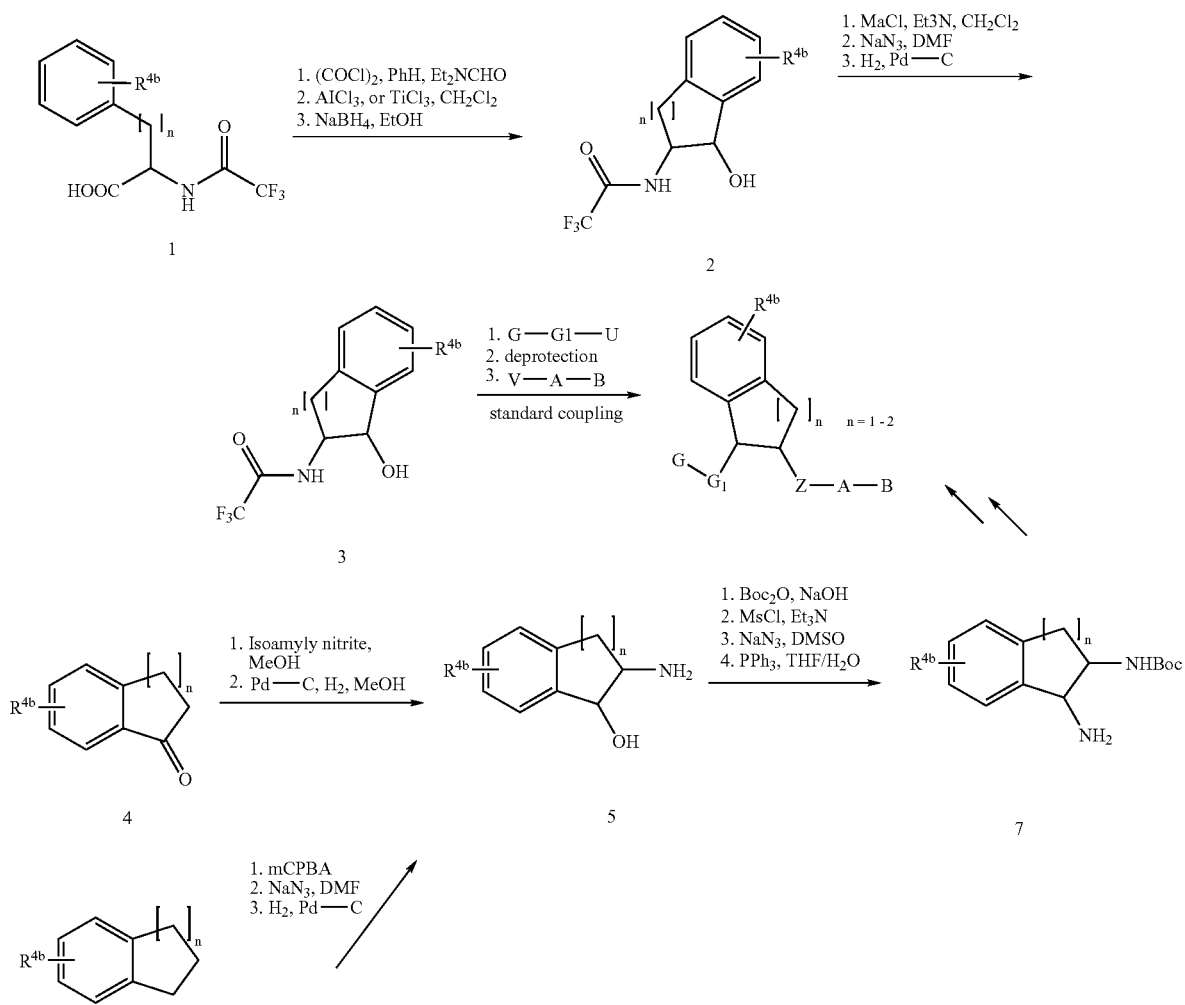

Enantiomencally pure product can be prepared from enatiomerically pure 5:

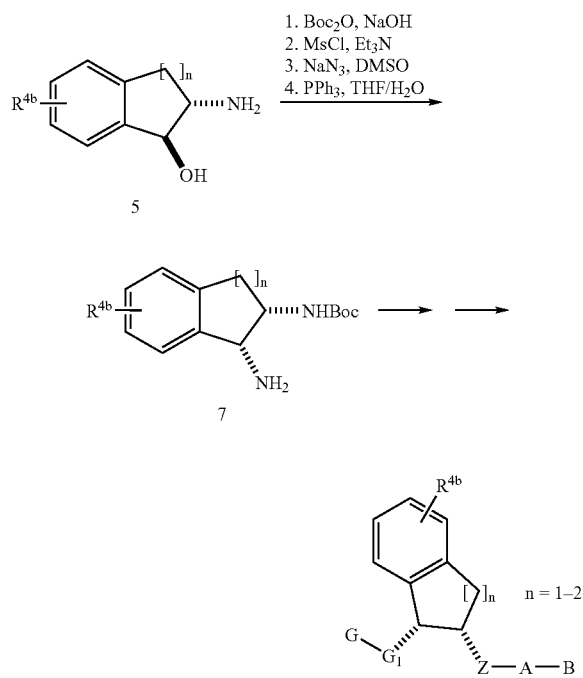

Scheme 18 depicts numerous spiro and bridged M intermediates that can be used to prepare compounds of the present invention. These intermediates can be prepared using methods known to those of ordinary skill in the art and using the methods described previously.

Scheme 18

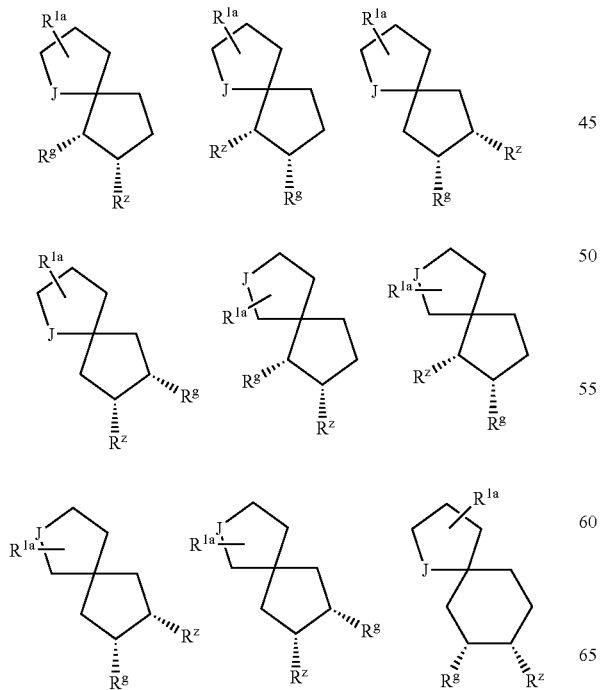

-continued

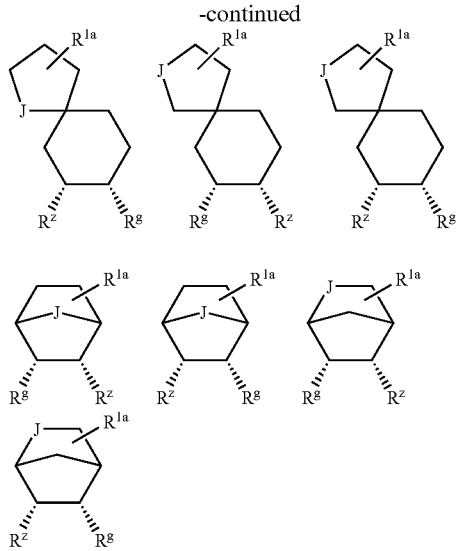

Scheme 19 depicts the synthesis of the spiro intermediates M of the present invention. Epoxidation of olefin 8 followed by displacement with TMSN$_3$ and reduction with 10-CSA can provide the amino alcohol intermediate 9. Protection of the amino and alcohol groups followed by nucleophilc addition to the carbonyl group and spiro ring formation can afford the spiro tetrahydrafuran intermediate 10. Compound 10 can undergo similar sequence of reactions described previously to give the compounds of the present invention.

Scheme 19

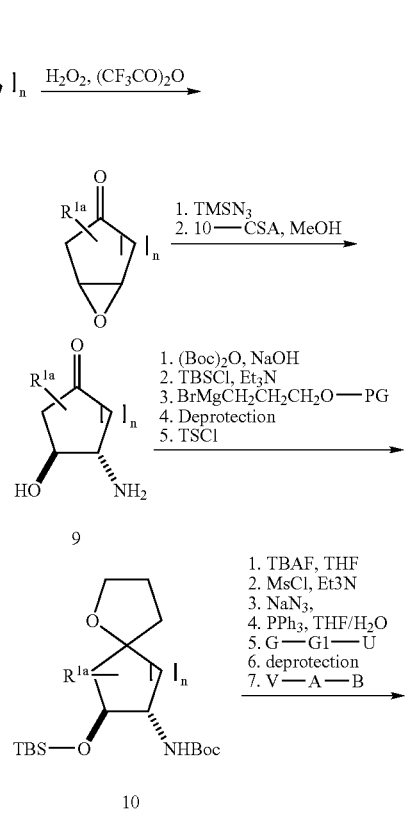

-continued

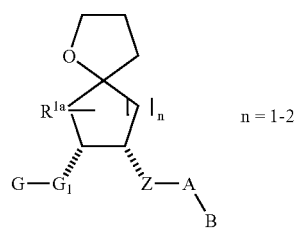

n = 1-2

Different diastereomers of compounds of the present invention can be prepared as shown in Scheme 20 with cyclopentyl as the central M ring. Starting from enantiomerically-pure commercially-available (1S, 2S)-2-benzyloxy cyclopentylamine, Boc protection followed by debenzylation gave alcohol 11. SN$_2$ displacement with NaN$_3$ of the mesylate of 11, followed by reduction of the azide afford the key intermediate 12. Amide formation as described previously provided two enantiomers 13 and 14. On the other hand, inversion of the stereo center of the alcohol 11 (p-NO$_2$—Ph—COOH, DEAD, PPh$_3$, THF; then NaOMe, MeOH) followed by the same sequence as for 13 and 14 afforded the other two enantiomers 16 and 17.

Scheme 20

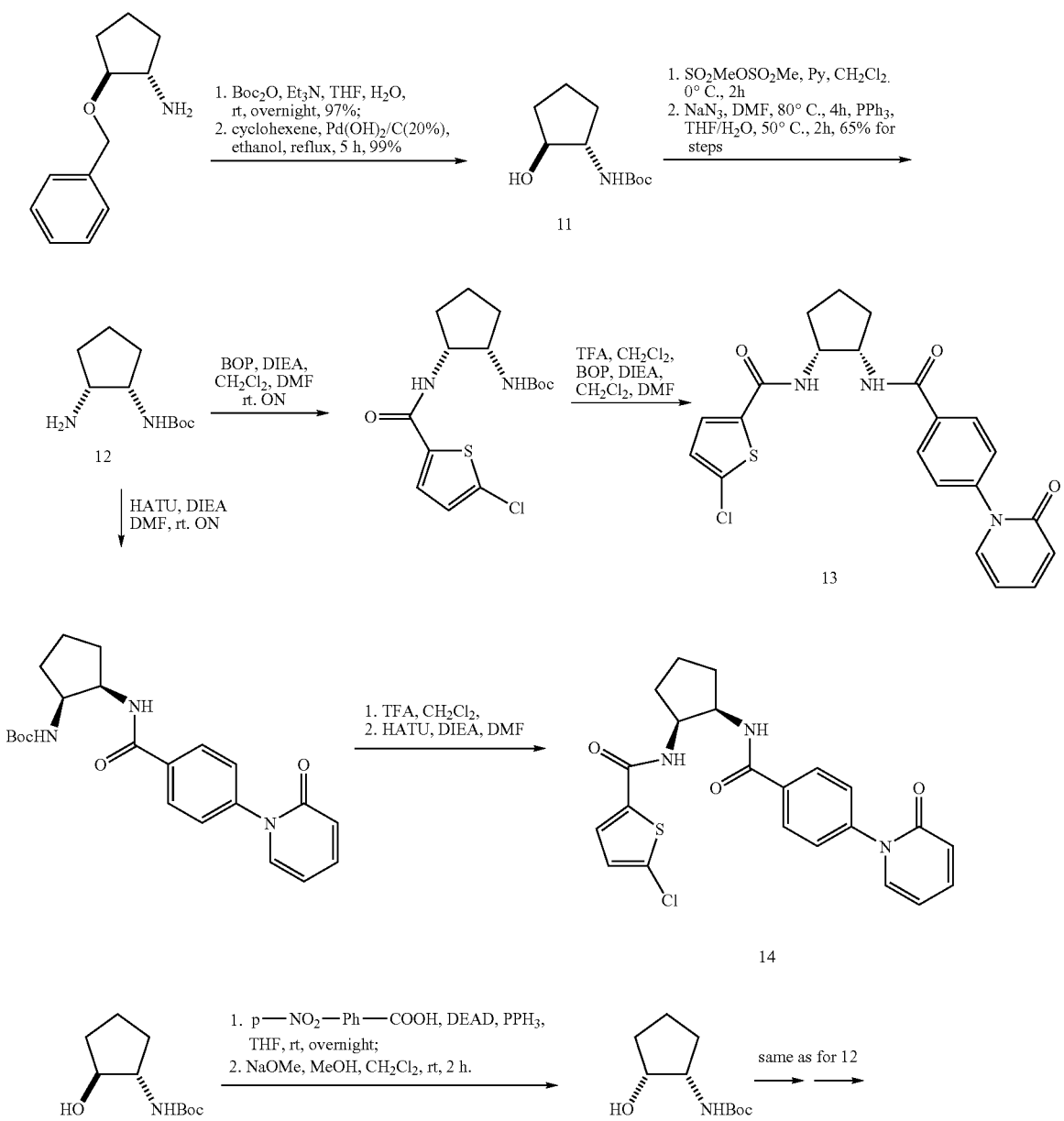

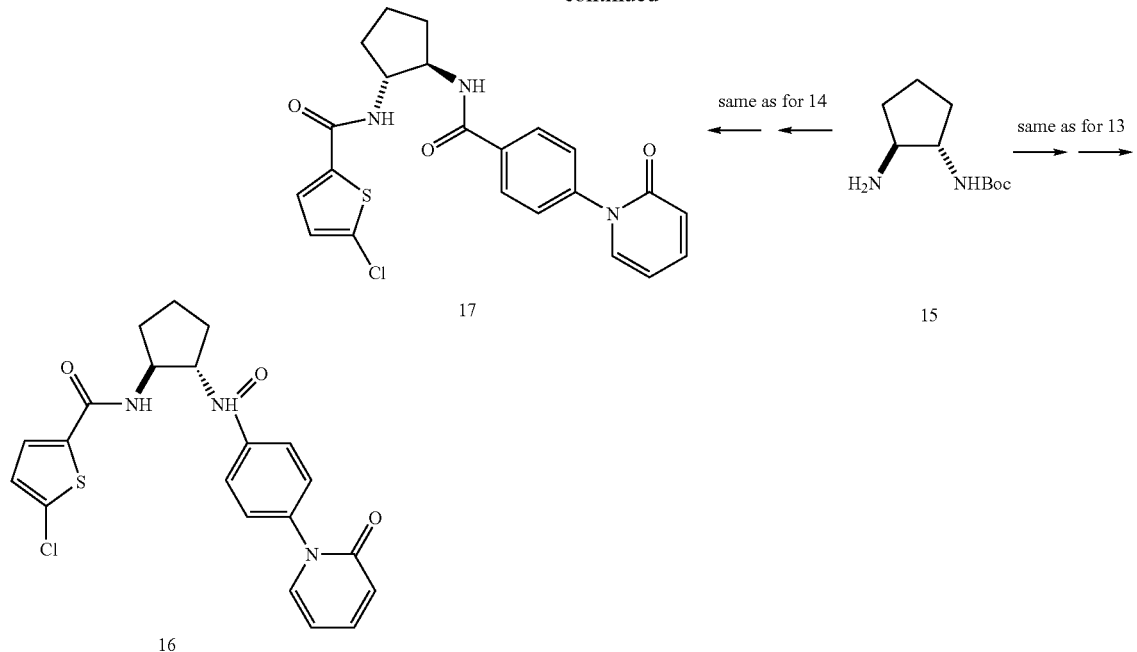

Diaminolactam derivatives 18 and 19 can be prepared from commercially available β-hydroxylactones as shown in Scheme 21. Dianion formation followed by treatment with trisyl azide and then hydrogenation should provide amino alcohol intermediate 20. Mesylation followed by replacement with NaN$_3$ should generate compound 21. The lactone 22 can then be transferred to the lactam 23 by treatment with NH$_2$R and mesylation, followed by ring formation with NaH. The final product 18 can be prepared from 23 by using reactions described previously to give compounds of the present invention.

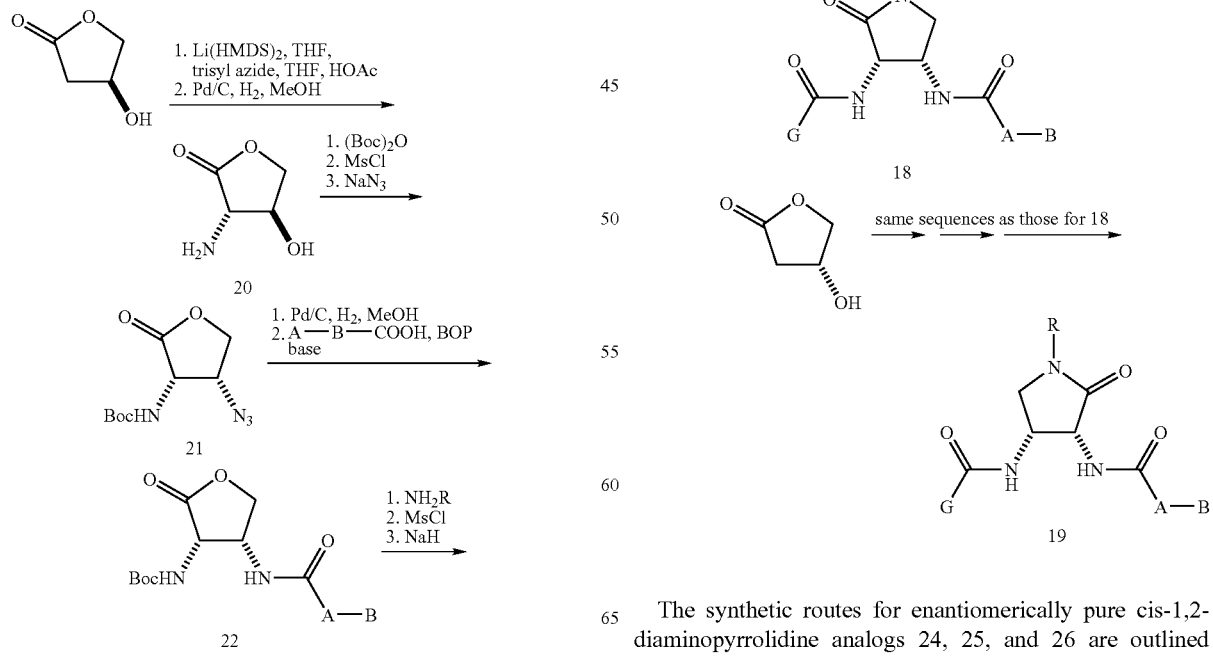

The synthetic routes for enantiomerically pure cis-1,2-diaminopyrrolidine analogs 24, 25, and 26 are outlined below in Scheme 22. Starting from commercially available 2,5-dihydro-1H-pyrrole, Fmoc-protection followed by epoxidation with mCPBA should afford epoxide 27. Stereospecific ring opening of the neso epoxide with TMS azide in the presence of Jacobson's chiral chromium(III) catalyst 28, followed by TMS deprotection with 10-CSA should afford the trans azide 29 (see Jacobsen et al, U.S. Pat. No. 5,929,232). Hydrogenation of 29 followed by Boc-protection of the amino group should give intermediate 30. This enantiomerically pure trans Boc-protected amino alcohol can then be reacted with a freshly prepared toluene solution of $HN_3$ under Mitsonobu conditions to form the corresponding cis Boc-protected amino azide 31. Azide reduction and then Boc protection, followed by the sequences described previously should provide 32. The Fmoc group can then be removed with morpholine, and the free amine reacted with acetic anhydride, ethyl chloroformate, and methanesulfonyl chloride to generate desired final compounds 24, 25, and 26, respectively.

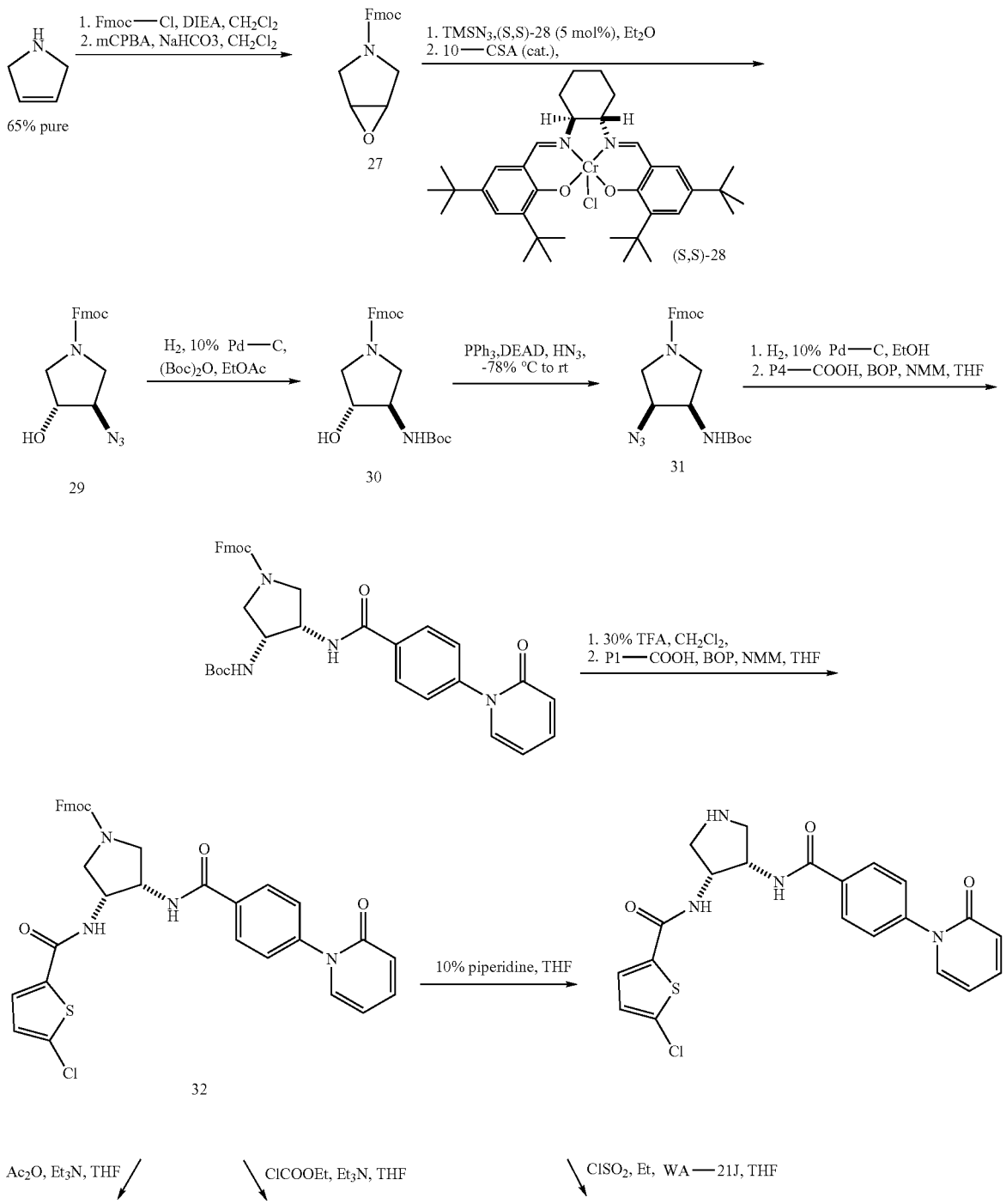

Scheme 22

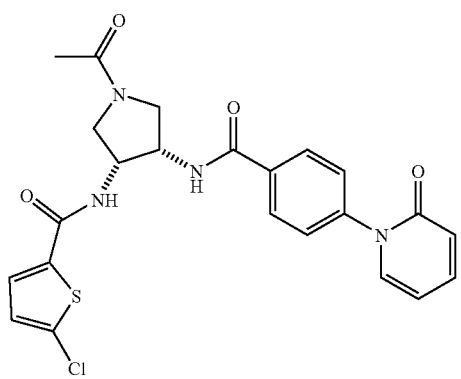

24

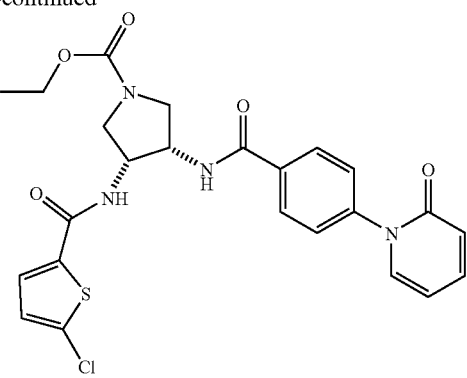

25

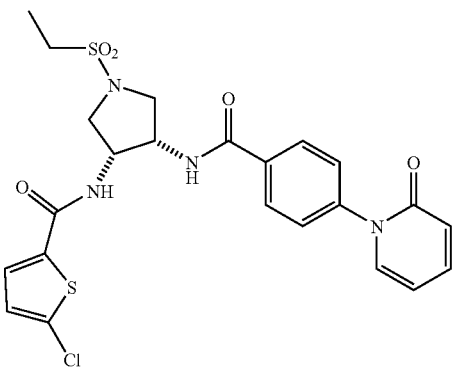

26

Utility

The compounds of this invention are inhibitors of factor Xa and are useful as anticoagulants for the treatment or prevention of thromboembolic disorders in mammals (i.e., factor Xa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular or cerebrovascular thromboembolic disorders, and thromboembolic disorders in the chambers of the heart. The term "thromboembolic disorders" as used herein also includes specific disorders selected from, but not limited to, unstable angina or other acute coronary syndromes, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Diapharma/Chromogenix, West Chester, Ohio) was measured both in the absence and presence of compounds of the present invention. Hydrolysis of the substrate resulted in the release of pNA, which was monitored spectrophotometrically by measuring the increase in absorbance at 405 nm. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 min and the velocities (rate of absorbance change vs. time) were measured in the time frame of 25–30 min. The following relationship was used to calculate $K_i$ values:

$$(v_o-v_s)/v_s = I/(K_i(1+S/K_m))$$

where:
  $v_o$ is the velocity of the control in the absence of inhibitor;
  $v_s$ is the velocity in the presence of inhibitor;
  I is the concentration of inhibitor;
  $K_i$ is the dissociation constant of the enzyme:inhibitor complex;
  S is the concentration of substrate;
  $K_m$ is the Michaelis constant.

Compounds tested in the above assay are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM. Still more preferred compounds of the present invention have $K_i$'s of $\leq 0.001$ μM. Using the methodology described above, a number of compounds of the present invention were found to exhibit $K_i$'s of $\leq 10$ μM, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After 40 min, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The compounds of the present invention may also be useful as inhibitors of serine proteases, notably human thrombin, Factor VIIa, Factor IXa, Factor XIa, urokinase, plasma kallikrein, and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 min of incubation, thrombin activity was assayed by monitoring the rate of increase in absorbance at 405 nm that arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 10 μm, thereby confirming the utility of the compounds of the present invention as effective thrombin inhibitors.

The compounds are administered to a mammal in a therapeutically effective amount. By "therapeutically effective amount" it is meant an amount of a compound of the present invention that, when administered alone or in combination with an additional therapeutic agent to a mammal, is effective to treat a thromboembolic condition or disease.

The compounds of the present invention can be administered alone or in combination with one or more additional therapeutic agents. By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Additional therapeutic agents include other anti-coagulant or coagulation inhibitory agents, anti-platelet or platelet inhibitory agents, thrombin inhibitors, thrombolytic or fibrinolytic agents, anti-arrythmic agents, anti-hypertensive agents, calcium channel blockers (L-type and T-type), cardiac glycosides, diruetics, mineralocorticoid receptor antagonists, phospodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid receptor antagonist), anti-infective agents, anti-viral agents, anti-bacterial agents, and anti-fungal agents.

Other anticoagulant agents (or coagulation inhibitory agents) that may be used in combination with the, compounds of this invention include warfarin and heparin (either unfractionated heparin or any commercially available low molecular weight heparin, for example LOVENOX™), synthetic pentasaccharide, direct acting thrombin inhibitors including hirudin and argatrobanas, factor VIIa, IXa, XIa inhibitors, well as other factor Xa inhibitors such as those described in the publications identified above under Background of the Invention.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytics or fibrinolytic agents (or thrombolytics or fibrinolytics), as used herein, denote agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K$^+$ channel openers such as $I_{Ach}$ inhibitors, and $I_{Kur}$ inhibitors (e.g., compounds such as those disclosed in WO01/40231).

Examples of suitable anti-hypertensive agents for use in combination with the compounds of the present invention include: alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat and nitrates); and P-blockers (e.g., propanolol, nadolo, or carvedilol).

Examples of suitable cardiac glycosides for use in combination with the compounds of the present invention include digitalis and ouabain.

Examples of suitable mineralocorticoid receptor antagonists for use in combination with the compounds of the present invention include sprionolactone and eplirinone.

Examples of suitable cholesteroulipid lowering agents and lipid profile therapies for use in combination with the compounds of the present invention include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protien tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-coagulants for use in combination with the compounds of the present invention include heparins (e.g., unfractioned and low molecular weight heparins such as enoxaparin and dalteparin).

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each (i.e., a synergistic combination). A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

Compounds of the present invention may further be useful as diagnostic agents and adjuncts. For example, the present compounds may be useful in maintaining whole and fractionated blood in the fluid phase such as required for analytical and biological testing.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/min during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, 18th ed., Mack Publishing Company, Easton, Pa., 1990, a standard reference text in this field.

Where the compounds of this invention are combined with other anticoagulant agents, for example, a daily dosage may be about 0.1 to 100 milligrams of the compound of The present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of The present invention and about 50 to 150 milligrams of the anti-platelet agent, preferably about 0.1 to 1 milligrams of the compound of The present invention and about 1 to 3 milligrams of antiplatelet agents, per kilogram of patient body weight.

Where the compounds of The present invention are administered in combination with thrombolytic agent, typically a daily dosage may be about 0.1 to 1 milligrams of the compound of The present invention, per kilogram of patient body weight and, in the case of the thrombolytic agents, the usual dosage of the thrombolyic agent when administered alone may be reduced by about 70–80% when administered with a compound of The present invention.

Where two or more of the foregoing second therapeutic agents are administered with the compound of The present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of The present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Other features of the invention will become apparent in the course of the following descriptions of exemplary embodiments that are afforded for illustration of the invention and are not intended to be limiting thereof.

EXAMPLES

Example 1

(1R,2S)-5-Chloro-thiophene-2-carboxylic acid {2-[4-(2-oxo-2H-pyridin-1-yl)-benzoylamino]-cyclopentyl}-amide

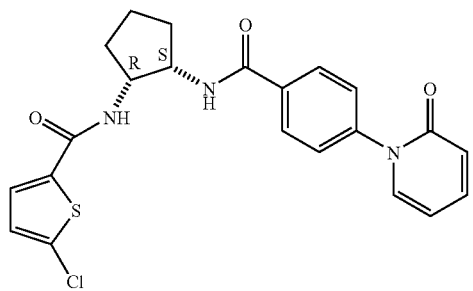

Part A

To a solution of (1S,2S)-2-benzyloxycyclopentyl-amine (9.8 g, 51.2 mmol) in THF (150 mL) was added Et$_3$N (13.6 mL, 0.10 mol) and (Boc)$_2$O (12.30 g, 56.4 mmol) sequentially at 0° C. The reaction mixture was stirred overnight at room temperature and diluted with EtOAc (200 mL). The organic phase was washed with H$_2$O, brine, and dried (Na$_2$SO$_4$). The solvent was evaporated to afford (1S, 2S)-2-benzyloxy-cyclopentyl-carbamic acid tert-butyl ester (14.90 g, 100%) as a slightly yellow solid. MS m/z 293.0 ([M+H]$^+$).

Part B

The product from Part A (10.0 mg, 34.2 mmol) was dissolved in ethanol (100 mL), Pd/C (800 mg, 5%) was added. The reaction mixture was hydrogenated at 25 psi with stirring for 4 h, and filtered through a pad of Celite®. The filtrate was evaporated to afford (1S,2S)-2-hydroxy-cyclopentyl-carbamic acid tert-butyl ester (6.84 g, 99%) as a white solid. MS m/z 202.0 ([M+H]$^+$).

Part C

To a solution of the product from Part B (4.95 g, 24.6 mmol) in CH$_2$Cl$_2$ (50 mL) were added Et$_3$N (4.11 mL, 29.51 mmol) and MsCl (2.09 g, 27.05 mmol) sequentially at 0° C. The reaction mixture was stirred for 2 h at 0° C., then quenched with H$_2$O, and extracted with EtOAc (3×50 mL). The organic phase was washed with H$_2$O, brine, and dried (Na$_2$SO$_4$). The solvent was evaporated to afford (1S,2S)-methanesulfonic acid 2-tert-butoxycarbonylamino-cyclopentyl ester (6.35 g, 92%) as a white solid. MS m/z 297.0 ([M+NH$_4$]$^+$).

Part D

NaN$_3$ (4.40 g, 67.7 mmol) was added to a solution of the product from Part C (6.30 g, 22.6 mmol) in DMF (50 mL), and the reaction mixture was heated at 80° C. for 12 h with vigorous stirring. The reaction was cooled to room temperature, poured into water, and extracted with EtOAc (4×100 mL). The extracts were combined; washed with H$_2$O, aqueous LiCl (10%), and brine; and dried (Na$_2$SO$_4$). The solvent was evaporated, and the residue was taken to next step without purification. The residue was then dissolved in ethanol (200 mL) and Pd/C (300 mg, 5%) was added. The reaction mixture was hydrogenated at 1 atm with stirring for 24 h, and filtered through a pad of Celite®. The filtrate was evaporated to afford (1S,2R)-2-amino-cyclopentyl-carbamic acid tert-butyl ester (6.84 g, 99%) as a white solid. MS m/z 201.0 ([M+H]$^+$).

Part E

The product from Part D (150 mg, 0.75 mmol) and 5-chloro-thiophene-2-carboxylic acid (101 mg, 0.62 mmol) were dissolved in DMF (2 mL) and cooled to 0° C. To the above solution were added HATU (354 mg, 0.93 mmol) and DIEA (0.22 mL, 1.24 mmol), and it was stirred overnight. The reaction mixture was diluted with ethyl acetate; washed with water, aqueous LiCl (10%), and brine; and dried (MgSO$_4$). After evaporation of the solvent, the residue was purified on silica gel using 50% EtOAc-Hexane to afford (1S,2R)-{2-[(5-chloro-thiophene-2-carbonyl)-amino]-cyclopentyl}-carbamic acid tert-butyl ester (115 mg, 54%) as a white solid. MS m/z 367.6 ([M+Na]$^+$).

Part F

The product from Part E (115 mg, 0.33 mmol) was suspended in CH$_2$Cl$_2$ (1 mL), and TFA (1 mL) was added. A clear solution was obtained and stirred for 2 h at ambient temperature. The resulting solution was concentrated, and the residue was partitioned between EtOAc and aqueous Na$_2$CO$_3$. The aqueous phase was extracted with EtOAc (3×10 mL), and the extracts were combined, washed with brine, and dried (Na$_2$SO$_4$). Evaporation of the solvent afforded (1R,2S)-5-chloro-thiophene-2-carboxylic acid (2-amino-cyclopentyl)-amide (80 mg, 98%) as a white solid which was taken to next step without purification. MS m/z 245.0 ([M+H]$^+$).

Part G

The product from Part F (40 mg, 0.16 mmol) and 4-(2-oxo-2H-pyridin-1-yl)-benzoic acid (35 mg, 0.16 mmol) were dissolved in DMF (1 mL) and cooled to 0° C. To the above solution was added HATU (73 mg, 0.19 mmol) and DIEA (0.042 mL, 0.24 mmol), and it was stirred overnight. The reaction mixture was diluted with ethyl acetate; washed with water, aqueous LiCl (10%), and brine, and dried (MgSO$_4$). After evaporation of the solvent, the residue was purified on silica gel using 5% CH$_3$OH—CH$_2$Cl$_2$, and then crystallized in CH$_2$Cl$_2$-EtOAc-Hexane to afford the title product (41 mg, 58%) as a white crystal. $^1$H NMR (400 MHz, CD$_3$OD) δ 1.60–1.76 (m, 1H), 1.77–1.89 (m, 2H), 1.90–2.04 (m, 1H), 2.04–2.26 (m, 2H), 4.35–4.62 (m, 2H), 6.38–6.55 (m, 1H), 6.56–6.70 (m, 1H), 6.88–7.02 (m, 1H), 7.36–7.51 (m, 3H), 7.55–7.68 (m, 2H), 7.77–7.97 (m, 2H); HRMS (ESI) m/z calcd for C$_{22}$H$_{21}$ClN$_3$O$_3$S ([M+H]$^+$) 442.0992. found 442.1003.

Using a procedure similar to that of Example 1, the Examples 2–11 were prepared:

Example 2

(1S,2R)-5-Chloro-thiophene-2-carboxylic acid {2-[4-(2-oxo-2H-pyridin-1-yl)-benzoylamino]-cyclopentyl}-amide

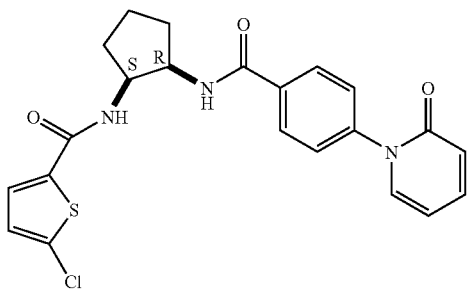

$^1$H NMR (CD$_3$OD) δ 7.83 (d, J=8.8 Hz, 2H), 7.61 (m, 2H), 7.46 (d, J=4.0 Hz, 1H), 7.43 (d, J=8.4 Hz, 2H), 6.94 (d, J=4.0 Hz, 1H), 6.61 (d, J=9.2 Hz, 1H), 6.47 (td, J=7.0, 1.4 Hz, 1H), 4.49 (m, 2H), 2.13–1.63 (m, 6H) ppm. HRMS(ESI) calcd for C$_{22}$H$_{21}$SClN$_3$O$_3$ (M+H) 442.0993. found 442.0986.

Example 3

(1R,2S)-3-Chloro-1H-indole-6-carboxylic acid {2-[4-(2-oxo-2H-pyridin-1-yl)-benzoylamino]-cyclopentyl}-amide

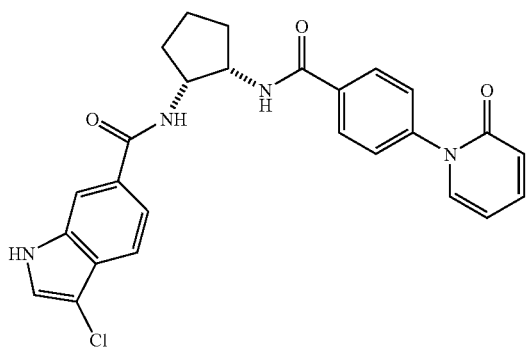

Anal. LC/MS (ESI) 475.07 (M+H), 473.07 (M−H), t$_R$=2.90 min (10%–90% MeOH in H$_2$O with 10 mM NH$_4$OAc in a 4-min run).

Example 4

(1R,2S)-5-Chloro-thiophene-2-carboxylic acid {2-[4-(2-oxo-piperidin-1-yl)-benzoylamino]-cyclopentyl}-amide

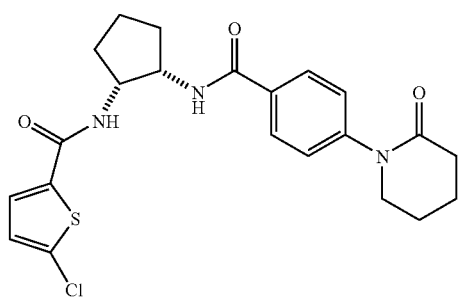

$^1$H NMR (400 MHz, CDCl$_3$) δ 7.70 (d, J=8.7 Hz, 2H), 7.28 (d, J=4.1 Hz, 1H), 7.24 (d, J=8.7 Hz, 2H), 6.82 (d, J=4.1 Hz, 1H), 4.36 (m, 1H), 4.25 (m, 1H), 3.64 (m, 2H), 2.58 (m, 2H), 2.15 (m, 2H), 1.97 (m, 4H), 1.76 (m, 4H) ppm.

Example 5

(1R,2S)-3-Chloro-1H-indole-6-carboxylic acid {2-[4-(2-oxo-piperidin-1-yl)-benzoylamino]-cyclopentyl}-amide

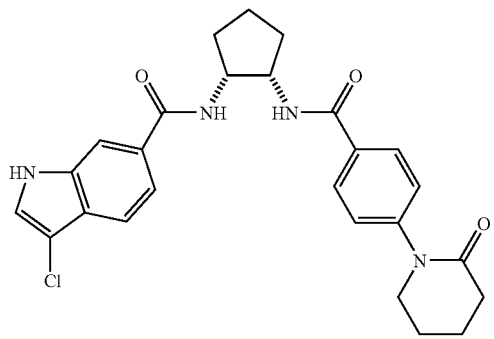

$^1$H NMR (400 MHz, methanol-d$_4$) δ 9.82 (s, br, 1H), 7.71 (d, J=8.3 Hz, 2H), 7.52 (d, J=8.2 Hz, 1H), 7.41 (d, J=8.3 Hz, 1H), 7.31 (m, 1H), 7.20 (m, 1H), 7.15 (d, J=8.3 Hz, 2H), 4.46 (m, 2H), 3.60 (m, 2H), 2.57 (m, 2H), 2.04 (m, 2H), 1.95 (m, 4H), 1.58 (m, 4H) ppm. LC-MS (ESI) 479.16 (M+H), t$_R$=2.99 min (10–90% MeOH in H$_2$O with 10 mM NH4OAc

Example 6

(1S,2R)-4-methoxy-phenyl-carboxylic acid {2-[4-(2-oxo-2H-pyridin-1-yl)-benzoylamino]-cyclopentyl}-amide

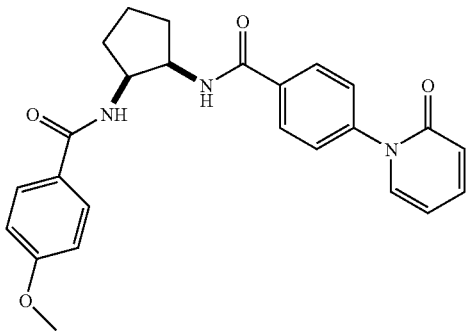

$^1$H NMR (CD$_3$OD) δ 7.84 (d, J=8.8 Hz, 2H), 7.71 (d, J=9.2 Hz, 2H), 7.60 (m, 2H), 7.43 (d, J=8.8 Hz, 2H), 6.91 (d, J=8.8 Hz, 2H), 6.61 (d, J=8.8 Hz, 1H), 6.47 (dt, J=6.7, 1.1 Hz, 1H), 4.52 (m, 2H), 3.79 (s, 3H), 2.21 (m, 2H), 1.94 (m, 1H), 1.85 (m, 2H), 1.69 (m, 1H) ppm. LCMS (ESI) 432.4 (M+H), t$_R$=1.66 min (10–90% CH$_3$CN in H$_2$O in a 4-min run). HRMS (ESI) calcd for C$_{25}$H$_{26}$N$_3$O$_4$ (M+H) for 432.1924. found 432.1908.

Example 7

(1S,2R)-5-Chloro-1H-indole-2-carboxylic acid {2-[4-(2-oxo-2H-pyridin-1-yl)-benzoylamino]-cyclopentyl}-amide

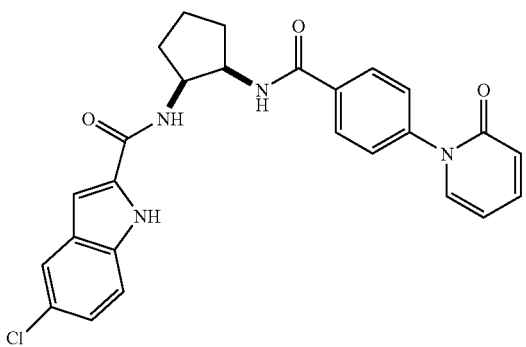

$^1$H NMR (CD$_3$OD) 7.82 (d, J=8.8 Hz, 2H), 7.60 (m, 1H), 7.52 (m, 2H), 7.38 (m, 3H), 7.13 (m, 1H), 6.98 (s, 1H), 6.60 (d, J=9.2 Hz, 1H), 6.45 (td, J=6.6, 1.1 Hz, 1H), 4.55 (m, 2H), 2.15 (m, 2H), 1.98 (m, 1H), 1.89 (m, 2H), 1.72 (m, 1H) ppm. LCMS (ESI) t$_R$=2.04 min (10–90% CH$_3$CN in H$_2$O in a 4-min run), 475.4 (M+H), HRMS (ESI) calcd for C$_{26}$H$_{24}$ClN$_4$O$_3$ (M+H) 475.1538. found 475.1543.

Example 8

(1R,2S)-5-Chloro-1H-indole-2-carboxylic acid {2-[4-(2-oxo-2H-pyridin-1-yl)-benzoylamino]-cyclopentyl}-amide

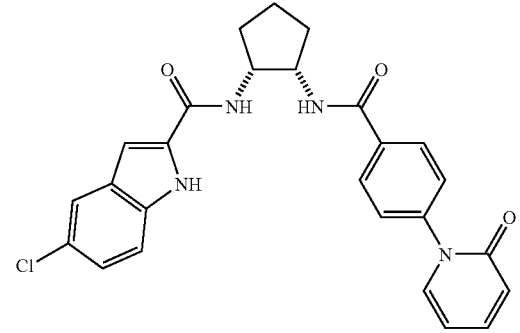

$^1$H NMR (Methanol-d$_4$) δ 7.82 (d, J=8.6 Hz, 2H), 7.59 (td, J=7.3, 2.7 Hz, 1H), 7.53 (d, J=2.0 Hz, 1H), 7.48 (dd, J=6.7, 1.7 Hz, 1H), 7.37 (m, 3H), 7.14 (dd, J=8.3, 2.5 Hz, 1H), 6.99 (d, J=1.3 Hz, 1H), 6.60 (d, J=9.3 Hz, 1H), 6.45 (dt, J=6.8, 1.3 Hz, 1H), 4.55 (m, 2H), 2.15 (m, 2H), 1.98 (m, 1H), 1.88 (m, 2H), 1.71 (m, 1H) ppm. Anal. LC/MS (ESI) 475.07 (M+H), 473.12 (M−H), t$_R$=3.09 min (10%–90% MeOH in H$_2$O with 10 mM NH$_4$OAc in a 4-min run).

Example 9

(1R,2S)-5-Chloro-thiophene-2-carboxylic acid {2-[4-(2-oxo-2H-pyridin-1-yl)-benzoylamino]-cyclohexyl}-amide

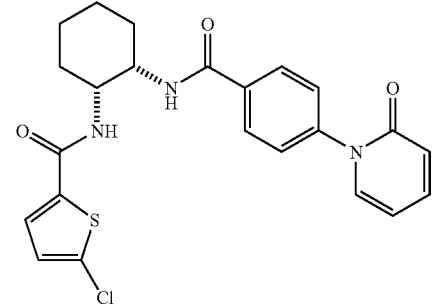

$^1$H NMR (400 MHz, CDCl$_3$) δ 7.70 (d, J=8.7 Hz, 2H), 7.28 (d, J=4.1 Hz, 1H), 7.24 (d, J=8.7 Hz, 2H), 6.82 (d, J=4.1 Hz, 1H), 4.36 (m, 1H), 4.25 (m, 1H), 3.64 (m, 2H), 2.58 (m, 2H), 2.15 (m, 2H), 1.97 (m, 4H), 1.76 (m, 4H) ppm.

--- in a 4-min run). HRMS (ESI) m/z calcd for C$_{26}$H$_{28}$ClN$_4$O$_3$ ([M+H]$^+$) 479.1850. found 479.1856.

Example 10

(1R,2S)-3-Chloro-1H-indole-6-carboxylic acid {2-[4-(2-oxo-2H-pyridin-1-yl)-benzoylamino]-cyclohexyl}-amide

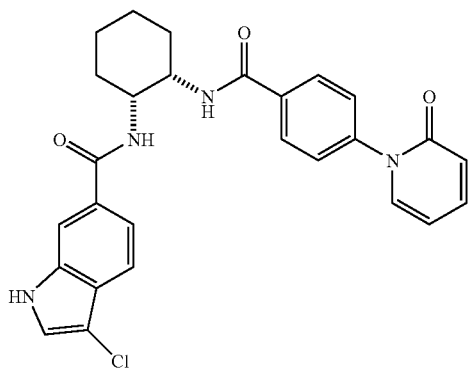

$^1$H NMR (DMSO-D$_6$) δ 8.01 (d, 1H), 7.92 (d, 1H), 7.88 (m, 3H), 7.51 (m, 2H), 7.38 (m, 3H), 6.35 (d, 1H), 6.30 (t, 1H), 4.13(m, 1H), 3.91 (m, 1H), 1.78 (m, 2H), 1.59 (m, 4H), 1.30 (m, 2H) ppm. LC/MS (ESI) 489.2 (M+H).

Example 11

(1R,2S)-3-Chloro-1H-indole-6-carboxylic acid {2-[4-(2-oxo-piperidin-1-yl)-benzoylamino]-cyclohexyl}-amide

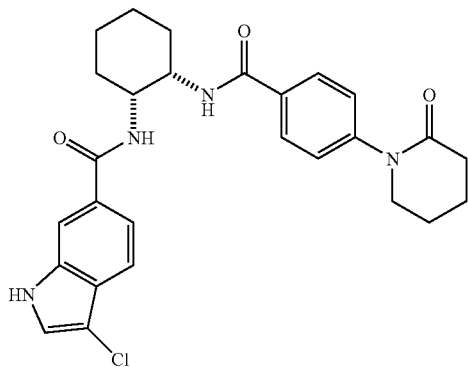

$^1$H NMR (methanol-d$_3$): δ 7.89 (s, 1H), 7.84 (d, J=8.6 Hz, 2H), 7.56 (m, 2H), 7.41 (s, 1H), 7.36 (d, J=8.4 Hz, 2H), 4.45 (m, 2H), 3.69 (t, J=6.1 Hz, 2H), 2.53 (t, J=6.3 Hz, 2H), 1.96 (m, 6H), 1.82 (m, 2H), 1.61 (m, 2H) ppm. LC/MS (ESI) 493.2 (M+H).

Example 12

(1R,2S)-N-(5-Chloro-pyridin-2-yl)-N'-{2-[4-(2-oxo-2H-pyridin-1-yl)-benzoylamino]-cyclopentyl}-oxalamide

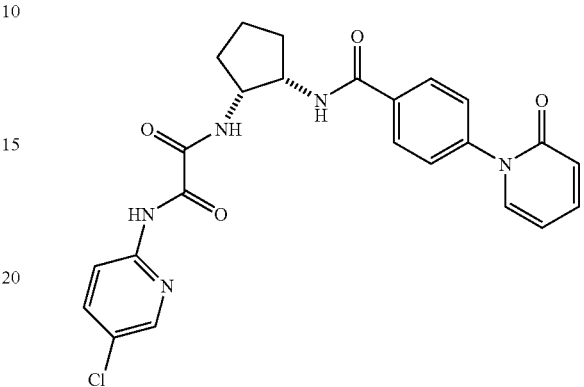

Part A

To a stirred solution of 2-amino-5-chloropyridine (0.645 gm 5.0 mmol) in CH$_2$Cl$_2$ (15 mL) was added Et$_3$N (0.80 mL, 6.0 mL, 1.2 eq) followed by addition of ethyl chlorooxoacetate (0.56 mL, 5.0 mmol, 1.0 eq). The mixture was stirred at rt for 2 h. It was diluted with EtOAc; washed with H$_2$O and brine; dried (Na$_2$SO$_4$); and purified by silica gel chromatography to give pure N-(5-chloro-pyridin-2-yl)-oxalamic acid ethyl ester as a white solid (389 mg, yield: 34%). $^1$H NMR (400 MHz, methanol-d$_4$) δ 8.16 (d, J=2.4 Hz, 1H), 7.97 (d, J=9.4 Hz, 1H), 7.66 (dd, J=8.9, 2.6 Hz, 1H), 4.19 (q, J=6.6 Hz, 2H), 1.20 (t, J=6.6 Hz, 3H) ppm. MS (ESI) 227.0 (M−H).

Part B

The product from Part A (228.6 mg, 1.0 mmol) and (1R,2S)-(2-Amino-cyclopentyl)-carbamic acid tert-butyl ester (200 mg, 1.0 mmol. 1.0 eq) were stirred in MeOH (2 mL) at rt for 1 day. The solvent was evaporated to give almost pure {2-[(5-chloro-pyridin-2-ylaminooxalyl)-amino]-cyclopentyl}-carbamic acid tert-butyl ester (383 mg, yield: 100%). $^1$H NMR (400 MHz, methanol-d$_4$) δ 8.17 (m, 1H), 8.01 (m, 1H), 7.69 (m, 1H), 4.06 (m, 1H), 3.88 (m, 1H), 1.84 (m, 2H), 1.44 (m, 4H), 1.23 (m, 9H) ppm. MS (ESI) 383.1 (M+H), 380.9 (M−H).

Part C

Following the same sequence of Part F and Part G in Example 1, but using the product of part B as one of the starting materials, the title compound was obtained. $^1$H NMR (400 MHz, methanol-d$_4$) δ 8.52 (d, 1H), 8.32 (d, 1H), 8.18 (d, 2H), 8.03 (dd, 1H), 7.76 (m, 2H), 7.63 (d, 2H), 6.83 (d, 1H), 6.64 (t, 1H) ppm. HRMS (ESI) calcd. 480.1439 for C$_{24}$H$_{23}$ClN$_5$O$_4$ (M+H). found 480.1461.

Examples 13–15 were obtained using the same procedure as that of Example 1.

Example 13

(1S,3R,4S)-3-[(3-Chloro-1H-indole-6-carbonyl)-amino]-4-[4-(2-oxo-2H-pyridin-1-yl)-benzoylamino]-cyclopentanecarboxylic acid methyl ester

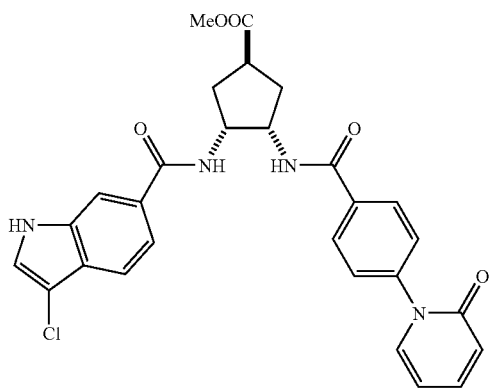

$^1$H NMR (400 MHz, DMSO-$d_6$) δ 11.71 (s, br, 1H), 8.36 (d, J=8.2 Hz, 1H), 8.25 (d, J=8.2 Hz, 1H), 8.00 (d, J=9.1 Hz, 2H), 7.76 (d, J=2.7 Hz, 1H), 7.72 (m, 2H), 7.61 (m, 1H), 7.58 (d, J=8.8 Hz, 2H), 6.58 (d, J=9.2 Hz, 1H), 6.43 (td, J=7.0, 1.0 Hz, 1H), 4.67 (m, 2H), 3.76 (s, 3H), 3.36 (m, 1H), 2.27 (m, 4H) ppm. LC-MS (ESI) 533.18 (M+H), 555.17 (M+Na), $t_R$=1.56 min (10–90% MeOH in H$_2$O with 0.1% TFA in a 2-min run). HRMS (ESI) m/z calcd for C$_{28}$H$_{26}$ClN$_4$O$_5$ ([M+H]$^+$) 533.1592. found 533.1595.

Example 14

(1S,3R,4S)-3-[(5-Chloro-thiophene-2-carbonyl)-amino]-4-[4-(2-oxo-2H-pyridin-1-yl)-benzoylamino]-cyclopentanecarboxylic acid methyl ester

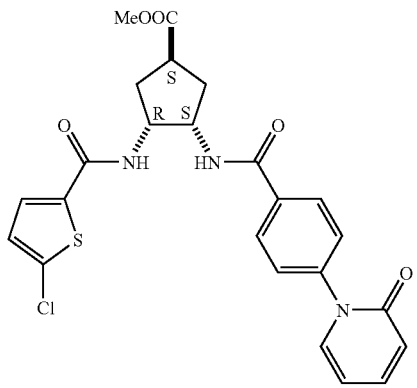

$^1$H NMR (400 MHz, CDCl$_3$) δ 7.78 (d, J=8.2 Hz, 1H), 7.62 (m, 2H), 7.35 (m, 2H), 6.84 (d, J=6.0 Hz, 1H), 6.77 (d, J=9.2 Hz, 1H), 6.47 (t, J=8.8 Hz, 1H), 4.54 (m, 1H), 4.47 (m, 1H), 3.70 (s, 3H), 3.11 (m, 1H), 2.36 (m, 2H), 2.18 (m, 2H) ppm. LC-MS (ESI) 500.12 (M+H), 522.11 (M+Na), $t_R$=1.47 min (10–90% MeOH in H$_2$O with 0.1% TFA in a 2-min run). HRMS (ESI) m/z calcd for C$_{24}$H$_{23}$ClN$_3$O$_5$S ([M+H]$^+$) 500.1047. found 500.1042.

Example 15

(1R,2S,4S)-5-Chloro-thiophene-2-carboxylic acid {4-(2-methoxy-ethylcarbamoyl)-2-[4-(2-oxo-2H-pyridin-1-yl)-benzoylamino]-cyclopentyl}-amide

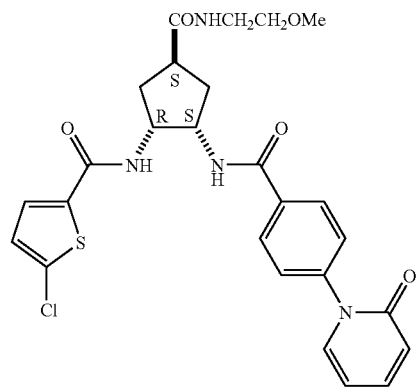

$^1$H NMR (500 MHz, methanol-$d_4$) δ 7.86 (d, J=8.4 Hz, 1H), 7.61 (m, 2H), 7.48 (d, J=4.0 Hz, 1H), 7.46 (d, J=8.6 Hz, 2H), 6.97 (d, J=4.1 Hz, 1H), 6.63 (d, J=9.2 Hz, 1H), 6.49 (td, J=6.6, 1.3 Hz, 1H), 4.69 (m, 2H), 3.26 (m, 2H), 3.36 (m, 2H), 3.35 (s, 3H), 3.14 (m, 1H), 2.26 (m, 2H), 2.17 (m, 2H) ppm. LC-MS (ESI) 543.00 (M+H), $t_R$=2.61 min (10–90% MeOH in H$_2$O with 10 mM NH$_4$OAc in a 4-min run).

Example 16

(1R,2S)-3-Chloro-1H-indole-6-carboxylic acid {2-[4-(3-oxo-morpholin-4-yl)-benzoylamino]-cyclohexyl}-amide

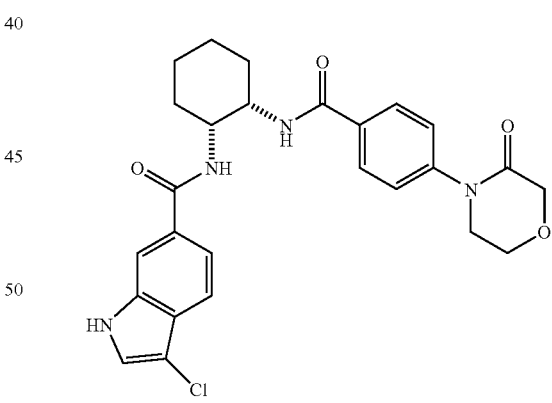

Part A

A mixture of 4-fluorobenzoate (1.75 g, 10.5 mmol) and morpholine (3.1 g, 35 mmol, 3.3 eq) was heated at 120° C. for 2 days. To the cooled mixture was added H$_2$O. The precipitate was filtered and rinsed with H$_2$O. It was dried in vacuo to give 4-morpholin-4-yl-benzoic acid ethyl ester (2.35 g, yield: 95.9%). $^1$H NMR (CDCl$_3$) δ 7.92(d, J=8.8 Hz, 2H), 6.84 (d, J=9.2 Hz, 2H), 4.31 (q, J=7.0 Hz, 2H), 3.84 (t, J=5.0 Hz, 4H), 3.26 (t, J=4.9 Hz, 4H), 1.35 (t, J=7.1 Hz, 3H) ppm. LC/MS (ESI)(10–90% MeOH in H$_2$O with 10 mM NH$_4$Ac in a 4-min run): 236.26 (M+H), $t_R$=3.02 min.

Part B

To the product from Part A (0.90 g) in CH₂Cl₂ were added benzyltriethylammonium chloride (2.05 g) and KMnO₄ (1.62 g). The resulting mixture was heated at 50° C. for 3 h. It was cooled and poured into aqueous NaHSO₃. It was extracted with CH₂Cl₂, washed with H₂O and brine (2×), dried over MgSO₄, filtered, and concentrated to dryness. The residue was purified by FCC (silica gel, Hexanes: EtOAc=1:0 to 0:1) to give 4-(3-oxo-morpholin-4-yl)-benzoic acid ethyl ester as white crystals (0.56 g, yield: 58.9%). ¹H NMR (CDCl₃) δ 8.10 (d, J=8.8 Hz, 2H), 7.47 (d, J=8.7 Hz, 2H), 4.39 (q, J=7.1 Hz, 2H), 4.37 (s, 2H), 4.06 (m, 2H), 3.82 (m, 2H), 1.41 (t, J=7.1 Hz, 3H) ppm. LC/MS (ESI) (10–90% MeOH in H₂O with 10 mM NH₄Ac in a 4-min run), 250.26 (M+H), $t_R$=2.27 min.

Part C

The product from Part B (0.50 g, 2.0 mmol) was stirred in EtOH (10 mL). 1N NaOH (5 mL) was added. The mixture was stirred at rt for 2 h. The solvent was evaporated. The residue was acidified with 1N HCl, extracted with CH₂Cl₂ (3×), dried over MgSO₄, filtered, and concentrated to dryness to give 4-(3-oxo-morpholin-4-yl)-benzoic acid (0.41 g). LC/MS (ESI) 222.2 (M+H).

Part D

Following the procedure described in Part D to Part G in Example 1, but using 4-(3-oxo-morpholin-4-yl)-benzoic acid and (1S,2R)-(2-amino-cyclohexyl)-carbamic acid tert-butyl ester as the starting materials, the title compound was prepared. ¹H NMR (methanol-d₄): δ 7.86 (s, 1H), 7.81 (m, 1H), 7.71 (d, J=8.8 Hz, 2H), 7.51 (m, 2H), 7.38 (s, 1H), 6.57 (d, J=8.8 Hz, 1H), 4.25 (m, 2H), 4.02 (s, 2H), 3.68 (m, 2H), 3.30 (m, 2H), 1.72 (m, 6H), 1.51 (m, 2H) ppm. LC/MS (ESI) 495.2 (M+H).

Example 17

(1R,2S)-3-Chloro-1H-indole-6-carboxylic acid {2-[4-(3-oxo-morpholin-4-yl)-benzoylamino]-cyclopentyl}-amide

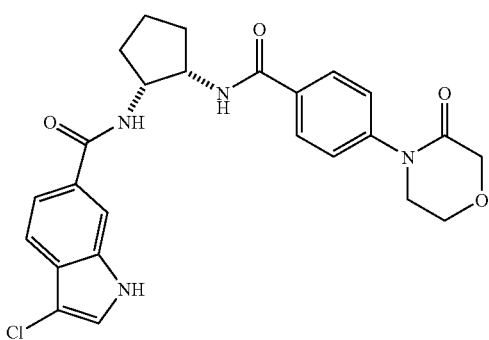

Using a procedure similar to that for Example 16, the title compound was prepared. ¹H NMR (CDCl₃): δ 9.25 (s, br, 1H), 7.72 (d, 2H), 7.68 (d, 1H), 7.39 (m, 3H), 7.32 (m, 1H), 6.91 (m, 1H), 4.41 (m, 2H), 4.05 (m, 2H), 3.74 (m, 2H), 2.25 (m, 2H), 2.01 (m, 3H), 1.69 (m, 1H) ppm. HRMS (ESI) calcd. C₂₅H₂₆ClN₄O₄ ([M+H]⁺) for 481.1643. found 481.1629.

Example 18

Cis-3-Chloro-1H-indole-6-carboxylic acid {2-[4-(2-oxo-2H-pyridin-1-yl)-phenylcarbamoyl]-cyclohexyl}-amide

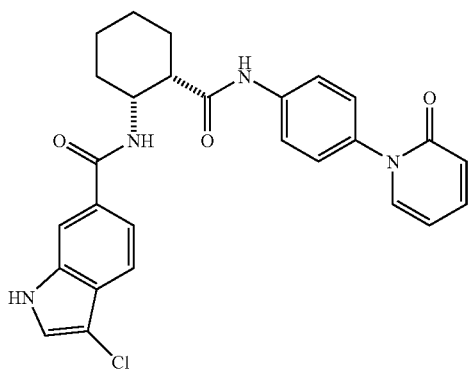

Using a procedure similar to that for Example 1, the title compound was prepared but using 2-tert-Butoxycarbonylamino-cyclohexanecarboxylic acid as one of the starting materials, the title compound was prepared. LRMS (ESI) 489.2 (M+H).

Example 19

(1R,2S)-3-Chloro-1H-indole-6-carboxylic acid {2-[3-methyl-4-(2-oxo-2H-pyridin-1-yl)-benzoylamino]-cyclohexyl}-amide

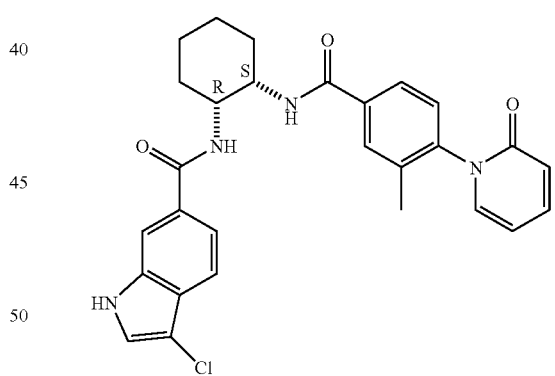

Following the same procedures as those used for Example 1, but using 3-methyl-4-(2-oxo-2H-pyridin-1-yl)-benzoic acid as one of the starting materials, the title compound was obtained. Reverse-phase HPLC (30–90% MeOH in H₂O with 0.1% TFA in a 10-min run, $t_R$=9.46 min) afforded the pure title compound (15 mg, yield: 23.7%). ¹H NMR (methanol-d₄) δ 7.91 (d, J=3.3 Hz, 1H), 7.79 (m, 2H), 7.69 (t, J=9.0 Hz, 1H), 7.58 (m, 2H), 7.49 (d, J=8.6 Hz, 1H), 7.41 (m, 1H), 7.31 (dd, J=7.8, 3.0 Hz, 1H), 6.68 (d, J=9.0 Hz, 1H), 6.53 (td, J=6.9, 1.3 Hz, 1H), 4.46 (m, 2H), 2.15, 2.12 (2×s, 3H), 1.94–1.83 (m, 6H), 1.61 (m, 2H) ppm. HRMS (ESI) calcd. C₂₈H₂₈ClN₄O₃ ([M+H]⁺) for 503.1850. found 503.1859.

Example 20

(1R,2S)-3-Chloro-1H-indole-6-carboxylic acid {2-[3-methyl-4-(2-oxo-2H-pyridin-1-yl)-benzoylamino]-cyclopentyl}-amide

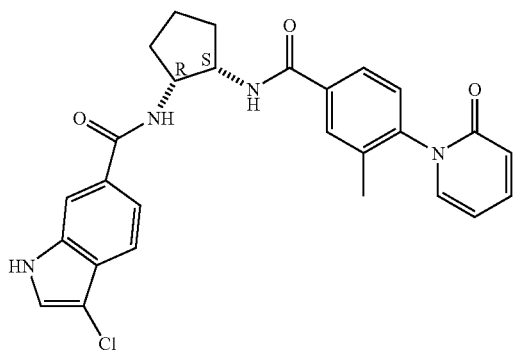

Using the same procedure as that for Example 1, the title compound was obtained. $^1$H NMR (400 MHz, Methanol-$d_4$) δ 7.65 (d, J=7.0 Hz, 1H), 7.59 (m, 1H), 7.53 (m, 2H), 7.40 (d, J=5.8 Hz, 2H), 7.29 (dd, J=7.0, 2.9 Hz, 1H), 7.24 (d, J=2.6 Hz, 1H), 7.11 (t, J=8.9 Hz, 1H), 6.52 (d, J=8.9 Hz, 1H), 6.37 (td, J=6.4, 1.9 Hz, 1H), 4.45 (m, 2H), 2.05 (m, 2H), 1.92, 1.83 (2×s, 3H, Me), 1.82 (m, 1H), 1.74 (m, 2H), 1.58 (m, 1H) ppm. HRMS (ESI) m/z calcd for $C_{27}H_{26}ClN_4O_3$ ([M+H]$^+$) 489.1693. found 489.1674.

Example 21

(1R,2S)-3-Chloro-1H-indole-6-carboxylic acid {2-[4-(2-oxo-azepan-1-yl)-benzoylamino]-cyclohexyl}-amide

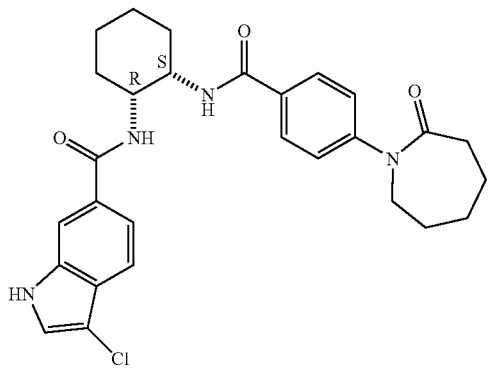

Part A

A mixture of methyl 4-iodobenzoate (5.24 g, 20.0 mmol), caprolactam (2.26 g, 20.0 mmol), $K_2CO_3$ (3.58 g, mmol), CuI (1.53 g, mmol), and 1,10-phenantroline (1.45 g, 35 mmol, 3.3 eq) was heated at 120–125° C. for 15 h. To the cooled mixture was added EtOAc/$H_2O$. The organic layer was washed with $H_2O$ and brine, dried over $MgSO_4$, filtered, and concentrated to dryness. The residue was purified by flash chromatography (hexanes:EtOAc=1:1 to 0:1) to give pure 4-(2-oxo-azepan-1-yl)-benzoic acid methyl ester as a white solid (2.56 g, yield: 51.8%). $^1$H NMR (DMSO-$d_6$) δ 8.01 (d, J=8.6 Hz, 2H), 7.31 (d, J=8.6 Hz, 2H), 3.87 (s, 3H), 3.76 (m, 2H), 2.68 (m, 2H), 1.79 (m, 4H) ppm. LC-MS (ESI) 248.28 (M+H), $t_R$=2.69 min (10–90% MeOH in $H_2O$ with 10 mM $NH_4OAc$ in a 4-min run).

Part B

The product from Part A (1.34 g, 5.42 mmol) was stirred in 1N NaOH (20 mL) and MeOH (50 mL) for 2 h. The solvents were evaporated. It was acidified via addition of conc. HCl. The precipitate was filtered, rinsed with $H_2O$, and dried in vacuo to give 4-(2-oxo-azepan-1-yl)-benzoic acid (1.02 g, yield: 83.9%). MS (ESI) 234.2 (M+H).

Part C

To the mixture of the product from Part B (30 mg) and 3-chloro-1H-indole-6-carboxylic acid (30 mg) in DMF (0.5 mL) were added BOP (58 mg) and 4-methyl morpholine (0.05 mL). The mixture was stirred at rt for 1.5 h. It was then added to EtOAc/$H_2O$. The organic layer was concentrated. The residue was dissolved in MeOH, filtered, and purified via reverse phase HPLC (35–90% MeOH in $H_2O$ with 0.1% TFA, $t_R$=10.68 min) to give the title compound. $^1$H NMR (methanol-$d_4$) δ 8.77 (br, s, 1H), 7.77 (m, 4H), 7.63 (m, 2H), 7.45 (d, J=8.4 Hz, 2H), 7.24 (d, J=8.8 Hz, 2H), 4.43 (m, 2H), 3.89 (m, 2H), 3.73 (m, 2H), 2.75 (m, 2H), 2.65 (m, 2H), 1.92 (m, 12H), 1.56 (m, 2H) ppm; HRMS (ESI) m/z calcd for $C_{28}H_{32}ClN_4O_3$ ([M+H]$^+$) 507.2163. found 507.2179.

Example 22

(1R,2S)-3-Chloro-1H-indole-6-carboxylic acid {2-[4-(2-oxo-azepan-1-yl)-benzoylamino]-cyclopentyl}-amide

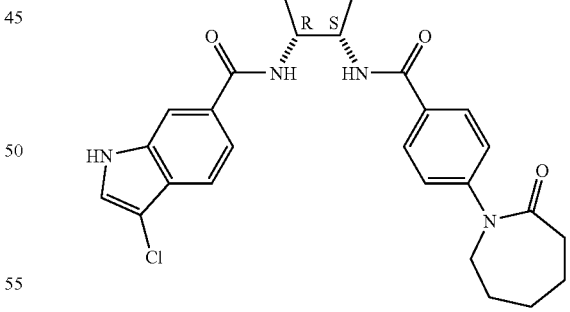

Using a procedure similar to that for Example 21, but using (1R,2S)-3-chloro-1H-indole-6-carboxylic acid (2-amino-cyclopentyl)-amide as one of the starting materials, the title compound was prepared. $^1$H NMR (400 MHz, methanol-$d_4$) δ 7.77 (m, 1H), 7.74 (d, J=8.8 Hz, 2H), 7.50 (m, 2H), 7.37 (s, 1H), 7.23 (dd, J=6.6, 1.7 Hz, 2H), 4.45 (m, 2H), 3.78 (m, 2H), 2.69 (m, 2H), 2.15 (m, 2H), 1.95 (m, 1H), 1.81 (m, 8H), 1.68 (m, 1H) ppm. HRMS (ESI) m/z calcd for $C_{27}H_{30}ClN_4O_3$ ([M+H]$^+$) 492.1928. found 492.1991.

Example 23

(1R,2S)-N-[2-(6-Chloro-naphthalene-2-sulfonylamino)-cyclohexyl]-4-(2-oxo-2H-pyridin-1-yl)-benzamide

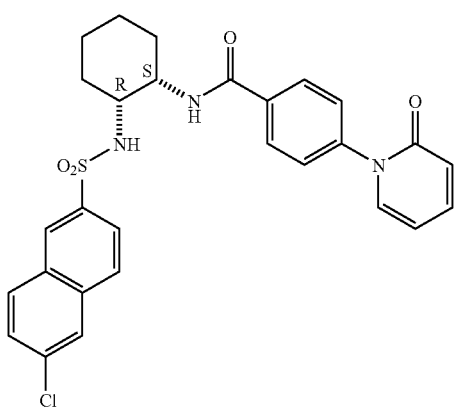

Using a procedure similar to that for Example 10, but using 6-chloro-naphthalene-2-sulfonyl chloride as one of the starting materials, the title compound was prepared. $^1$H NMR (methanol-d$_4$) δ 8.18 (m, 1H), 7.76 (d, J=8.9 Hz, 1H), 7.70 (m, 1H), 7.64 (m, 1H), 7.59 (m, 1H), 7.44 (m, 4H), 7.34 (dd, J=8.8, 2.0 Hz, 1H), 7.12 (d, J=8.6 Hz, 2H), 6.49 (d, J=9.1 Hz, 1H), 6.34 (td, J=6.8, 1.3 Hz, 1H), 3.72 (m, 1H), 3.63 (m, 1H), 1.62–1.11 (m, 8H) ppm. HRMS (ESI) calcd. for C$_{28}$H$_{27}$ClN$_3$O$_4$S (M+H) 536.1411. found 536.1415.

Example 24

(1R,2S)-3-Chloro-1H-indole-6-carboxylic acid {2-[4-(2-oxo-pyrrolidin-1-yl)-benzoylamino]-cyclohexyl}-amide

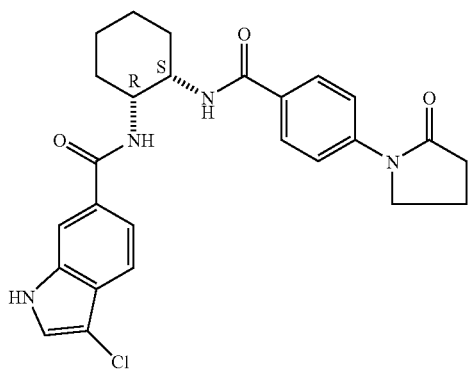

Using a procedure similar to that for Example 21, but using 4-(2-oxo-pyrrolidin-1-yl)-benzoic acid as one of the starting materials, the title compound was prepared. It was purified by reverse phase HPLC (30–90% MeOH in H$_2$O with 0.1% TFA, t$_R$=11.14 min in a 15-min run). $^1$H NMR (CDCl$_3$) δ 9.59 (br, s, 1H), 8.05 (s, 1H), 7.69 (m, 3H), 7.55 (d, J=8.3 Hz, 2H), 7.43 (m, 3H), 4.56 (m, 1H), 4.34 (m, 1H), 3.76 (t, J=7.0 Hz, 2H), 2.60 (t, J=7.0 Hz, 2H), 2.16 (m, 2H), 1.99–1.61 (m, 6H) ppm. LC/MS (ESI) 479.05, 481.04 (M+H), 477.07, 479.07 (M–H), t$_R$=3.15 min (10–90% MeOH in H$_2$O with 10 mM NH$_4$OAc in a 4-min run).

Example 25

(1R,2S)-N-(5-Chloro-pyridin-2-yl)-N'-{2-[4-(2-oxo-2H-pyridin-1-yl)-benzoylamino]-cyclohexyl}-oxalamide

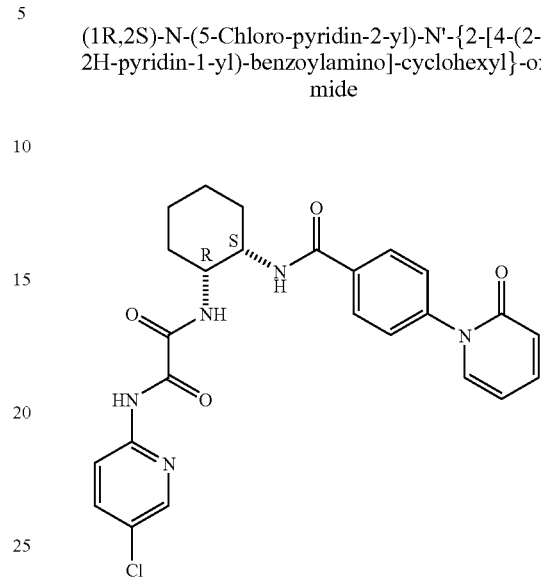

Using a procedure similar to that for Example 12, the title compound was obtained. $^1$H NMR (methanol-d$_4$) δ 8.31 (m, 1H), 8.17 (d, J=8.8 Hz, 1H), 7.90 (d, J=8.4 Hz, 2H), 7.83 (dd, J=9.2, 2.6 Hz, 1H), 7.61 (m, 2H), 7.46 (d, J=8.8 Hz, 2H), 6.62 (d, J=9.2 Hz, 1H), 6.48 (td, J=6.6, 0.9 Hz, 1H), 4.35 (m, 2H), 1.84 (m, 6H), 1.57 (m, 2H) 1.29 (m, 2H) ppm. HRMS (ESI) calcd. for C$_{25}$H$_{25}$ClN$_5$O$_4$ (M+H) 494.1595. found 494.1603.

Example 26

(1R,2S)-3-Chloro-1H-indole-6-carboxylic acid {2-[4-(1,1-dioxo-1λ$^6$-isothiazolidin-2-yl)-benzoylamino]-cyclohexyl}-amide

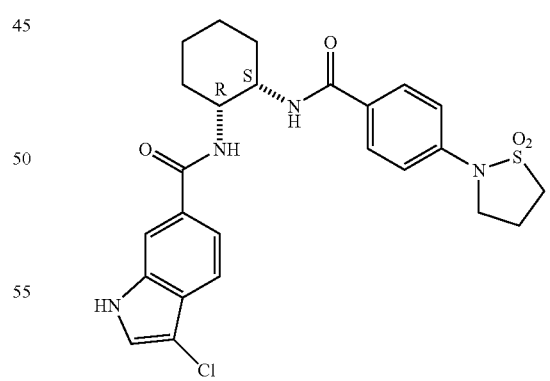

Part A

Methyl 4-aminobenzoate (1.34 g, 8.87 mmol) and [1,2]oxathiolane 2,2-dioxide (1.02 g, 8.36 mmol) were heated at 100–110° C for 1 h. The cooled residue was washed with 1N HCl and water and air-dried to give 4-(3-sulfo-propylamino)-benzoic acid methyl ester (1.62 g, yield: 71%). $^1$H NMR (DMSO-d$_6$) δ 7.70 (d, J=8.7 Hz, 2H), 6.65 (d, J=8.7

Hz, 2H), 5.88 (br, s, NH+SO₃H), 3.19 (t, J=7.0 Hz, 2H), 2.63 (t, J=7.3 Hz, 2H), 1.87 (quint, J=7.0 Hz, 2H). LC/MS (ESI) 256.22 (M+H)⁺, $t_R$=2.21 min (10–90% MeOH in H₂O with 10 mM NH₄OAc in a 4-min run).

Part B

The Product from Part A (0.50 g, 1.83 mmol) was heated in refluxing POCl₃ (20 mL) for 4 h. After cooling, the mixture was carefully decanted into ice water. The resulting solution was neutralized with 4N NaOH. The precipitate was filtered, washed with H₂O, air-dried to give 4-(1,1-dioxo-1λ⁶-isothiazolidin-2-yl)-benzoic acid methyl ester as a white solid (0.44 g, yield: 94.2%). ¹H NMR (methanol-d₄) δ 7.89 (d, J=9.0 Hz, 2H), 7.20 (d, J=9.0 Hz, 2H), 3.78 (s, 3H), 3.75 (t, J=6.6 Hz, 2H), 3.38 (t, J=6.5 Hz, 2H), 2.44 (m, 2H) ppm. LC/MS (ESI) 256.22 (M+H)⁺, $t_R$=2.21 min (10–90% MeOH in H₂O with 10 mM NH₄OAc in a 4-min run).

Part C

The product from Part B (0.36 g, 1.41 mmol) and 1N NaOH (6 mL) were heated in MeOH (20 mL) at 50° C. for 2 h. The solvents were evaporated. The residue was acidified with conc. HCl. The precipitate was filtered, rinsed with H₂O, and air-dried to give 4-(1,1-dioxo-1λ⁶-isothiazolidin-2-yl)-benzoic acid (0.33 g, yield: 99%).

Part D

The product from Part C (28 mg, 0.12 mmol), (1R,2S)-3-chloro-1H-indole-6-carboxylic acid (2-amino-cyclohexyl)-amide (36 mg, 0.12 mmol), BOP (57 mg, 0.13 mmol, 1.1 eq), and 4-methylmorpholine (0.02 mL, 1.5 eq) were stirred at room temperature for 1 h. H₂O was added. The solvents were evaporated. The residue was dissolved in MeOH, and purified by reverse phase HPLC (20–90% MeOH in H₂O with 0.1% TFA, $t_R$=9.86 min in a 10-min run) to give the title compound (26 mg, yield: 42.2%). ¹H NMR (methanol-d₄) δ 7.90 (s, 1H), 7.81 (d, J=8.8 Hz, 2H), 7.56 (m, 2H), 7.41 (s, 1H), 7.28 (d, J=8.8 Hz, 2H), 4.41 (m, 2H), 3.81 (t, J=6.5 Hz, 2H), 3.46 (t, J=7.3 Hz, 2H), 2.52 (quint, J=7.0 Hz, 2H), 1.92–1.78 (m, 6H), 1.60 (m, 2H) ppm. LC/MS (ESI) 515.41 (M+H), 513.34 (M−H), $t_R$=3.10 min (10–90% MeOH in H₂O in a 4-min run). HRMS (ESI) calcd. 515.1520 for $C_{25}H_{28}ClN_4O_4S$ (M+H). found 515.1522.

Example 27

(1R,2S)-3-Chloro-1H-indole-6-carboxylic acid {2-[4-(2-oxo-tetrahydro-pyrimidin-1-yl)-benzoylamino]-cyclohexyl}-amide

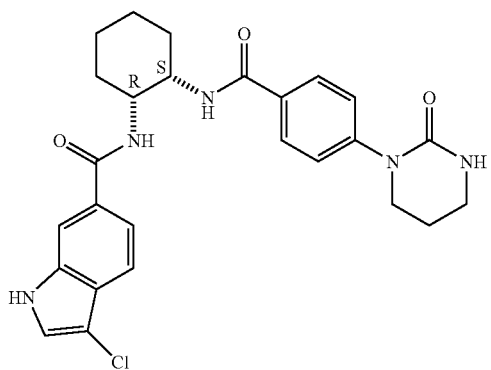

Part A

Methyl 4-aminobenzoate (3.0 g, 20.0 mmol) and 1-chloro-3-isocyanato-propane (2.0 mL, 20.0 mmol) were stirred in THF (50 mL) at room temperature overnight. The solvents were evaporated. A THF (50 mL) solution of the residue (5.0 g, 18.51 mmol) was added to a stirred solution of NaH (60%, 0.93 g, 23.25 mmol) in THF (60 mL) portionwise at room temperature. The mixture was stirred for 3.5 h. It was evaporated. H₂O was added. It was extracted with CH₂Cl₂, dried over MgSO₄, filtered, and concentrated to dryness to give pure 4-(2-oxo-tetrahydro-pyrimidin-1-yl)-benzoic acid methyl ester as a white solid (2.15 g, yield: 49.6%). ¹H NMR (DMSO-d₆) δ 7.88 (d, J=8.5 Hz, 2H), 7.48 (d, J=8.6 Hz, 2H), 6.82 (s, br, 1H), 3.68 (m, 2H), 3.34 (s, 3H), 3.23 (m, 2H), 1.96 (m, 2H) ppm. LC-MS (ESI) 235.23 (M+H), $t_R$=2.17 min (10–90% MeOH in H₂O in a 4-min run).

Part B

The Product from Part A (200 mg, 0.85 mmol) and 1N NaOH (5 mL) were heated in MeOH (20 mL) at room temperature for 4 h. The solvents were evaporated. The residue was acidified with conc. HCl. The precipitate was filtered, rinsed with H₂O, and air-dried to give 4-(2-oxo-tetrahydro-pyrimidin-1-yl)-benzoic acid (156 mg, yield: 83%). 1H NMR (DMSO-d₆) δ 7.86 (d, J=8.6 Hz, 2H), 7.44 (d, J=8.6 Hz, 2H), 6.78 (s, br, 1H), 3.69 (m, 2H), 3.23 (m, 2H), 1.96 (m, 2H) ppm.

Part C

The product from Part B (24 mg, 0.11 mmol), (1R,2S)-3-chloro-1H-indole-6-carboxylic acid (2-amino-cyclohexyl)-amide (32 mg, 0.11 mmol), BOP (64 mg, 0.14 mmol, 1.3 eq), and 4-methylmorpholine (0.02 mL, 1.5 eq) were stirred in DMF (0.4 mL) at room temperature for 1.5 h. H₂O was added. The solvents were evaporated. The residue was dissolved in MeOH, and purified by reverse phase HPLC (20–90% MeOH in H₂O with 0.1% TFA, $t_R$=8.09 min in a 10-min run) to give the title compound (13 mg, yield: 24.0%). ¹H NMR (methanol-d₄) δ 7.92 (s, 1H), 7.83 (d, J=8.5 Hz, 2H), 7.60 (s, 2H), 7.42 (m, 2H), 4.46 (m, 2H), 3.77 (t, J=5.7 Hz, 2H), 3.43 (t, J=5.8 Hz, 2H), 2.12 (t, J=5.8 Hz, 2H), 1.95–1.85 (m, 6H), 1.65 (m, 2H) ppm. LC/MS (ESI) 494.40 (M+H), 492.35 (M−H), $t_R$=3.09 min (10–90% MeOH in H₂O with 10 mM NH₄OAc in a 4-min run). HRMS (ESI) calcd. 494.1959 for $C_{26}H_{29}ClN_5O_3$ (M+H). found 494.1964.

Example 28

(1R,2S)-3-Chloro-1H-indole-6-carboxylic acid {2-[4-(2-oxo-[1,3]oxazinan-3-yl)-benzoylamino]-cyclohexyl}-amide

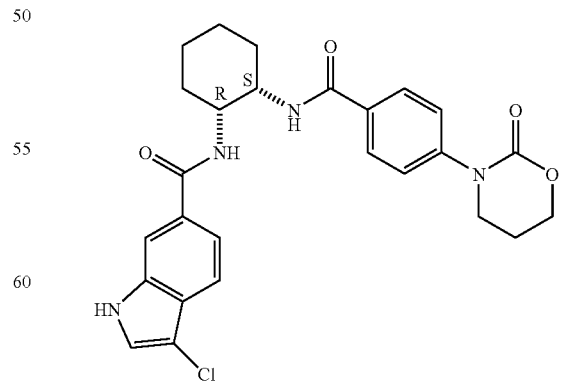

Using a procedure similar to that for Example 27, but using 4-(2-oxo-[1,3]oxazinan-3-yl)-benzoic acid as one of the starting materials, the title compound was prepared. It was purified by reverse phase HPLC (30–90% MeOH in H₂O with 0.1% TFA, $t_R$=9.91 min in a 15-min run): ¹H NMR (CDCl₃) δ 7.90 (s, 1H), 7.84 (d, J=8.8 Hz, 2H), 7.57 (s, 2H), 7.45 (d, J=8.8 Hz, 2H), 7.41 (s, 1H), 4.46 (t+m, 4H), 3.77 (t, J=6.0 Hz, 2H), 2.21 (m, 2H), 1.98–1.79 (m, 6H), 1.62 (m, 2H) ppm. LC/MS (ESI) 495.06, 497.06 (M+H), 493.097, 495.08 (M–H), $t_R$=3.02 min (10–90% MeOH in H₂O with 10 mM NH₄OAc in a 4-min run).

Example 29

(1R,2S)-3-Chloro-1H-indole-6-carboxylic acid {2-[2-fluoro-4-(2-oxo-2H-pyridin-1-yl)-benzoylamino]-cyclohexyl}-amide

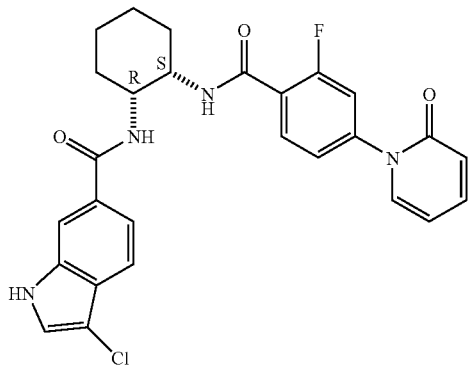

Part A

A mixture of 4-bromo-2-fluoro-benzoic acid methyl ester (1.17 g, 5.0 mmol), 2-hydroxypyridine (0.72 g, 7.5 mmol, 1.5 eq), K₂CO₃ (1.38 g, 10.0 mmol, 2.0 eq), CuI (0.48 g, 2.5 mmol, 0.5 eq), and N,N'-dimethylethylenediamine (0.22 mL, 2.6 mmol, 0.5 eq) was heated in refluxing toluene (6 mL) for 8 h. After cooling, EtOAc was added. The mixture was filtered through a pad of silica gel and rinsed with EtOAc. The desired fractions were concentrated in vacuo to give essentially pure 2-fluoro-4-(2-oxo-2H-pyridin-1-yl)-benzoic acid methyl ester (1.05 g, yield: 84%). ¹H NMR (CDCl₃) δ 8.07 (t, J=8.0 Hz, 1H), 7.14 (m, 1H), 7.33–7.27 (m, 3H), 6.64 (m, 1H), 6.28 (m, 1H), 3.96 (s, 3H) ppm. LC/MS (ESI) 248.05 (M+H), $t_R$=2.05 min (10–90% MeOH in H₂O with 10 mM NH₄OAc in a 4-min run).

Part B

Following the same procedure as that of Part C in Example 20, 2-fluoro-4-(2-oxo-2H-pyridin-1-yl)-benzoic acid was obtained. ₁H NMR (CDCl₃) δ 7.98 (t, J=8.2 Hz, 1H), 7.70 (dd, J=6.8, 1.2 Hz, 1H), 7.53 (m, 2H), 7.40 (dd, J=8.3, 1.4 Hz, 1H), 6.51 (d, J=9.2 Hz, 1H), 6.36 (t, J=8.4 Hz, 1H) ppm. LC/MS (ESI) 234.05 (M+H), $t_R$=0.68 min (10–90% MeOH in H₂O with 10 mM NH₄OAc in a 4-min run).

Part C

Following the same procedure as that for Example 27, but using the product of part B as one of the starting materials, the title compound was obtained. It was purified by reverse phase HPLC (30–90% MeOH in H₂O with 0.1% TFA in a 12-min run, $t_R$=9.81 min). ¹H NMR (CDCl₃) δ 9.05 (br, s, 1H), 8.14 (m, 1H), 7.61–7.26 (m, 6H), 6.78 (m, 1H), 6.44 (m, 1H), 4.42 (m, 4H), 2.09–1.26 (m, 8H) ppm. LC/MS (ESI) 505.07, 507.05 (M+H), $t_R$=3.17 min (10–90% MeOH in H₂O with 10 mM NH₄OAc in a 4-min run).

Example 30

(1R,2S)-4-Chloro-phenylcarboxylic acid {2-[4-(2-oxo-2H-pyridin-1-yl)-benzoylamino]-cyclohexyl}-amide

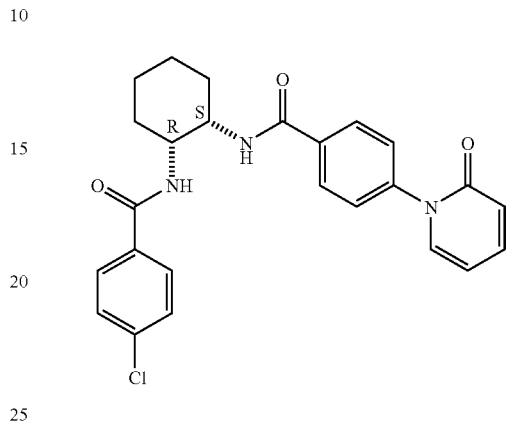

Using the same procedure as that for Example 1, the title compound was obtained. ¹H NMR (CDCl₃) δ 7.93 (d, J=8.5 Hz, 2H), 7.78 (d, J=8.6 Hz, 2H), 7.45 (m, 6H), 6.73 (d, J=9.2 Hz, 1H), 6.38 (t, J=6.8, 1.0 Hz, 1H), 4.31 (m, 2H), 2.03 (m, 2H), 1.70 (m, 6H) ppm. LC/MS (ESI) 450.080, 452.06 (M+H), 448.50, 450.09 (M–H), $t_R$=1.63 min (10–90% MeOH in H₂O with 10 mM NH₄OAc in a 2-min run).

Example 31

(1R,2S)-3-Chloro-1H-indole-6-carboxylic acid {2-[4-(2-oxo-2H-pyridin-1-yl)-benzoylamino]-indan-1-yl}-amide Part A

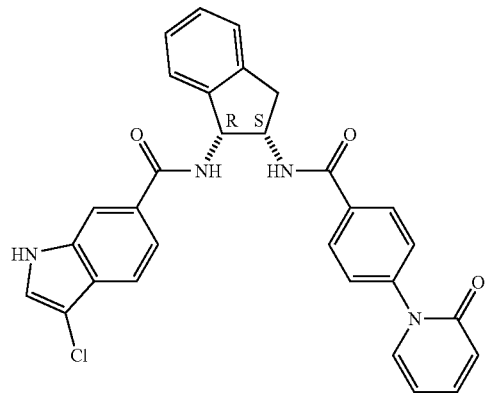

To a solution of (1R,2S)-1-amino-indan-2-ol (5.04 g, 33.8 mmol) in THF (50 mL) cooled at 0° C. were sequentially added triethylamine (5.65 mL, 40.6 mmol) and (Boc)₂O (7.37 g, 33.8 mmol). The reaction mixture was stirred overnight at room temperature, quenched with H₂O, and extracted with EtOAc (3×50 mL). The organic extracts were combined, washed with water and brine, and dried (MgSO₄). Removal of the solvent gave the (1R,2S)-(2- hydroxy-indan-1-yl)-carbamic acid tert-butyl ester (8.39 g, 99%) as a white solid, which was taken to the next step without purification. MS m/z 250 [(M+H)+].

Part B

The product from Part A (2.49 g, 10 mmol), p-nitrobenzoic acid (1.67 g, 10 mmol), and triphenylphosphine (4.20 g, 16 mmol) were dissolved in THF (20 mL) and cooled to 0° C. A solution of DEAD (2.26 g, 13 mmol) in THF (10 mL) was added dropwise over 10 min. The reaction mixture was stirred for 30 min at 0° C. and 4 h at room temperature, and then concentrated. The residue was dissolved in EtOAc (100 mL), washed with $Na_2CO_3$ (sat'd) and brine, and dried ($MgSO_4$). The solvent was removed. The residue was purified on silica gel, using 2% EtOAc-$CHCl_3$, and crystallized from EtOAc-hexane to afford (1R,2R)-4-nitro-benzoic acid 1-tert-butoxycarbonylamino-indan-2-yl ester (4.50 g, 57%) as a white solid. MS m/z 399 [(M+H)+].

Part C

A solution of product from Part B (4.0 g, 10 mmol) in $CH_2Cl_2$ (20 mL) was added to a solution of $NaOCH_3$ in $CH_3OH$ (25% wt, 6.86 mL) over 10 min at 0° C. The reaction mixture was stirred for 2 h at 0° C., and then quenched with $H_2O$, extracted with EtOAc (3×50 mL). The extracts were combined, washed with $H_2O$ and brine, and dried ($Na_2SO_4$). After evaporation of the solvent, the residue was chromatographed on silica gel using 10–50% EtOAc-$CH_2Cl_2$ (gradient) to afford (1R,2R)-(2-hydroxy-indan-1-yl)-carbamic acid tert-butyl ester (1.94 g, 78%) as a white solid. MS m/z 250 [(M+H)+].

Part D

To a solution of the product from Part C (1.0 g, 4.01 mmol) in $CH_2Cl_2$ (10 mL) cooled at 0° C. were sequentially added triethylamine (0.73 mL, 5.21 mmol) and MsCl (0.34 mL, 4.41 mmol). The reaction mixture was stirred for 2 hours at 0° C., quenched with $H_2O$, and extracted with EtOAc (3×20 mL). The organic extracts were combined, washed with water and brine, and dried ($MgSO_4$). The solvent was evaporated, and the residue was purified via silica gel chromatography with 10–30% (gradient) EtOAc-hexane to afford (1R,2R)-methanesulfonic acid 1-tert-butoxycarbonylamino-indan-2-yl ester (1.24 g, 95%) as a white solid. MS m/z 328 [(M+H)+].

Part E $NaN_3$ (739 mg, 11.4 mmol) was added to a solution of the product from Part D (1.24 g, 3.79 mmol) in DMF (20 mL), and the reaction mixture was heated at 100° C. for 2 h with vigorous stirring. The reaction mixture was cooled to room temperature, poured into water, and extracted with EtOAc (4×50 mL). The extracts were combined; washed with $H_2O$, aqueous LiCl (10%), and brine; and dried ($Na_2SO_4$). The solvent was evaporated, and the residue was filtered through a pad of silica gel and washed with 30% EtOAc-hexanes (200 mL). The filtrate was evaporated to afford (1R,2S)-(2-azido-indan-1-yl)-carbamic acid tert-butyl ester (487 mg, 47%) as a white solid. MS m/z 275 [(M+H)+].

Part F

To a solution of the product of Part E (470 mg, 1.71 mmol) in ethanol (100 mL) was added Pd/C (100 mg, 5%). The reaction mixture was hydrogenated at 50 psi with stirring for 6 h and filtered through a pad of Celite®. The filtrate was evaporated to afford (1R,2S)-(2-amino-indan-1-yl)-carbamic acid tert-butyl ester (400 mg, 94%) as a white solid. MS m/z 249 [(M+H)+].

Part G

The product of Part F (50 mg, 0.2 mmol) and 4-(2-oxo-2H-pyridin-1-yl)-benzoic acid (44 mg, 0.2 mmol) were dissolved in DMF (1 mL). To this solution were sequentially added diisopropylethylamine (0.7 mL, 0.4 mmol) and BOP (133 mg, 0.3 mL). After stirring for 3 h at room temperature, the reaction mixture was diluted with ethyl acetate; washed with water, aqueous LiCl (10%), and brine; and dried ($MgSO_4$). After evaporation of the solvent, the residue was purified on silica gel using 5% $CH_3OH$—$CH_2Cl_2$ to afford (1R,2S)-{2-[4-(2-oxo-2H-pyridin-1-yl)-benzoylamino]-indan-1-yl}-carbamic acid tert-butyl ester (85 mg, 96%) as a white solid. MS m/z 468 [(M+Na)+].

Part H

The product from Part G (85 mg, 0.19 mmol) was suspended in $CH_2Cl_2$ (1 mL), and TFA (1 mL) was added. A clear solution was obtained and stirred for 2 h at ambient temperature. The resulting solution was concentrated, and the residue was partitioned between EtOAc and aqueous $Na_2CO_3$. The aqueous layer was extracted with EtOAc (3×10 mL). The extracts were combined, washed with brine, and dried ($Na_2SO_4$). Evaporation of the solvent afforded (1R,2S)-N-(1-amino-indan-2-yl)-4-(2-oxo-2H-pyridin-1-yl)-benzamide (40 mg, 61%) as a white solid which was taken to next step without purification. MS m/z 346 [(M+H)+].

Part I

To the product from Part H (15 mg, 0.043 mmol) and 3-chloro-1H-indole-6-carboxylic acid (8.5 mg, 0.043 mmol), dissolved in DMF (0.4 mL), were sequentially added diisopropylethylamine (0.015 mL, 0.086 mmol) and BOP (28.5 mg, 0.065 mmol). After stirring for 4 h at room temperature, the reaction mixture was diluted with ethyl acetate; washed with water, aqueous LiCl (10%), and brine; and dried ($MgSO_4$). The solvent was evaporated, and the residue was purified by HPLC to afford the title compound (8.5 mg, 39%) as a white solid. HPLC purity >96%, $t_R$=1.84 min (10–90% MeOH in $H_2O$ with 0.2% $H_3PO_4$ in a 2-min run). HRMS (ESI) m/z calcd for $C_{30}H_{24}ClN_4O_3$ ([M+H]+) 523.1537. found 523.1557.

Using the same procedure as that for Example 31, Examples 32–37 were obtained:

Example 32

(1R,2S)-5-Chloro-thiophene-2-carboxylic acid {2-[4-(2-oxo-2H-pyridin-1-yl)-benzoylamino]indan-1-yl}-amide

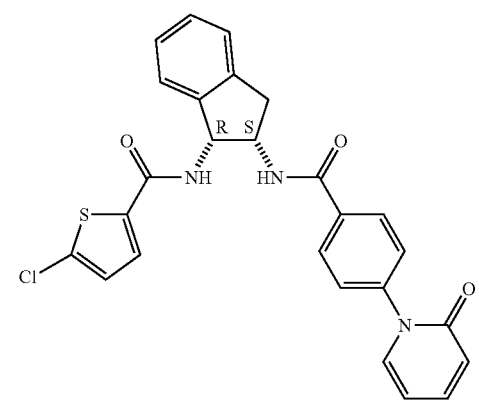

$^1$H NMR (400 Hz, DMSO-$d_6$) δ 8.26 (d, J=9.1 Hz, 1H), 8.04 (m 1H), 7.99 (d, J=4.5 Hz, 2H), 7.92–7.74 (m, 6H), 7.70 (d, J=9.1 Hz, 1H), 7.52 (d, J=4.5 Hz, 1H), 7.06 (d, J=9.1 Hz, 1H), 6.86 (td, J=6.9, 1.2 Hz, 1H) ppm, 6.24 (m, 1H), 5.55 (m, 1H), 3.88 (dd, J=16.2, 7.3 Hz, 1H), 3.65 (dd, J=16.4, 5.0 Hz, 1H) ppm. HPLC purity >96%, $t_R$=1.79 min (10–90% MeOH in $H_2O$ with 0.2% $H_3PO_4$ in a 2-min run). HRMS (ESI) m/z calcd 490.0992 for $C_{26}H_{21}ClN_3O_3S$ ([M+H]$^+$). found 490.1001.

Example 33

(1S,2R)-5-Chloro-thiophene-2-carboxylic acid {1-[4-(2-oxo-2H-pyridin-1-yl)-benzoylamino]-indan-2-yl}-amide

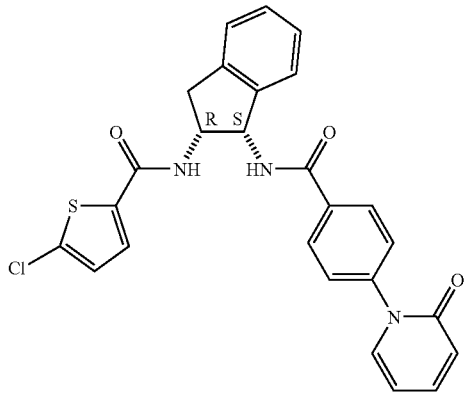

$^1$H NMR (400 Hz, DMSO-$d_6$) δ 8.61 (d, J=8.6 Hz, 1H), 8.38 (d, J=8.4 Hz, 1H), 7.95 (d, J=8.6 Hz, 2H), 7.66 (dd, J=6.5, 1.9 Hz, 1H), 7.61 (d, J=3.8 Hz, 1H). 7.53 (m, 1H), 7.50 (d, J=8.7 Hz, 2H), 7.32 (m, 3H), 7.14 (d, J=3.8 Hz, 1H), 6.49 (d, J=9.0 Hz, 1H), 6.33 (t, J=6.7, 1.3 Hz, 1H) ppm. LC-MS (ESI) 489.96 (M+H), 487.98 (M−H), $t_R$=1.66 min (10–90% MeOH in $H_2O$ with 10 mM $NH_4OAc$ in a 2-min run). HRMS (ESI) m/z calcd 490.0992 for $C_{26}H_{21}ClN_3O_3S$ ([M+H]$^+$). found 490.1000.

Example 34

(1S,2R)-3-Chloro-1H-indole-6-carboxylic acid {1-[4-(2-oxo-2H-pyridin-1-yl)-benzoylamino]-indan-2-yl}-amide

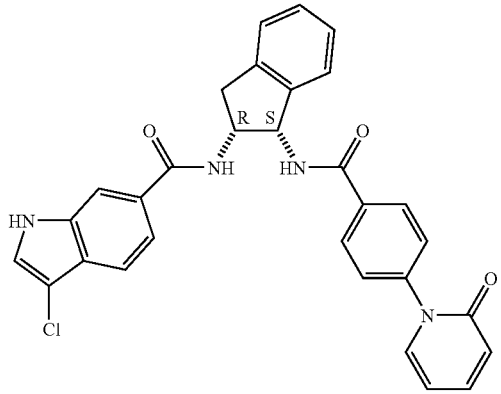

HRMS (ESI) m/z calcd for $C_{30}H_{24}ClN_4O_3$ ([M+H]$^+$) 523.1537. found 523.1536.

Example 35

(1S,2R)-3-Chloro-1H-indole-6-carboxylic acid {2-[4-(2-oxo-2H-pyridin-1-yl)-benzoylamino]-indan-1-yl}-amide LC-MS (ESI) 523.15 (M+H), 545.14 (M+Na), $t_R$=1.75 min (10–90% MeOH in $H_2O$ with 0.1% TFA in a 2-min run). HRMS (ESI) m/z calcd for $C_{30}H_{24}ClN_4O_3$ ([M+H]$^+$) 523.1537. found 523.1556.

Example 36

(1S,2R)-5-Chloro-thiophene-2-carboxylic acid {2-[4-(2-oxo-2H-pyridin-1-yl)-benzoylamino]-indan-1-yl}-amide $^1$H NMR (400 Hz, CDCl$_3$) δ 8.96 (d, J=9.0 Hz, 1H), 7.71 (d, J=4.0 Hz, 1H), 7.55 (m, 1H), 7.50 (d, J=8.8 Hz, 2H), 7.35 (m, 2H), 7.13 (t, J=7.3 Hz, 1H), 7.11 (d, J=7.7 Hz, 1H), 7.06 (dd, J=7.0, 2.9 Hz, 1H), 6.90 (m, 1H), 6.88 (d, J=4.0 Hz, 1H), 6.61 (d, J=9.2 Hz, 1H), 6.36 (dt, J=6.9, 1.4 Hz, 1H), 6.25 (br, 2H), 5.91 (m, 1H), 4.99 (m, 1H), 3.31 (dd, J=16.7, 5.7 Hz, 1H), 3.04 (d, J=16.7 Hz, 1H) ppm. LC-MS (ESI) 490.09 (M+H), 512.07 (M+Na), $t_R$=1.71 min (10–90% MeOH in $H_2O$ with 0.1% TFA in a 2-min run). HRMS (ESI) m/z calcd for $C_{26}H_{21}ClN_3O_3S$ ([M+H]$^+$) 490.0992. found 490.1008.

Example 37

(1R,2S)-3-Chloro-1H-indole-6-carboxylic acid {1-[4-(2-oxo-2H-pyridin-1-yl)-benzoylamino]-indan-2-yl}-amide

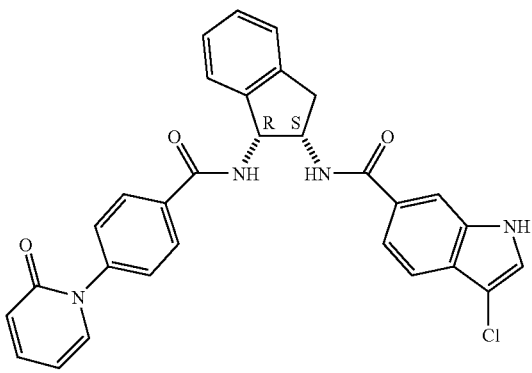

$^1$H NMR (400 Hz, methanol-$d_4$) δ 7.78 (d, J=9.2 Hz, 2H), 7.66 (s, 1H), 7.51 (m, 2H), 7.45 (dd, J=7.0, 1.8 Hz, 1H), 7.38 (m, 2H). 7.30 (d, J=Hz, 2H), 7.26–7.18 (m, 4H), 6.52 (d, J=9.0 Hz, 1H), 6.37 (t, J=6.9, 1.3 Hz, 1H), 5.73 (m, 1H), 5.03 (q, J=7.4 Hz, 1H), 3.28 (dd, J=16.1, 7.6 Hz, 1H), 3.16 (dd, J=16.3, 6.7 Hz, 1H) ppm. LC-MS (ESI) 523.16 (M+H), 545.16 (M+Na), $t_R$=1.75 min (10–90% MeOH in $H_2O$ with 0.1% TFA in a 2-min run). HRMS (ESI) m/z calcd for $C_{30}H_{24}ClN_4O_3$ ([M+H]$^+$) 523.1522. found 523.1537.

Example 38

Cis-3-Chloro-1H-indole-6-carboxylic acid {2-[4-(2-oxo-2H-pyridin-1-yl)-benzenesulfonylmethyl]-cyclohexyl}-amide

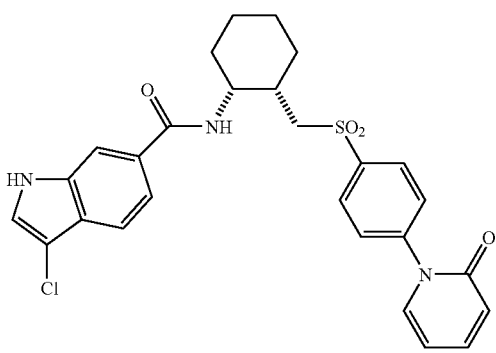

Part A

To a stirred solution of the HCl salt of cis-(2-amino-cyclohexyl)-methanol (1.0 g, 6.17 mmol) were sequentially added Et$_3$N (1.72 mL, 2.0 eq) and (Boc)$_2$O (1.41 g, 6.48 mmol, 1.05 eq). The mixture was stirred at rt for 4 h. It was partitioned between CH$_2$Cl$_2$ and H$_2$O. The organic layers were washed with brine, dried (MgSO$_4$), filtered, and concentrated to dryness to give cis-(2-hydroxymethyl-cyclohexyl)-carbamic acid tert-butyl ester as a colorless foam (1.38 g, yield: 98%).

Part B

The product of Part A (1.36 g, 5.94 mmol) and Et$_3$N (1.24 mL, 8.91 mmol, 1.5 eq) were stirred in CH$_2$Cl$_2$ (20 mL) at 0° C. MsCl (0.50 mL, 6.53 mmol, 1.1 eq) was added dropwise. The mixture was stirred for 40 min at 0° C. It was extracted with CH$_2$Cl$_2$, washed with brine, dried (MgSO$_4$), filtered, and concentrated to dryness to give cis-methanesulfonic acid 2-tert-butoxycarbonylamino-cyclohexylmethyl ester (1.79 g, yield: 98%).

Part C

The product of Part B (1.78 g, 5.80 mmol) was stirred in DMF (10 mL). KSAc (1.98 g, 17.40 mmol, 3.0 eq) was added. The resulting mixture was stirred at 50° C. for 2 h. It was partitioned between EtOAc and H$_2$O. The organic layer was washed with brine, dried (MgSO$_4$), and concentrated to dryness. The residue was purified by silica gel chromatography (0–100% EtOAc/hexanes) to give pure cis-thioacetic acid S-(2-tert-butoxycarbonylaminocyclohexyl-methyl) ester (1.08 g, yield: 67%). Analytical LC/MS (ESI) 288.09 (M+H), $t_R$=3.52 min, (10%-90% MeOH in H$_2$O with 10 mM NH$_4$OAc in a 4-min run). $^1$H NMR (CDCl$_3$) δ 4.65 (m, 1H), 3.92 (m, 1H), 2.83 (m, 2H), 2.32 (s, 3H), 1.78–1.55 (m, 4H), 1.54–1.20 (m, 4H), 1.45 (s, 9H) ppm.

Part D

The product from Part C (0.40 g, 1.39 mmol) was stirred in MeOH (10 mL) at 0° C. 1N NaOH (2.8 mL, 2.80 mmol) was added. The resulting mixture was stirred at 0° C. for 1 h. 6N HCl (10 mL) and MeOH (5 mL) were added. The mixture was heated from rt to 100° C. within 1 h. It was evaporated, azetroped with toluene (2×), and vacuum dried to give crude HCl salt of cis-(2-amino-cyclohexyl)-methanethiol (0.337 g).

Part E

The product from Part D (0.14 g, 0.78 mmol), 1-(4-iodophenyl)-1H-pyridin-2-one (0.30 g, 1.01 mmol), K$_2$CO$_3$ (0.48 g, mmol, 3.48 mmol, 3.5 eq), ethylene glycol (0.11 mL, 2 eq), and CuI (90 mg, 0.47 mmol) were stirred in isopropanol (1.5 mL) at reflux overnight. After cooling, CH$_2$Cl$_2$ was added, and the mixture was filtered through a silica gel pad and rinsed with CH$_2$Cl$_2$. The organic layer was washed with 1N HCl (3×). The aqueous layer was basified, extracted with CH$_2$Cl$_2$ (3×), dried (MgSO$_4$), filtered, and concentrated to dryness to give cis-1-[4-(2-Amino-cyclohexylmethyl-sulfanyl)-phenyl]-1H-pyridin-2-one (54 mg, yield: 22%). Anal. LC/MS (ESI) 315.10 (M+H), $t_R$=1.33 min, (10%-90% MeOH/H$_2$O with 10 mM NH$_4$OAc in a 2-min run).

Part F

The product from Part E (100 mg, 0.32 mmol) was stirred in MeOH (1.5 mL). A solution of Oxone® (250 mg) in H$_2$O (1.5 mL) was added. The mixture was stirred for 50 min at rt. Sat'd NaHCO$_3$ was added. The solvents were evaporated to dryness. CHCl$_3$ was added; the solids were filtered off; and the solvent was evaporated to give crude cis-1-[4-(2-amino-cyclohexylmethanesulfonyl)-phenyl]-1H-pyridin-2-one (96 mg, yield: 87%).

Part G

The product from Part F (15 mg, 0.043 mmol), 3-chloro-1H-indole-6-carboxylic acid (10.1 mg, 1.2 eq), BOP (28.5 mg, 1.5 eq), and NMM (0.012 mL, 2.5 eq) were stirred in DMF (0.4 mL) at rt for 5 h. It was concentrated and purified by reverse phase HPLC (30%–90% MeOH/H₂O with 0.1% TFA) to give the title compound. ¹H NMR (CDCl₃) δ 8.01 (d, J=8.4 Hz, 2H), 7.76 (s, 1H), 7.59 (m, 1H), 7.57 (d, J=8.4 Hz, 2H), 7.49 (t, J=8.4, 1.4 Hz, 1H), 7.39 (d, J=8.4 Hz, 1H), 7.29 (m, 1H), 6.72 (d, J=9.2 Hz, 1H), 6.41 (d, J=7.4 Hz, 1H), 6.35 (t, J=6.7 Hz, 1H), 4.28 (m, 1H), 3.37 (dd, J=14.2, 3.2 Hz, 1H), 3.08 (dd, J=14.6, 8.2 Hz, 1H), 2.74 (m, 1H), 1.80 (m, 2H), 1.72 (m, 1H), 1.58 (m, 5H) ppm. Analytical LC/MS(ESI) 524.07 (M+H), 522.13 (M−H), t_R=1.71 min, (10%–90% MeOH in H₂O with 10 mM NH₄OAc in a 2-min run).

Examples 39–43 were obtained using the same procedure as that of Example 38.

Example 39

Cis-5-Chloro-thiophene-2-carboxylic acid {2-[4-(2-oxo-2H-pyridin-1-yl)-benzenesulfonylmethyl]-cyclohexyl}-amide

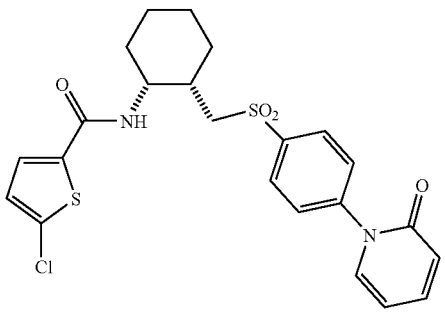

¹H NMR (CDCl₃) δ 8.05 (d, J=8.5 Hz, 2H), 7.62 (d, J=8.5 Hz, 2H), 7.53 (m, 1H), 7.38 (dd, J=6.8, 1.6 Hz, 1H), 7.34 (d, J=4.01 Hz, 1H), 6.90 (d, J=4.01 Hz, 1H), 6.80 (d, J=9.1 Hz, 1H), 6.42 (t, J=6.7 Hz, 1H), 4.22 (m, 1H), 3.43 (dd, J=14.4, 5.2 Hz, 1H), 3.02 (dd, J=14.0, 5.8 Hz, 1H), 2.66 (m, 1H), 1.90–1.52 (m, 8H) ppm.

Analytical LC/MS(ESI) 491.01 (M+H), 489.05 (M−H), t_R=1.67 min, (10%–90% MeOH in H₂O with 10 mM NH₄OAc in a 2-min run).

Example 40

Cis-N-[2-(4-Chloro-benzenesulfinylmethyl)-cyclohexyl]-4-(2-oxo-2H-pyridin-1-yl)-benzamide

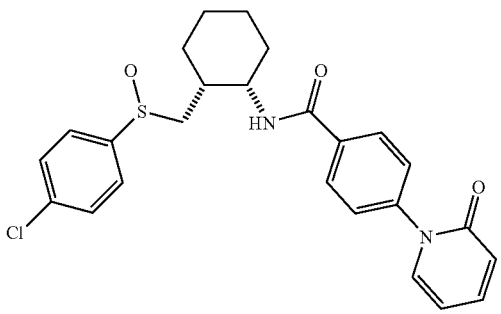

¹H NMR (CDCl₃) δ 7.98 (m, 2H), 7.61 (d, J=8.4 Hz, 2H), 7.51–7.48 (m, 6H), 6.82 (d, J=9.2 Hz, 1H), 6.43 (t, J=6.5 Hz, 1H), 4.49 (m, 1H), 3.02 (m, 1H), 2.65 (m, 2H), 2.60 (m, 1H), 1.92 (m, 2H), 1.63 (m, 3H), 1.51 (m, 2H), 1.29 (m, 1H) ppm.

Analytical LC/MS(ESI) 469.02 (M+H), 467.07 (M−H), t_R=1.63 min (10%–90% MeOH/H₂O with 10 mM NH₄OAc in a 2-min run).

Example 41

Cis-N-[2-(4-Chloro-benzenesulfonylmethyl)-cyclohexyl]-4-(2-oxo-2H-pyridin-1-yl)-benzamide

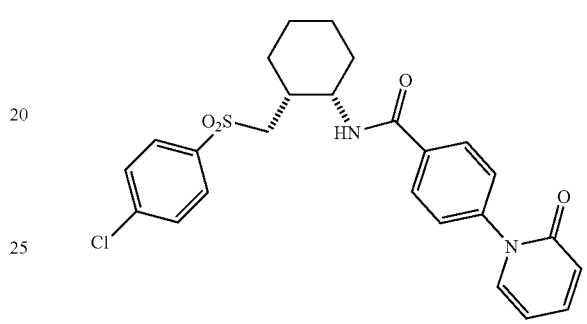

¹H NMR (CDCl₃) δ 7.85 (d, J=7.9 Hz, 2H), 7.78 (d, J=8.3 Hz, 2H), 7.57 (t, J=7.0 Hz, 1H), 7.42 (m, 4H), 7.10 (d, J=7.5 Hz, 1H), 6.80 (d, J=9.2 Hz, 1H), 6.46 (t, J=6.6 Hz, 1H), 4.20 (m, 1H), 3.38 (dd, J=15.0, 3.3 Hz, 1H), 2.97 (d, J=14.5, 7.5 Hz, 1H), 2.53 (m, 1H), 1.86 (m, 1H), 1.73 (m, 1H), 1.53 (m, 6H) ppm. Analytical LC/MS ESI t_R=1.59 min, 485.04 (M+H), 483.07 (M−H), (10%–90% MeOH in H₂O with 10 mM NH₄OAc in a 2-min run).

Example 42

Cis-5-Chloro-thiophene-2-sulfonic acid {2-[4-(2-oxo-2H-pyridin-1-yl)-benzenesulfonylmethyl]-cyclohexyl}-amide

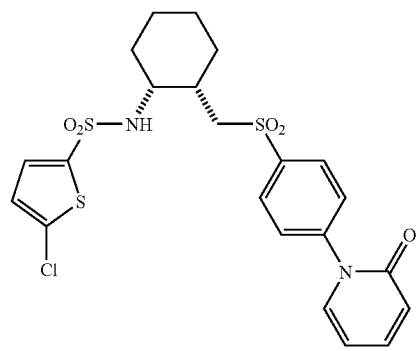

¹H NMR (CDCl₃) δ 8.07 (d, J=8.5 Hz, 2H), 7.64 (d, J=8.5 Hz, 2H), 7.48 (td, J=9.1, 1.8 Hz, 1H), 7.41 (d, J=4.0 Hz, 1H), 7.38 (m, 1H), 6.92 (m, 1H), 6.75 (d, J=9.2 Hz, 1H), 6.38 (t, J=6.9 Hz, 1H) ppm. Analytical LC/MS(ESI) 527.00 (M+H), 525.03 (M−H), t_R=1.72 min (10%–90% MeOH in H₂O with 10 mM NH₄OAc in a 2-min run).

Example 43

Cis-1-(4-Chloro-phenyl)-3-{2-[4-(2-oxo-2H-pyridin-1-yl)-benzenesulfonylmethyl]-cyclohexyl}-urea

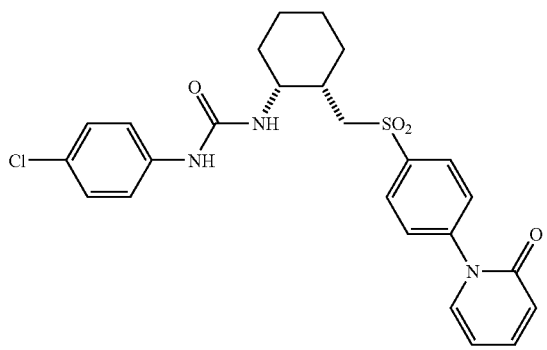

Analytical LC/MS ESI $t_R$=1.72 min, 500.04 (M+H), 498.12 (M−H) (10%–90% MeOH in $H_2O$ with 10 mM $NH_4OAc$ in a 2-min run).

Example 44

Cis-3-Chloro-1H-indole-6-carboxylic acid {1-cyclopropanecarbonyl-3-[4-(2-oxo-2H-pyridin-1-yl)-benzoylamino]-piperidin-4-yl}-amide

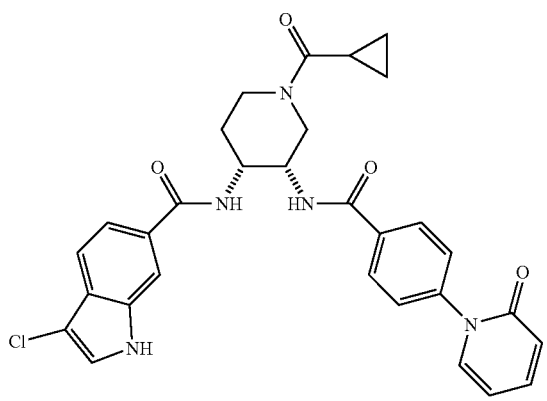

Part A

Trans-4-benzyloxycarbonylamino-3-hydroxy-piperidine-1-carboxylic acid tert-butyl ester (1.06 g, 3.04 mmol) and $Et_3N$ (0.56 mL, 4.02 mmol, 1.3 eq) were stirred in $CH_2Cl_2$ (10 mL) at 0° C. under $N_2$. MsCl (0.27 mL, 3.47 mmol, 1.1 eq) was added dropwise. The resulting mixture was stirred for 1 h. It was extracted with $CH_2Cl_2$ and $H_2O$, washed with brine, dried ($MgSO_4$), filtered, and concentrated to dryness. The residue was dissolved in DMSO (8 mL), and $NaN_3$ (0.79 g, 12.16 mmol, 4.0 eq) was added. The mixture was stirred at 90–95° C. for overnight. After cooling, the mixture was partitioned between EtOAc and $H_2O$. The organic layer was washed with $H_2O$ and brine, dried, filtered, and concentrated to dryness to give cis-3-azido-4-benzyloxy-carbonylamino-piperidine-1-carboxylic acid tert-butyl ester (1.1 g).

Part B

The product from Part A (1.1 g, 2.94 mmol) and $PPh_3$ (4.8 g, 18.3 mmol) were stirred in THF (100 mL) and $H_2O$ (3 mL), heated at 65° C. for 14 h, cooled, and partitioned between EtOAc and 1N HCl. The mixture was washed with 1N HCl (4×20 mL). The aqueous layer was basified with $Na_2CO_3$, extracted with $CH_2Cl_2$ (3×), dried over $MgSO_4$, filtered, and concentrated to give crude amine (0.41 g). LC/MS (ESI) 350.12, 351.12 (M+H), 348.08 (M−H), $t_R$=2.97 min (10%–90% MeOH in $H_2O$ with 10 mM $NH_4OAc$ in a 4-min run).

Part C

The product from Part B (0.39 g, 1.12 mmol), 4-(2-oxo-2H-pyridin-1-yl)-benzoic acid (0.34 g, 1.58 mmol, 1.4 eq), BOP (0.74 g, 1.70 mmol, 1.5 eq), and DIEA (0.66 mL) were stirred in DMF (5 mL) at rt for 1.5 h. The mixture was partitioned between EtOAc and $H_2O$, washed with brine, dried ($MgSO_4$), filtered, and concentrated to dryness. The residue was purified by flash chromatography (silica gel, EtOAc) to give cis-4-benzyloxycarbonylamino-3-[4-(2-oxo-2H-pyridin-1-yl)-benzoylamino]-piperidine-1-carboxylic acid tert-butyl ester (520 mg, yield: 85.2%). $^1$H NMR ($CDCl_3$) δ 7.86 (d, J=8.5 Hz, 2H), 7.41–7.27 (m, H), 6.65 (d, J=9.2 Hz, 1H), 6.28 (t, J=6.8 Hz, 1H), 5.09 (m, 2H), 4.39 (m, 1H), 3.92 (m, 2H), 3.23 (m, 1H), 3.04 (m, 1H), 1.93–1.69 (m, 3H), 1.46 (m, 10H) ppm. LC/MS (ESI) 447.45 (M-Boc+H), 391.45 (M-t-Bu+H), $t_R$=3.16 min (10%–90% MeOH in $H_2O$ with 10 mM $NH_4OAc$ in a 4-min run).

Part D

The product from Part C (82 mg, 0.15 mmol) was stirred in TFA (2 mL) and $CH_2Cl_2$ (2 mL) at rt for 1 h. The solvents were evaporated to dryness. The residue was dissolved in $CH_2Cl_2$ (5 mL). $Et_3N$ (0.05 mL) was added followed by the addition of cyclopropanecarbonyl chloride (0.015 mL, 0.165 mmol, 1.1 eq). The resulting mixture was stirred at rt for 3 h. $H_2O$ was added. The mixture was then extracted with $CH_2Cl_2$, dried ($MgSO_4$), filtered, and concentrated to dryness to give cis-{1-cyclopropanecarbonyl-3-[4-(2-oxo-2H-pyridin-1-yl)-benzoylamino]-piperidin-4-yl}-carbamic acid benzyl ester (77 mg). LC/MS (ESI) 515.09 (M+H), $t_R$=2.74 min (10%–90% MeOH in $H_2O$ with 10 mM $NH_4OAc$ in a 4-min run).

Part E

The product from Part D (77 mg, 0.15 mmol) was stirred in $CH_3CN$ (1.5 mL). TMSI (0.05 mL, mmol) was added dropwise. The mixture was stirred for 5 min. MeOH was added. It was partitioned between (3:1 $CH_2Cl_2$:MeOH and $H_2O$). The organic layer was concentrated and vacuum dried to give crude cis-N-(4-amino-1-cyclopropanecarbonyl-piperidin-3-yl)-4-(2-oxo-2H-pyridin-1-yl)-benzamide. LC/MS (ESI) 381.06 (M+H), 379.08 (M−H), $t_R$=1.51 min (10%–90% MeOH in $H_2O$ with 10 mM $NH_4OAc$ in a 4-min run). The amine (38 mg, 0.10 mmol), 3-chloro-1H-indole-6-carboxylic acid (20 mg, 0.10 mmol), BOP (57 mg, 0.13 mmol, 1.3 eq), and 4-methylmorpholine (0.02 mL, 0.18 mmol, 1.8 eq) were stirred in DMF (0.5 mL) at rt for 1.5 h. The reaction mixture was concentrated. The residue was dissolved in MeOH and purified by reverse phase HPLC (30–90% MeOH in $H_2O$ with 0.1% TFA) to give the title compound. LC/MS (ESI) 558.47, 560.48 (M+H), 556.43, 558.36 (M−H), $t_R$=2.89 min (10%-90% MeOH in $H_2O$ with 10 mM $NH_4OAc$ in a 4-min run).

Example 45

Cis-5-Chloro-thiophene-2-carboxylic acid {1-cyclopropanecarbonyl-3-[4-(2-oxo-2H-pyridin-1-yl)-benzoylamino]-piperidin-4-yl}-amide

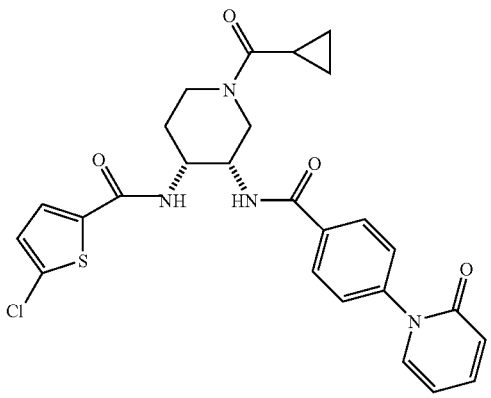

Using a procedure similar to that of Example 44, but using 5-chloro-thiophene-2-carboxylic acid as one of the starting materials, the title compound was prepared. It was purified by reverse phase HPLC (30–90% MeOH in H$_2$O with 0.1% TFA): Anal. LC/MS (ESI) 525.40, 527.39 (M+H), 523.35, 525.36 (M–H), t$_R$=2.76 min (10%-90% MeOH in H$_2$O with 10 mM NH$_4$OAc in a 4-min run).

Example 46

Cis-1H-Indole-6-carboxylic acid {1-cyclopropanecarbonyl-4-[4-(2-oxo-2H-pyridin-1-yl)-benzoylamino]-piperidin-3-yl}-amide

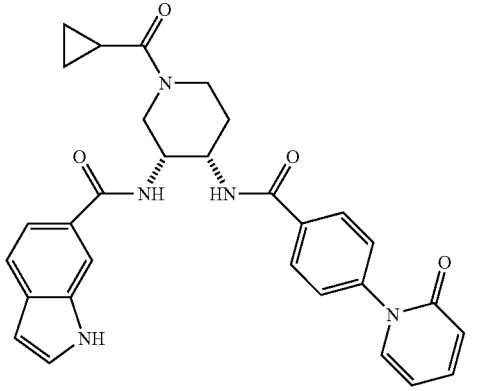

Using a procedure similar to that of Example 44, the title compound was prepared. It was purified by reverse phase HPLC (30–90% MeOH in H$_2$O with 0.1% TFA). 1H NMR (methanol-d$_4$) δ 7.95 (m, 2H), 7.89 (s, 1H), 7.62 (m, 3H), 7.49 (m, 3H), 7.42 (d, J=3.1 Hz, 1H), 6.63 (d, J=9.2 Hz, 1H), 6.51 (d, J=3.1 Hz, 1H), 6.49 (t, J=6.7 Hz, 1H), 4.60 (m, 4H), 3.62 (m, 1H), 3.07 (m, 1H), 2.02 (m, 3H), 0.78 (m, 3H), 0.53 (m, 1H) ppm. Anal. LC/MS (ESI) 524.11 (M+H), 522.15 (M–H), t$_R$=1.61 min (10%–90% MeOH in H$_2$O with 10 mM NH$_4$OAc in a 2-min run).

Examples 47–55 were obtained using the same procedure as that of Example 1.

Example 47

(1R,2S)-4-Chloro-phenylcarboxylic acid {2-[4-(2-oxo-2H-pyridin-1-yl)-benzoylamino]-cyclopentyl}-amide

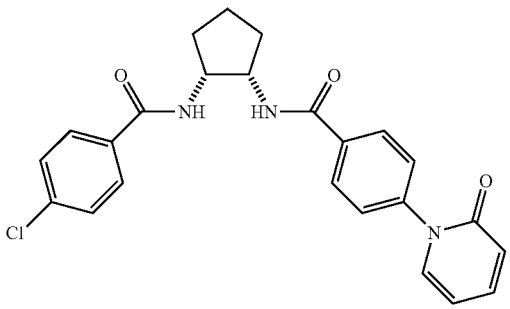

Anal. LC/MS (ESI) 450.08 (M+H), 448.10 (M–H), t$_R$=1$^{59}$ min (10%–90% MeOH in H$_2$O with 10 mM NH$_4$OAc in a 2-min run).

Example 48

(1R,2S)-4-Chloro-3-fluorophenylcarboxylic acid {2-[4-(2-oxo-2H-pyridin-1-yl)-benzoylamino]-cyclopentyl}-amide

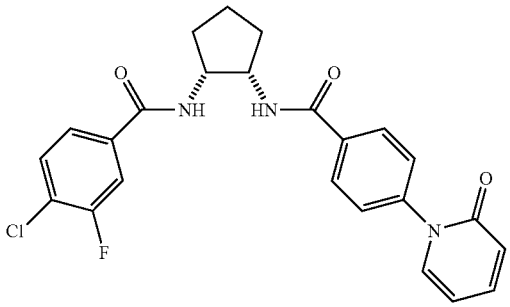

$^1$H NMR (methanol-d$_4$) δ 7.74 (m, 2H), 7.60 (m, 2H), 7.52 (d, J=8.4 Hz, 1H), 7.45 (m, 1H), 7.37 (m, 1H), 7.31 (d, J=8.2 Hz, 2H), 6.76 (d, J=9.1 Hz, 1H), 6.51 (t, J=7.2 Hz, 1H), 4.45 (m, 2H), 2.18 (m, 2H), 1.97 (m, 1H), 1.86–1.66 (m, 4H) ppm.

Example 49

(1R,2S)-4-Chloro-3-methylphenylcarboxylic acid {2-[4-(2-oxo-2H-pyridin-1-yl)-benzoylamino]-cyclopentyl}-amide

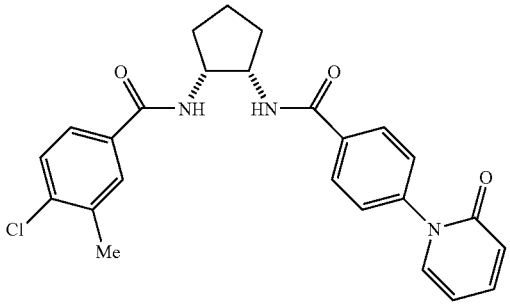

¹H NMR (methanol-d₄) δ 7.79 (d, J=8.3 Hz, 2H), 7.57 (s, 1H), 7.55 (m, 1H), 7.52 (dd, J=7.9, 1.5 Hz, 2H), 7.36 (m, 1H), 7.31 (m, 2H), 6.72 (d, J=9.2 Hz, 1H), 6.45 (t, J=6.7 Hz, 1H), 4.42 (m, 2H), 2.33 (s, 3H), 2.16 (m, 2H), 1.97 (m, 1H), 1.89–1.66 (m, 4H) ppm.

Example 50

(1R,2S)-4-Chloro-3-,methoxylphenylcarboxylic acid {2-[4-(2-oxo-2H-pyridin-1-yl)-benzoylamino]-cyclopentyl}-amide

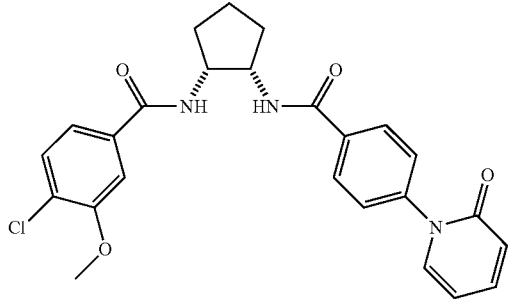

¹H NMR (methanol-d₄) δ 7.77 (d, J=8.0 Hz, 3H), 7.56 (td, J=8.7, 1.7 Hz, 1H), 7.45 (m, 2H), 7.35 (dd, J=8.7, 1.4 Hz, 1H), 7.31 (m, 2H), 6.69 (d, J=9.2 Hz, 1H), 6.44 (t, J=6.9 Hz, 1H), 4.45 (m, 2H), 3.86 (s, 3H), 2.16 (m, 2H), 1.97 (m, 1H), 1.86–1.67 (m, 4H) ppm.

Example 51

(1R,2S)-5-Methyl-thiophene-2-carboxylic acid {2-[4-(2-oxo-2H-pyridin-1-yl)-benzoylamino]-cyclopentyl}-amide

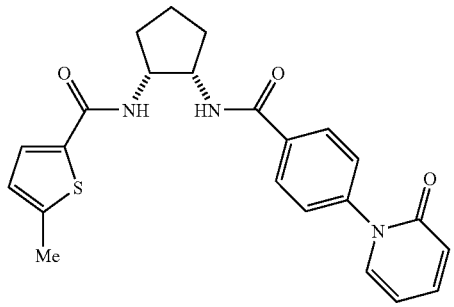

¹H NMR (methanol-d₄) δ 7.86 (d, J=8.5 Hz, 2H), 7.60 (m, 2H), 7.45 (m, 3H), 6.75 (d, J=3.7 Hz, 1H), 6.63 (d, J=9.2 Hz, 1H), 6.48 (t, J=9.2 Hz, 1H), 4.49 (m, 2H), 2.46 (s, 3H), 2.12 (m, 2H), 1.96 (m, 1H), 1.84 (m, 2H), 1.69 (m, 1H) ppm. Anal. LC/MS (ESI) 422.12, 423.13 (M+H), 420.25, 421.25 (M−H), $t_R$=1.37 min (10%–90% MeOH in H₂O with 10 mM NH₄OAc in a 2-min run).

Example 52

(1R,2S)-1H-Indole-6-carboxylic acid {2-[4-(2-oxo-2H-pyridin-1-yl)-benzoylamino]-cyclopentyl}-amide

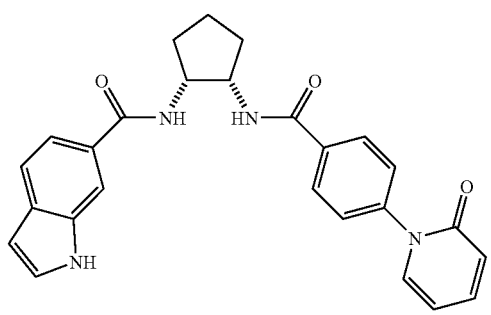

¹H NMR (methanol-d₄) δ 7.88 (d, J=8.5 Hz, 2H), 7.80 (s, 1H), 7.56 (m, 3H), 7.42 (d, J=8.4 Hz, 2H), 7.34 (m, 1H), 6.75 (d, J=3.7 Hz, 1H), 6.62 (d, J=9.2 Hz, 1H), 6.47 (m, 2H), 4.58 (m, 2H), 2.17 (m, 2H), 1.976 (m, 1H), 1.86 (m, 2H), 1.70 (m, 1H) ppm. Anal. LC/MS (ESI) 441.15, 442.15 (M+H), 439.26, 438.25 (M−H), $t_R$=1.37 min (10%–90% MeOH in H₂O with 10 mM NH₄OAc in a 2-min run).

Example 53

(1R,2S)-6-Chloro-naphthalene-2-carboxylic acid {2-[4-(2-oxo-2H-pyridin-1-yl)-benzoylamino]-cyclohexyl}-amide

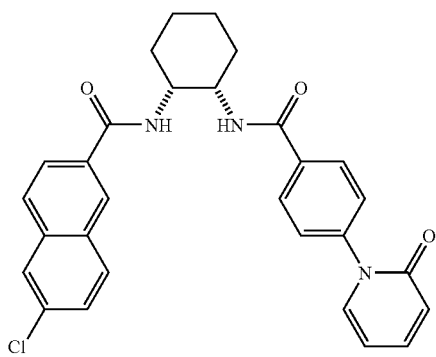

¹H NMR (methanol-d₄) δ 7.88 (d, J=8.5 Hz, 2H), 7.80 (s, 1H), 7.56 (m, 3H), 7.42 (d, J=8.4 Hz, 2H), 7.34 (m, 1H), 6.75 (d, J=3.7 Hz, 1H), 6.62 (d, J=9.2 Hz, 1H), 6.47 (m, 2H), 4.58 (m, 2H), 2.17 (m, 2H), 1.976 (m, 1H), 1.86 (m, 2H), 1.70 (m, 1H) ppm. Anal. LC/MS (ESI) 441.15, 442.15 (M+H), 439.26, 438.25 (M−H), $t_R$=1.37 min (10%–90% MeOH in H₂O with 10 mM NH₄OAc in a 2-min run).

Example 54

(1R,2S)-6-Chloro-1H-indole-2-carboxylic acid {2-[4-(2-oxo-2H-pyridin-1-yl)-benzoylamino]-cyclopentyl}-amide

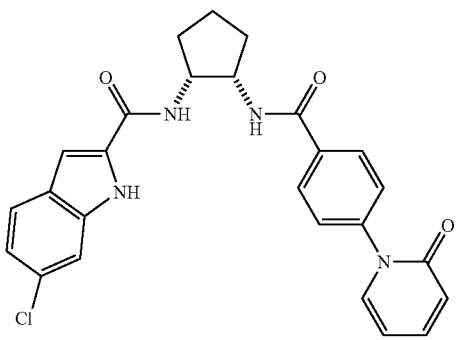

¹H NMR (Methanol-d₄) δ 7.84 (d, J=8.3 Hz, 2H), 7.61 (td, J=7.2, 2.2 Hz, 1H), 7.53 (d, J=8.3 Hz, 2H), 7.40 (m, 3H), 7.04 (s, 1H), 7.01 (dd, J=8.6, 1.9 Hz, 1H), 6.61 (d, J=9.3 Hz, 1H), 6.46 (dt, J=6.9, 1.3 Hz, 1H), 4.55 (m, 2H), 2.16 (m, 2H), 2.00 (m, 1H), 1.89 (m, 2H), 1.69 (m, 1H) ppm. Anal. LC/MS (ESI) 475.08, 477.09 (M+H), 473.12, 475.14 (M−H), $t_R$=min (10%–90% MeOH in H₂O with 10 mM NH₄OAc in a 4-min run).

Example 55

(1R,2S)-5-Chloro-2H-indole-2-carboxylic acid {2-[4-(2-oxo-2H-pyridin-1-yl)-benzoylamino]-cyclopentyl}-amide

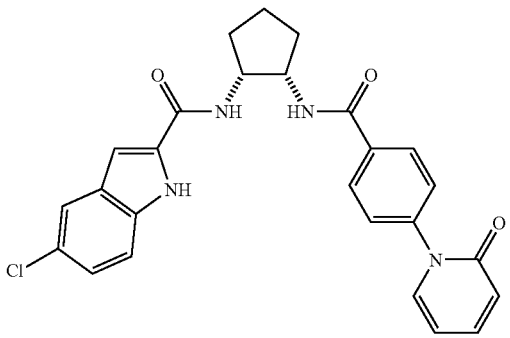

¹H NMR (Methanol-d₄) δ 7.82 (d, J=8.6 Hz, 2H), 7.59 (td, J=7.3, 2.7 Hz, 1H), 7.53 (d, J=2.0 Hz, 1H), 7.48 (dd, J=6.7, 1.7 Hz, 1H), 7.37 (m, 3H), 7.14 (dd, J=8.3, 2.5 Hz, 1H), 6.99 (d, J=1.3 Hz, 1H), 6.60 (d, J=9.3 Hz, 1H), 6.45 (dt, J=6.8, 1.3 Hz, 1H), 4.55 (m, 2H), 2.15 (m, 2H), 1.98 (m, 1H), 1.88 (m, 2H), 1.71 (m, 1H) ppm. Anal. LC/MS (ESI) 475.07 (M+H), 473.12 (M−H), $t_R$=3.09 min (10%–90% MeOH in H₂O with 10 mM NH₄OAc in a 4-min run).

Example 56

(1R,2S)-5-Chloro-thiophene-2-carboxylic acid {2-[4-(2-oxo-2H-pyridin-1-yl)-benzylamino]-cyclopentyl}-amide

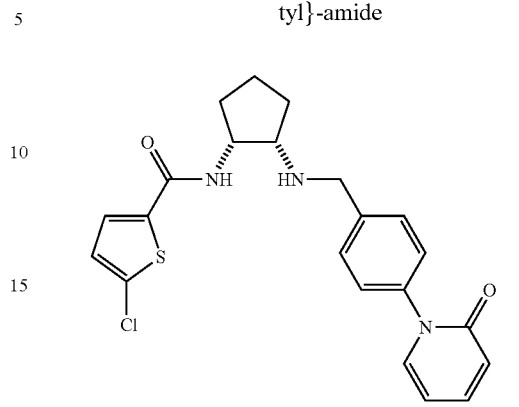

Part A

To a stirred solution of 4-(2-oxo-2H-pyridin-1-yl)-benzoic acid (0.31 g, 1.4 mmol) in THF (12 mL) was added Et₃N (0.30 mL, 2.15 mmol, 1.5 eq) followed by dropwise addition of ClCOOEt (0.16 mL, 1.2 eq) at 0° C. under N₂. The mixture was stirred for 1 h at 0° C., filtered, and rinsed with THF. The THF solution was stirred at 0° C., MeOH (3 mL) was added followed by portionwise addition of NaBH₄ (0.26 g, 6.8 mmol). The mixture was stirred at 0° C. for 20 min, sat'd Na₂SO₄ added, extracted with CH₂Cl₂, dried (MgSO₄), filtered, and concentrated to dryness to give 4-(2-oxo-2H-pyridin-1-yl)-benzaldehyde (0.17 g) as a tan solid.

Part B

The product from Part A (20 mg) and (1R,2S)-5-chloro-thiophene-2-carboxylic acid (2-amino-cyclopentyl)-amide were stirred in dichloroethane (1.5 mL) at rt. NaBH(OAc)₃ (150 mg) was added followed by the addition of 1 drop of HOAc. The mixture was stirred at rt for 2.5 h. H₂O was added. The mixture was extracted with CH₂Cl₂, concentrated, and purified by reverse phase HPLC to give the title compound. ¹H NMR (methanol-d₄) δ 7.72 (d, J=8.5 Hz, 1H), 7.65 (d, J=Hz, 2H), 7.58 (d, J=Hz, 1H), 7.47 (d, J=8.4 Hz, 2H), 7.04 (d, J=4.1 Hz, 1H), 6.63 (d, J=9.1 Hz, 1H), 6.49 (t, J=7.7 Hz, 1H), 4.58 (m, 2H), 2.17 (m, 2H), 1.97 (m, 1H), 1.86 (m, 2H), 1.70 (m, 1H) ppm. Anal. LC/MS (ESI) 441.15, 442.15 (M+H), 439.26, 438.25 (M−H), $t_R$=1.37 min (10%–90% MeOH in H₂O with 10 mM NH₄OAc in a 2-min run).

Example 57

(1R,2S)-3-Chloro-1H-indole-6-carboxylic acid {2-[4-(2-oxo-2H-pyridin-1-yl)-benzylamino]-cyclohexyl}-amide

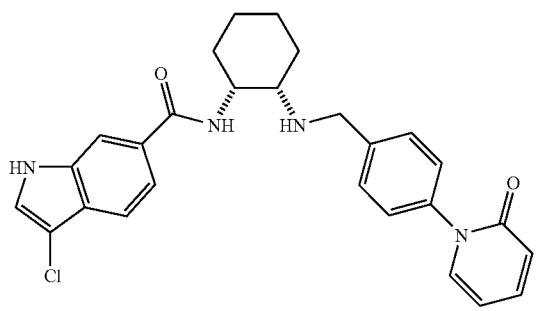

Using the same procedure as that of Example 56, the title compound was obtained. ¹H NMR (methanol-d₄) δ 7.72 (d, J=8.5 Hz, 1H), 7.65 (d, J=Hz, 2H), 7.58 (d, J=Hz, 1H), 7.47 (d, J=8.4 Hz, 2H), 7.04 (d, J=4.1 Hz, 1H), 6.63 (d, J=9.1 Hz, 1H), 6.49 (t, J=7.7 Hz, 1H), 4.58 (m, 2H), 2.17 (m, 2H), 1.976 (m, 1H), 1.86 (m, 2H), 1.70 (m, 1H) ppm. Anal. LC/MS (ESI) 441.15, 442.15 (M+H), 439.26, 438.25 (M−H), $t_R$=1.37 min (10%–90% MeOH in H₂O with 10 mM NH₄OAc in a 2-min run).

Example 58

(1R,2S)-N-{2-[(5-Chloro-thiophen-2-ylmethyl)-amino]-cyclopentyl}-4-(2-oxo-2H-pyridin-1-yl)-benzamide

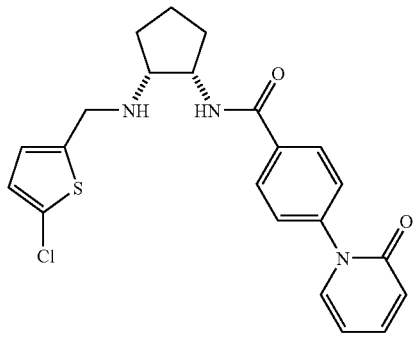

Using the same procedure as that of Example 56, the title compound was obtained. ¹H NMR (CDCl₃) δ 7.94 (dd, J=6.6, 1.9 Hz, 2H), 7.49 (dd, J=6.6, 2.0 Hz, 2H), 7.40 (td, J=6.7, 1.9 Hz, 1H), 7.33 (ddd, J=6.9, 1.9, 0.7 Hz, 1H), 6.71 (d, J=3.9 Hz, 1H), 6.67 (d, J=6.9 Hz, 1H), 6.66 (m, 1H), 6.26 (dt, J=6.6, 1.3 Hz, 1H), 4.20 (m, 1H), 3.89 (AB, J=14.68 Hz, 2H), 3.23 (m, 1H), 2.13 (m, 1H), 1.96 (m, 1H), 1.77 (m, 2H), 1.57 (m, 2H) ppm. Anal. LC/MS (ESI) 428.21, 430.20 (M+H), $t_R$=2.63 min (10%–90% MeOH in H₂O with 0.1% TFA in a 4-min run).

Example 59

(1R,2S)-3-Chloro-1H-indole-6-carboxylic acid {2-[4-(2-oxo-2H-pyrazin-1-yl)-benzoylamino]-cyclohexyl}-amide

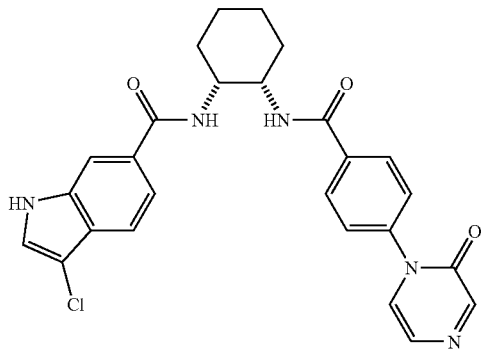

Part A

Methyl 4-amino-benzoate (3.58 g, 23.70 mmol) and N-Boc glycine (4.15 g, 23.70 mmol) were stirred in DMF (50 mL) at room temperature. BOP (11.52 g, 26.07 mmol) was added followed by the addition of DIEA (6.18 mL, 35.55 mmol). The resulting mixture was stirred at rt for 1.5 h. It was quenched with sat'd NaHCO₃ and EtOAc. The organic layer was washed with H₂O, brine (3×), dried (MgSO₄), and concentrated to dryness to give 4-(2-tert-butoxycarbonylamino-acetylamino)-benzoic acid methyl ester (7.18 g, yield: 98%). ¹H NMR (CDCl₃) δ 9.16 (s, br, 1H), 7.96 (d, J=8.4 Hz, 2H), 7.65 (d, J=8.4 Hz, 2H), 3.98 (s, 2H), 3.89 (s, 3H), 1.45 (s, 9H) ppm.

Part B

The product from Part A (2.56 g, 8.31 mmol) was stirred in CH₂Cl₂ (20 mL) and TFA (10 mL) for 1.5 h. The solvents were evaporated, and the residue was dried in vacuo to give 4-(2-amino-acetylamino)-benzoic acid methyl ester (1.62 g, yield: 100%). Anal. LC/MS (ESI) 209.02 (M+H), $t_R$=1.34 min (10%–90% MeOH in H₂O with 10 mM NH₄OAc in a 4-min run).

Part C

The product from Part B (1.62 g, 8.31 mmol) was stirred in MeOH (20 mL) at −40° C. under N₂. Glyoxal (40% et in H₂O, 6.20 g) was added followed by the dropwise addition of NaOH (0.50 g, 12.5 mmol) in H₂O (1 mL). The resulting mixture was stirred at −40° C. to 5° C. for 3 h. 1N HCl was added, and the solvents were evaporated. H₂O was added. The precipitate was collected by filtration to give pure 4-(2-oxo-2H-pyrazin-1-yl)-benzoic acid methyl ester as tan solids (1.01 g, yield: 55%). Anal. LC/MS (ESI) 231.04 (M+H), $t_R$=1.77 min (10%–90% MeOH in H₂O with 10 mM NH₄OAc in a 4-min run).

Part D

The product from part C (120 mg, 0.52 mmol) was stirred in MeOH (15 mL) and 1N NaOH (3 mL) at 50° C. for 2 h. The solvents were evaporated. It was acidified by 1N HCl, and the solids were collected by filtration to give 4-(2-oxo-2H-pyrazin-1-yl)-benzoic acid (85 mg, yield: 76%). Anal. LC/MS (ESI) 216.91 (M+H), 214.96 (M−H), $t_R$=0.40 min (10%–90% MeOH in H₂O with 10 mM NH₄OAc in a 4-min run).

Part E

The product from Part D (30 mg), 3-chloro-1H-indole-6-carboxylic acid (70 mg), BOP (154 mg), and NMM (0.05 mL) were stirred at rt for 1 h. The mixture was quenched with H₂O and evaporated. The residue was dissolved in MeOH and purified by reverse phase HPLC (35–90% MeOH in H₂O with 0.1% TFA) to give the title compound. ¹H NMR (CDCl₃) δ 9.48 (s, br, 1H), 8.23 (s, 1H), 7.92 (m, 2H), 7.82 (d, J=8.5 Hz, 2H), 7.59 (d, J=8.5 Hz, 1H), 7.46 (m, 2H), 7.26 (m, 2H), 7.15 (d, J=4.7 Hz, 1H), 4.52 (m, 1H), 4.26 (m, 1H), 2.07–1.89 (m, 3H), 1.71–1.59 (m, 5H) ppm. Anal. LC/MS (ESI) 492.13, 490.13 (M+H), $t_R$=2.97 min (10%–90% MeOH in H₂O with 10 mM NH₄OAc in a 4-min run).

Example 60

(1R,2S)-5-Chloro-thiophene-2-carboxylic acid {1-[4-(2-oxo-2H-pyrazin-1-yl)-benzoylamino]-indan-2-yl}-amide

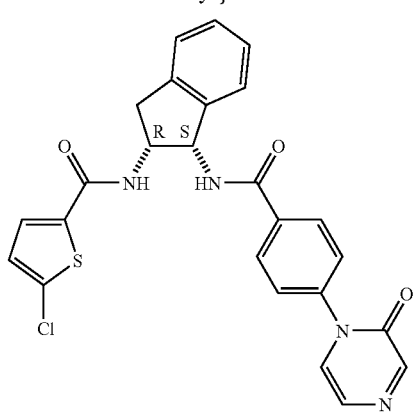

Using the same procedure as that of Example 59, the title compound was obtained. ¹H NMR (500 Hz, CDCl₃) δ 8.17 (s, 1H), 7.87 (d, J=8.1 Hz, 2H), 7.47 (d, J=4.5 Hz, 1H), 7.42 (d, J=8.2 Hz, 2H), 7.31 (m, 3H), 7.25 (d, J=4.5 Hz, 1H), 7.20 (dd J=4.4, 0.8 Hz, 1H), 7.14 (d, J=7.6 Hz, 1H), 6.86 (d, J=4.2 Hz, 1H), 5.63 (t, J=7.1 Hz, 1H), 4.89 (m, 1H), 3.46 (dd, J=16.3, 7.1 Hz, 1H), 3.18 (dd, J=16.3, 5.7 Hz, 1H) ppm. LC-MS (ESI) 491.03 (M+H), $t_R$=2.99 min (10–90% MeOH in H₂O with 10 mM NH₄OAc in a 4-min run).

Example 61

Cis-3-Chloro-1H-indole-6-carboxylic acid {2-[4-(2-oxo-2H-pyridin-1-yl)-benzenesulfonylamino]-cyclohexyl}-amide

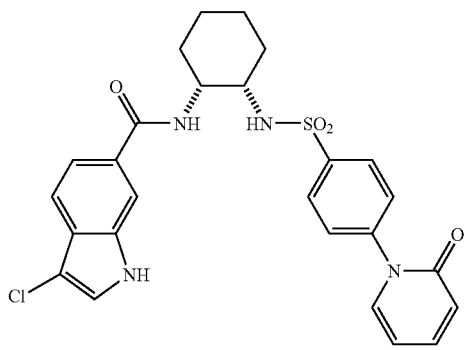

Part A

Cis-1,2-diaminocyclohexane (0.70 g, 6.86 mmol) was stirred in CH₂Cl₂ (40 mL) at 0° C. under N₂. A solution of 4-iodobenzenesulfonic acid (0.85 g, 2.81 mmol) in CH₂Cl₂ (20 mL) was added dropwise to the above solution. It was stirred for 30 min at 0° C. LC/MS showed completion of the reaction. It was washed with 1N HCl. The aqueous solution was basified with 1N NaOH until formation of a cloudy solution. It was extracted with CH₂Cl₂ (3×), washed with brine, dried (MgSO₄), and concentrated to dryness to give cis-N-(2-amino-cyclohexyl)-4-iodobenzenesulfonamide (0.37 g, yield: 35%). ¹H NMR (400 MHz, CDCl₃) δ 7.86 (d, J=6.8 Hz, 2H), 7.60 (d, J=6.7 Hz, 2H), 3.15 (m, 1H), 2.84 (m, 1H), 1.48 (m, 10H) ppm.

Part B

The product from Part A (0.9 g, 0.76 mmol) and (0.40 g, 1.24 mmol) were stirred in DMF (2 mL) under N₂. CuI (72 mg, 0.38 mmol) was added. The resulting mixture was stirred at 130° C. overnight, filtered through Celite®, and washed with CH₂Cl₂. The filtrate was concentrated to dryness. The residue was filtered through a clean-up cartridge using MeOH, then ammonia in MeOH as the eluants to give almost pure N-(2-amino-cyclohexyl)-4-(2-oxo-2H-pyridin-1-yl)-benzenesulfonamide (95 mg, yield: 36%). LC-MS (ESI) 381.06 (M+H), $t_R$=2.26 min (10–90% MeOH in H₂O with 0.1% TFA in a 4-min run).

Part C

The product from Part B (30 mg), 3-chloro-1H-indole-6-carboxylic acid (20 mg), BOP (45 mg), and NMM (0.02 mL) were stirred in DMF (1 mL) at rt for 40 min. It was quenched with H₂O, and purified by reverse-phase HPLC to give pure title compound. ¹H NMR (400 MHz, CDCl₃) δ 9.63 (s, br, 1H), 7.88 (d, J=8.1 Hz, 2H), 7.68 (s, 1H), 7.47 (m, 2H), 7.24 (m, 3H), 6.93 (m, 2H), 6.70 (d, J=9.2 Hz, 1H), 6.29 (t, J=6.8 Hz, 1H), 6.25 (s, br, 1H), 4.07 (m, 1H), 3.68 (m, 1H), 1.71–1.46 (m, 8H) ppm. LC-MS (ESI) 525.06 (M+H), $t_R$=3.04 min (10–90% MeOH in H₂O with 10 mM NH₄OAc in a 4-min run).

Examples 62–67 were obtained using the same procedure as that of Example 1.

Example 62

(1R,2S,4S)-5-Chloro-thiophene-2-carboxylic acid {4-dimethylcarbamoyl-2-[4-(2-oxo-2H-pyridin-1-yl)-benzoylamino]-cyclopentyl}-amide

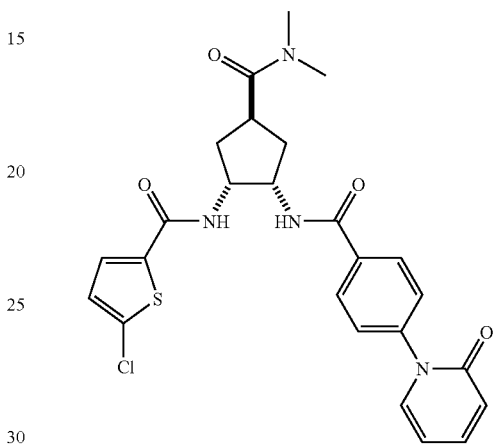

¹H NMR (500 MHz, methanol-d₄) δ 7.87 (d, J=8.1 Hz, 2H), 7.62 (m, 2H), 7.51 (d, J=4.1 Hz, 1H), 7.46 (d, J=8.4 Hz, 2H), 6.97 (d, J=4.0 Hz, 1H), 6.63 (d, J=9.1 Hz, 1H), 6.50 (dt, J=6.6, 1.4 Hz, 1H), 4.66 (m, 2H), 3.60 (m, 1H), 3.12 (s, 3H), 2.95 (s, 3H), 2.27 (m, 2H), 2.15 (m, 2H) ppm. Anal. LC/MS (ESI) 513.17, 515.16 (M+H), $t_R$=2.67 min (10%–90% MeOH in H₂O with 0.1% TFA in a 4-min run).

Example 63

(1R,2S,4S)-5-Chloro-thiophene-2-carboxylic acid {4-cyclopropylcarbamoyl-2-[4-(2-oxo-2H-pyridin-1-yl)-benzoylamino]-cyclopentyl}-amide

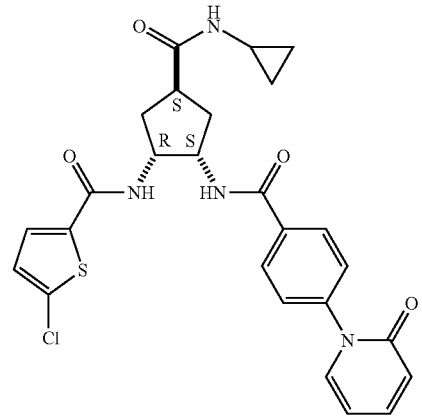

¹H NMR (methanol-d₄) δ 7.86 (d, J=8.5 Hz, 2H), 7.60 (m, 2H), 7.47 (m, 3H), 6.97 (d, J=3.9 Hz, 1H), 6.63 (d, J=9.1 Hz, 1H), 6.49 (dt, J=6.6, 1.3 Hz, 1H), 4.68 (m, 2H), 3.06 (m, 1H), 2.65 (m, 1H), 2.24 (m, 2H), 2.14 (m, 2H), 0.72 (m, 2H), 0.49 (m, 2H) ppm. Anal. LC/MS (ESI) 428.21, 430.20 (M+H), $t_R$=2.63 min (10%–90% MeOH in H$_2$O with 0.1% TFA in a 4-min run).

Example 64

(1R,2S,4S)-5-Chloro-thiophene-2-carboxylic acid {4-(morpholine-4-carbonyl)-2-[4-(2-oxo-2H-pyridin-1-yl)-benzoylamino]-cyclopentyl}-amide

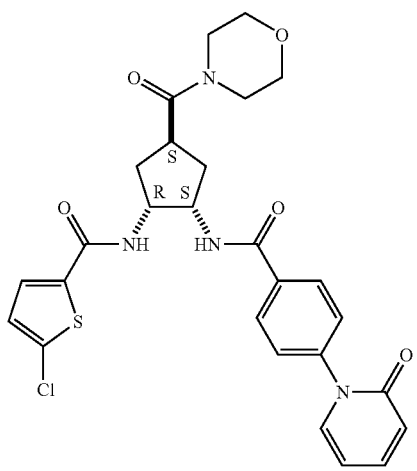

$^1$H NMR (methanol-d$_4$) δ 7.81 (d, J=8.5 Hz, 2H), 7.55 (m, 2H), 7.41 (m, 3H), 6.90 (d, J=3.9 Hz, 1H), 6.56 (d, J=9.1 Hz, 1H), 6.42 (t, J=7.2 Hz, 1H), 4.57 (m, 2H), 3.60 (m, 4H), 3.55 (m, 4H), 2.24 (m, 2H), 2.09 (m, 2H) ppm. Anal. LC/MS (ESI) 555.18, 557.20 (M+H), $t_R$=2.68 min (10%–90% MeOH in H$_2$O with 0.1% TFA in a 4-min run).

Example 65

Cis-3-Chloro-1H-indole-6-carboxylic acid {1-methyl-3-[4-(2-oxo-2H-pyridin-1-yl)-benzoylamino]-piperidin-4-yl}-amide

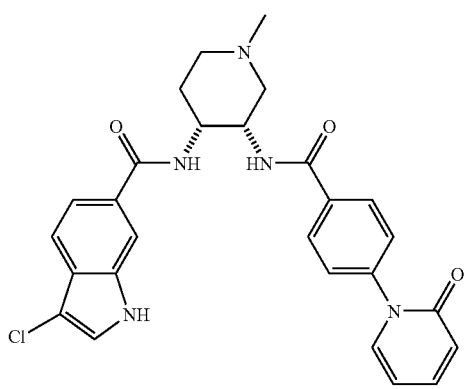

Part A

Cis-4-Benzyloxycarbonylamino-3-[4-(2-oxo-2H-pyridin-1-yl)-benzoylamino]-piperidine-1-carboxylic acid tert-butyl ester (285 mg, 0.52 mmol) was stirred in TFA (3 mL) and CH$_2$Cl$_2$ (5 mL) at rt for 1.5 h. LC/MS showed completion of the reaction (447.33 (M+H), $t_R$=2.23 min, 10–90% MeOH in H$_2$O with 10 mM NH$_4$OAc in a 4-min run). The solvents were evaporated. Half of the residue (0.26 mmol) was dissolved in CH$_3$CN (2 mL). HCHO (37% wt in H$_2$O, 0.20 mL) was added, followed by the addition of NaCNBH$_3$ (78 mg). The resulting mixture was stirred at rt for 40 min. HOAc was added dropwise to neutralize the mixture. The resulting mixture was stirred for additional 1 h, extracted with EtOAc (3×), dried over MgSO$_4$, filtered, and concentrated to dryness to give crude cis-{1-methyl-3-[4-(2-oxo-2H-pyridin-1-yl)-benzoylamino]-piperidin-4-yl}-carbamic acid benzyl ester (130 mg). Anal. LC/MS (ESI) 461.14 (M+H), $t_R$=2.63 min (10%–90% MeOH in H$_2$O with 10 mM NH$_4$OAc in a 4-min run).

Part B

The product from Part A (130 mg) was stirred in CH$_3$CN (2 mL) at rt. TMSI (0.20 mL) was added. The resulting mixture was stirred for 1.5 h. The solvents were evaporated and dried under vacuum. The residue was dissolved in DMF (2 mL), and 3-chloro-1H-indole-6-carboxylic acid (73 mg), BOP (245 mg), and NMM (0.25 mL) were added. The resulting mixture was stirred at rt for 1 h. H$_2$O was added. It was concentrated and purified by reverse-phase HPLC to give pure title compound.

Anal. LC/MS (ESI) 504.12 (M+H), 502.17 (M−H), $t_R$=2.86 min (10%–90% MeOH in H$_2$O with 10 mM NH$_4$OAc in a 4-min run).

Example 66

Cis-3-Chloro-1H-indole-6-carboxylic acid {1-isopropyl-3-[4-(2-oxo-2H-pyridin-1-yl)-benzoylamino]-piperidin-4-yl}-amide

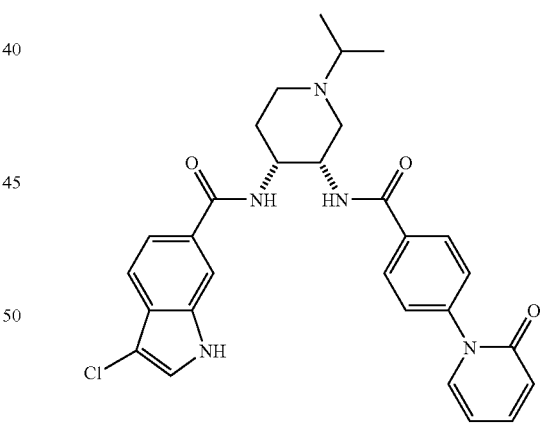

Part A

Cis-{3-[4-(2-Oxo-2H-pyridin-1-yl)-benzoylamino]-piperidin-4-yl}-carbamic acid benzyl ester (0.26 mmol) was dissolved in CH$_3$CN (1.5 ml). Iodoisopropane (0.04 mL) was added, followed by the addition of Na$_2$CO$_3$ (70 mg). The resulting mixture was stirred at 80° C. overnight. After cooling, it was extracted with EtOAc (3×), dried over MgSO$_4$, filtered, and concentrated to dryness to give crude cis-{1-isopropyl-3-[4-(2-oxo-2H-pyridin-1-yl)-benzoylamino]-piperidin-4-yl}-carbamic acid benzyl ester (115 mg).

Part B

The product from Part A (115 mg) was stirred in CH₃CN (2 mL) at rt. TMSI (0.20 mL) was added. The resulting mixture was stirred for 1.5 h. The solvents were evaporated and dried under vacuum. The residue was dissolved in DMF (2 mL). 3-Chloro-1H-indole-6-carboxylic acid (70 mg), BOP (220 mg), and NMM (0.20 mL) were added. The resulting mixture was stirred at rt for 1 h. H₂O was added. It was concentrated and purified by reverse-phase HPLC to give pure title compound. ¹H NMR (methanol-d₄) δ 8.07 (d J=8.2 Hz, 1H), 7.96 (m, 1H), 7.83 (s, 1H), 7.50–7.36 (m, 7H), 6.60 (m, 1H), 6.45 (m, 1H), 4.94 (m, 1H), 4.51 (m, 1H), 3.71–3.52 (m, 3H), 3.34 (m, 1H), 2.46 (m, 1H), 2.28 (m, 1H), 2.12 (m, 1H), 1.37 (m, 6H) ppm. Anal. LC/MS (ESI) 532.16 (M+H), 530.21 (M−H), $t_R$=3.04 min (10%–90% MeOH in H₂O with 10 mM NH₄OAc in a 4-min run).

Following the same procedure as that for Example 1, Examples 67–73 were prepared.

Example 67

(1R,2S)-6-Chloro-benzo[b]thiophene-2-carboxylic acid {2-[4-(2-oxo-2H-pyridin-1-yl)-benzoylamino]-cyclopentyl}-amide

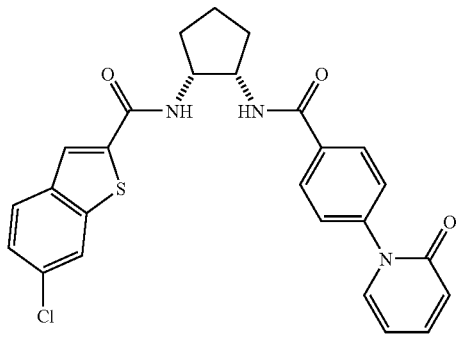

Anal. LC/MS (ESI) 492.2 (M+H).

Example 68

(1R,2S)-6-Chloro-benzo[b]thiophene-2-carboxylic acid {2-[4-(2-oxo-2H-pyridin-1-yl)-benzoylamino]-cyclohexyl}-amide

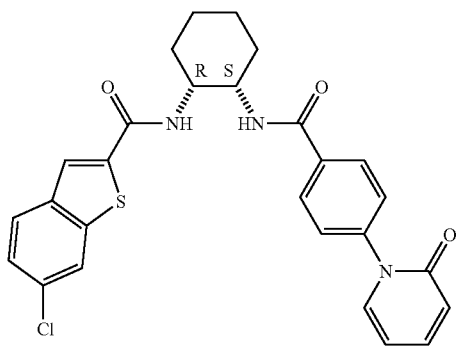

Anal. LC/MS (ESI) 506.2 (M+H).

Example 69

(1R,2S)-5-Chloro-thiophene-2-carboxylic acid {2-[2-fluoro-4-(2-oxo-2H-pyridin-1-yl)-benzoylamino]-cyclopentyl}-amide

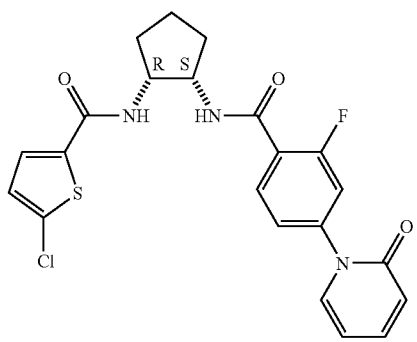

Anal. LC/MS (ESI) 460.2 (M+H).

Example 70

(1R,2S)-5-Chloro-thiophene-2-carboxylic acid {2-[4-(2-oxo-2H-pyrazin-1-yl)-benzoylamino]-cyclopentyl}-amide

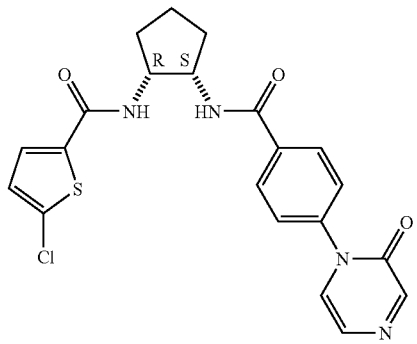

Anal. LC/MS (ESI) 443.2 (M+H).

Example 71

(1R,2S)-6-Chloro-benzo[b]thiophene-2-carboxylic acid {2-[4-(2-oxo-2H-pyrazin-1-yl)-benzoylamino]-cyclohexyl}-amide

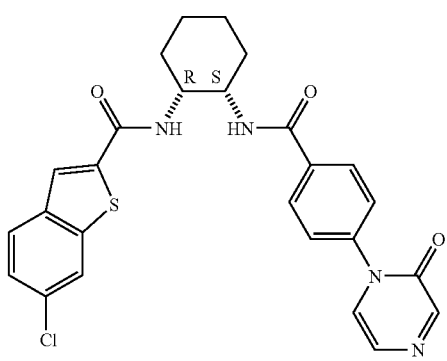

Anal. LC/MS (ESI) 507.2 (M+H).

Example 72

(1S,2R)-2-Oxo-2H-[1,2']bipyridinyl-5'-carboxylic acid {2-[(5-chloro-thiophene-2-carbonyl)-amino]-cyclopentyl}-amide

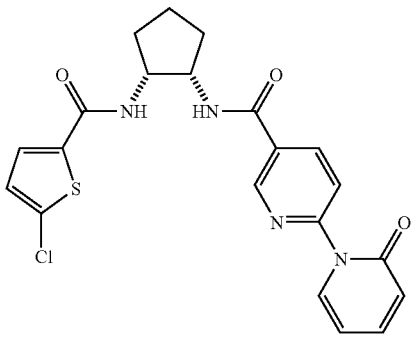

Anal. LC/MS (ESI) 443.2 (M+H).

Example 73

(1R,2S)-5-Chloro-thiophene-2-carboxylic acid {2-[3-methyl-4-(2-oxo-2H-pyridin-1-yl)-benzoylamino]-cyclopentyl}-amide

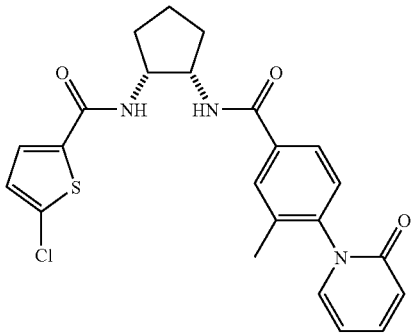

Anal. LC/MS (ESI) 456.2 (M+H).

Example 74

(3R,4S)-3-[(5-Chloro-thiophene-2-carbonyl)-amino]-4-[4-(2-oxo-2H-pyridin-1-yl)-benzoylamino]-pyrrolidine-1-carboxylic acid 9H-fluoren-9-yl methyl ester

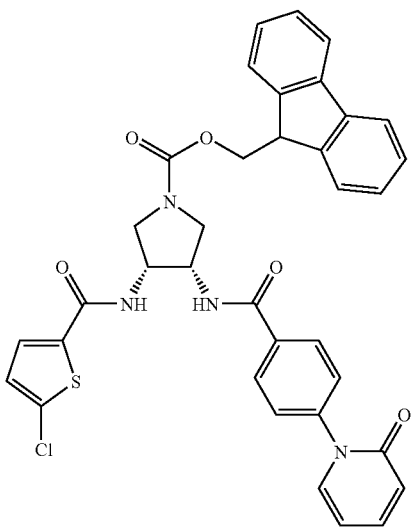

Part A

To a solution of 3-pyrroline (25.0 g, 0.36 mol) in $CH_2Cl_2$ (500 mL) at 0° C. was added $Et_3N$ (60 mL, 0.42 mol), followed by Fmoc-Cl (103 g, 0.39 mole) at 0° C. The reaction mixture was stirred at 0° C. for 1 h, then 30 minutes at it. The reaction mixture was partitioned between $H_2O$ (250 mL) and $CH_2Cl_2$ (150 mL×3). The organic phase was washed with brine and dried over $Na_2SO_4$. The solvent was evaporated, and the residue was purified on silica gel using 5 to 70% EtOAc in hexanes as eluting solvents to afford 2,5-dihydro-pyrrole-1-carboxylic acid 9H-fluoren-9-ylmethyl ester (99 g, 95%) as a white solid. MS m/z 314.0 ([M+Na]$^+$).

Part B

The product from Part A (15.0 g, 51.5 mmol) was dissolved in $CH_2Cl_2$ (100 mL) and m-CPBA (13.3 g, 77.7 mmol) was added. The reaction mixture was stirred at rt overnight. The reaction mixture was filtered through a pad of Celite®, and the filter cake was washed with $CH_2Cl$ (150 mL×2). The filtrate was washed with 10% $K_2CO_3$ (100 mL), sat. $NaHCO_3$ (100 mL), and dried over $Na_2SO_4$. The organic solvent was evaporated and purified on silica gel using 50% EtOAc in hexanes as eluting solvent to afford 6-oxa-3-azabicyclo[3.1.0]hexane-3-carboxylic acid 9H-fluoren-9-ylmethyl ester (8.1 g, 52%) as a white solid. MS m/z 308.0 ([M+H]$^+$).

Part C

To a solution of (S,S)-N,N'-bis(3,5-di-tert-butyl-salicylidene)-1,2-cyclohexane-diaminochromium(III) chloride (293 mg, 0.46 mmol) in $Et_2O$ (2 mL) was add the product from Part B (7.1 g, 23.1 mmol) in $Et_2O$ (6 mL) and THF (1 mL). The reaction mixture was stirred at rt for 20 minutes and was added $TMSN_3$ (4.6 mL, 34.7 mmol). The reaction mixture was stirred at rt for 42 h. The solvent was evaporated under pressure, and the residue was purified by silica gel using 0 to 80% EtOAc in hexane to yield (3R,4R)-3-azido-4-trimethylsilanyl-pyrrolidine-1-carboxylic acid 9H-fluoren-9-ylmethyl ester (7.85 g, 81%) as a white powder. MS m/z 422.0 ([M+H]$^+$).

Part D

To a solution of the product from Part C (5.7 g, 13.5 mmol) in MeOH (20 mL) was added 10-CSA (315 mg, 1.35 mmol). The reaction mixture was stirred at rt for 30 minutes. The solvent was evaporated under pressure and was partitioned between $H_2O$ (100 mL) and EtOAc (100 mL). The organic solvent was further washed with $H_2O$ (20 mL) and brine and dried over $Na_2SO_4$. The solvent was evaporated under pressure to afford (3R,4R)-3-azido-4-hydroxy-pyrrolidine-1-carboxylic acid 9H-fluoren-9-ylmethyl ester (4.0 g, 85%) as a white powder. MS m/z 351.0 ([M+H]$^+$).

Part E

To a solution of the product from Part D (4 g, 11.43 mmol) in EtOAc (40 mL) was added $(Boc)_2O$ (3.3 g, 15 mmol), followed by 10% Pd/C (400 mg). The reaction mixture was stirred at rt under $H_2$ for overnight. The catalyst was filtered through a cake of Celite®. The filtrate was evaporated under pressure and was purified on silica gel using 30% to 80% EtOAc in hexane as eluting solvent to afford (3R,4R)-(9H-fluoren-9-yl)methyl 3-(tert-butoxycarbonylamino)-4-hydroxypyrrolidine-1-carboxylate (4.2 g, 87%) as a white powder. MS m/z 447.6 ([M+Na]$^+$).

Part F

To a mixture of $NaN_3$ (650 mg), $H_2O$ (650 µl), and toluene (4 mL) was added conc. $H_2SO_4$ (135 µl) at 0° C. The reaction mixture was stirred at 0° C. for 30 minutes then 15° C. for another 30 minutes. The solution was cooled to 0° C. and Na₂SO₄ added to dry up excess H₂O. To a solution of PPh₃ (248 mg, 0.943 mmol) in THF (6 mL), cooled to −78° C., was added DEAD (148 μl), followed by a HN₃/toluene solution (680 μl). The reaction mixture was stirred between −74° C. to −60° C. until the solution was clear. A solution of the product from Part E (100 mg, 0.236 mmol) in THF (7 mL) was added as one portion at −78° C. The reaction mixture was stirred at −78° C. for 2 h until the reaction was completed and then quenched with MeOH (5 mL). The solvent was evaporated under pressure, and the residue was purified using 0 to 20% EtOAc in hexane as eluting solvent to afford (3S,4R)-3-azido-4-tert-butoxycarbonylamino-pyrrolidine-1-carboxylic acid 9H-fluoren-9-ylmethyl ester (95 mg, 90%) as a white powder. MS m/z 472 ([M+Na]⁺).

Part G

To a solution of the product from Part F (100 mg, 0.236 mmol) dissolved in MeOH (5 mL) was added 10% Pd/C (10 mg). The reaction mixture was stirred at rt under H₂ for 1 h. The catalyst was filtered through a cake of Celite®, and the filtrate was evaporated under pressure to afford (3S,4R)-3-amino-4-tert-butoxycarbonylamino-pyrrolidine-1-carboxylic acid 9H-fluoren-9-ylmethyl ester (90 mg, 90%) as a white powder. MS m/z 424 ([M+H]⁺).

Part H

To a solution of 4-(2-oxopyridin-1(2H)-yl)benzoic acid (78 mg, 0.362 mmol) in THF (3 mL) and DMF (300 μl) was added a solution of the product from Part G (90 mg, 0.212 mmol) in THF (2 mL), followed by NMM (54 μl, 0.49 mmol). The reaction mixture was stirred at rt for 4 h and diluted with EtOAc (10 mL). The organic layer was washed with H₂O (3 mL), 1N HCl (3 mL), sat.NaHCO₃ (3 mL), and brine and dried over Na₂SO₄. The solvent was evaporated under pressure, and the residue was purified on silica gel using 0 to 5% MeOH in CH₂Cl₂ as the eluting solvent to afford (3R,4S)-3-tert-butoxycarbonylamino-4-[4-(2-oxo-2H-pyridin-1-yl)-benzoylamino]-pyrrolidine-1-carboxylic acid 9H-fluoren-9-ylmethyl ester (63 mg, 44%) as a white powder. MS m/z 643 ([M+Na]⁺).

Part I

To a solution of the product from Part H (30 mg, 0.048 mmol) in THF (1 mL) was added 30% TFA. The reaction was stirred at rt for 1 h. The solvent was evaporated under pressure to afford the unmasked crude amine-TFA salt, (3R,4S)-3-amino-4-[4-(2-oxo-2H-pyridin-1-yl)-benzoylamino]-pyrrolidine-1-carboxylic acid 9H-fluoren-9-ylmethyl ester trifluoroacetic acid salt, as a white foam. This crude product was used without further purification.

Part J

To a suspension of 2-Chlorothiopene-5-carboxylic acid (8.7 mg, 0.068 mmol) in THF (1 mL) was added Bop-reagent (23.5 mg, 0.106 mmol), followed by the crude amine and NMM (8.7 μl, 0.079 mmol). The reaction mixture was stirred at rt overnight. Then, the reaction mixture was partitioned between 1N HCl (2 mL) and EtOAc (2 mL). The organic layer was washed with sat. NaHCO₃ and brine and dried over Na₂SO₄. The solvent was evaporated under pressure, and the residue was purified on silica gel using 5 to 10% MeOH in CH₂Cl₂ to afford the title compound (30 mg, 93%) as a white powder. MS m/z 666 ([M+H]⁺).

Example 75

(3R,4S)-5-Chloro-thiophene-2-carboxylic acid {4-[4-(2-oxo-2H-pyridin-1-yl)-benzoylamino]-pyrrolidin-3-yl}-amide

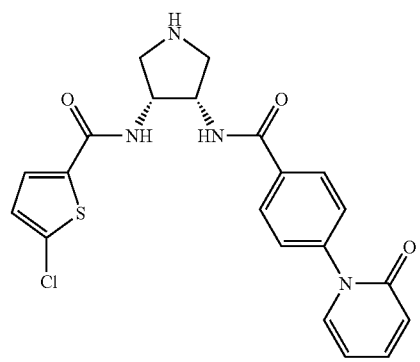

To a solution of the product of Example 74 (30 mg, 0.045 mmol) in THF (1 mL) was added 10% piperidine (100 μl). The reaction mixture was stirred at rt for 3 h and purified on Prep HPLC (Luna 10μ, C₁₈ ₂₅ₓ₁₀₀ mm) using 0 to 100% ACN in H₂O as mobile phase to afford 5-chloro-N-((3R,4S)-4-(4-(2-oxopyridin-1(2H)-yl)benzamido)pyrrolidin-3-yl)thiophene-2-carboxamide (16 mg, 81%) as a white lyophillate. MS m/z 443 ([M+H]⁺).

Using a procedure similar to that of Examples 74 and 75, the Examples 76 and 77 were prepared.

Example 76

(3R,4S)-3-[(3-Chloro-1H-indole-6-carbonyl)-amino]-4-[4-(2-oxo-2H-pyridin-1-yl)-benzoylamino]-pyrrolidine-1-carboxylic acid 9H-fluoren-9-ylmethyl ester

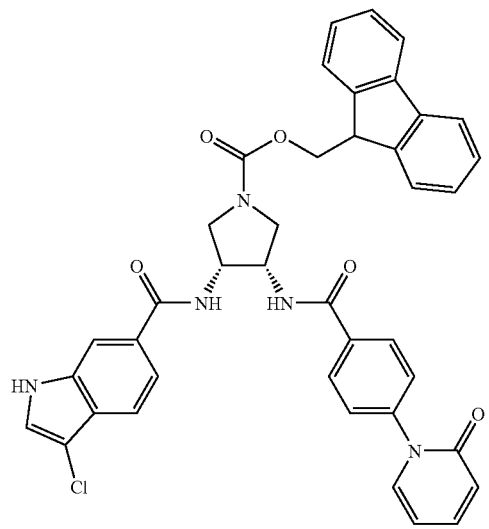

MS m/z 699 ([M+H]⁺).

Example 77

(3R,4S)-3-Chloro-1H-indole-6-carboxylic acid {4-[4-(2-oxo-2H-pyridin-1-yl)-benzoylamino]-pyrrolidin-3-yl}-amide

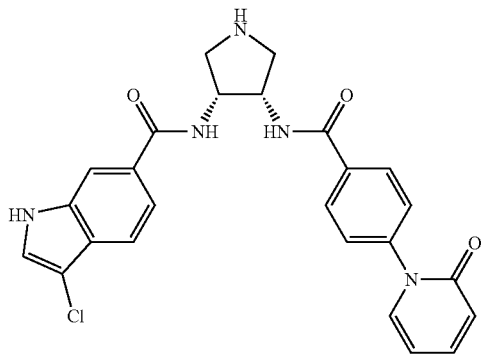

MS m/z 476 ([M+H]+).

Example 78

(3R,4S)-5-Chloro-thiophene-2-carboxylic acid {1-acetyl-4-[4-(2-oxo-2H-pyridin-1-yl)-benzoylamino]-pyrrolidin-3-yl}-amide

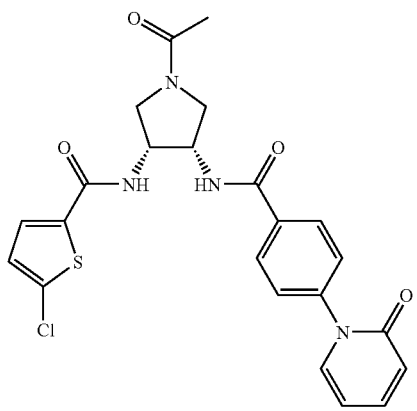

To a solution of Example 75 (6 mg, 0.013 mmol) in THF (200 µl) at 0° C. was added Et₃N (3 µl, 0.021 mmol) followed by the acetic anhydride (5 µl, 0.04 mmol). The reaction mixture was stirred at 0° C. for 5 minutes and then at rt for 10 minutes. The solvent was evaporated under pressure, and the residue was purified by preparative HPLC using 0 to 100% B over 10 minutes (Column, Luna 10µ, C18 25×100 mm; Solvent A, 10% ACN +90% H₂O with 0.1% TFA; Solvent B, 90% ACN+10% H₂O with 0.1% TFA) to afford the title compound (2.8 mg, 48%) as a white lyophilite. MS m/z 486 ([M+H]+).

Example 79

(3R,4S)-3-Chloro-1H-indole-5-carboxylic acid {1-acetyl-4-[4-(2-oxo-2H-pyridin-1-yl)-benzoylamino]-pyrrolidin-3-yl}-amide

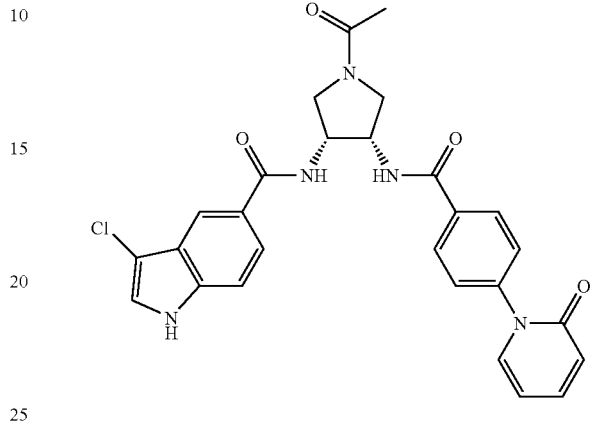

To a solution of Example 77 (3.5 mg, 0.008 mmol) was in THF (500 µl) was added WA-21 J resin (10 mg). The reaction mixture was stirred at rt for 5 minutes, followed by the acetic chloride (5 µl). The reaction mixture was stirred at rt for 10 minutes and was purified by Preparative HPLC (Column, Luna 10µ, C18 25×100 mm) using 0 to 100% B over 10 minutes gradient (Solvent A, 10% ACN+90% H₂O with 0.1% TFA; Solvent B, 90% ACN+10% H₂O with 0.1% TFA) to afford the title compound (2.2 mg, 54%) as a white lyophilite. MS m/z 518 ([M+H]+).

Using a procedure similar to that of Example 79, Examples 80 to 93 were prepared.

Example 80

(3R,4S)-5-Chloro-thiophene-2-carboxylic acid {1-cyclopropanecarbonyl-4-[4-(2-oxo-2H-pyridin-1-yl)-benzoylamino]-pyrrolidin-3-yl}-amide

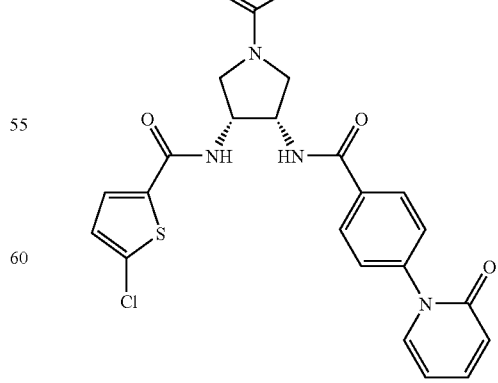

MS m/z 512 ([M+H]+).

Example 81

(3R,4S)-5-Chloro-thiophene-2-carboxylic acid {1-(2,2-dimethyl-propionyl)-4-[4-(2-oxo-2H-pyridin-1-yl)-benzoylamino]-pyrrolidin-3-yl}-amide

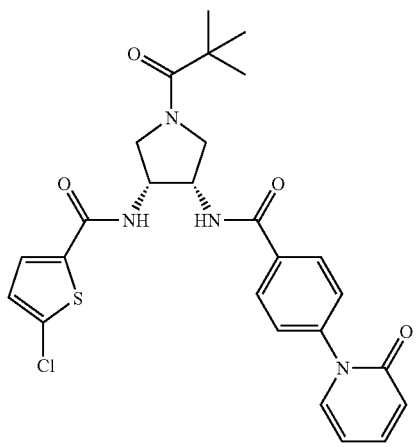

MS m/z 786 ([M+H]$^+$).

Example 82

(3R,4S)-5-Chloro-thiophene-2-carboxylic acid {4-[4-(2-oxo-2H-pyridin-1-yl)-benzoylamino]-1-propionyl-pyrrolidin-3-yl}-amide

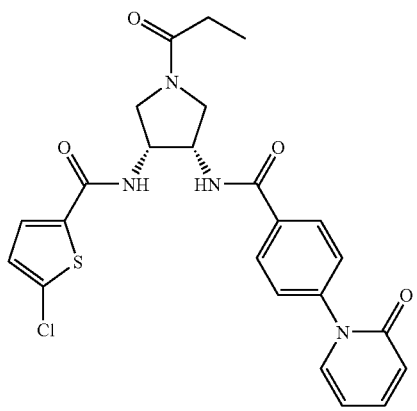

MS m/z 499 ([M+H]$^+$).

Example 83

(3R,4S)-5-Chloro-thiophene-2-carboxylic acid {1-(2-methoxy-acetyl)-4-[4-(2-oxo-2H-pyridin-1-yl)-benzoylamino]-pyrrolidin-3-yl}-amide

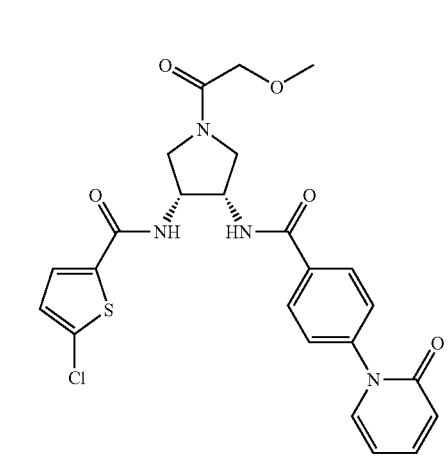

MS m/z 515 ([M+H]$^+$).

Example 84

(3R,4S)-5-Chloro-thiophene-2-carboxylic acid {1-isobutyryl-4-[4-(2-oxo-2H-pyridin-1-yl)-benzoylamino]-pyrrolidin-3-yl}-amide

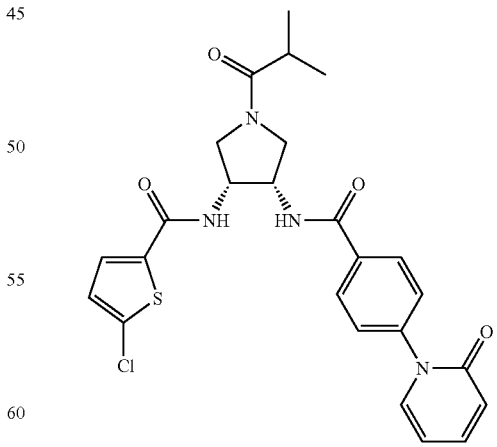

MS m/z 513 ([M+H]$^+$).

Example 85

(3R,4S)-5-Chloro-thiophene-2-carboxylic acid {1-benzoyl-4-[4-(2-oxo-2H-pyridin-1-yl)-benzoylamino]-pyrrolidin-3-yl}-amide

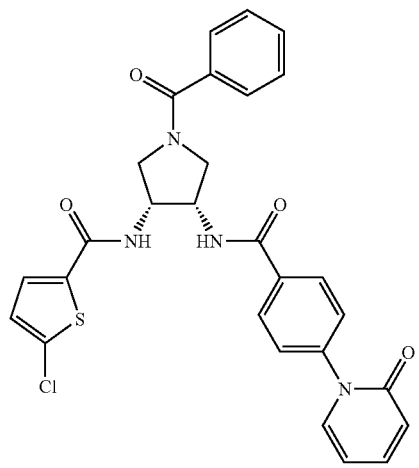

MS m/z 547 ([M+H]$^+$).

Example 86

(3R,4S)-5-Chloro-thiophene-2-carboxylic acid {1-methanesulfonyl-4-[4-(2-oxo-2H-pyridin-1-yl)-benzoylamino]-pyrrolidin-3-yl}-amide

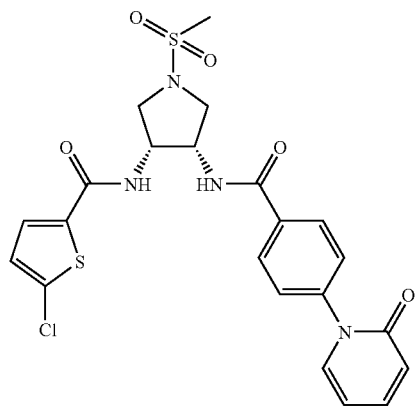

MS m/z 522 ([M+H]$^+$).

Example 87

(3R,4S)-5-Chloro-thiophene-2-carboxylic acid {1-ethanesulfonyl-4-[4-(2-oxo-2H-pyridin-1-yl)-benzoylamino]-pyrrolidin-3-yl}-amide

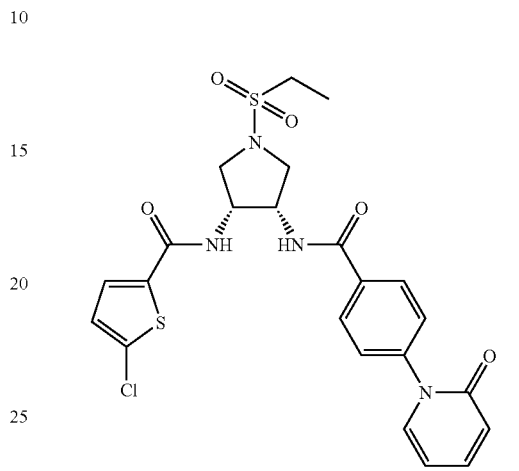

MS m/z 535 ([M+H]$^+$).

Example 88

(3R,4S)-5-Chloro-thiophene-2-carboxylic acid [4-[4-(2-oxo-2H-pyridin-1-yl)-benzoylamino]-1-(propane-2-sulfonyl)-pyrrolidin-3-yl]-amide

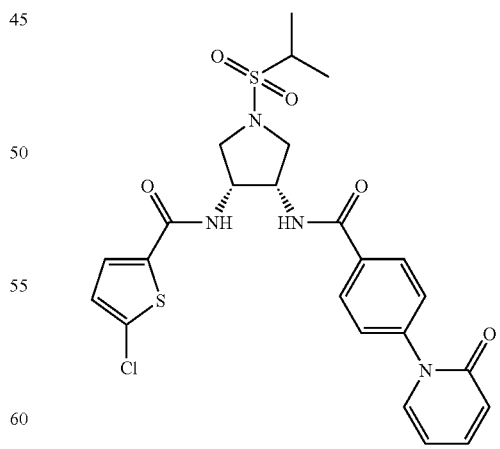

MS m/z 550 ([M+H]$^+$).

Example 89

(3R,4S)-5-Chloro-thiophene-2-carboxylic acid [4-[4-(2-oxo-2H-pyridin-1-yl)-benzoylamino]-1-(pyrrolidine-1-carbonyl)-pyrrolidin-3-yl]-amide

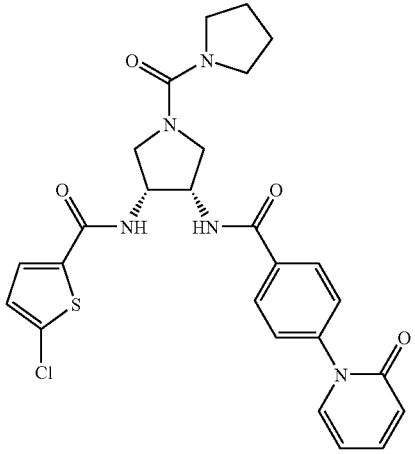

MS m/z 540 ([M+H]+).

Example 90

(3R,4S)-3-[(3-Chloro-1H-indole-5-carbonyl)-amino]-4-[4-(2-oxo-2H-pyridin-1-yl)-benzoylamino]-pyrrolidine-1-carboxylic acid ethyl ester

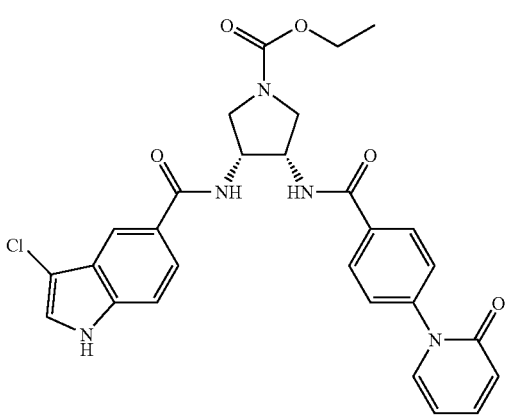

To a solution of Example 77 (5 mg, 0.0113 mmol) in THF (200 μl) was added sat. NaHCO$_3$ (200 μl), followed by ethyl chlorofomate (5 μl). The reaction mixture was stirred at rt for 25 minutes. The layers were separated and the aqueous layer was washed further with THF (1 mL). The organic layers were combined and dried over Na$_2$SO$_4$. The solvent was evaporated under pressure, and the residue was purified by Preparative HPLC ((Column, Luna 10μ, C18 25×100 mm) using 0 to 100% B over 10 minutes gradient (Solvent A, 10% ACN+90% H2O with 0.1% TFA; Solvent B, 90% ACN+10% H$_2$O with 0.1% TFA) to afford the title compound (4.2 mg, 80%) as a white lyophillate. MS m/z 515 ([M+H]+).

Using a procedure similar to that of Example 90, Examples 91 to 93 were prepared.

Example 91

(3R,4S)-3-[(5-Chloro-thiophene-2-carbonyl)-amino]-4-[4-(2-oxo-2H-pyridin-1-yl)-benzoylamino]-pyrrolidine-1-carboxylic acid methyl ester

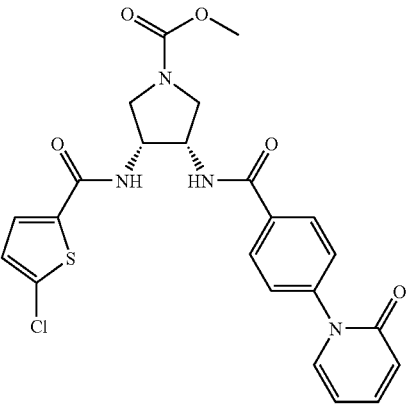

MS m/z 501 ([M+H]+).

Example 92

(3R,4S)-3-[(5-Chloro-thiophene-2-carbonyl)-amino]-4-[4-(2-oxo-2H-pyridin-1-yl)-benzoylamino]-pyrrolidine-1-carboxylic acid ethyl ester

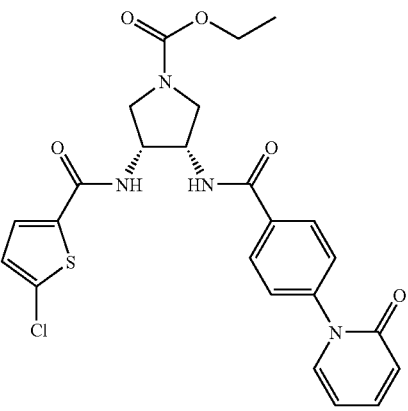

MS m/z 515 ([M+H]+).

Example 93

(3R,4S)-3-[(5-Chloro-thiophene-2-carbonyl)-amino]-4-[4-(2-oxo-2H-pyridin-1-yl)-benzoylamino]-pyrrolidine-1-carboxylic acid 2-methoxyethyl ester

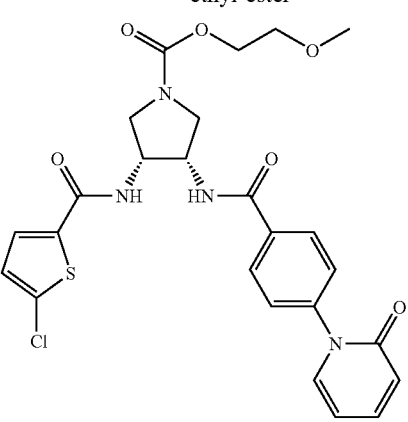

MS m/z 545 ([M+H]+).

Example 94

(1S,3R,4S)-3-[(5-Chloro-thiophene-2-carbonyl)-amino]-4-[4-(2-oxo-2H-pyridin-1-yl)-benzoylamino]-cyclopentanecarboxylic acid

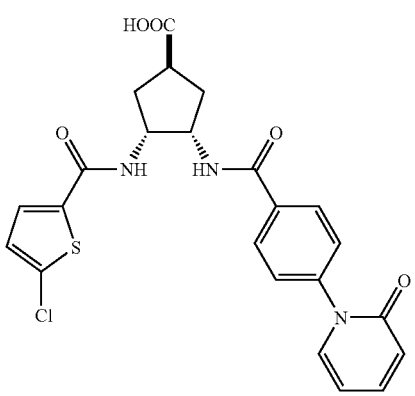

The product from Example 16 (440 mg) was stirred in THF (6 mL) at 0° C. H$_2$O (1.5 mL) was added, followed by LiOH (50 mg). The mixture was stirred at 0° C. for 2 h. TLC showed completion of the reaction. It was concentrated, acidified with TFA, and purified by RPHPLC (CH$_3$CN/H$_2$O with 0.1% TFA) to give the title compound. MS (ESI) 486.1 (M+H).

Example 95

(1R,2S,4S)-5-Chloro-thiophene-2-carboxylic acid {4-hydroxymethyl-2-[4-(2-oxo-2H-pyridin-1-yl)-benzoylamino]-cyclopentyl}-amide

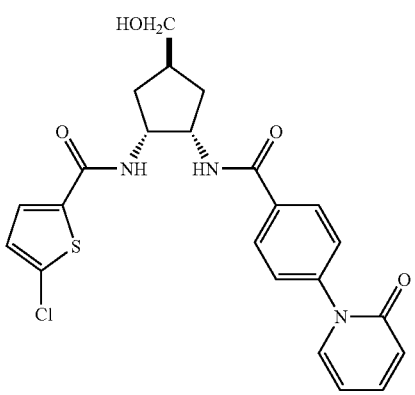

The product from Example 94 (0.22 g, 0.45 mmol) was stirred in THF (10 mL) at 0° C., Et$_3$N (0.095 mL, 0.68 mmol, 1.5 eq) was added followed by dropwise addition of ClCOOEt (0.051 mL, 0.54 mmol, 1.2 eq). The mixture was stirred at 0° C. for 1 h. It was filtered and rinsed with THF (10 mL). The THF solution was stirred at 0° C. MeOH (5 mL) was added followed by addition of NaBH$_4$ (0.25 mg, 6.6 mmol). The resulting mixture was stirred at 0° C. for 1 h. LC/MS showed completion of the reaction. EtOAc was added, it was washed with NH$_4$Cl, H$_2$O, and brine. The organic layer was concentrated, and purified by reverse phase HPLC (MeOH/H$_2$O in 0.1% TFA) to give pure title compound. LC-MS (ESI) 472.12, 474.04 (M+H), 488.06 (M+Na), t$_R$=2.54 min (10–90% MeOH in H$_2$O with 0.1% TFA in a 4-min run).

Example 96

(1S,2R)-5-Chloro-thiophene-2-carboxylic acid {1-[4-(2-oxo-piperidin-1-yl)-benzoylamino]-indan-2-yl}-amide

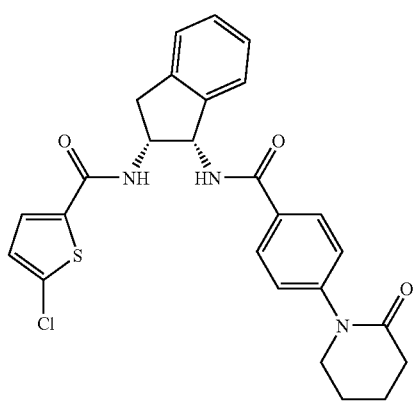

Following a similar synthetic sequence as that of Example 59, the title compound was obtained. LC-MS (ESI) 494.07, 496.11 (M+H), t$_R$=3.19 min (10–90% MeOH in H$_2$O with 0.1% TFA in a 4-min run).

Example 97

(3S,4R)-5-Chloro-thiophene-2-carboxylic acid {4-[4-(2-oxo-2H-pyridin-1-yl)-benzoylamino]-tetrahydro-furan-3-yl}-amide

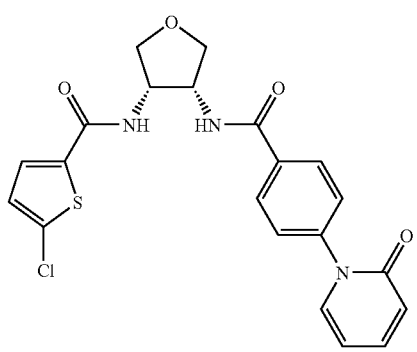

Following a similar procedure as that of Example 74, but using 3,4-epoxytetrahydrofuran as one of the starting materials instead of, the title compound was obtained. $^1$H NMR (400 MHz, methanol-d$_4$) δ 7.86 (dd, J=6.6, 1.9 Hz, 2H), 7.61 (m, 2H), 7.48 (m, 3H), 6.96 (d, J=4.0 Hz, 1H), 6.65 (d, J=9.1 Hz, 1H), 6.50 (td, J=7.0, 1.0 Hz, 1H), 4.86 (m, 2H), 4.15 (m, 2H), 3.91 (m, 2H) ppm. LC-MS (ESI) 444.12, 446.11 (M+H), 466.10 (M+Na), t$_R$=2.50 min (10–90% MeOH in H$_2$O with 0.1% TFA in a 4-min run).

Example 98

(3S,R4)-3-Chloro-1H-indole-6-carboxylic acid {4-[4-(2-oxo-2H-pyridin-1-yl)-benzoylamino]-tetrahydro-furan-3-yl}-amide

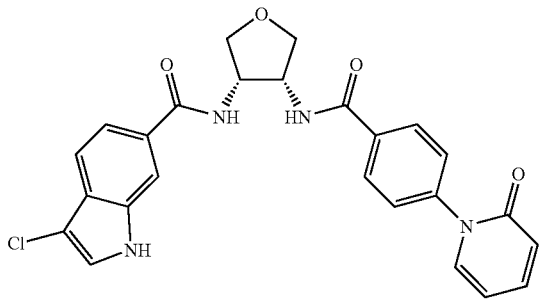

Following the similar procedure as that of Example 97, the title compound was obtained. LC-MS (ESI) 477.07, 479.12 (M+H), $t_R$=2.79 min (10–90% MeOH in H$_2$O with 0.1% TFA in a 4-min run).

Following the same procedure as that of Example 1, Examples 99–110 were prepared and purified:

Example 99

(1R,2S)-6-Chloro-naphthalene-2-carboxylic acid {2-[4-(2-oxo-2H-pyridin-1-yl)-benzoylamino]-cyclopentyl}-amide

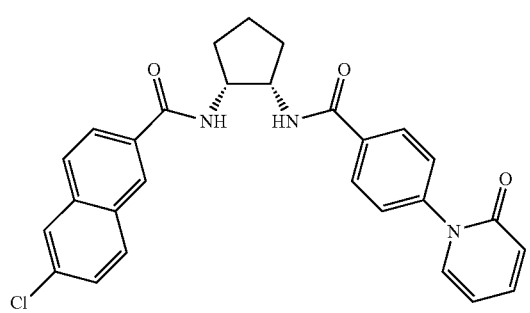

MS m/z 486 ([M+H]$^+$).

Example 100

(1R,2S)-5-Chloro-3a,7a-dihydro-benzo[b]thiophene-2-carboxylic acid {2-[4-(2-oxo-2H-pyridin-1-yl)-benzoylamino]-cyclopentyl}-amide

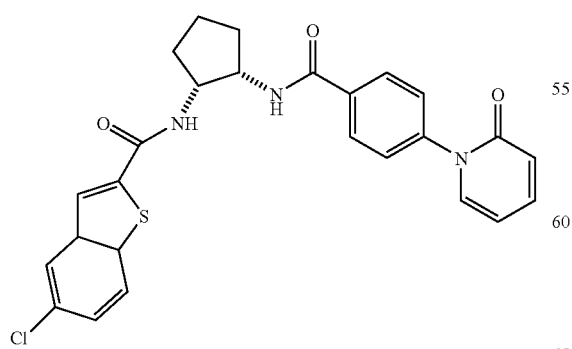

MS (ESI) 494.1 (M+H).

Example 101

(1R,2S)-3-Chloro-phenyl-carboxylic acid {2-[4-(2-oxo-2H-pyridin-1-yl)-benzoylamino]-cyclopentyl}-amide

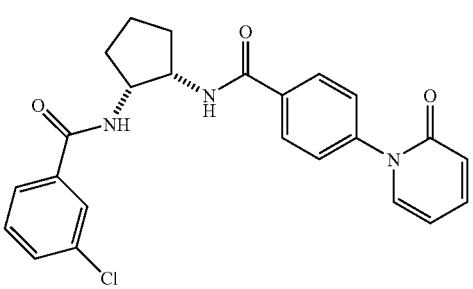

MS m/z 436 ([M+H]$^+$).

Example 102

(1R,2S)-2-Chloro-phenyl-carboxylic acid {2-[4-(2-oxo-2H-pyridin-1-yl)-benzoylamino]-cyclopentyl}-amide

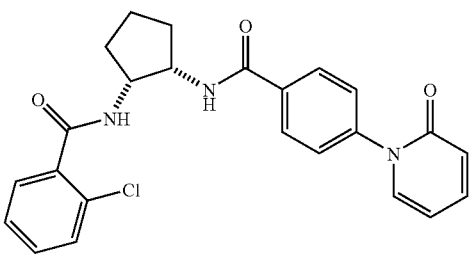

LC-MS (ESI) 436.12, 438.13 (M+H), 458.09 (M+Na), $t_R$=2.31 min (10–90% MeOH in H$_2$O with 10 mM NH$_4$OAc in a 4-min run).

Example 103

(1R,2S)-3,4-Dichloro-phenyl-carboxylic acid {2-[4-(2-oxo-2H-pyridin-1-yl)-benzoylamino]-cyclopentyl}-amide

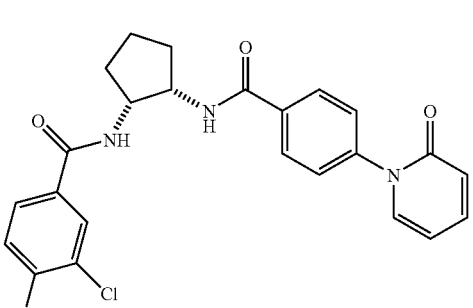

LC-MS (ESI) 469.99 (M+H), $t_R$=3.04 min (10–90% MeOH in H$_2$O with 0.1% TFA in a 4-min run).

Example 104

(1R,2S)-4-Chloro-2-fluoro-phenyl-carboxylic acid {2-[4-(2-oxo-2H-pyridin-1-yl)-benzoylamino]-cyclopentyl}-amide

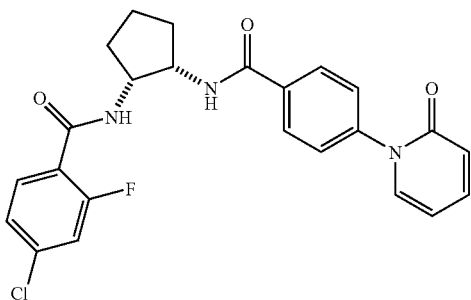

LC-MS (ESI) 454.14, 456.16 (M+H), $t_R$=2.72 min (10–90% MeOH in H$_2$O with 0.1% TFA in a 4-min run).

Example 105

(1R,2S)-2,4-Dichloro-phenyl-carboxylic acid {2-[4-(2-oxo-2H-pyridin-1-yl)-benzoylamino]-cyclopentyl}-amide

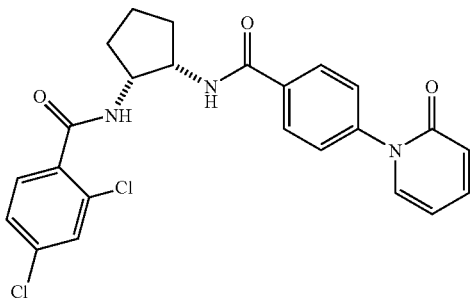

LC-MS (ESI) 469.99 (M+H), $t_R$=2.77 min (10–90% MeOH in H$_2$O with 10 mM NH$_4$OAc in a 4-min run).

Example 106

(1R,2S)-4-Chloro-2-methyl-phenyl-carboxylic acid {2-[4-(2-oxo-2H-pyridin-1-yl)-benzoylamino]-cyclopentyl}-amide

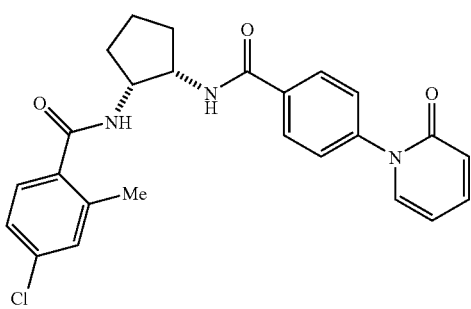

LC-MS (ESI) 450.17, 452.19 (M+H), $t_R$=2.80 min (10–90% MeOH in H$_2$O with 10 mM NH$_4$OAc in a 4-min run).

Example 107

(1R,2S)-4-Methoxy-phenyl-carboxylic acid {2-[4-(2-oxo-2H-pyridin-1-yl)-benzoylamino]-cyclopentyl}-amide

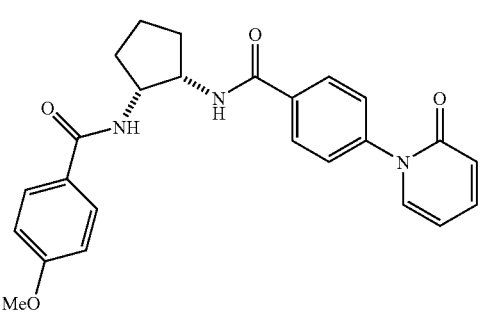

LC-MS (ESI) 432.24 (M+H), 430.23 (M–H), $t_R$ 2.41 min (10–90% MeOH in H$_2$O with 10 mM NH$_4$OAc in a 4-min run).

Example 108

(1R,2S)-3-Methoxy-phenyl-carboxylic acid {2-[4-(2-oxo-2H-pyridin-1-yl)-benzoylamino]-cyclopentyl}-amide

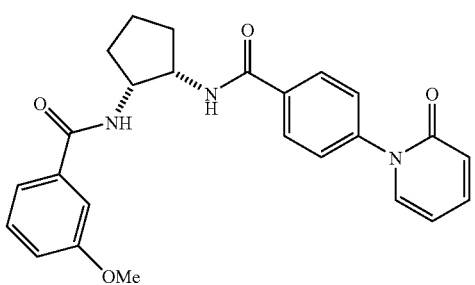

LC-MS (ESI) 432.12 (M+H), $t_R$=2.44 min (10–90% MeOH in H$_2$O with 10 mM NH$_4$OAc in a 4-min run).

Example 109

(1R,2S)-2-Chloro-thiazole-5-carboxylic acid {2-[4-(2-oxo-2H-pyridin-1-yl)-benzoylamino]-cyclopentyl}-amide

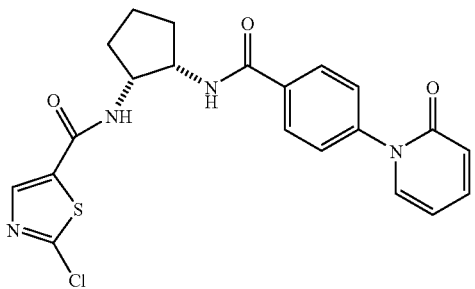

MS m/z 447 ([M+H]$^+$).

Example 110

(1R,2S)-N-{2-[3-(4-Chloro-phenyl)-ureido]-cyclopentyl}-4-(2-oxo-2H-pyridin-1-yl)-benzamide

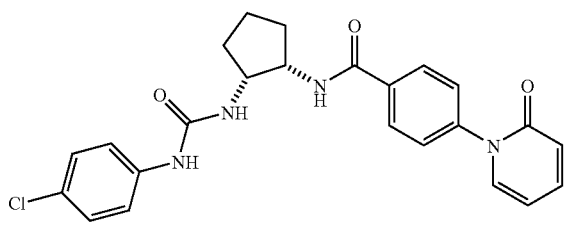

LC-MS (ESI) 451.13 (M+H), 473.09 (M+Na), $t_R$=2.92 min (10–90% MeOH in H$_2$O with 0.1% TFA in a 4-min run).

Example 111

(1S,2R)-[2,2']Bithiophenyl-5-carboxylic acid {2-[4-(2-oxo-2H-pyridin-1-yl)-benzoylamino]-cyclopentyl}-amide

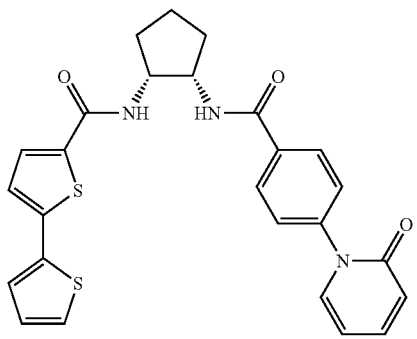

MS m/z 490 ([M+H]$^+$).

Example 112

Cis-3-[(3-Chloro-1H-indole-6-carbonyl)-amino]-4-[4-(2-oxo-2H-pyridin-1-yl)-benzoylamino]-piperidine-1-carboxylic acid tert-butyl ester

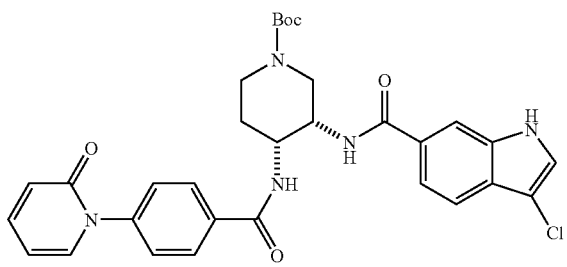

Part A 1,2,3,6-Tetrahydropyridine (7.30 g, 0.0878 mmol) was dissolved in 10% aqueous Na$_2$CO$_3$ (30 mL). The solution was cooled to 0° C. Di-tert-butyl dicarbonate (19.4 g, 887 mmol) was added portion wise over 20 min. The solution was stirred at 0° C. for 1 hr, warmed to rt, and stirred overnight. The reaction solution was partitioned between Et$_2$O and saturated NaCl. The organic layer was dried over MgSO$_4$ and concentrated in vacuo to give 3,6-dihydro-2H-pyridine-1-carboxylic acid tert-butyl ester as a yellow oil (14.9 g, 93%). LC-MS: (M+H): 184.

Part B

The product from Part A (14.9 g, 81.4 mmol) was dissolved in CH$_2$Cl$_2$ (100 mL), and the solution was cooled in an ice-water bath. m-CPBA (18.25 g, 106 mmol) in CH$_2$Cl$_2$ (200 mL) was then added over 30 min. The reaction mixture was allowed to warm to rt and stirred overnight. The mixture was washed with 5% aqueous K$_2$CO$_3$ (2×100 mL) and saturated NaCl (2×100 mL), dried over MgSO$_4$, and concentrated in vacuo to yield a white foam. Further purification by flash chromatography (ISCO system, 20% EtOAc/Hex) gave 7-oxa-3-aza-bicyclo[4.1.0]heptane-3-carboxylic acid tert-butyl ester as a colorless oil (10.96 g, 67%). LC-MS: (M+H): 200.

Part C

The product from Part B (930 mg, 4.67 mmol), NaN$_3$ (364 mg, 5.60 mmol), NH$_4$Cl (300 mg, 5.60 mmol), CH$_3$OH (6 mL), and H$_2$O (4 mL) were refluxed overnight. The solution was reduced in vacuo, and CH$_2$Cl$_2$ (50 mL) added. The mixture was then washed with saturated NaCl (2×20 mL), dried over MgSO$_4$, and evaporated to give 873 mg of trans-4-azido-3-hydroxy-piperidine-1-carboxylic acid tert-butyl ester. LC-MS: (M+Na): 265.

Part D

The product from part C (873 mg, 3.60 mmol) was dissolved in CH$_3$OH (12 mL), and the mixture was hydrogenated overnight in the presence of 10% Pd/C (218 mg, 25% weight) at rt and atmospheric pressure. The catalyst was removed by filtration, and the solution reduced in vacuo to give trans-4-amino-3-hydroxy-piperidine-1-carboxylic acid tert-butyl ester as a colorless oil (779 mg). LC-MS: (M+Na+H)$^+$: 240.

The crude material (779 mg, 3.60 mmol) was dissolved in THF (22 mL) and H$_2$O (5 mL) along with Et$_3$N (1.5 mL) and (Cbz)$_2$O (1.14 g, 3.98 mmol). The mixture was stirred at ambient temperature overnight. After solvent removal, the residue was mixed with ether; washed with 10% citric acid, H$_2$O, saturated NaHCO$_3$, and brine; dried; and, evaporated to yield a brown oil. The desired compound, cis 4-benzyloxycarbonylamino-3-hydroxy-piperidine-1-carboxylic acid tert-butyl ester, was obtained as a white foam (607 mg) after purification by flash column chromatography (ISCO system 42% EtOAc/Hex). LC-MS: (M+Na)$^+$: 373.

Part E

The product from Part D (607 mg, 1.73 mmol), Et$_3$N (0.313 mL, 2.25 mmol), and CH$_2$Cl$_2$ (6 mL) were stirred at 0° C. under N$_2$. To this mixture was added dropwise MsCl (0.15 mL, 1.90 mmol), and stirring was continued for 2 h. CH$_2$Cl$_2$ (10 mL) was added, and the mixture was washed with H$_2$O and brine, dried over MgSO$_4$, filtered, and concentrated to dryness to yield the mesylate as an oily residue. LC-MS: (M+Na): 451.

The mesylate residue was dissolved in DMSO (4.5 mL), and NaN$_3$ (450 mg, 6.92 mmol) was added. The mixture was stirred at 93° C. overnight. After cooling, the mixture was partitioned between EtOAc and H$_2$O. The organic layer was washed with H$_2$O and brine, dried, and concentrated to dryness to give Cis-3-azido-4-benzyloxycarbonylamino-piperidine-1-carboxylic acid tert-butyl ester (610 mg). LC-MS: (M+H)⁺: 350.

Part F

A mixture of the product from Part E (610 mg, 1.62 mmol), PPh₃ (2.65 g, 10.11 mmol), THF (55 mL), and H₂O (1.7 mL) was heated at 65° C. overnight. Upon cooling, the reaction mixture was partitioned between EtOAc (30 mL) and 1N HCl (30 mL). The organic phase was washed with 1N HCl (4×25 mL). The combined aqueous layers were basified with Na₂CO₃, extracted with CH₂Cl₂ (4×30 mL), dried over MgSO₄, filtered, and concentrated to give crude cis-3-amino-4-benzyloxycarbonylamino-piperidine-1-carboxylic acid tert-butyl ester (500 mg). LC-MS: (M+H)⁺: 350.

Part G

The product from part F (500 mg, 1.431 mmol) was mixed with 10% Na₂CO₃ (20 mL) and cooled with an ice-water bath. To the cooled mixture was added a cooled (0° C.) dioxane solution (7 mL) of Fmoc-Cl (374 mg, 1.445 mmol). The reaction mixture was stirred for 2 hr. EtOAc (50 mL) was added. The mixture was washed with brine, dried over MgSO₄, filtered, and evaporated. The crude product was purified by flash chromatography (ISCO system 35% EtOAc/Hexane) to yield cis-4-benzyloxycarbonylamino-3-(9H-fluoren-9-ylmethoxycarbonylamino)-piperidine-1-carboxylic acid tert-butyl ester as a white foam (430 mg). LC-MS: (M+Na)⁺: 594.

Part H

The product from Part G (430 mg, 0.752 mmol) was dissolved in CH₃OH (5 mL) and hydrogenated in the presence of 10% Pd/C (108 mg, 25% weight) at rt and atmospheric pressure. After 3.5 h, the catalyst was removed and the organic phase concentrated to give cis-tert-butyl 3-(((9H-fluoren-9-yl)methoxy)carbonylamino)-4-aminopiperidine-1-carboxylate (317 mg). LC-MS: (M+H): 438

Part I

The product from part H (317 mg, 0.725 mmol) was dissolved in CH₂Cl₂ (10 mL) and cooled to 0° C. Et₃N (0.303 mL, 2.175 mmol) was added, followed by freshly prepared 4-(2-oxopyridin-1(2H)-yl)benzoyl chloride (203 mg, 0.870 mmol). The reaction mixture was stirred at rt overnight. Saturated NaHCO₃ solution (10 mL) was then added. The mixture extracted with EtOAc (2×30 mL), washed with brine (2×20 mL), dried over MgSO₄, and concentrated. The crude product was purified by flash chromatography (ISCO system 100% EtOAc) to yield cis-3-(9H-fluoren-9-ylmethoxycarbonylamino)-4-[4-(2-oxo-2H-pyridin-1-yl)-benzoylamino]-piperidine-1-carboxylic acid tert-butyl ester as a colorless oil (120 mg). LC-MS: (M+Na): 657.

Part J

The product from part I (120 mg) was dissolved in THF (5 mL) and cooled to 0° C. Piperidine (0.5 mL) was then added. The mixture was stirred at rt for 3 h, and a white precipitate formed. The mixture was extracted with EtOAc (20 mL) and washed with 1 N HCl (4×15 mL). The aqueous layer was basified with NaHCO₃, extracted with CH)Cl₂ (4×20 mL), dried over MgSO₄, filtered, and concentrated to give crude cis-3-amino-4-[4-(2-oxo-2H-pyridin-1-yl)-benzoylamino]-piperidine-1-carboxylic acid tert-butyl ester (120 mg) as a slightly yellow oil. LC-MS: (M+H): 413.

Part K

The product from part J (120 mg, 0.296 mmol) was dissolved in THF (5 mL) and cooled to 0° C. 6-Chloro-indole-3-carboxylic acid (56 mg, 0.296 mmol), BOP (170 mg, 0.384 mmol), and nMM (58 µl, 0.532 mmol) were then added. The yellow solution was stirred overnight at rt. The mixture was partitioned between EtOAc (20 mL) and 1 N HCl (10 mL). The organic layer was washed with NaHCO₃ and brine and dried. The crude product was purified by silica gel flash column chromatography (10% MeOH/EtOAc) to give the title compound as an off-white solid (60 mg). LC-MS: (M+Na): 612.

Example 113

Cis-3-Chloro-1H-indole-6-carboxylic acid {4-[4-(2-oxo-2H-pyridin-1-yl)-benzoylamino]-piperidin-3-yl}-amide

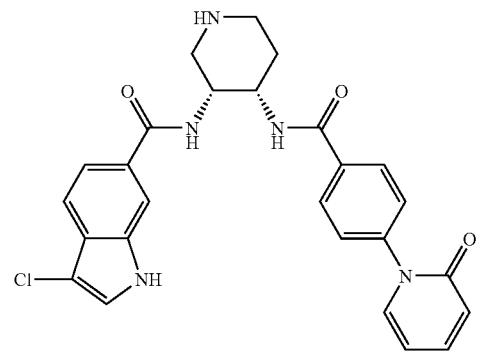

The N-Boc protected compound from Example 112 (15 mg, 0.0254 mmol) was dissolved in CH₂Cl₂ (2 mL) at 0° C. TFA (1.0 mL) was then added. The mixture was warmed to rt and stirred for 1 h. The solvent was removed in vacuo to give a yellow oil. The crude material was dissolved in MeOH and purified by reverse phase HPLC to give the title compound in a nearly quantitative yield. LC-MS: (M+H)⁺: 490.

Example 114

Cis-5-Chloro-thiophene-2-carboxylic acid {1-cyclopropanecarbonyl-4-[4-(2-oxo-2H-pyridin-1-yl)-benzoylamino]-piperidin-3-yl}-amide

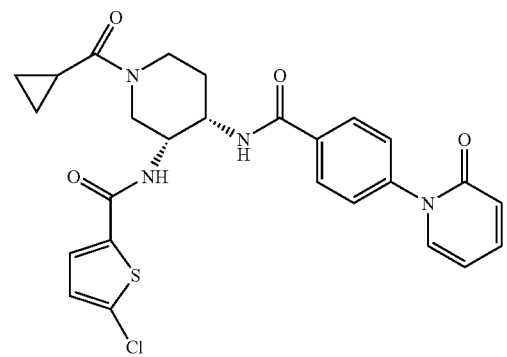

Part A

Cis-3-amino-4-benzyloxycarbonylamino-piperidine-1-carboxylic acid tert-butyl ester (450 mg, 1.288 mmol), from Part F of Example 112, was added to a cooled mixture (0° C.) of 5-chloro-thiophen-carboxylic chloride (233 mg, 1.288 mmol), Et$_3$N (0.54 mL, 3.864 mmol), and CH$_2$Cl$_2$ (10 mL). The mixture stirred overnight at rt. EtOAc (70 mL) was added. The mixture was washed with brine, and the organic phase dried over MgSO$_4$ and concentrated. The crude product was purified by silica gel flash column chromatography (30% MeOH/EtOAc) to yield cis-4-benzyloxycarbonylamino-3-[(5-chloro-thiophene-2-carbonyl)-amino]-piperidine-1-carboxylic acid tert-butyl ester as a white solid (236 mg). LC-MS: (M-100): 394.

Part B

The product from part A (79 mg, 0.160 mmol) was dissolved in CH$_2$Cl$_2$ (2 mL) and cooled to 0° C. TFA (1.2 mL) was then added. The reaction mixture was stirred for 1.5 h at rt and the solvent removed in vacuo to give a yellow oil (63 mg) of the free amine as a TFA salt. To this residue was added CH$_2$Cl$_2$ (4 mL). The solution was cooled to 0° C. Et$_3$N (0.05 mL) was added, followed by cyclopropanecarbonyl chloride (16 µL). Stirring at rt continued for 2 h. The reaction mixture was quenched with H$_2$O (20 mL), extracted with CH$_2$Cl$_2$ (3×20 mL), dried over MgSO$_4$, and concentrated to give cis-{3-[(5-chloro-thiophene-2-carbonyl)-amino]-1-cyclopropanecarbonyl-piperidin-4-yl}-carbamic acid benzyl ester as a yellow solid (74 mg). LC-MS: (M+H): 462.

Part C

The product from part B (74 mg, 0.160 mmol) was dissolved in CH$_3$CN (1.5 mL) and cooled to 0° C. TMSI (55 µL, 0.383 mmol) was then added. The mixture was stirred for 5 min. EtOAc (20 mL) was added, and the reaction mixture extracted with 1N HCl (4×15 mL). The aqueous layers were combined, basified with NaHCO$_3$, and extracted with CH$_2$Cl$_2$ (4×20 mL). The combined organic phases were dried over MgSO$_4$, filtered, and concentrated to give cis-5-chloro-thiophene-2-carboxylic acid (4-amino-1-cyclopropanecarbonyl-piperidin-3-yl)-amide as a colorless oil (50 mg). LC-MS: (M+H): 328.

Part D

The amine from Part C was dissolved in CH$_2$Cl$_2$ (5 mL) and cooled to 0° C. Et$_3$N (0.064 mL) was added, followed by 4-(2-oxo-2H-pyridin-1-yl)-benzoic acid chloride (39 mg, 0.167 mmol). The mixture was stirred at rt for 2 h and concentrated. The residue was dissolved in MeOH and purified by reverse phase HPLC to give the title compound as an off-white solid (23.7 mg). LC-MS: (M)$^+$: 525. $^1$H NMR (500 MHz, CD$_3$OD-d6) δ 7.91 (d, J=8.74 Hz, 2H), 7.63 (m, 2H), 7.55 (m, 1H), 7.48 (t, J=9.41 Hz, 3H), 7.03 (m, 1H), 6.63 (d, J=8.74 Hz, 1H), 6.49 (t, J=6.72 Hz, 1H), 4.49 (m, 3H), 4.32 (m, 1H), 3.60 (m, 1H), 1.96 (m, 3H), 0.73 (m, 4H) ppm.

Alternative Preparation: The free NH compound from Example 113 (0.025 mmol, 1 eq) was mixed with WA-21J dianion resin from SUPELCO (10 mg) in THF (2 mL). 1.1 equivalent of sulfonyl chloride, carbamoyl chloride or acid chloride was then added and the reaction mixture stirred for 30 min. The resin was removed by filtration and the solvent evaporated. The crude material was purified by preparative HPLC (Column YMC S5 ODS 20×100 mm gradient elution with methanol/water/0.1% TFA solution) to yield the title compound.

Example 115

Cis-3-Chloro-1H-indole-6-carboxylic acid {1-methanesulfonyl-4-[4-(2-oxo-2H-pyridin-1-yl)-benzoylamino]-piperidin-3-yl}-amide

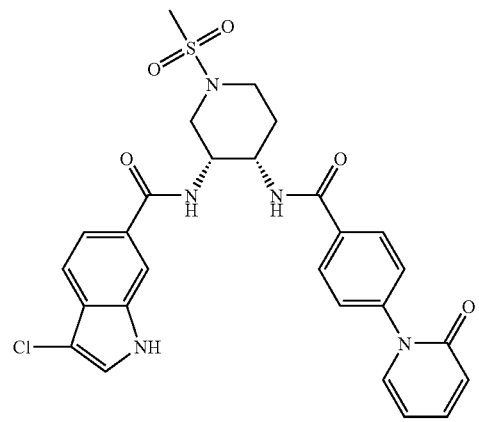

The N-Boc protected compound from Example 112 (15 mg, 0.0254 mmol) was deprotected with TFA and then reacted with methyl sulfonyl chloride (2.9 µl, 0.0381 mmol) to provide the title compound. LC-MS: (M)$^+$: 568.

Example 116

Cis-3-Chloro-1H-indole-6-carboxylic acid {1-acetyl-4-[4-(2-oxo-2H-pyridin-1-yl)-benzoylamino]-piperidin-3-yl}-amide

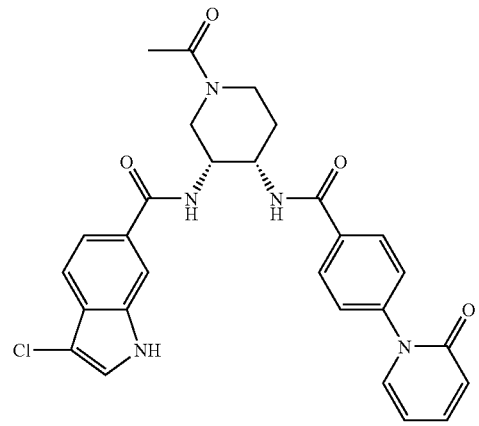

The N-Boc protected compound from Example 112 (15 mg, 0.0254 mmol) was deprotected with TFA and then reacted with acetyl chloride (2.0 µl, 0.0279 mmol) to provide the title compound. LC-MS: (M+H)$^+$: 532.

Example 117

Cis-3-[(3-Chloro-1H-indole-6-carbonyl)-amino]-4-[4-(2-oxo-2H-pyridin-1-yl)-benzoylamino]-piperidine-1-carboxylic acid ethyl ester

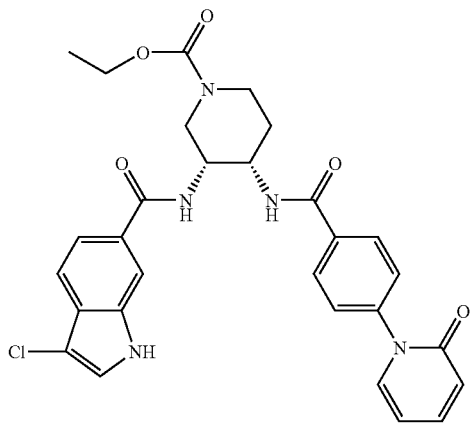

The N-Boc protected compound from Example 112 (10 mg, 0.0169 mmol) was deprotected with TFA and then reacted with ethyl chloro formate (1.8 µl, 0.0186 mmol) to provide the title compound. LC-MS: (M)+: 562

Example 118

Cis-3-Chloro-1H-indole-6-carboxylic acid {1-dimethylcarbamoyl-4-[4-(2-oxo-2H-pyridin-1-yl)-benzoylamino]-piperidin-3-yl}-amide

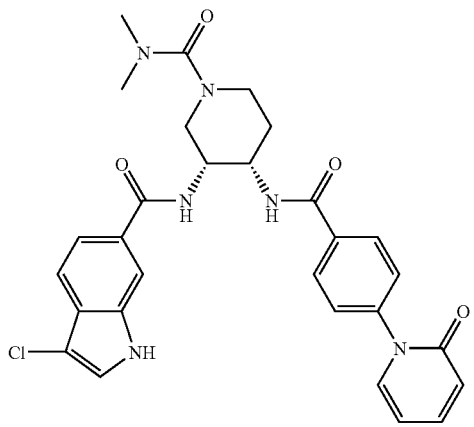

The N-Boc protected compound from Example 112 (10 mg, 0.0169 mmol) was deprotected with TFA and then reacted with dimethylcarbamic chloride (1.7 µl, 0.0186 mmol) to provide the title compound. LC-MS: (M+H)+: 562.

Example 119

Cis-3-Chloro-1H-indole-6-carboxylic acid {1-cyclopropanecarbonyl-4-[4-(2-oxo-2H-pyridin-1-yl)-benzoylamino -piperidin-3-yl}-amide

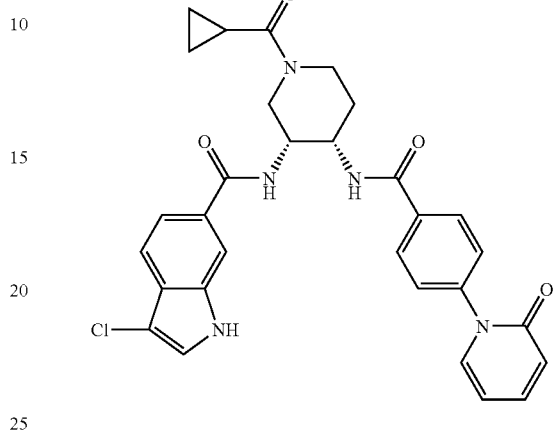

The N-Boc protected compound from Example 112 (15 mg, 0.0254 mmol) was deprotected with TFA and then reacted with cyclopropane carbonyl chloride (2.54 µl, 0.0380 mmol) to provide the title compound. LC-MS: (M)+: 558

Example 120

Cis-4-[(3-Chloro-1H-indole-6-carbonyl)-amino]-3-[4-(2-oxo-piperidin-1-yl)-benzoylamino]-piperidine-1-carboxylic acid tert-butyl ester

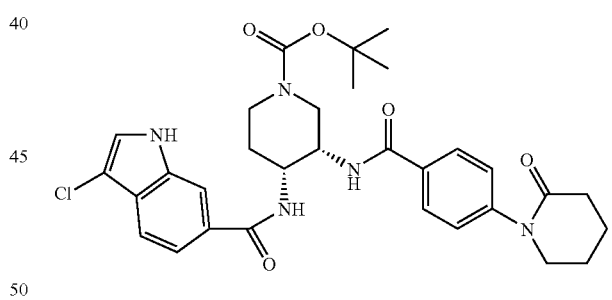

Part A 4-(2-oxopyridin-1(2H)-yl)benzoic acid (1 g, 4.6 mmol) was ]mixed with 10 mL of 1,2-dichloroethane. To this suspension was added SOCl₂ (6 mL), and the mixture was refluxed for 1.5 h. The mixture was reduced in vacuo. The remaining traces of SOCl₂ were removed by adding 1,2-dichloroethane (2×5 mL) and evaporating to dryness to yield 4-(2-oxopyridin-1(2H)-yl)benzoyl chloride as a white solid.

Part B

Cis-3-amino-4-benzyloxycarbonylamino-piperidine-1-carboxylic acid tert-butyl ester (332.1 mg, 0.95 mmol), from Example 112 Part F, was mixed with 10 mL of CH₂Cl₂ and 96 mg (0.95 mmol) of triethylamine. The resulting solution was cooled with an ice-water bath. Freshly prepared 4-(2-oxopyridin-1(2H)-yl)benzoyl chloride (222 mg, 0.95 mmol), from part A, was added portion wise. Stirring was continued at rt overnight. CH$_2$Cl$_2$ (10 mL) was added, and the solution was washed with water (3×3 mL). The organic phase was dried over MgSO$_4$, filtered, and evaporated to yield cis-4-Benzyloxycarbonylamino-3-[4-(2-oxo-2H-pyridin-1-yl)-benzoylamino]-piperidine-1-carboxylic acid tert-butyl ester (343.2 mg) as a crude oil, which was further purified by flash chromatography (ISCO system; 10 g cartridge Eluent AcOEt/Hexane 20%). $^1$H NMR (400 MHz, CDCl$_3$) δ 7.83 (d, J=8.4 Hz, 2H), 7.42–7.24 (m, 8H), 7.06 (d, J=6.5 Hz, 1H), 6.62 (d, J=9.1 Hz, 1H), 6.27 (t, 1H), 5.06 (s, 2H), 4.34 (bs, 1H), 4.08 (bs, 1H), 3.87 (m, 1H), 3.16 (d, J=13.4 Hz, 1H), 2.98 (t, 1H), 1.85 (bs, 1H), 1.65 (m, 1H), 1.39 (m, 9H), ppm. LC-MS (ESI) 569.24 [M+Na]$^+$, $t_R$=6.331 min (Shimadzu Phenomenex S5 ODS 4.6 ×50 mm Luna flow rate 2.5 mL/mn; detection at 220 nM; Gradient elution 0% to 100% B over 8 min; (A=10% MeOH, 90% H2O, 0.2% H3PO4 & B=90% MeOH, 10% H$_2$O, 0.2% H$_3$PO$_4$)).

HRMS (ESI) m/z calcd for C$_{30}$H$_{35}$N$_4$O$_6$ [M+Na]$^+$ 569.2376. Found 569.2353.

Part C

The product from part B (185 mg, 0.338 mmol) was added to ethanol (10 mL) and hydrogenated in the presence of Pd/C 10%. After stirring at rt overnight and under H$_2$ atmosphere (atmospheric pressure), the catalyst was removed by filtration over Celite® 545. The organic phase was concentrated to yield 140 mg (quantitative yield) of Cis-4-amino-3-[4-(2-oxo-piperidin-1-yl)-benzoylamino]-piperidine-1-carboxylic acid tert-butyl ester, which was used without further purification. Anal. LC/MS (ESI) Shimadzu Phenomenex C18; 4.6×50 mm Luna; flow rate 4 mL/mn; detection at 220 nM; Gradient elution 0% to 100% B over 4 min; (A=10% MeOH, 90% H$_2$O, 0.1% TFA & B=90% MeOH, 10% H$_2$O, 0.1% TFA); 833.67 (2M+H), $t_R$=2.30 min.

Part D

3-Chloro-1H-indole-6-carboxylic acid (200 mg) was mixed with 3 mL of SOCl$_2$. The mixture was refluxed for 1 h and evaporated to dryness. Benzene (2 mL) was added and evaporated twice in order to eliminate residual SOCl$_2$. The dark oil was triturated in ether/CH$_2$Cl$_2$ to yield 3-chloro-1H-indole-6-carbonyl chloride as a dark solid, which was used without further purification.

Part E

The product from part C (63.3 mg, 0.152 mmol) was dissolved in anhydrous CH$_2$Cl$_2$ (2 mL). The mixture was cooled with an ice-water bath. Triethylamine (35 mg, 0.164 mmol)(TEA) was added followed by the freshly prepared product from part D (32.5 mg, 0.152 mmol). The stirring continued for 15 min, and the cold bath was removed. After stirring overnight at rt, CH$_2$Cl$_2$ (10 mL) was added, and the mixture washed twice with water (5 mL), dried over MgSO$_4$, and concentrated under reduced pressure to yield a dark solid (84.7 mg). The analytically pure title compound (4 mg) was obtained after two successive liquid chromatographies: first by the ISCO system flash chromatography (4 g cartridge Eluent AcOEt/Hexane 30%) and then using IST isolute flash cartridge (2 g cartridge, Eluent CH$_2$Cl$_2$ then 3% MeOH/CH$_2$Cl$_2$). $^1$H NMR (400 MHz, CDCl$_3$) δ 8.85 (b, 1H), 7.91–7.63 (m, 4H), 7.33–7.1 (m, 4H), 4.46 (m, 1H), 4.12 (m, 2H), 3.64 (m, 2H), 3.15 (m, 1H), 2.98 (m, 1H), 2.56 (m, 2H), 2.56 (m, 1H), 1.95 (m, 2H), 1.48 (m, 9H), ppm. LC-MS (ESI) 616.32 [M+Na]$^+$, $t_R$=6.465 min (Shimadzu Phenomenex S5 ODS 4.6×50 mm Luna flow rate 2.5 mL/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{31}$H$_{37}$ClN$_5$O$_5$ [M+Na]$^+$ 616.2303. Found 616.2277.

Example 121

Cis-4-[(3-Chloro-1H-indole-6-carbonyl)-amino]-3-[4-(2-oxo-2H-pyridin-1-yl)-benzoylamino]-piperidine-1-carboxylic acid tert-butyl ester

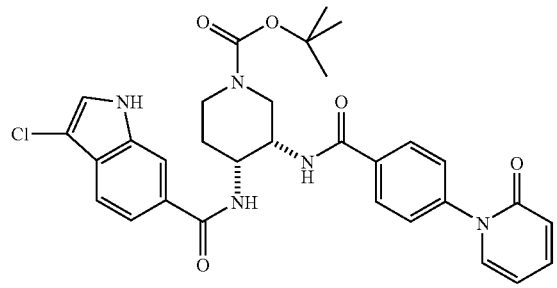

Part A

Part B from Example 120 (150 mg, 0.274 mmol) was mixed with 3 mL of a 4M HCl, dioxane solution. The mixture was stirred at rt for three days. Evaporation of the solvent quantitatively yielded cis-N-(4-amino-piperidin-3-yl)-4-(2-oxo-2H-pyridin-1-yl)-benzamide di-HCl salt as a white solid, which was used without further purification. HPLC: Shimadzu Phenomenex S5 ODS 4.6×50 mm Luna flow rate 2.5 mL/mn; detection at 220 nM; Gradient elution 0% to 100% B over 4 min; (A=10% MeOH, 90% H$_2$O, 0.2% H$_3$PO$_4$ & B=90% MeOH, 10% H$_2$O, 0.2% H$_3$PO$_4$). $t_R$=0.25 min.

Part B

A suspension of the product from part A (35.8 mg, 0.1 mmol) in 1 mL of anhydrous methanol was cooled to −20° C. To the suspension was added 0.5M MeONa/MeOH solution (0.6 mL, 0.3 mmol) dropwise. By the end of the addition, a homogenous solution had formed. Di-tert-butyl dicarbonate (14 mg, 0.063 mmol) was dissolved in MeOH (0.5 mL) and then added to the homogenous solution. This mixture was stirred for 2 h at a temperature between −20° C. and −15° C. CH$_2$Cl$_2$ (5 mL) was added, and the mixture washed with water (3×1 mL). The organic phase was dried over MgSO$_4$ and evaporated to yield cis-4-amino-3-[4-(2-oxo-2H-pyridin-1-yl)-benzoylamino]-piperidine-1-carboxylic acid tert-butyl ester HPLC: Shimadzu Phenomenex S5 ODS 4.6×50 mm Luna flow rate 4 mL/mn; detection at 220 nM; Gradient elution 0% to 100% B over 4 min; (A=10% MeOH, 90% H$_2$O, 0.2% H$_3$PO4 & B=90% MeOH, 10% H2O, 0.2% H$_3$PO$_4$). $t_R$=1.929 min. (36 mg, 87%) as a solid.

Part C

The product from part B (36 mg, 0.087 mmol) was dissolved in anhydrous CH$_2$Cl$_2$. TEA (100 µL) was added followed by freshly prepared 3-chloro-1H-indole-6-carbonyl chloride (18.7 mg, 0.087 mmol). The mixture was stirred at rt overnight, washed with water (3×1 mL), dried over MgSO$_4$, and concentrated to yield 53.3 mg of crude title compound which was purified by preparative HPLC. Shimadzu Phenomenex S5 50×4.6 mm Luna; flow rate 2.5 mL/mn; detection at 220 nM; Gradient elution 0% to 100%

B over 20 min; (A=10% MeOH, 90% H₂O, 0.2% H₃PO₄ & B=90% MeOH, 10% H₂O, 0.2% H₃PO₄); Retention time=6.308 min. LC-MS (ESI) 612. [M+Na]⁺, HRMS (ESI) m/z calcd for $C_{31}H_{33}ClN_5O_5$ [M+H]⁺ 590.21703. Found 590.2178. ¹H NMR (500 MHz, MeOD-D₃) δ 8.02 (d, J=8.7 Hz, 1H), 7.96–7.90 (m, 2H), 7.88 (s, 1H), 7.66–7.48 (m, 5H), 7.4 (d, J=9.4 Hz, 1H), 6.63 (dd, J=9.4 Hz and 3.36 Hz, 1H), 6.49 (m, 1H). 4.65 (m, 0.5H), 4.45 (m, 1H), 4.30 (m, 0.5H), 4.12 (m, 0.5H), 3.65 (m, 0.5H), 3.56 (m, 1H), 3.12 (m, 0.5H), 3.07 (m, 0.5H), 2.36 (m, 0.5H), 2.2(m, 0.5H), 2.03 (m, 1H), 1.92 (m, 1H), 1.6–1.2 (bs, 9H), ppm.

Example 122

Cis-3-Chloro-1H-indole-6-carboxylic acid {1-methanesulfonyl-3-[4-(2-oxo-2H-pyridin-1-yl)-benzoylamino]-piperidin-4-yl}-amide

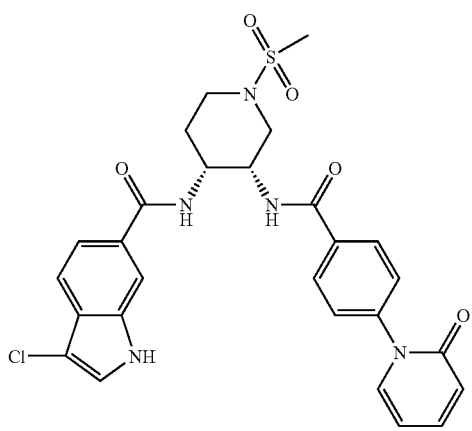

The N-Boc protected compound from Example 121 (4.4 mg, 0.009 mmol) was deprotected with TFA and then reacted with methyl sulfonyl chloride (0.76 μl, 0.01 mmol) to provide the title compound. LC-MS: (M)⁺: 568.

Example 123

Cis-3-Chloro-1H-indole-6-carboxylic acid {1-acetyl-3-[4-(2-oxo-2H-pyridin-1-yl)-benzoylamino]-piperidin-4-yl}-amide

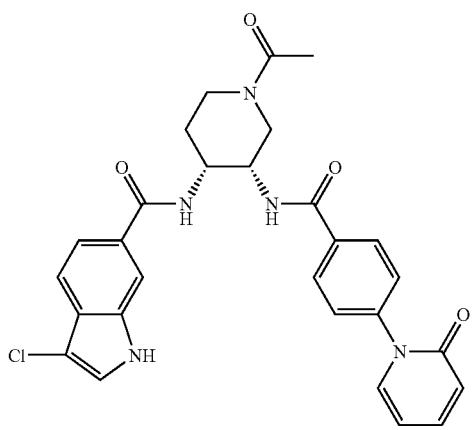

The N-Boc protected compound from Example 121 (4.4 mg, 0.009 mmol) was deprotected with TFA and then reacted with acetyl chloride (0.7 μl, 0.01 mmol) to provide the title compound. LC-MS: (M+H)⁺: 532.

Example 124

Cis-3-Chloro-1H-indole-6-carboxylic acid {1-dimethylcarbamoyl-3-[4-(2-oxo-2H-pyridin-1-yl)-benzoylamino]-piperidin-4-yl}-amide

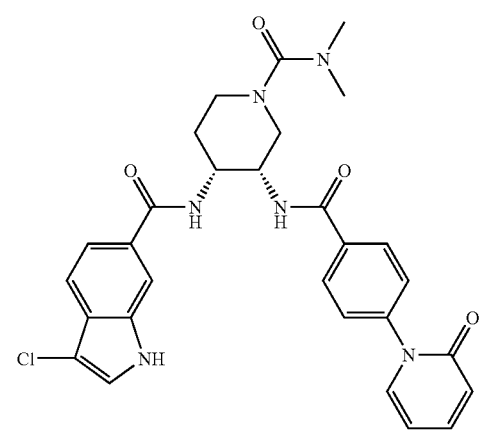

The N-Boc protected compound from Example 121 (4.4 mg, 0.009 mmol) was deprotected with TFA and then reacted with dimethylcarbamic chloride (0.91 μl, 0.01 mmol) to provide the title compound. LC-MS: (M)⁺: 561.

Example 125

Cis-{1-Cyclopropanecarbonyl-3-[4-(2-oxo-2H-pyridin-1-yl)-benzoylamino]-piperidin-4-yl}-carbamic acid benzyl ester

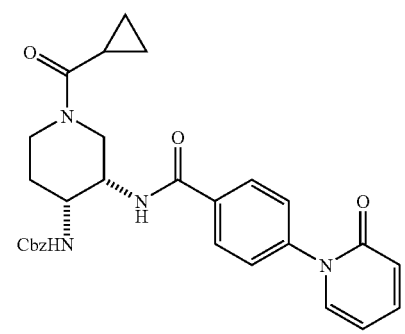

Part A

Cis-4-Benzyloxycarbonylamino-3-[4-(2-oxo-2H-pyridin-1-yl)-benzoylamino]-piperidine-1-carboxylic acid tert-butyl ester (22.2 mg, 0.041 mmol) was dissolved in 2 mL of anhydrous $CH_2Cl_2$ To this solution was added 2 mL of trifluoroacetic acid (TFA). The mixture was stirred for one hour at rt. The solvent was removed in vacuo to yield cis-{3-[4-(2-Oxo-2H-pyridin-1-yl)-benzoylamino]-piperidin-4-yl}-carbamic acid benzyl ester, $CF_3COOH$ salt (42.7 mg) as a viscous oil, which was used without any further purification. Anal. LC/MS (ESI) Shimadzu Phenomenex C18; 4.6×50 mm Luna; flow rate 4 mL/mn; detection at 220 nM; Gradient elution 0% to 100% B over 4 min; (A=10% MeOH, 90% $H_2O$, 0.1% TFA & B=90% MeOH, 10% H2O, 0.1% TFA); 447.24 $(M+H)^+$, $t_R$=2.15 min.

Part B

The product from part A (42.7 mg, 0.076 mmol) was dissolved in 8 μL of $CH_2Cl_2$. To this mixture was added TEA (15.4 mg, 0.152 mmol, 2 equivalent) followed by cyclopropanecarbonyl chloride (8.7 mg, 0.084 mmol, 1.1 equivalent). The resulting solution was stirred overnight at rt. $CH_2Cl_2$ (10 mL) was added, and the solution washed with water (3×3 mL). The organic phase was dried over $MgSO_4$, filtered, and evaporated to dryness to yield the title compound (47.7 mg) as a pale yellow oil. The oil was purified by flash chromatography (ISCO system, 4 g cartridge, gradient elution 0% to 100% B over 59 min; (A=Hexane & B=AcOEt)) to yield 33.5 mg (86% yield) of the title compound as an amorphous solid. $^1H$ NMR (400 MHz, $CDCl_3$) δ 7.75 (d, J=8 Hz, 2H), 7.57 (bs, 1H), 7.36–7.16 (m, 8H), 6.51 (d, J=8.7 Hz, 1H), 6.41 (d, J=7.4 Hz, 1H). 6.25 (t, 1H), 5.0 (s, 2H), 4.33 (m, 1H),-4.2–3.9 (m, 2H), 3.3 (m, 1H), 2.76 (m, 1H), 1.97 (m, 1H), 1.8–1.45 (in, 2H), 0.81 (m, 2H), 0.62 (m, 2H), 0.39 (m, 1H), ppm. LC-MS (ESI) 515.34 $[M+H]^+$; $t_R$=5.128 min (Shimadzu Phenomenex S5 ODS 4.6×50 mm Luna flow rate 2.5 mL/mn; detection at 220 nM; Gradient elution 0% to 100% B over 8 min; (A=10% MeOH, 90% $H_2O$, 0.2% $H_3PO_4$ & B=90% MeOH, 10% $H_2O$, 0.2% $H_3PO_4$)). HRMS (ESI) m/z calcd for $C_{29}H_{31}N_4O_5$ $[M+H]^+$ 515.2295. Found 515.2290.

Using a procedure similar to that of Example 79, Examples 126 and 127 were prepared.

Example 126

(3R,4S)-3-(2-chlorothiophene-5-carboxamido)-N-methyl-4-(4-(2-oxopyridin-1(2H)-yl)benzamido) pyrrolidine-1-carboxamide

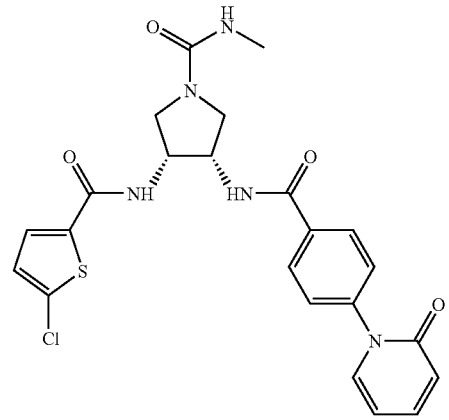

MS m/z 500.2 $([M+H]^+)$.

Example 127

(3R,4S)-3-(2-chlorothiophene-5-carboxamido)-N,N-dimethyl-4-(4-(2-oxopyridin-1(2H)-yl)benzamido) pyrrolidine-1-carboxamide

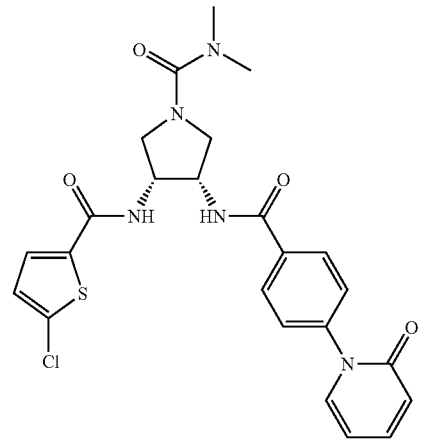

MS m/z 514.2 $([M+H]^+)$.

Examples 128–429, shown in Table 1 below, can be prepared by following the procedures of Examples 1–127.

TABLE 1

| Example | Name |
|---|---|
| 128. | (1R,2S)-5-Chloro-thiophene-2-carboxylic acid {2-[4-(3-oxo-morpholin-4-yl)-benzoylamino]-cyclopentyl}-amide |
| 129. | (1R,2S)-5-Chloro-thiophene-2-carboxylic acid {2-[4-(2-oxo-2H-pyrazin-1-yl)-benzoylamino]-cyclopentyl}-amide |
| 130. | (1R,2S)-5-Chloro-thiophene-2-carboxylic acid {2-[4-(2-oxo-azepan-1-yl)-benzoylamino]-cyclopentyl}-amide |
| 131. | (1R,2S)-5-Chloro-thiophene-2-carboxylic acid {2-[4-(1,1-dioxo-1λ⁶-[1,2]thiazinan-2-yl)-benzoylamino]-cyclopentyl}-amide |
| 132. | (1R,2S)-5-Chloro-thiophene-2-carboxylic acid {2-[4-(2-oxo-[1,3]oxazinan-3-yl)-benzoylamino]-cyclopentyl}-amide |
| 133. | (1R,2S)-5-Chloro-thiophene-2-carboxylic acid {2-[4-(2-oxo-tetrahydro-pyrimidin-1-yl)-benzoylamino]-cyclopentyl}-amide |
| 134. | (1R,2S)-5-Chloro-thiophene-2-carboxylic acid {2-[4-(4-methyl-2-oxo-piperazin-1-yl)-benzoylamino]-cyclopentyl}-amide |
| 135. | (1R,2S)-5-Chloro-thiophene-2-carboxylic acid {2-[4-(2-oxo-pyrrolidin-1-yl)-benzoylamino]-cyclopentyl}-amide |

TABLE 1-continued

| Example | Name |
|---|---|
| 136. | (1R,2S)-5-Chloro-thiophene-2-carboxylic acid {2-[2-fluoro-4-(3-oxo-morpholin-4-yl)-benzoylamino]-cyclopentyl}-amide |
| 137. | (1R,2S)-5-Chloro-thiophene-2-carboxylic acid {2-[2-fluoro-4-(2-oxo-2H-pyrazin-1-yl)-benzoylamino]-cyclopentyl}-amide |
| 138. | (1R,2S)-5-Chloro-thiophene-2-carboxylic acid {2-[2-fluoro-4-(2-oxo-azepan-1-yl)-benzoylamino]-cyclopentyl}-amide |
| 139. | (1R,2S)-5-Chloro-thiophene-2-carboxylic acid (2-[2-fluoro-4-(1,1-dioxo-1$\lambda^6$-[1,2]thiazinan-2-yl)-benzoylamino]-cyclopentyl}-amide |
| 140. | (1R,2S)-5-Chloro-thiophene-2-carboxylic acid {2-[2-fluoro-4-(2-oxo-[1,3]oxazinan-3-yl)-benzoylamino]-cyclopentyl}-amide |
| 141. | (1R,2S)-5-Chloro-thiophene-2-carboxylic acid {2-[2-fluoro-4-(2-oxo-tetrahydro-pyrimidin-1-yl)-benzoylamino]-cyclopentyl}-amide |
| 142. | (1R,2S)-5-Chloro-thiophene-2-carboxylic acid {2-[2-fluoro-4-(2-oxo-piperazin-1-yl)-benzoylamino]-cyclopentyl}-amide |
| 143. | (1R,2S)-5-Chloro-thiophene-2-carboxylic acid {2-[2-fluoro-4-(2-oxo-pyrrolidin-1-yl)-benzoylamino]-cyclopentyl}-amide |
| 144. | (1R,2S)-3-Chloro-1H-indole-6-carboxylic acid {2-[4-(4-methyl-2-oxo-piperazin-1-yl)-benzoylamino]-cyclopentyl}-amide |
| 145. | (1R,2S)-3-Chloro-1H-indole-6-carboxylic acid {2-[2-fluoro-4-(2-oxo-piperidin-1-yl)-benzoylamino]-cyclopentyl}-amide |
| 146. | (1R,2S)-3-Chloro-1H-indole-6-carboxylic acid {2-[2-fluoro-4-(3-oxo-morpholin-4-yl)-benzoylamino]-cyclopentyl}-amide |
| 147. | (1R,2S)-3-Chloro-1H-indole-6-carboxylic acid {2-[2-fluoro-4-(2-oxo-2H-pyrazin-1-yl)-benzoylamino]-cyclopentyl}-amide |
| 148. | (1R,2S)-3-Chloro-1H-indole-6-carboxylic acid {2-[2-fluoro-4-(2-oxo-azepan-1-yl)-benzoylamino]-cyclopentyl}-amide |
| 149. | (1R,2S)-3-Chloro-1H-indole-6-carboxylic acid {2-[2-fluoro-4-(2-oxo-[1,3]oxazinan-3-yl)-benzoylamino]-cyclopentyl}-amide |
| 150. | (1R,2S)-3-Chloro-1H-indole-6-carboxylic acid {2-[2-fluoro-4-(2-oxo-tetrahydro-pyrimidin-1-yl)-benzoylamino]-cyclopentyl}-amide |
| 151. | (1R,2S)-3-Chloro-1H-indole-6-carboxylic acid {2-[2-fluoro-4-(4-methyl-2-oxo-piperazin-1-yl)-benzoylamino]-cyclopentyl}-amide |
| 152. | 5-chloro-N-((1R,2S,4S)-4-(hydroxymethyl)-2-(4-(2-oxoazepan-1-yl)benzamido)cyclopentyl)thiophene-2-carboxamide |
| 153. | 5-chloro-N-((1R,2S,4S)-4-(hydroxymethyl)-2-(4-(2-oxopyrazin-1(2H)-yl)benzamido)cyclopentyl)thiophene-2-carboxamide |
| 154. | 5-chloro-N-((1R,2S,4S)-2-(3-chloro-4-(2-oxopyridin-1(2H)-yl)benzamido)-4-(hydroxymethyl)cyclopentyl)thiophene-2-carboxamide |
| 155. | 5-chloro-N-((1R,2S,4S)-4-(hydroxymethyl)-2-(4-(3-oxomorpholino)benzamido)cyclopentyl)thiophene-2-carboxamide |
| 156. | 5-chloro-N-((1R,2S,4S)-4-(hydroxymethyl)-2-(4-(2-oxo-tetrahydropyrimidin-1(2H)-yl)benzamido)cyclopentyl)thiophene-2-carboxamide |
| 157. | 5-chloro-N-((1R,2S,4S)-4-(hydroxymethyl)-2-(4-(4-methyl-2-oxopiperazin-1-yl)benzamido)cyclopentyl)thiophene-2-carboxamide |
| 158. | 5-chloro-N-((1R,2S,4S)-4-(hydroxymethyl)-2-(4-(2-oxopyrrolidin-1-yl)benzamido)cyclopentyl)thiophene-2-carboxamide |
| 159. | 5-chloro-N-((1R,2S,4S)-4-(hydroxymethyl)-2-(4-(2-oxo-1,3-oxazinan-3-yl)benzamido)cyclopentyl)thiophene-2-carboxamide |
| 160. | 5-chloro-N-((1R,2S,4S)-4-(hydroxymethyl)-2-(4-(2-oxopiperidin-1-yl)benzamido)cyclopentyl)thiophene-2-carboxamide |
| 161. | (3R,4S)-5-Chloro-thiophene-2-carboxylic acid {1-cyclopropanecarbonyl-4-[4-(2-oxo-piperidin-1-yl)-benzoylamino]-pyrrolidin-3-yl}-amide |
| 162. | (3R,4S)-5-Chloro-thiophene-2-carboxylic acid {1-cyclopropanecarbonyl-4-[2-fluoro-4-(2-oxo-2H-pyridin-1-yl)-benzoylamino]-pyrrolidin-3-yl}-amide |
| 163. | (3R,4S)-5-Chloro-thiophene-2-carboxylic acid {1-cyclopropanecarbonyl-4-[4-(2-oxo-2H-pyrazin-1-yl)-benzoylamino]-pyrrolidin-3-yl}-amide |
| 164. | 5-chloro-N-((3R,4S)-1-(2-(methylamino)-2-oxoethyl)-4-(4-(2-oxopyridin-1(2H)-yl)benzamido)pyrrolidin-3-yl)thiophene-2-carboxamide |
| 165. | (3R,4S)-5-Chloro-thiophene-2-carboxylic acid {1-methyl-4-[4-(2-oxo-piperidin-1-yl)-benzoylamino]-pyrrolidin-3-yl}-amide |
| 166. | (3R,4S)-5-Chloro-thiophene-2-carboxylic acid {1-methyl-4-[2-fluoro-4-(2-oxo-2H-pyridin-1-yl)-benzoylamino]-pyrrolidin-3-yl}-amide |
| 167. | (3R,4S)-5-Chloro-thiophene-2-carboxylic acid {1-methyl-4-[4-(2-oxo-2H-pyrazin-1-yl)-benzoylamino]-pyrrolidin-3-yl}-amide |
| 168. | (3R,4S)-5-Chloro-thiophene-2-carboxylic acid {1-methyl-4-[4-(2-oxo-2H-pyridin-1-yl)-benzoylamino]-pyrrolidin-3-yl}-amide |
| 169. | (3R,4S)-5-Chloro-thiophene-2-carboxylic acid {4-[4-(2-oxo-2H-pyridin-1-yl)-benzoylamino]-tetrahydro-furan-3-yl}-amide |
| 170. | (3R,4S)-5-Chloro-thiophene-2-carboxylic acid {4-[4-(2-oxo-2H-pyrazin-1-yl)-benzoylamino]-tetrahydro-furan-3-yl}-amide |
| 171. | (7R,8S)-5-Chloro-thiophene-2-carboxylic acid {8-[4-(2-oxo-2H-pyridin-1-yl)-benzoylamino]-1-oxa-spiro[4.4]non-7-yl}-amide |

TABLE 1-continued

| Example | Name |
|---|---|
| 172. | (7R,8S)-5-Chloro-thiophene-2-carboxylic acid {8-[4-(2-oxo-piperidin-1-yl)-benzoylamino]-1-oxa-spiro[4.4]non-7-yl}-amide |
| 173. | (3R,4S)-3-Chloro-1H-indole-6-carboxylic acid {1-cyclopropanecarbonyl-4-[2-fluoro-4-(2-oxo-2H-pyridin-1-yl)-benzoylamino]-pyrrolidin-3-yl}-amide |
| 174. | (3R,4S)-3-Chloro-1H-indole-6-carboxylic acid {4-[2-fluoro-4-(2-oxo-2H-pyridin-1-yl)-benzoylamino]-tetrahydro-furan-3-yl}-amide |
| 175. | (3R,4S)-3-Chloro-1H-indole-6-carboxylic acid {4-[4-(2-oxo-2H-pyridin-1-yl)-benzoylamino]-tetrahydro-furan-3-yl}-amide |
| 176. | (7R,8S)-3-Chloro-1H-indole-6-carboxylic acid {8-[4-(2-oxo-2H-pyridin-1-yl)-benzoylamino]-1-oxa-spiro[4.4]non-7-yl}-amide |
| 177. | (7R,8S)-3-Chloro-1H-indole-6-carboxylic acid {8-[4-(2-oxo-piperidin-1-yl)-benzoylamino]-1-oxa-spiro[4.4]non-7-yl}-amide |
| 178. | (3R,4S)-5-Chloro-1H-indole-2-carboxylic acid {1-cyclopropane-carbonyl-4-[2-fluoro-4-(2-oxo-2H-pyridin-1-yl)-benzoylamino]-pyrrolidin-3-yl}-amide |
| 179. | (3R,4S)-5-Chloro-1H-indole-2-carboxylic acid {4-[2-fluoro-4-(2-oxo-2H-pyridin-1-yl)-benzoylamino]-tetrahydro-furan-3-yl}-amide |
| 180. | (3R,4S)-5-Chloro-1H-indole-2-carboxylic acid {4-[4-(2-oxo-2H-pyridin-1-yl)-benzoylamino]-tetrahydro-furan-3-yl}-amide |
| 181. | (7R,8S)-5-Chloro-1H-indole-2-carboxylic acid {8-[4-(2-oxo-2H-pyridin-1-yl)-benzoylamino]-1-oxa-spiro[4.4]non-7-yl}-amide |
| 182. | (7R,8S)-5-Chloro-1H-indole-2-carboxylic acid {8-[4-(2-oxo-piperidin-1-yl)-benzoylamino]-1-oxa-spiro[4.4]non-7-yl}-amide |
| 183. | methyl 2-((3R,4S)-3-(2-chlorothiophene-5-carboxamido)-4-(4-(2-oxopyridin-1(2H)-yl)benzamido)pyrrolidin-1-yl)acetate |
| 184. | (3R,4S)-3-[(5-Chloro-thiophene-2-carbonyl)-amino]-4-[4-(2-oxo-piperidin-1-yl)-benzoylamino]-pyrrolidine-1-carboxylic acid methyl ester |
| 185. | N-((3R,4S)-1-(2-amino-2-oxoethyl)-4-(4-(2-oxopyridin-1(2H)-yl)benzamido)pyrrolidin-3-yl)-5-chlorothiophene-2-carboxamide |
| 186. | (3R,4S)-5-Chloro-thiophene-2-carboxylic acid {1-acetyl-4-[4-(2-oxo-piperidin-1-yl)-benzoylamino]-pyrrolidin-3-yl}-amide |
| 187. | 5-chloro-N-((3R,4S)-1-(2-morpholino-2-oxoethyl)-4-(4-(2-oxopyridin-1(2H)-yl)benzamido)pyrrolidin-3-yl)thiophene-2-carboxamide |
| 188. | (3R,4S)-5-Chloro-thiophene-2-carboxylic acid {1-methanesulfonyl-4-[4-(2-oxo-piperidin-1-yl)-benzoylamino]-pyrrolidin-3-yl}-amide |
| 189. | (3R,4S)-3-[(5-Chloro-thiophene-2-carbonyl)-amino]-4-[4-(2-oxo-2H-pyridin-1-yl)-benzoylamino]-pyrrolidine-1-carboxylic acid dimethylamide |
| 190. | (3R,4S)-3-[(5-Chloro-thiophene-2-carbonyl)-amino]-4-[4-(2-oxo-piperidin-1-yl)-benzoylamino]-pyrrolidine-1-carboxylic acid dimethylamide |
| 191. | (3R,4S)-5-Chloro-thiophene-2-carboxylic acid {4-[4-(2-oxo-piperidin-1-yl)-benzoylamino]-tetrahydro-furan-3-yl}-amide |
| 192. | (3R,4S)-5-Chloro-thiophene-2-carboxylic acid {1,1-dioxo-4-[4-(2-oxo-piperidin-1-yl)-benzoylamino]-tetrahydro-1$\lambda^6$-thiophen-3-yl}-amide |
| 193. | (3R,4S)-3-[(3-Chloro-1 H-indole-6-carbonyl)-amino]-4-[4-(2-oxo-2H-pyridin-1-yl)-benzoylamino]-pyrrolidine-1-carboxylic acid methyl ester |
| 194. | (3R,4S)-3-[(3-Chloro-1 H-indole-6-carbonyl)-amino]-4-[4-(2-oxo-piperidin-1-yl)-benzoylamino]-pyrrolidine-1-carboxylic acid methyl ester |
| 195. | (3R,4S)-3-Chloro-4S-indole-6-carboxylic acid {1-acetyl-4-[4-(2-oxo-2H-pyridin-1-yl)-benzoylamino]-pyrrolidin-3-yl}-amide |
| 196. | (3R,4S)-3-Chloro-1H-indole-6-carboxylic acid {1-acetyl-4-[4-(2-oxo-piperidin-1-yl)-benzoy lamino]-pyrrolidin-3-yl}-amide |
| 197. | (3R,4S)-3-Chloro-1H-indole-6-carboxylic acid {1-methanesulfonyl-4-[4-(2-oxo-2H-pyridin-1-yl)-benzoylamino]-pyrrolidin-3-yl}-amide |
| 198. | (3R,4S)-3-Chloro-1H-indole-6-carboxylic acid {1-methanesulfonyl-4-[4-(2-oxo-piperidin-1-yl)-benzoylamino]-pyrrolidin-3-yl}-amide |
| 199. | (3R,4S)-3-Chloro-1H-indole-6-carboxylic acid {1-dimethylcarbamoyl-4-[4-(2-oxo-2H-pyridin-1-yl)-benzoylamino]-pyrrolidin-3-yl}-amide |
| 200. | (3R,4S)-3-Chloro-1H-indole-6-carboxylic acid {1-dimethylcarbamoyl-4-[4-(2-oxo-piperidin-1-yl)-benzoylamino]-pyrrolidin-3-yl}-amide |
| 201. | (3R,4S)-3-Chloro-1H-indole-6-carboxylic acid {4-[4-(2-oxo-piperidin-1-yl)-benzoylamino]-tetrahydro-furan-3-yl}-amide |
| 202. | (3R,4S)-3-Chloro-1H-indole-6-carboxylic acid {1,1-dioxo-4-[4-(2-oxo-piperidin-1-yl)-benzoylamino]-tetrahydro-1$\lambda^6$-thiophen-3-yl}-amide |
| 203. | (1R,2S,4R)-3-Chloro-1H-indole-6-carboxylic acid {4-dimethylcarbamoyl-2-[4-(2-oxo-2H-pyridin-1-yl)-benzoylamino]-cyclohexyl}-amide |
| 204. | (1R,2S,4R)-3-Chloro-1H-indole-6-carboxylic acid {4-dimethylcarbamoyl-2-[4-(2-oxo-piperidin-1-yl)-benzoylamino]-cyclohexyl}-amide |
| 205. | (1R,2S,4R)-3-Chloro-1H-indole-6-carboxylic acid {4-dimethylcarbamoyl-2-[4-(3-oxo-morpholin-4-yl)-benzoylamino]-cyclohexyl}-amide |

TABLE 1-continued

| Example | Name |
|---|---|
| 206. | (1R,2S,4R)-3-Chloro-1H-indole-6-carboxylic acid {4-dimethylcarbamoyl-2-[4-(2-oxo-2H-pyrazin-1-yl)-benzoylamino]-cyclohexyl}-amide |
| 207. | (1R,2S,5S)-3-Chloro-1H-indole-6-carboxylic acid {5-dimethylcarbamoyl-2-[4-(2-oxo-piperidin-1-yl)-benzoylamino]-cyclohexyl}-amide |
| 208. | (1R,2S,5S)-3-Chloro-1H-indole-6-carboxylic acid {5-dimethylcarbamoyl-2-[4-(2-oxo-2H-pyridin-1-yl)-benzoylamino]-cyclohexyl}-amide |
| 209. | (1R,2S,5S)-3-Chloro-1H-indole-6-carboxylic acid {5-dimethylcarbamoyl-2-[2-fluoro-4-(2-oxo-2H-pyridin-1-yl)-benzoylamino]-cyclohexyl}-amide |
| 210. | (1R,2S,5S)-3-Chloro-1H-indole-6-carboxylic acid {5-dimethylcarbamoyl-2-[2-fluoro-4-(2-oxo-piperidin-1-yl)-benzoylamino]-cyclohexyl}-amide |
| 211. | (1R,2S,4R)-3-Chloro-1H-indole-6-carboxylic acid {4-dimethylcarbamoyl-2-[2-fluoro-4-(2-oxo-2H-pyridin-1-yl)-benzoylamino]-cyclohexyl}-amide |
| 212. | (1R,2S,4R)-3-Chloro-1H-indole-6-carboxylic acid {4-dimethylcarbamoyl-2-[2-fluoro-4-(2-oxo-piperidin-1-yl)-benzoylamino]-cyclohexyl}-amide |
| 213. | (1R,2S,4R)-3-Chloro-1H-indole-6-carboxylic acid {4-methoxy-2-[4-(2-oxo-2H-pyridin-1-yl)-benzoylamino]-cyclohexyl}-amide |
| 214. | (1R,2S,4R)-3-Chloro-1H-indole-6-carboxylic acid {4-methoxymethyl-2-[4-(2-oxo-2H-pyridin-1-yl)-benzoylamino]-cyclohexyl}-amide |
| 215. | (1R,2S,4R)-3-Chloro-1H-indole-6-carboxylic acid {4-methoxymethyl-2-[4-(2-oxo-2H-pyridin-1-yl)-benzoylamino]-cyclohexyl}-amide |
| 216. | (1R,2S,4R)-3-Chloro-1H-indole-6-carboxylic acid {4-dimethylcarbamoylmethyl-2-[4-(2-oxo-2H-pyridin-1-yl)-benzoylamino]-cyclohexyl}-amide |
| 217. | (1R,2S,5S)-3-Chloro-1H-indole-6-carboxylic acid {5-methoxy-2-[4-(2-oxo-2H-pyridin-1-yl)-benzoylamino]-cyclohexyl}-amide |
| 218. | (1R,2S,5S)-3-Chloro-1H-indole-6-carboxylic acid {5-methoxymethyl-2-[4-(2-oxo-2H-pyridin-1-yl)-benzoylamino]-cyclohexyl}-amide |
| 219. | (1R,2S,5S)-3-Chloro-1H-indole-6-carboxylic acid {5-methoxymethyl-2-[4-(2-oxo-2H-pyridin-1-yl)-benzoylamino]-cyclohexyl}-amide |
| 220. | (1R,2S 5S)-3-Chloro-1H-indole-6-carboxylic acid {5-dimethylcarbamoylmethyl-2-[4-(2-oxo-2H-pyridin-1-yl)-benzoylamino]-cyclohexyl}-amide |
| 221. | (3S,4R)-3-Chloro-1H-indole-6-carboxylic acid {1-dimethylcarbamoyl-3-[4-(2-oxo-2H-pyridin-1-yl)-benzoylamino]-piperidin-4-yl}-amide |
| 222. | (3S,4R)-3-Chloro-1H-indole-6-carboxylic acid {1-dimethylcarbamoyl-3-[4-(2-oxo-piperidin-1-yl)-benzoylamino]-piperidin-4-yl}-amide |
| 223. | (3S,4R)-3-Chloro-1H-indole-6-carboxylic acid {1-cyclopropanecarbonyl-3-[4-(2-oxo-2H-pyridin-1-yl)-benzoylamino]-piperidin-4-yl}-amide |
| 224. | (3S,4R)-3-Chloro-1H-indole-6-carboxylic acid {1-cyclopropanecarbonyl-3-[4-(2-oxo-piperidin-1-yl)-benzoylamino]-piperidin-4-yl}-amide |
| 225. | (3S,4R)-4-[(3-Chloro-1H-indole-6-carbonyl)-amino]-3-[4-(2-oxo-2H-pyridin-1-yl)-benzoylamino]-piperidine-1-carboxylic acid methyl ester |
| 226. | (3S,4R)-4-[(3-Chloro-1H-indole-6-carbonyl)-amino]-3-[4-(2-oxo-piperidin-1-yl)-benzoylamino]-piperidine-1-carboxylic acid methyl ester |
| 227. | (3S,4R)-3-Chloro-1H-indole-6-carboxylic acid {1-acetyl-3-[4-(2-oxo-2H-pyridin-1-yl)-benzoylamino]-piperidin-4-yl}-amide |
| 228. | (3S,4R)-3-Chloro-1H-indole-6-carboxylic acid {1-acetyl-3-[4-(2-oxo-piperidin-1-yl)-benzoylamino]-piperidin-4-yl}-amide |
| 229. | (3S,4R)-3-Chloro-1H-indole-6-carboxylic acid {1-methanesulfonyl-3-[4-(2-oxo-2H-pyridin-1-yl)-benzoylamino]-piperidin-4-yl}-amide |
| 230. | (3S,4R)-3-Chloro-1H-indole-6-carboxylic acid {1-methanesulfonyl-3-[4-(2-oxo-piperidin-1-yl)-benzoylamino]-piperidin-4-yl}-amide |
| 231. | (3S,4R)-3-Chloro-1H-indole-6-carboxylic acid {1-(1-methoxy-cyclopropanecarbonyl)-3-[4-(2-oxo-2H-pyridin-1-yl)-benzoylamino]-piperidin-4-yl}-amide |
| 232. | (3S,4R)-3-Chloro-1H-indole-6-carboxylic acid {1-(1-methoxy-cyclopropanecarbonyl)-3-[4-(2-oxo-piperidin-1-yl)-benzoylamino]-piperidin-4-yl}-amide |
| 233. | (3R,4S)-3-[(3-Chloro-1H-indole-6-carbonyl)-amino]-4-[4-(2-oxo-2H-pyridin-1-yl)-benzoylamino]-piperidine-1-carboxylic acid methyl ester |
| 234. | (3R,4S)-3-[(3-Chloro-1H-indole-6-carbonyl)-amino]-4-[4-(2-oxo-piperidin-1-yl)-benzoylamino]-piperidine-1-carboxylic acid methyl ester |
| 235. | (3R,4S)-3-Chloro-1H-indole-6-carboxylic acid {1-cyclopropanecarbonyl-4-[4-(2-oxo-2H-pyridin-1-yl)-benzoylamino]-piperidin-3-yl}-amide |
| 236. | (3R,4S)-3-Chloro-1H-indole-6-carboxylic acid {1-cyclopropanecarbonyl-4-[4-(2-oxo-piperidin-1-yl)-benzoylamino]-piperidin-3-yl}-amide |

TABLE 1-continued

| Example | Name |
|---|---|
| 237. | (3R,4S)-3-[(3-Chloro-1H-indole-6-carbonyl)-amino]-4-[4-(2-oxo-2H-pyridin-1-yl)-benzoylamino]-piperidine-1-carboxylic acid methyl ester |
| 238. | (3R,4S)-3-[(3-Chloro-1H-indole-6-carbonyl)-amino]-4-[4-(2-oxo-piperidin-1-yl)-benzoylamino]-piperidine-1-carboxylic acid methyl ester |
| 239. | (3R,4S)-3-Chloro-1H-indole-6-carboxylic acid {1-acetyl-4-[4-(2-oxo-2H-pyridin-1-yl)-benzoylamino]-piperidin-3-yl}-amide |
| 240. | (3R,4S)-3-Chloro-1H-indole-6-carboxylic acid {1-acetyl-4-[4-(2-oxo-piperidin-1-yl)-benzoylamino]-piperidin-3-yl}-amide |
| 241. | (3R,4S)-3-Chloro-1H-indole-6-carboxylic acid {1-methanesulfonyl-4-[4-(2-oxo-piperidin-1-yl)-benzoylamino]-piperidin-3-yl}-amide |
| 242. | (3R,4S)-3-Chloro-1H-indole-6-carboxylic acid {1-methanesulfonyl-4-[4-(2-oxo-2H-pyridin-1-yl)-benzoylamino]-piperidin-3-yl}-amide |
| 243. | (3R,4S)-3-Chloro-1H-indole-6-carboxylic acid {1-(1-methoxy-cyclopropanecarbonyl)-4-[4-(2-oxo-2H-pyridin-1-yl)-benzoylamino]-piperidin-3-yl}-amide |
| 244. | (3R,4S)-3-Chloro-1H-indole-6-carboxylic acid {1-(1-methoxy-cyclopropanecarbonyl)-4-[4-(2-oxo-piperidin-1-yl)-benzoylamino]-piperidin-3-yl}-amide |
| 245. | (3S,4R)-3-Chloro-1H-indole-6-carboxylic acid {3-[4-(2-oxo-2H-pyridin-1-yl)-benzoylamino]-tetrahydro-pyran-4-yl}-amide |
| 246. | (3S,4R)-3-Chloro-1H-indole-6-carboxylic acid {3-[4-(2-oxo-piperidin-1-yl)-benzoylamino]-tetrahydro-pyran-4-yl}-amide |
| 247. | (3S,4R)-3-Chloro-1H-indole-6-carboxylic acid {1,1-dioxo-3-[4-(2-oxo-2H-pyridin-1-yl)-benzoylamino]-hexahydro-1$\lambda^6$-thiopyran-4-yl}-amide |
| 248. | (3S,4R)-3-Chloro-1H-indole-6-carboxylic acid {1,1-dioxo-3-[4-(2-oxo-piperidin-1-yl)-benzoylamino]-hexahydro-1$\lambda^6$-thiopyran-4-yl}-amide |
| 249. | (3R,4S)-3-Chloro-1H-indole-6-carboxylic acid {4-[4-(2-oxo-piperidin-1-yl)-benzoylamino]-tetrahydro-pyran-3-yl}-amide |
| 250. | (3R,4S)-3-Chloro-1H-indole-6-carboxylic acid {4-[4-(2-oxo-2H-pyridin-1-yl)-benzoylamino]-tetrahydro-pyran-3-yl}-amide |
| 251. | (3R,4S)-3-Chloro-1H-indole-6-carboxylic acid {1,1-dioxo-4-[4-(2-oxo-2H-pyridin-1-yl)-benzoylamino]-hexahydro-1$\lambda^6$-thiopyran-3-yl}-amide |
| 252. | (3R,4S)-3-Chloro-1H-indole-6-carboxylic acid {1,1-dioxo-4-[4-(2-oxo-piperidin-1-yl)-benzoylamino]-hexahydro-1$\lambda^6$-thiopyran-3-yl}-amide |
| 253. | (7S,8R)-3-Chloro-1H-indole-6-carboxylic acid {7-[4-(2-oxo-2H-pyridin-1-yl)-benzoylamino]-1-oxa-spiro[4.5]dec-8-yl}-amide |
| 254. | (7R,8S)-3-Chloro-1H-indole-6-carboxylic acid {8-[4-(2-oxo-2H-pyridin-1-yl)-benzoylamino]-1-oxa-spiro[4.5]dec-7-yl}-amide |
| 255. | (3R,4S)-3-Chloro-1H-indole-6-carboxylic acid {8-[4-(2-oxo-2H-pyridin-1-yl)-benzoylamino]-1-oxa-spiro[4.4]non-7-yl}-amide |
| 256. | (2R,3S)-3-Chloro-1H-indole-6-carboxylic acid {3-[4-(2-oxo-2H-pyridin-1-yl)-benzoylamino]-1,2,3,4-tetrahydro-naphthalen-2-yl}-amide |
| 257. | (3S,4R)-3-Chloro-1H-indole-6-carboxylic acid {1-methylcarbamoyl-3-[4-(2-oxo-2H-pyridin-1-yl)-benzoylamino]-piperidin-4-yl}-amide |
| 258. | (3R,4S)-{4-[(3-Chloro-1H-indole-6-carbonyl)-amino]-3-[4-(2-oxo-2H-pyridin-1-yl)-benzoylamino]-piperidin-1-yl}-acetic acid methyl ester |
| 259. | (3R,4S)-3-{4-[(3-Chloro-1H-indole-6-carbonyl)-amino]-3-[4-(2-oxo-2H-pyridin-1-yl)-benzoylamino]-piperidin-1-yl}-propionic acid methyl ester |
| 260. | (3S,4R)-3-Chloro-1H-indole-6-carboxylic acid {1-(morpholine-4-carbonyl)-3-[4-(2-oxo-2H-pyridin-1-yl)-benzoylamino]-piperidin-4-yl}-amide |
| 261. | (3S,4R)-3-Chloro-1H-indole-6-carboxylic acid {1-benzoyl-3-[4-(2-oxo-2H-pyridin-1-yl)-benzoylamino]-piperidin-4-yl}-amide |
| 262. | (3S,4R)-3-Chloro-1H-indole-6-carboxylic acid {1-(2-methoxy-2-methyl-propionyl)-3-[4-(2-oxo-2H-pyridin-1-yl)-benzoylamino]-piperidin-4-yl}-amide |
| 263. | (3S,4R)-3-Chloro-1H-indole-6-carboxylic acid {1-(1-hydroxy-cyclopropanecarbonyl)-3-[4-(2-oxo-2H-pyridin-1-yl)-benzoylamino]-piperidin-4-yl}-amide |
| 264. | (3S,4R)-3-Chloro-1H-indole-6-carboxylic acid {1-(2-hydroxy-2-methyl-propionyl)-3-[4-(2-oxo-2H-pyridin-1-yl)-benzoylamino]-piperidin-4-yl}-amide |
| 265. | (3S,4R)-3-Chloro-1H-indole-6-carboxylic acid {1-cyclopropylcarbamoyl-3-[4-(2-oxo-2H-pyridin-1-yl)-benzoylamino]-piperidin-4-yl}-amide |
| 266. | (3S,4R)-3-Chloro-1H-indole-6-carboxylic acid {1-(3-methoxy-2,2-dimethyl-propionyl)-3-[4-(2-oxo-2H-pyridin-1-yl)-benzoylamino]-piperidin-4-yl}-amide |
| 267. | (3S,4R)-3-Chloro-1H-indole-6-carboxylic acid {1-(3-hydroxy-2,2-dimethyl-propionyl)-3-[4-(2-oxo-2H-pyridin-1-yl)-benzoylamino]-piperidin-4-yl}-amide |
| 268. | (3S,4R)-3-Chloro-1H-indole-6-carboxylic acid {1-[(2-methoxy-ethyl)-methyl-carbamoyl]-3-[4-(2-oxo-2H-pyridin-1-yl)-benzoylamino]-piperidin-4-yl}-amide |

TABLE 1-continued

| Example | Name |
|---|---|
| 269. | (3S,4R)-3-Chloro-1H-indole-6-carboxylic acid {1-[(2-hydroxy-ethyl)-methyl-carbamoyl]-3-[4-(2-oxo-2H-pyridin-1-yl)-benzoylamino]-piperidin-4-yl}-amide |
| 270. | (3S,4R)-4-[(3-Chloro-1H-indole-6-carbonyl)-amino]-3-[4-(2-oxo-2H-pyridin-1-yl)-benzoylamino]-piperidine-1-carboxylic acid ethyl ester |
| 271. | (3S,4R)-3 Chloro-1H-indole-6-carboxylic acid {1-(azetidine-1-carbonyl)-3-[4-(2-oxo-2H-pyridin-1-yl)-benzoylamino]-piperidin-4-yl}-amide |
| 272. | (3S,4R)-4-[(3-Chloro-1H-indole-6-carbonyl)-amino]-3-[4-(2-oxo-2H-pyridin-1-yl)-benzoylamino]-piperidine-1-carboxylic acid 2-methoxy-ethyl ester |
| 273. | (3S,4R)-3-Chloro-1H-indole-6-carboxylic acid {1-(3-fluoro-pyrrolidine-1-carbonyl)-3-[4-(2-oxo-2H-pyridin-1-yl)-benzoylamino]-piperidin-4-yl}-amide |
| 274. | (3S,4R)-3-Chloro-1H-indole-6-carboxylic acid {1-cyclobutanecarbonyl-3-[4-(2-oxo-2H-pyridin-1-yl)-benzoylamino]-piperidin-4-yl}-amide |
| 275. | (3S,4R)-3-Chloro-1H-indole-6-carboxylic acid {1-cyclopentanecarbonyl-3-[4-(2-oxo-2H-pyridin-1-yl)-benzoylamino]-piperidin-4-yl}-amide |
| 276. | 18-no structure: (3S,4R)-3-Chloro-1H-indole-6-carboxylic acid [3-[4-(2-oxo-2H-pyridin-1-yl)-benzoylamino]-1-(pyrrolidine-1-carbonyl)-piperidin-4-yl]-amide |
| 277. | 17-no structure: (3S,4R)-3-Chloro-1H-indole-6-carboxylic acid {1-(3-hydroxy-pyrrolidine-1-carbonyl)-3-[4-(2-oxo-2H-pyridin-1-yl)-benzoylamino]-piperidin-4-yl}-amide |
| 278. | (3S,4S)-5-Chloro-thiophene-2-carboxylic acid {1-methyl-2-oxo-4-[4-(2-oxo-2H-pyridin-1-yl)-benzoylamino]-pyrrolidin-3-yl}-amide |
| 279. | (3S,4S)-5-Chloro-thiophene-2-carboxylic acid {1-methyl-2-oxo-4-[4-(2-oxo-piperidin-1-yl)-benzoylamino]-pyrrolidin-3-yl}-amide |
| 280. | (3S,4S)-5-Chloro-thiophene-2-carboxylic acid {1-methyl-2-oxo-4-[4-(3-oxo-morpholin-4-yl)-benzoylamino]-pyrrolidin-3-yl}-amide |
| 281. | (3S,4S)-5-Chloro-thiophene-2-carboxylic acid {1-methyl-2-oxo-4-[4-(2-oxo-2H-pyrazin-1-yl)-benzoylamino]-pyrrolidin-3-yl}-amide |
| 282. | (3S,4S)-5-Chloro-thiophene-2-carboxylic acid {1-methyl-2-oxo-4-[4-(2-oxo-2H-pyridin-1-yl)-benzylamino]-pyrrolidin-3-yl}-amide |
| 283. | (3S,4S)-5-Chloro-thiophene-2-carboxylic acid {1-methyl-2-oxo-4-[4-(2-oxo-piperidin-1-yl)-benzylamino]-pyrrolidin-3-yl}-amide |
| 284. | (3S,4S)-5-Chloro-thiophene-2-carboxylic acid {1-methyl-2-oxo-4-[4-(3-oxo-morpholin-4-yl)-benzylamino]-pyrrolidin-3-yl}-amide |
| 285. | (3S,4S)-5-Chloro-thiophene-2-carboxylic acid {1-methyl-2-oxo-4-[4-(2-oxo-2H-pyrazin-1-yl)-benzylamino]-pyrrolidin-3-yl}-amide |
| 286. | (3R,4R)-5-Chloro-thiophene-2-carboxylic acid {1-methyl-5-oxo-4-[4-(2-oxo-2H-pyridin-1-yl)-benzoylamino]-pyrrolidin-3-yl}-amide |
| 287. | (3R,4R)-5-Chloro-thiophene-2-carboxylic acid {1-methyl-5-oxo-4-[4-(2-oxo-piperidin-1-yl)-benzoylamino]-pyrrolidin-3-yl}-amide |
| 288. | (3R,4R)-5-Chloro-thiophene-2-carboxylic acid {1-methyl-5-oxo-4-[4-(3-oxo-morpholin-4-yl)-benzoylamino]-pyrrolidin-3-yl}-amide |
| 289. | (3R,4R)-5-Chloro-thiophene-2-carboxylic acid {1-methyl-5-oxo-4-[4-(2-oxo-2H-pyrazin-1-yl)-benzoylamino]-pyrrolidin-3-yl}-amide |
| 290. | (3R,4R)-5-Chloro-thiophene-2-carboxylic acid {1-methyl-5-oxo-4-[4-(2-oxo-2H-pyridin-1-yl)-benzylamino]-pyrrolidin-3-yl}-amide |
| 291. | (3R,4R)-5-Chloro-thiophene-2-carboxylic acid {1-methyl-5-oxo-4-[4-(2-oxo-piperidin-1-yl)-benzylamino]-pyrrolidin-3-yl}-amide |
| 292. | (3R,4R)-5-Chloro-thiophene-2-carboxylic acid {1-methyl-5-oxo-4-[4-(3-oxo-morpholin-4-yl)-benzylamino]-pyrrolidin-3-yl}-amide |
| 293. | (3R,4R)-5-Chloro-thiophene-2-carboxylic acid {1-methyl-5-oxo-4-[4-(2-oxo-2H-pyrazin-1-yl)-benzylamino]-pyrrolidin-3-yl}-amide |
| 294. | (1R,2S)-5-Chloro-thiophene-2-carboxylic acid {2-[4-(2-oxo-piperazin-1-yl)-benzoylamino]-cyclopentyl}-amide |
| 295. | (1R,2S)-3-Chloro-1H-indole-6-carboxylic acid {2-[4-(2-oxo-2H-pyrazin-1-yl)-benzoylamino]-cyclopentyl}-amide |
| 296. | (1R,2S)-3-Chloro-1H-indole-6-carboxylic acid {2-[4-(2-oxo-[1,3]oxazinan-3-yl)-benzoylamino]-cyclopentyl}-amide |
| 297. | (1R,2S)-3-Chloro-1H-indole-6-carboxylic acid {2-[4-(2-oxo-tetrahydro-pyrimidin-1-yl)-benzoylamino]-cyclopentyl}-amide |
| 298. | (1R,2S)-3-Chloro-1H-indole-6-carboxylic acid {2-[4-(2-oxo-piperazin-1-yl)-benzoylamino]-cyclopentyl}-amide |
| 299. | (1R,2S)-3-Chloro-1H-indole-6-carboxylic acid {2-[4-(1,1-dioxo-1$\lambda^6$-[1,2]thiazinan-2-yl)-benzoylamino]-cyclopentyl}-amide |
| 300. | (1R,2S)-5-Chloro-thiophene-2-carboxylic acid {2-[4-(2-oxo-2H-pyrazin-1-yl)-phenylcarbamoyl]-cyclopentyl}-amide |
| 301. | (1R,2S)-5-Chloro-thiophene-2-carboxylic acid {2-[4-(2-oxo-[1,3]oxazinan-3-yl)-phenylcarbamoyl]-cyclopentyl}-amide |
| 302. | (1R,2S)-5-Chloro-thiophene-2-carboxylic acid {2-[4-(2-oxo-tetrahydro-pyrimidin-1-yl)-phenylcarbamoyl]-cyclopentyl}-amide |

TABLE 1-continued

| Example | Name |
|---|---|
| 303. | (1R,2S)-5-Chloro-thiophene-2-carboxylic acid {2-[4-(1,1-dioxo-1$\lambda^6$-[1,2]thiazinan-2-yl)-phenylcarbamoyl]-cyclopentyl}-amide |
| 304. | (1R,2S)-5-Chloro-thiophene-2-carboxylic acid {2-[4-(2-oxo-piperazin-1-yl)-phenylcarbamoyl]-cyclopentyl}-amide |
| 305. | (1R,2S)-5-Chloro-thiophene-2-carboxylic acid {2-[4-(2-oxo-azepan-1-yl)-phenylcarbamoyl]-cyclopentyl}-amide |
| 306. | (1R,2S)-3-Chloro-1H-indole-6-carboxylic acid {2-[4-(2-oxo-2H-pyrazin-1-yl)-phenylcarbamoyl]-cyclopentyl}-amide |
| 307. | (1R,2S)-3-Chloro-1H-indole-6-carboxylic acid {2-[4-(2-oxo-[1,3]oxazinan-3-yl)-phenylcarbamoyl]-cyclopentyl}-amide |
| 308. | (1R,2S)-3-Chloro-1H-indole-6-carboxylic acid {2-[4-(2-oxo-tetrahydro-pyrimidin-1-yl)-phenylcarbamoyl]-cyclopentyl}-amide |
| 309. | (1R,2S)-3-Chloro-1H-indole-6-carboxylic acid {2-[4-(2-oxo-piperazin-1-yl)-phenylcarbamoyl]-cyclopentyl}-amide |
| 310. | (1R,2S)-3-Chloro-1H-indole-6-carboxylic acid {2-[4-(1,1-dioxo-1$\lambda^6$-[1,2]thiazinan-2-yl)-phenylcarbamoyl]-cyclopentyl}-amide |
| 311. | (1R,2S)-3-Chloro-1H-indole-6-carboxylic acid {2-[4-(2-oxo-azepan-1-yl)-phenylcarbamoyl]-cyclopentyl}-amide |
| 312. | (3R,4S)-3-Chloro-1H-indole-6-carboxylic acid {1,1-dioxo-4-[4-(2-oxo-2H-pyridin-1-yl)-benzoylamino]-tetrahydro-1$\lambda^6$-thiophen-3-yl}-amide |
| 313. | (3R,4S)-3-Chloro-1H-indole-6-carboxylic acid {1,1-dioxo-4-[4-(2-oxo-piperidin-1-yl)-benzoylamino]-tetrahydro-1$\lambda^6$-thiophen-3-yl}-amide |
| 314. | (3R,4S)-3-[(5-Chloro-thiophene-2-carbonyl)-amino]-4-[4-(2-oxo-2H-pyridin-1-yl)-phenylcarbamoyl]-pyrrolidine-1-carboxylic acid methyl ester |
| 315. | (3R,4S)-1-Acetyl-4-[(5-chloro-thiophene-2-carbonyl)-amino]-pyrrolidine-3-carboxylic acid [4-(2-oxo-2H-pyridin-1-yl)-phenyl]-amide |
| 316. | (3R,4S)-4-[(5-Chloro-thiophene-2-carbonyl)-amino]-1-methanesulfonyl-pyrrolidine-3-carboxylic acid [4-(2-oxo-2H-pyridin-1-yl)-phenyl]-amide |
| 317. | (3R,4S)-4-[(5-Chloro-thiophene-2-carbonyl)-amino]-pyrrolidine-1,3-dicarboxylic acid 1-dimethylamide 3-{[4-(2-oxo-2H-pyridin-1-yl)-phenyl]-amide} |
| 318. | (3R,4S)-4-[(5-Chloro-thiophene-2-carbonyl)-amino]-tetrahydro-furan-3-carboxylic acid [4-(2-oxo-2H-pyridin-1-yl)-phenyl]-amide |
| 319. | (3R,4S)-5-Chloro-thiophene-2-carboxylic acid {1,1-dioxo-4-[4-(2-oxo-2H-pyridin-1-yl)-phenylcarbamoyl]-tetrahydro-1$\lambda^6$-thiophen-3-yl}-amide |
| 320. | (3R,4S)-3-[(3-Chloro-1H-indole-6-carbonyl)-amino]-4-[4-(2-oxo-2H-pyridin-1-yl)-phenylcarbamoyl]-pyrrolidine-1-carboxylic acid methyl ester |
| 321. | (3R,4S)-3-Chloro-1H-indole-6-carboxylic acid {1-acetyl-4-[4-(2-oxo-2H-pyridin-1-yl)-phenylcarbamoyl]-pyrrolidin-3-yl}-amide |
| 322. | (3R,4S)-3-Chloro-1H-indole-6-carboxylic acid {1-methanesulfonyl-4-[4-(2-oxo-2H-pyridin-1-yl)-phenylcarbamoyl]-pyrrolidin-3-yl}-amide |
| 323. | (3R,4S)-3-Chloro-1H-indole-6-carboxylic acid {4-[4-(2-oxo-2H-pyridin-1-yl)-phenylcarbamoyl]-tetrahydro-furan-3-yl}-amide |
| 324. | (3R,4S)-3-Chloro-1H-indole-6-carboxylic acid (1-dimethylcarbamoyl-4-{[4-(2-oxo-2H-pyridin-1-yl)-phenylamino]-methyl}-pyrrolidin-3-yl)-amide |
| 325. | (3R,4S)-3-Chloro-1H-indole-6-carboxylic acid {1,1-dioxo-4-[4-(2-oxo-2H-pyridin-1-yl)-phenylcarbamoyl]-tetrahydro-1$\lambda^6$-thiophen-3-yl}-amide |
| 326. | (1R,2S)-3-Chloro-1H-indole-6-carboxylic acid {2-[4-(1,1-dioxo-1$\lambda^6$-[1,2]thiazinan-2-yl)-benzoylamino]-cyclohexyl}-amide |
| 327. | (1R,2S)-3-Chloro-1H-indole-6-carboxylic acid {2-[4-(2-oxo-azepan-1-yl)-benzoylamino]-cyclohexyl}-amide |
| 328. | (1R,2S)-3-Chloro-1H-indole-6-carboxylic acid {2-[4-(4-methyl-2-oxo-piperazin-1-yl)-benzoylamino]-cyclohexyl}-amide |
| 329. | (1R,2S)-3-Chloro-1H-indole-6-carboxylic acid {2-[4-(2-oxo-2H-pyrazin-1-yl)-phenylcarbamoyl]-cyclohexyl}-amide |
| 330. | (1R,2S)-3-Chloro-1H-indole-6-carboxylic acid {2-[4-(2-oxo-[1,3]oxazinan-3-yl)-phenylcarbamoyl]-cyclohexyl}-amide |
| 331. | (1R,2S)-3-Chloro-1H-indole-6-carboxylic acid {2-[4-(2-oxo-tetrahydro-pyrimidin-1-yl)-phenylcarbamoyl]-cyclohexyl}-amide |
| 332. | (1R,2S)-3-Chloro-1H-indole-6-carboxylic acid {2-[4-(2-oxo-piperazin-1-yl)-phenylcarbamoyl]-cyclohexyl}-amide |
| 333. | (1R,2S)-3-Chloro-1H-indole-6-carboxylic acid {2-[4-(1,1-dioxo-1$\lambda^6$-[1,2]thiazinan-2-yl)-phenylcarbamoyl]-cyclohexyl}-amide |
| 334. | (1R,2S)-3-Chloro-1H-indole-6-carboxylic acid {2-[4-(2-oxo-azepan-1-yl)-phenylcarbamoyl]-cyclohexyl}-amide |
| 335. | (1R,2S)-3-Chloro-1H-indole-6-carboxylic acid {2-[4-(3-oxo-morpholin-4-yl)-phenylcarbamoyl]-cyclohexyl}-amide |
| 336. | (1R,2S,4R)-3-Chloro-1H-indole-6-carboxylic acid {4-methoxy-2-[4-(2-oxo-2H-pyrazin-1-yl)-benzoylamino]-cyclohexyl}-amide |
| 337. | (1R,2S,4R)-3-Chloro-1H-indole-6-carboxylic acid {4-methoxy-2-[4-(2-oxo-piperidin-1-yl)-benzoylamino]-cyclohexyl}-amide |

TABLE 1-continued

| Example | Name |
|---|---|
| 338. | (1R,2S,4R)-3-Chloro-1H-indole-6-carboxylic acid {4-methoxy-2-[4-(3-oxo-morpholin-4-yl)-benzoylamino]-cyclohexyl}-amide |
| 339. | (1R,2S,5S)-3-Chloro-1H-indole-6-carboxylic acid {5-dimethylcarbamoyl-2-[4-(2-oxo-2H-pyrazin-1-yl)-benzoylamino]-cyclohexyl}-amide |
| 340. | (1R,2S,5S)-3-Chloro-1H-indole-6-carboxylic acid {5-dimethylcarbamoyl-2-[4-(3-oxo-morpholin-4-yl)-benzoylamino]-cyclohexyl}-amide |
| 341. | (1R,2S,5S)-3-Chloro-1H-indole-6-carboxylic acid {5-methoxy-2-[4-(2-oxo-2H-pyrazin-1-yl)-benzoylamino]-cyclohexyl}-amide |
| 342. | (1R,2S,5S)-3-Chloro-1H-indole-6-carboxylic acid {5-methoxy-2-[4-(2-oxo-piperidin-1-yl)-benzoylamino]-cyclohexyl}-amide |
| 343. | (1R,2S,5S)-3-Chloro-1H-indole-6-carboxylic acid {5-methoxy-2-[4-(3-oxo-morpholin-4-yl)-benzoylamino]-cyclohexyl}-amide |
| 344. | (1R,2S,4S)-4-[(3-Chloro-1H-indole-6-carbonyl)-amino]-cyclohexane-1,3-dicarboxylic acid 1-dimethylamide 3-{[4-(2-oxo-2H-pyridin-1-yl)-phenyl]-amide} |
| 345. | (1R,2S,4S)-3-Chloro-1H-indole-6-carboxylic acid {4-methoxy-2-[4-(2-oxo-2H-pyridin-1-yl)-phenylcarbamoyl]-cyclohexyl}-amide |
| 346. | (1R,2S,5S)-2-[(3-Chloro-1H-indole-6-carbonyl)-amino]-cyclohexane-1,4-dicarboxylic acid 4-dimethylamide 1-{[4-(2-oxo-2H-pyridin-1-yl)-phenyl]-amide} |
| 347. | (1R,2S,5S)-3-Chloro-1H-indole-6-carboxylic acid {5-methoxy-2-[4-(2-oxo-2H-pyridin-1-yl)-phenylcarbamoyl]-cyclohexyl}-amide |
| 348. | (3S,4R)-3-Chloro-1H-indole-6-carboxylic acid {3-[4-(2-oxo-2H-pyridin-1-yl)-phenylcarbamoyl]-tetrahydro-pyran-4-yl}-amide |
| 349. | (3S,4R)-3-Chloro-1H-indole-6-carboxylic acid {1,1-dioxo-3-[4-(2-oxo-2H-pyridin-1-yl)-phenylcarbamoyl]-hexahydro-1$\lambda^6$-thiopyran-4-yl}-amide |
| 350. | (3R,4S)-3-Chloro-1H-indole-6-carboxylic acid {3-[4-(2-oxo-2H-pyridin-1-yl)-phenylcarbamoyl]-tetrahydro-pyran-3-yl}-amide |
| 351. | (3R,4S)-3-Chloro-1H-indole-6-carboxylic acid {1,1-dioxo-3-[4-(2-oxo-2H-pyridin-1-yl)-phenylcarbamoyl]-hexahydro-1$\lambda^6$-thiopyran-3-yl}-amide |
| 352. | (3S,4R)-4-[(3-Chloro-1H-indole-6-carbonyl)-amino]-piperidine-1,3-dicarboxylic acid 1-dimethylamide 3-{[4-(2-oxo-2H-pyridin-1-yl)-phenyl]-amide} |
| 353. | (3S,4R)-3-Chloro-1H-indole-6-carboxylic acid{1-cyclopropanecarbonyl-3-[4-(2-oxo-2H-pyridin-1-yl)-phenylcarbamoyl]-piperidin-4-yl}-amide |
| 354. | (3S,4R)-4-[(3-Chloro-1H-indole-6-carbonyl)-amino]-3-[4-(2-oxo-2H-pyridin-1-yl)-phenylcarbamoyl]-piperidine-1-carboxylic acid methyl ester |
| 355. | (3S,4R)-3-Chloro-1H-indole-6-carboxylic acid {1-acetyl-3-[4-(2-oxo-2H-pyridin-1-yl)-phenylcarbamoyl]-piperidin-4-yl}-amide |
| 356. | (3S,4R)-3-Chloro-1H-indole-6-carboxylic acid {1-methanesulfonyl-3-[4-(2-oxo-2H-pyridin-1-yl)-phenylcarbamoyl]-piperidin-4-yl}-amide |
| 357. | (3S,4R)-3-Chloro-1H-indole-6-carboxylic acid {1-(1-methoxy-cyclopropanecarbonyl)-3-[4-(2-oxo-2H-pyridin-1-yl)-phenylcarbamoyl]-piperidin-4-yl}-amide |
| 358. | (3R,4S)-3-[(3-Chloro-1H-indole-6-carbonyl)-amino]-4-[4-(2-oxo-2H-pyridin-1-yl)-phenylcarbamoyl]-piperidine-1-carboxylic acid methyl ester |
| 359. | (3R,4S)-3-Chloro-1H-indole-6-carboxylic acid {1-cyclopropanecarbonyl-4-[4-(2-oxo-2H-pyridin-1-yl)-phenylcarbamoyl]-piperidin-3-yl}-amide |
| 360. | (3R,4S)-3-[(3-Chloro-1H-indole-6-carbonyl)-amino]-4-{2-[4-(2-oxo-2H-pyridin-1-yl)-phenyl]-acetyl}-piperidine-1-carboxylic acid methyl ester |
| 361. | (3R,4S)-3-Chloro-1H-indole-6-carboxylic acid {1-acetyl-4-[4-(2-oxo-2H-pyridin-1-yl)-phenylcarbamoyl]-piperidin-3-yl}-amide |
| 362. | (3R,4S)-3-Chloro-1H-indole-6-carboxylic acid {1-methanesulfonyl-4-[4-(2-oxo-2H-pyridin-1-yl)-phenylcarbamoyl]-piperidin-3-yl}-amide |
| 363. | (3R,4S)-3-Chloro-1H-indole-6-carboxylic acid {1-(1-methoxy-cyclopropanecarbonyl)-4-[4-(2-oxo-2H-pyridin-1-yl)-phenylcarbamoyl]-piperidin-3-yl}-amide |
| 364. | (5S,6R)-5-Chloro-thiophene-2-carboxylic acid {5-[4-(2-oxo-2H-pyridin-1-yl)-benzoylamino]-6,7-dihydro-5H-[1]pyrindin-6-yl}-amide |
| 365. | (5S,6R)-5-Chloro-thiophene-2-carboxylic acid {5-[4-(2-oxo-2H-pyridin-1-yl)-benzoylamino]-6,7-dihydro-5H-[2]pyrindin-6-yl}-amide |
| 366. | (5S,6R)-5-Chloro-thiophene-2-carboxylic acid {7-[4-(2-oxo-2H-pyridin-1-yl)-benzoylamino]-6,7-dihydro-5H-[2]pyrindin-6-yl}-amide |
| 367. | (5S,6R)-5-Chloro-thiophene-2-carboxylic acid {7-[4-(2-oxo-2H-pyridin-1-yl)-benzoylamino]-6,7-dihydro-5H-[1]pyrindin-6-yl}-amide |
| 368. | (1S,2R)-5-Chloro-thiophene-2-carboxylic acid {4-fluoro-1-[4-(2-oxo-2H-pyridin-1-yl)-benzoylamino]-indan-2-yl}-amide |

TABLE 1-continued

| Example | Name |
|---|---|
| 369. | (1S,2R)-5-Chloro-thiophene-2-carboxylic acid {4-methoxy-1-[4-(2-oxo-2H-pyridin-1-yl)-benzoylamino]-indan-2-yl}-amide |
| 370. | (1S,2R)-5-Chloro-thiophene-2-carboxylic acid {4-cyano-1-[4-(2-oxo-2H-pyridin-1-yl)-benzoylamino]-indan-2-yl}-amide |
| 371. | (6R,7S)-5-Chloro-thiophene-2-carboxylic acid {4-methyl-7-[4-(2-oxo-2H-pyridin-1-yl)-benzoylamino]-6,7-dihydro-5H-[1]pyrindin-6-yl}-amide |
| 372. | (1S,2R)-5-Chloro-thiophene-2-carboxylic acid {4-methanesulfonyl-1-[4-(2-oxo-2H-pyridin-1-yl)-benzoylamino]-indan-2-yl}-amide |
| 373. | (1S,2R)-5-Chloro-thiophene-2-carboxylic acid {4-(1-hydroxy-1-methyl-ethyl)-1-[4-(2-oxo-2H-pyridin-1-yl)-benzoylamino]-indan-2-yl}-amide |
| 374. | (6S,7R)-3-Chloro-1H-indole-6-carboxylic acid {6-[4-(2-oxo-2H-pyridin-1-yl)-benzoylamino]-6,7-dihydro-5H-[1]pyrindin-7-yl}-amide |
| 375. | (6S,7R)-3-Chloro-1H-indole-6-carboxylic acid {6-[4-(2-oxo-2H-pyridin-1-yl)-benzoylamino]-6,7-dihydro-5H-[2]pyrindin-7-yl}-amide |
| 376. | (5R,6S)-3-Chloro-1H-indole-6-carboxylic acid {6-[4-(2-oxo-2H-pyridin-1-yl)-benzoylamino]-6,7-dihydro-5H-[2]pyrindin-5-yl}-amide |
| 377. | (5R,6S)-3-Chloro-1H-indole-6-carboxylic acid {6-[4-(2-oxo-2H-pyridin-1-yl)-benzoylamino]-6,7-dihydro-5H-[1]pyrindin-5-yl}-amide |
| 378. | 5-Chloro-thiophene-2-carboxylic acid (2-{2-oxo-2-[4-(2-oxo-2H-pyrazin-1-yl)-phenyl]-ethyl}-cyclopentyl)-amide |
| 379. | N-{2-[2-(5-Chloro-thiophen-2-yl)-2-oxo-ethyl]-cyclopentyl}-4-(2-oxo-2H-pyrazin-1-yl)-benzamide |
| 380. | N-{2-[2-(5-Chloro-thiophen-2-yl)-2-oxo-ethyl]-cyclopentyl}-4-(2-oxo-2H-pyridin-1-yl)-benzamide |
| 381. | 5-Chloro-thiophene-2-carboxylic acid (2-{2-oxo-2-[4-(2-oxo-2H-pyridin-1-yl)-phenyl]-ethyl}-cyclopentyl)-amide |
| 382. | 5-Chloro-thiophene-2-carboxylic acid (1-methanesulfonyl-4-{oxo-2-[4-(2-oxo-2H-pyridin-1-yl)-phenyl]-ethyl}-pyrrolidin-3-yl)-amide |
| 383. | N-{4-[2-(5-Chloro-thiophen-2-yl)-2-oxo-ethyl]-1-methanesulfonyl-pyrrolidin-3-yl}-4-(2-oxo-2H-pyridin-1-yl)-benzamide |
| 384. | 3-[(3-Chloro-1H-indole-6-carbonyl)-amino]-4-[4-(2-oxo-2H-pyridin-1-yl)-benzylamino]-piperidine-1-carboxylic acid methyl ester |
| 385. | 3-[(3-Chloro-1H-indole-6-carbonyl)-amino]-4-[4-(2-oxo-2H-pyridin-1-yl)-benzenesulfonylmethyl]-piperidine-1-carboxylic acid methyl ester |
| 386. | 3-Chloro-1H-indole-6-carboxylic acid (1-methyl-4-{2-oxo-2-[4-(2-oxo-2H-pyridin-1-yl)-phenyl]-ethyl}-piperidin-3-yl)-amide |
| 387. | N-((3R,4S)-1-acetyl-4-(4-(3-oxomorpholino)benzamido)pyrrolidin-3-yl)-5-chlorothiophene-2-carboxamide |
| 388. | 5-chloro-N-((3R,4S)-4-(4-(3-oxomorpholino)benzamido)-1-propionylpyrrolidin-3-yl)thiophene-2-carboxamide |
| 389. | 5-chloro-N-((3R,4S)-4-(4-(2-oxopiperidin-1-yl)benzamido)-1-propionylpyrrolidin-3-yl)thiophene-2-carboxamide |
| 390. | 5-chloro-N-((3R,4S)-1-(3-methylbutanoyl)-4-(4-(2-oxopyridin-1(2H)-yl)benzamido)pyrrolidin-3-yl)thiophene-2-carboxamide |
| 391. | 5-chloro-N-((3R,4S)-1-(3-methylbutanoyl)-4-(4-(2-oxopiperidin-1-yl)benzamido)pyrrolidin-3-yl)thiophene-2-carboxamide |
| 392. | 5-chloro-N-((3R,4S)-1-(3-methylbutanoyl)-4-(4-(3-oxomorpholino)benzamido)pyrrolidin-3-yl)thiophene-2-carboxamide |
| 393. | 5-chloro-N-((3R,4S)-1-(2-cyclopropylacetyl)-4-(4-(2-oxopyridin-1(2H)-yl)benzamido)pyrrolidin-3-yl)thiophene-2-carboxamide |
| 394. | 5-chloro-N-((3R,4S)-1-(2-cyclobutylacetyl)-4-(4-(2-oxopyridin-1(2H)-yl)benzamido)pyrrolidin-3-yl)thiophene-2-carboxamide |
| 395. | 5-chloro-N-((3R,4S)-1-(2-cyclopentylacetyl)-4-(4-(2-oxopyridin-1(2H)-yl)benzamido)pyrrolidin-3-yl)thiophene-2-carboxamide |
| 396. | 5-chloro-N-((3R,4S)-4-(4-(2-oxopyridin-1(2H)-yl)benzamido)-1-(2-(tetrahydro-2H-pyran-4-yl)acetyl)pyrrolidin-3-yl)thiophene-2-carboxamide |
| 397. | 5-chloro-N-((3R,4S)-4-(4-(2-oxopyridin-1(2H)-yl)benzamido)-1-(2-(tetrahydro-2H-pyran-4-yl)acetyl)pyrrolidin-3-yl)thiophene-2-carboxamide |
| 398. | (3R,4S)-ethyl 3-(2-chlorothiophene-5-carboxamido)-4-(4-(2-oxopiperidin-1-yl)benzamido)pyrrolidine-1-carboxylate |
| 399. | (3R,4S)-ethyl 3-(2-chlorothiophene-5-carboxamido)-4-(4-(3-oxomorpholino)benzamido)pyrrolidine-1-carboxylate |
| 400. | 5-chloro-N-((3R,4S)-1-isopropyl-4-(4-(2-oxopyridin-1(2H)-yl)benzamido)pyrrolidin-3-yl)thiophene-2-carboxamide |
| 401. | 5-chloro-N-((3R,4S)-1-isopropyl-4-(4-(2-oxopiperidin-1-yl)benzamido)pyrrolidin-3-yl)thiophene-2-carboxamide |
| 402. | 5-chloro-N-((3R,4S)-1-isopropyl-4-(4-(3-oxomorpholino)benzamido)pyrrolidin-3-yl)thiophene-2-carboxamide |
| 403. | 5-chloro-N-((3R,4S)-1-isopropyl-4-(4-(2-oxopyrazin-1(2H)-yl)benzamido)pyrrolidin-3-yl)thiophene-2-carboxamide |
| 404. | 5-chloro-N-((3R,4S)-1-(2-hydroxyethyl)-4-(4-(2-oxopyridin-1(2H)-yl)benzamido)pyrrolidin-3-yl)thiophene-2-carboxamide |

TABLE 1-continued

| Example | Name |
|---|---|
| 405. | 5-chloro-N-((3R,4S)-1-(2-methoxyethyl)-4-(4-(2-oxopyridin-1(2H)-yl)benzamido)pyrrolidin-3-yl)thiophene-2-carboxamide |
| 406. | (3R,4S)-3-(2-chlorothiophene-5-carboxamido)-4-(4-(2-oxopyridin-1(2H)-yl)benzamido)pyrrolidine-1-carboxamide |
| 407. | (3R,4S)-3-(2-chlorothiophene-5-carboxamido)-N-methyl-4-(4-(2-oxopyridin-1(2H)-yl)benzamido)pyrrolidine-1-carboxamide |
| 408. | (3R,4S)-3-(2-chlorothiophene-5-carboxamido)-N-cyclopropyl-4-(4-(2-oxopyridin-1(2H)-yl)benzamido)pyrrolidine-1-carboxamide |
| 409. | (3R,4S)-3-(2-chlorothiophene-5-carboxamido)-N-cyclopentyl-4-(4-(2-oxopyridin-1(2H)-yl)benzamido)pyrrolidine-1-carboxamide |
| 410. | (3R,4S)-3-(2-chlorothiophene-5-carboxamido)-N-cyclopropyl-4-(4-(2-oxopyridin-1(2H)-yl)benzamido)pyrrolidine-1-carboxamide |
| 411. | (3R,4S)-isobutyl 3-(2-chlorothiophene-5-carboxamido)-4-(4-(2-oxopyridin-1(2H)-yl)benzamido)pyrrolidine-1-carboxylate |
| 412. | 5-chloro-N-((3R,4S)-1-cyclopropyl-4-(4-(2-oxopyridin-1(2H)-yl)benzamido)pyrrolidin-3-yl)thiophene-2-carboxamide |
| 413. | 5-chloro-N-((3R,4S)-1-(2-hydroxypropan-2-yl)-4-(4-(2-oxopyridin-1(2H)-yl)benzamido)pyrrolidin-3-yl)thiophene-2-carboxamide |
| 414. | 5-chloro-N-((3R,4S)-1-(1-(hydroxymethyl)cyclopropyl)-4-(4-(2-oxopyridin-1(2H)-yl)benzamido)pyrrolidin-3-yl)thiophene-2-carboxamide |
| 415. | 5-chloro-N-((3R,4S)-1-(methylsulfonyl)-4-(4-(2-oxopiperidin-1-yl)benzamido)pyrrolidin-3-yl)thiophene-2-carboxamide |
| 416. | 5-chloro-N-((3R,4S)-1-(ethylsulfonyl)-4-(4-(2-oxopiperidin-1-yl)benzamido)pyrrolidin-3-yl)thiophene-2-carboxamide |
| 417. | 5-chloro-N-((3R,4S)-1-(ethylsulfonyl)-4-(4-(2-oxopyridin-1(2H)-yl)benzamido)pyrrolidin-3-yl)thiophene-2-carboxamide |
| 418. | 5-chloro-N-((3R,4S)-1-(ethylsulfonyl)-4-(4-(3-oxomorpholino)-benzamido)pyrrolidin-3-yl)thiophene-2-carboxamide |
| 419. | 5-chloro-N-((3R,4S)-1-(methylsulfonyl)-4-(4-(3-oxomorpholino)benzamido)pyrrolidin-3-yl)thiophene-2-carboxamide |
| 420. | 5-chloro-N-((3R,4S)-4-(4-(2-oxopyridin-1(2H)-yl)benzamido)-1-(phenylsulfonyl)pyrrolidin-3-yl)thiophene-2-carboxamide |
| 421. | 5-chloro-N-((3R,4S)-1-(2-hydroxyethylsulfonyl)-4-(4-(2-oxopyridin-1(2H)-yl)benzamido)pyrrolidin-3-yl)thiophene-2-carboxamide |
| 422. | 5-chloro-N-((1R,2S,4S)-4-(methoxymethyl)-2-(4-(2-oxopyridin-1(2H)-yl)benzamido)cyclopentyl)thiophene-2-carboxamide |
| 423. | 5-chloro-N-((1R,2S,4S)-4-(ethoxymethyl)-2-(4-(2-oxopyridin-1(2H)-yl)benzamido)cyclopentyl)thiophene-2-carboxamide |
| 424. | 5-chloro-N-((1R,2S,4S)-4-((2-morpholinoethoxy)methyl)-2-(4-(2-oxopyridin-1(2H)-yl)benzamido)cyclopentyl)thiophene-2-carboxamide |
| 425. | 5-chloro-N-((1R,2S,4S)-4-hydroxy-2-(4-(2-oxopyridin-1(2H)-yl)benzamido)cyclopentyl)thiophene-2-carboxamide |
| 426. | 5-chloro-N-((1R,2S,4S)-4-methoxy-2-(4-(2-oxopyridin-1(2H)-yl)benzamido)cyclopentyl)thiophene-2-carboxamide |
| 427. | 5-chloro-N-((1R,2S,4S)-4-ethoxy-2-(4-(2-oxopyridin-1(2H)-yl)benzamido)cyclopentyl)thiophene-2-carboxamide |
| 428. | 5-chloro-N-((1R,2S,4S)-4-(morpholinomethoxy)-2-(4-(2-oxopyridin-1(2H)-yl)benzamido)cyclopentyl)thiophene-2-carboxamide |
| 429. | 5-chloro-N-((1R,2S,4S)-4-((methylamino)methyl)-2-(4-(2-oxopyridin-1(2H)-yl)benzamido)cyclopentyl)thiophene-2-carboxamide |

Numerous modifications and variations of the present invention are possible in light of the above teachings. It is therefore to be understood that within the scope of the appended claims, the invention may be practiced otherwise that as specifically described herein.

What is claimed is:

1. A compound selected from:

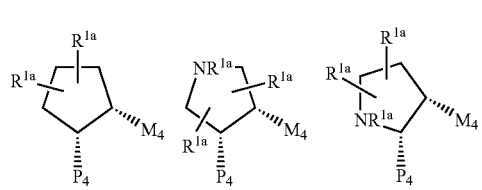

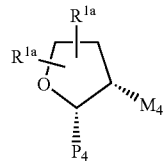

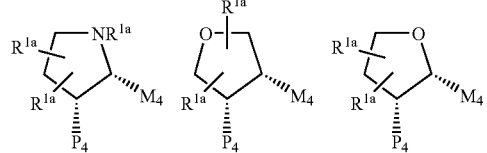

or a stereoisomer or pharmaceutically acceptable salt thereof, wherein:

one of $P_4$ and $M_4$ is -Z-A-B and the other -$G_1$-G;
G is a group of formula IIa or IIb:

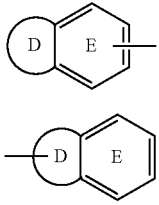

IIa

IIb ring D, including the two atoms of Ring E to which it is attached, is a 5–6 membered ring consisting of carbon atoms;
ring D is substituted with 0–2R and there are 0–3 ring double bonds;
E is selected from phenyl and pyridyl, and is substituted with 1–3 R;
alternatively, ring D is absent and ring E is selected from phenyl, pyrrolyl, and thienyl, and ring E is substituted with 1–3 R;
R is selected from H, $C_{1-4}$ alkyl, F, Cl, Br, I, OH, $OCH_3$, $OCH_2CH_3$, $OCH(CH_3)_2$, $OCH_2CH_2CH_3$, —CN, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $C(=NR^8)NR^7R^9$, $NHC(=NR^8)NR^7R^9$, $ONHC(=NR^8)NR^7R^9$, $NR^8CH(=NR^7)$, $(CR^8R^9)_tC(O)H$, $(CR^8R^9)_tC(O)R^{2c}$, $(CR^8R^9)_tNR^7R^8$, $(CR^8R^9)_tC(O)NR^7R^8$, $(CR^8R^9)_tNR^7C(O)R^7$, $(CR^8R^9)_tOR^3$, $(CR^8R^9)_tS(O)_pNR^7R^8$, $(CR^8R^9)_tNR^7S(O)_pR^7$, $(CR^8R^9)_tSR^3$, $(CR^8R^9)_tS(O)R^3$, $(CR^8R^9)_tS(O)_2R^3$, and $OCF_3$, provided that $S(O)_pR^7$ and $S(O)_2R^3$ form other than $S(O)_2H$ or $S(O)H$;
A is selected from: $C_{3-10}$ carbocycle substituted with 0–2 $R^4$ and substituted with 0–2 $R^4$;
B is

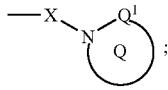

;

provided that Z and B are attached to different atoms on A and that the A-X-N moiety forms other than a N-N-N group;
$Q_1$ is selected from C=O and $SO_2$;
ring Q is a 6 membered monocyclic ring consisting of, in addition to the N-$Q_1$ group shown, carbon atoms, wherein: 0–2 double bonds are present within the ring and the ring is substituted with 0–2 $R^{4a}$;
X is absent;
$G_1$ is selected from $(CR^3R^{3a})_{1-5}$, $(CR^3R^{3a})_{0-2}CR^3=CR^3(CR^3R^{3a})_{0-2}$, $(CR^3R^{3a})_{0-2}C\equiv C(CR^3R^{3a})_{0-2}$, $(CR^3R^{3a})_u$ $C(O)(CR^3R^{3a})_w$, $(CR^3R^{3a})_uC(O)O(CR^3R^{3a})_w$, $(CR^3R^{3a})_uOC(O)(CR^3R^{3a})_w$, $(CR^3R^{3a})_uO(CR^3R^{3a})_w$, $(CR^3R^{3a})_uNR^{3b}(CR^3R^{3a})_w$, $(CR^3R^{3a})_uNR^{3e}(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uOC(O)NR^{3b}(CR^3R^{3a})_w$, $(CR^3R^{3a})_uNR^{3b}C(O)O(CR^3R^{3a})_w$, $(CR^3R^{3a})_uNR^{3b}C(O)NR^{3b}(CR^3R^{3a})_w$, $(CR^3R^{3a})_uNR^{3b}C(S)NR^{3b}(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^{3b}(CR^3R^{3a})_w$, $(CR^3R^{3a})_uNR^{3b}S(O)_2(CR^3R^{3a})_w$, $(CR^3R^{3a})_uS(O)_2NR^{3b}(CR^3R^{3a})_w$, $(CR^3R^{3a})_uNR^{3b}S(O)_2NR^{3b}(CR^3R^{34a})_w$, $(CR^3R^{3a})_uC(O)(CR^3R^{3a})_uC(O)(CR^3R^{3a})_w$, $(CR^3R^{3a})_uNR^{3b}(CR^3R^{3a})_uC(O)NR^{3b}(CR^3R^{3a})_w$, $(CR^3R^{3a})_uNR^{3b}C(O)(CR^3R^{3a})_uC(O)(CR^3R^{3a})_w$, $(CR^3R^{3a})_uC(O)(CR^3R^{3a})_uC(O)NR^{3b}(CR^3R^{3a})_w$, $(CR^3R^{3a})_uNR^{3b}C(O)(CR^3R^{3a})_uC(O)NR^{3b}(CR^3R^{3a})_w$, $(CR^3R^{3a})_uS(O)_2NR^{3b}C(O)(CR^3R^{3a})_w$, $(CR^3R^{3a})_uC(O)NR^{3b}S(O)_2(CR^3R^{3a})_w$, $(CR^3R^{3a})_uS(O)_2NR^{3b}C(O)NR^{3b}(CR^3R^{3a})_w$, $(CR^3R^{3a})_uNR^{3b}C(O)(CR^3R^{3a})_uC(S)NR^{3b}(CR^3R^{3a})_w$, and $(CR^3R^{3a})_uNR^{3b}C(S)(CR^3R^{3a})_uC(O)NR^{3b}(CR^3R^{3a})_w$, wherein u+w or u+u+w total 0, 1, 2, 3, or 4, and the right side of $G_1$ is attached to ring G, provided that $G_1$ does not form an N—S, $NCH_2N$, $NCH_2O$, or $NCH_2S$ bond with either group to which it is attached;
Z is selected from $(CR^3R^{3a})_{1-5}$, $(CR^3R^{3a})_{0-2}CR^3=CR^3(CR^3R^{3a})_{0-2}$, $(CR^3R^{3a})_{0-2}C\equiv C(CR^3R^{3a})_{0-2}$, $(CR^3R^{3a})_u$ $C(O)(CR^3R^{3a})_w$, $(CR^3R^{3a})_uC(O)O(CR^3R^{3a})_w$, $(CR^3R^{3a})_uOC(O)(CR^3R^{3a})_w$, $(CR^3R^{3a})_uO(CR^3R^{3a})_w$, $(CR^3R^{3a})_uNR^{3b}(CR^3R^{3a})_w$, $(CR^3R^{3a})_uNR^{3e}(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uOC(O)NR^{3b}(CR^3R^{3a})_w$, $(CR^3R^{3a})_uNR^{3b}C(O)O(CR^3R^{3a})_w$, $(CR^3R^{3a})_uNR^{3b}C(O)NR^{3b}(CR^3R^{3a})_w$, $(CR^3R^{3a})_uNR^{3b}C(S)NR^{3b}(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^{3b}(CR^3R^{3a})_w$, $(CR^3R^{3a})_uNR^{3b}S(O)_2(CR^3R^{3a})_w$, $(CR^3R^{3a})_uS(O)_2NR^{3b}(CR^3R^{3a})_w$, $(CR^3R^{3a})_uNR^{3b}S(O)_2NR^{3b}(CR^3R^{3a})_w$, $(CR^3R^{3a})_uC(O)(CR^3R^{3a})_uC(O)(CR^3R^{3a})_w$, $(CR^3R^{3a})_uNR^{3b}(CR^3R^{3a})_uC(O)NR^{3b}(CR^3R^{3a})_w$, $(CR^3R^{3a})_uNR^{3b}C(O)(CR^3R^{3a})_uC(O)(CR^3R^{3a})_w$, $(CR^3R^{3a})_uC(O)(CR^3R^{3a})_uC(O)NR^{3b}(CR^3R^{3a})_w$, $(CR^3R^{3a})_uNR^{3b}C(O)(CR^3R^{3a})_uC(O)NR^{3b}(CR^3R^{3a})_w$, $(CR^3R^{3a})_uS(O)_2NR^{3b}C(O)(CR^3R^{3a})_w$, $(CR^3R^{3a})_uC(O)NR^{3b}S(O)_2(CR^3R^{3a})_w$, $(CR^3R^{3a})_uS(O)_2NR^{3b}C(O)NR^{3b}(CR^3R^{3a})_w$, $(CR^3R^{3a})_uNR^{3b}C(O)(CR^3R^{3a})_uC(S)NR^{3b}(CR^3R^{3a})_w$, and $(CR^3R^{3a})_uNR^{3b}C(S)(CR^3R^{3a})_uC(O)NR^{3b}(CR^3R^{3a})_w$, wherein u+w or u+u+w total 0, 1, 2, 3, or 4, and the right side of Z is attached to ring A, provided that Z does not form an N—S, $NCH_2N$, $NCH_2O$, or $NCH_2S$ bond with either group to which it is attached;
$R^{1a}$, at each occurrence, is selected from H, $—(CR^3R^{3a})_r$ $—R^{1b}$, $—(CR^3R^{3a})_r—CR^3R^{1b}R^{1b}$, $—(CR^3R^{3a})_r—O—(CR^3R^{3a})_r—R^{1b}$, $—C_{2-6}$ alkenylene-$R^{1b}$, $—C_{2-6}$ alkynylene-$R^{1b}$, $—(CR^3R^{3a})_r—C(=NR^{1b})NR^3R^{1b}$, $NR^3CR^3R^{3a}R^{1c}$, $OCR^3R^{3a}R^{1c}$, $SCR^3R^{3a}R^{1c}$, $NR^3(CR^3R^{3a})_2(CR^3R^{3a})_rR^{1b}$, $C(O)NR^2(CR^3R^{3a})_2(CR^3R^{3a})_rR^{1b}$, $CO_2(CR^3R^{3a})_2(CR^3R^{3a})_rR^{1b}$, $O(CR^3R^{3a})_2(CR^3R^{3a})_rR^{1b}$, $S(CR^3R^{3a})_2(CR^3R^{3a})_rR^{1b}$, $S(O)_p(CR^3R^{3a})_rR^{1d}$, $O(CR^3R^{3a})_rR^{1d}$, $NR^3(CR^3R^{3a})_rR^{1d}$, $OC(O)NR^3(CR^3R^{3a})_rR^{1d}$, $NR^3C(O)NR^3(CR^3R^{3a})_r$ $R^{1d}$, $NR^3C(O)O(CR^3R^{3a})_rR^{1d}$, and $NR^3C(O)(CR^3R^{3a})_rR^{1d}$, provided that $R^{1a}$ forms other than an N-halo, N—S, O—O, or N—CN bond;
$R^{1b}$ is selected from H, $C_{1-3}$ alkyl, F, Cl, Br, I, —CN, $—NO_2$, —CHO, $(CF_2)_rCF_3$, $(CR^3R^{3a})_rOR^2$, $NR^2R^{2a}$, $C(O)R^{2b}$, $CO_2R^{2b}$, $OC(O)R^2$, $(CF_2)_rCO_2R^{2a}$, $S(O)_pR^{2b}$, $NR^2(CH_2)_rOR^2$, $C(=NR^{2c})NR^2R^{2a}$, $NR^2C(O)R^{2b}$, $NR^2C(O)NHR^2$, $NR^2C(O)_2R^{2a}$, $OC(O)NR^2R^{2a}$, $C(O)NR^2R^{2a}$, $C(O)NR^2R^{2b}$, $C(S)NR^2R^{2a}$, $C(O)NR^2(CH_2)_rOR^2$, $SO_2NR^2R^{2a}$, $NR^2SO_2R^2$, $C(O)NR^2SO_2R^2$, and $C_{3-6}$ carbocycle substituted with 0–2

$R^{4b}$ provided that $R^{1b}$ forms other than an O—O, N-halo, N—S, or N—CN bond;

$R^{1c}$ is selected from H, $CH(CH_2OR^2)_2$, $C(O)R^{2c}$, $C(O)NR^2R^{2a}$, $S(O)R^2$, $S(O)_2R^2$, and $SO_2NR^2R^{2a}$;

$R^{1d}$ is selected from $C_{3-6}$ carbocycle substituted with 0–2 $R^{4b}$;

$R^2$, at each occurrence, is selected from H, $CF_3$, $C_{1-6}$ alkyl, and $(CH_2)_r$—$C_{3-10}$ carbocycle substituted with 0–2 $R^{4b}$;

$R^{2a}$, at each occurrence, is selected from H, $CF_3$, $C_{1-6}$ alkyl, and —$(CH_2)_r$—$C_{3-10}$ carbocycle substituted with 0–2 $R^{4b}$;

$R^{2b}$, at each occurrence, is selected from $CF_3$, $C_{1-4}$ alkoxy substituted with 0–2 $R^{4b}$, $C_{1-6}$ alkyl substituted with 0–3$R^{4b}$, and $(CH_2)_r$—$C_{3-13}$ carbocycle substituted with 0–2 $R^{4b}$;

$R^{2c}$, at each occurrence, is selected from $CF_3$, OH, $C_{1-4}$ alkoxy, $C_{1-6}$ alkyl, and —$(CH_2)_r$—$C_{3-10}$ carbocycle substituted with 0–2 $R^{4b}$;

$R^3$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3a}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3b}$, at each occurrence, is selected from H, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, and —$(C_{0-4}$ alkyl)-5–10 membered carbocycle substituted with 0–3$R^{1a}$;

$R^{3c}$, at each occurrence, is selected from $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3d}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C_{1-4}$ alkyl-phenyl, and $C(=O)R^{3c}$;

$R^{3e}$, at each occurrence, is selected from H, $SO_2NHR^3$, $SO_2NR^3R^3$, $C(O)R^3$, $C(O)NHR^3$, $C(O)OR^{3f}$, $S(O)R^{3f}$, $S(O)_2R^{3f}$, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, and —$(C_{0-4}$ alkyl)-5–10 membered carbocycle substituted with 0–3 $R^{1a}$;

$R^{3f}$, at each occurrence, is selected from: $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, and —$(C_{0-4}$ alkyl)-5–10 membered carbocycle substituted with 0–3 $R^{1a}$;

$R^4$, at each occurrence, is selected from H, =O, $(CR^3R^{3a})_r$ $OR^2$, F, Cl, Br, I, $C_{1-4}$ alkyl, $(CR^3R^{3a})_r$CN, $(CR^3R^{3a})_r$ $NO_2$, $(CR^3R^{3a})_r$$NR^2R^{2a}$, $(CR^3R^{3a})_r$$C(O)R^{2c}$, $(CR^3R^{3a})_r$$NR^2C(O)R^{2b}$, $(CR^3R^{3a})_r$$C(O)NR^2R^{2a}$, $(CR^3R^{3a})_r$$NR^2C(O)NR^2R^{2a}$, $(CR^3R^{3a})_r$$C(=NR^2)NR^2R^{2a}$, $(CR^3R^{3a})_r$$C(=NS(O)_2R^5)NR^2R^{2a}$, $(CR^3R^{3a})_r$ $HC(=NR^2)NR^2R^{2a}$, $(CR^3R^{3a})_r$$C(O)NHC(=NR^2)NR^2R^{2a}$, $(CR^3R^{3a})_r$$SO_2NR^2R^{2a}$, $(CR^3R^{3a})_r$$NR^2SO_2NR^2R^{2a}$, $(CR^3R^{3a})_r$$NR^2SO_2$—$C_{1-4}$ alkyl, $(CR^3R^{3a})_r$$NR^2SO_2R^5$, $(CR^3R^{3a})_r$$S(O)_pR^{5a}$, $(CR^3R^{3a})_r$$(CF_2)_r$$CF_3$, $NHCH_2R^{1c}$, $OCH_2R^{1c}$, $SCH_2R^{1c}$, $NH(CH_2)_2(CH_2)_rR^{1b}$, $O(CH_2)_2(CH_2)_rR^{1b}$, $S(CH_2)_2(CH_2)_rR^{1b}$, and $(CR^3R^{3a})_r$-5–6 membered carbocycle substituted with 0–1 $R^5$;

$R^{4a}$, at each occurrence, is selected from H, =O, $(CR^3R^{3a})_r$$OR^2$, $(CR^3R^{3a})_r$F, $(CR^3R^{3a})_r$Br, $(CR^3R^{3a})_r$Cl, $C_{1-4}$ alkyl, $(CR^3R^{3a})_r$CN, $(CR^3R^{3a})_r$$NO_2$, $(CR^3R^{3a})_r$ $NR^2R^{2a}$, $(CR^3R^{3a})_r$$C(O)R^{2c}$, $(CR^3R^{3a})_r$$NR^2C(O)R^{2b}$, $(CR^3R^{3a})_r$$C(O)NR^2R^{2a}$, $(CR^3R^{3a})_r$ N=CHOR^3, $(CR^3R^{3a})_r$$C(O)NH(CH_2)_2NR^2R^{2a}$, $(CR^3R^{3a})_r$$NR^2C(O)NR^2R^{2a}$, $(CR^3R^{3a})_r$$C(=NR^2)NR^2R^{2a}$, $(CR^3R^{3a})_r$$NHC(=NR^2)NR^2R^{2a}$, $(CR^3R^{3a})_r$$SO_2NR^2R^{2a}$, $(CR^3R^{3a})_r$$NR^2SO_2NR^2R^{2a}$, $(CR^3R^{3a})_r$$NR^2SO_2$—$C_{1-4}$ alkyl, $(CR^3R^{3a})_r$$C(O)NHSO_2$—$C_{1-4}$ alkyl, $(CR^3R^{3a})$$NR^2SO_2R^5$, $(CR^3R^{3a})_r$$S(O)_pR^{5a}$, $(CR^3R^{3a})_r$$(CF_2)_r$$CF_3$, $(CR^3R^{3a})_r$-5–6 membered carbocycle substituted with 0–1 $R^5$;

$R^{4b}$, at each occurrence, is selected from H, =O, $(CH_2)_r$$OR^3$, $(CH_2)_r$F, $(CH_2)_r$Cl, $(CH_2)_r$Br, $(CH_2)_r$I, $C_{1-4}$ alkyl, $(CH_2)_r$CN, $(CH_2)_r$$NO_2$, $(CH_2)_r$$NR^3R^{3a}$, $(CH_2)_r$$C(O)R^3$, $(CH_2)_r$$C(O)OR^{3c}$, $(CH_2)_r$$NR^3C(O)R^{3a}$, $(CH_2)_r$—$C(O)NR^3R^{3a}$, $(CH_2)_r$$NR^3C(O)NR^3R^{3a}$, $(CH_2)_r$—$C(=NR^3)NR^3R^{3a}$, $(CH_2)_r$$NR^3C(=NR^3)NR^3R^{3a}$, $(CH_2)_r$ $SO_2NR^3R^{3a}$, $(CH_2)_r$$NR^3SO_2NR^3R^{3a}$, $(CH_2)_r$$NR^3SO_2$—$C_{1-4}$ alkyl, $(CH_2)_r$$NR^3SO_2CF_3$, $(CH_2)_r$$NR^3SO_2$-phenyl, $(CH_2)_r$$S(O)_pCF_3$, $(CH_2)_r$$S(O)_p$—$C_{1-4}$ alkyl, $(CH_2)_r$$S(O)_p$-phenyl, and $(CH_2)_r$$(CF_2)_r$$CF_3$;

$R^{4c}$, at each occurrence, is selected from H, $C_{1-4}$ alkyl, $(CR^3R^{3a})_{r1}$$OR^2$, $(CR^3R^{3a})_{r1}$F, $(CR^3R^{3a})_{r1}$Br, $(CR^3R^{3a})_{r1}$Cl, $(CR^3R^{3a})_{r1}$CN, $(CR^3R^{3a})_{r1}$$NO_2$, $(CR^3R^{3a})_{r1}$$NR^2R^{2a}$, $(CR^3R^{3a})_{r1}$$C(O)R^{2c}$, $(CR^3R^{3a})_{r1}$$NR^2C(O)R^{2b}$, $(CR^3R^{3a})_{r1}$$C(O)NR^2R^{2a}$, $(CR^3R^{3a})_{r1}$N=CHOR^3, $(CR^3R^{3a})_r$$C(O)NH(CH_2)_2NR^{22a}$, $(CR^3R^{3a})_{r1}$$NR^2C(O)NR^2R^{2a}$, $(CR^3R^{3a})_{r1}$$C(=NR^2)NR^2R^{2a}$, $(CR^3R^{3a})_{r1}$$NHC(=NR^2)NR^2R^{2a}$, $(CR^3R^{3a})_r$$SO_2NR^2R^{2a}$, $(CR^3R^{3a})_{r1}$$NR^2SO_2NR^2R^{2a}$, $(CR^3R^{3a})_{r1}$$NR^2SO_2$—$C_{1-4}$ alkyl, $(CR_3R^{3a})_r$$C(O)NHSO_2$-$C_{1-4}$ alkyl, $(CR^3R^{3a})_{r1}$$NR^2SO_2R^5$, $(CR^3R^{3a})_r$$S(O)_pR^{5a}$, $(CR^3R^{3a})_r$$(CF_2)_r$$CF_3$, and $(CR^3R^{3a})_r$-5–6 membered carbocycle substituted with 0–1 $R^5$;

$R^5$, at each occurrence, is selected from H, $C_{1-6}$ alkyl, =O, $(CH_2)_r$$OR^3$, F, Cl, Br, I, —CN, $NO_2$, $(CH_2)_r$$NR^3R^{3a}$, $(CH_2)_r$$C(O)R^3$, $(CH_2)_r$$C(O)OR^{3c}$, $(CH_2)_r$$NR^3C(O)R^{3a}$, $(CH_2)_r$$C(O)NR^3R^{3a}$, $(CH_2)_r$$NR^3C(O)NR^3R^{3a}$, $(CH_2)_r$$CH(=NOR^{3d})$, $(CH_2)_r$$C(=NR^3)NR^3R^{3a}$, $(CH_2)_r$$NR^3C(=NR^3)NR^3R^{3a}$, $(CH_2)_r$$SO_2NR^3R^{3a}$, $(CH_2)_r$$NR^3SO_2NR^3R^{3a}$, $(CH_2)_r$$NR^3SO_2$—$C_{1-4}$ alkyl, $(CH_2)_r$$NR^3SO_2CF_3$, $(CH_2)_r$$NR^3SO_2$-phenyl, $(CH_2)_r$$S(O)_pCF_3$, $(CH_2)_r$$S(O)_p$—$C_{1-4}$ alkyl, $(CH_2)_r$$S(O)_p$-phenyl, $(CF_2)_r$$CF_3$, phenyl substituted with 0–2 $R^6$, naphthyl substituted with 0–2 $R^6$, and benzyl substituted with 0–2 $R^6$;

$R^{5a}$, at each occurrence, is selected from $C_{1-6}$ alkyl, $(CH_2)_r$$OR^3$, $(CH_2)_r$$NR^3R^{3a}$, $(CH_2)_r$$C(O)R^3$, $(CH_2)_r$$C(O)OR^{3c}$, $(CH_2)_r$$NR^3C(O)R^{3a}$, $(CH_2)_r$$C(O)NR^3R^{3a}$, $(CF_2)_r$$CF_3$, phenyl substituted with 0–2 $R^6$, naphthyl substituted with 0–2 $R^6$, and benzyl substituted with 0–2 $R^6$, provided that $R^{5a}$ does not form a S—N or $S(O)_p$—$C(O)$ bond;

$R^6$, at each occurrence, is selected from H, OH, $(CH_2)_r$$OR^2$, Cl, F, Br, I, $C_{1-4}$ alkyl, —CN, $NO_2$, $(CH_2)_r$$NR^2R^{2a}$, $(CH_2)_r$$C(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkyl-$C(O)$—, $C_{1-6}$ alkyl-O—, $(CH_2)_n$-phenyl, $C_{1-4}$ alkyl-$OC(O)$—, $C_{6-10}$ aryl-O—, $C_{6-10}$ aryl-$OC(O)$—, $C_{6-10}$ aryl-$CH_2C(O)$—, $C_{1-4}$ alkyl-$C(O)O$—$C_{1-4}$ alkyl-$OC(O)$—, $C_{6-10}$ aryl-$C(O)O$—$C_{1-4}$ alkyl-$OC(O)$—, $C_{1-6}$ alkyl-$NH_2$—$C(O)$—, phenyl-$NH_2$—$C(O)$—, and phenyl-$C_{1-4}$ alkyl-$C(O)$—;

$R^8$, at each occurrence, is selected from H, $C_{1-6}$ alkyl, and $(CH_2)_n$-phenyl;

$R^9$, at each occurrence, is selected from H, $C_{1-6}$ alkyl, and $(CH_2)_n$-phenyl;

n, at each occurrence, is selected from 0, 1, 2, and 3;

p, at each occurrence, is selected from 0, 1, and 2;

r, at each occurrence, is selected from 0, 1, 2, 3, 4, 5, and 6;

r1, at each occurrence, is selected from 1, 2, 3, 4, 5, and 6; and t, at each occurrence, is selected from 0, 1, 2, and 3.

2. A compound according to claim 1, wherein:

G is selected from the group: 2-aminomethyl-4-chloro-phenyl; 2-aminosulfonyl-4-chloro-phenyl; 2-amido-4-chloro-phenyl; 4-chloro-2-methylsulfonyl-phenyl; 2-aminosulfonyl-4-fluoro-phenyl; 2-amido-4-fluoro-phenyl; 4-fluoro-2-methylsulfonyl-phenyl; 2-aminomethyl-4-bromo-phenyl; 2-aminosulfonyl-4-bromo-phenyl; 2-amido-4-bromo-phenyl; 4-bromo-2-methylsulfonyl-phenyl; 2-aminomethyl-4-methyl-phenyl; 2-aminosulfonyl-4-methyl-phenyl; 2-amido-4-methyl-phenyl; 2-methylsulfonyl-4-methyl-phenyl; 4-fluoro-pyrid-2-yl; 4-bromo-pyrid-2-yl; 4-methyl-pyrid-2-yl; 5-fluoro-thien-2-yl; 5-bromo-thien-2-yl; 5-methyl-thien-2-yl; 2-amido-4-methoxy-phenyl; 2-amido-phenyl; 2-aminomethyl-3-fluoro-phenyl; 2-aminomethyl-4-fluoro-phenyl; 2-aminomethyl-4-methoxy-phenyl; 2-aminomethyl-5-fluoro-phenyl; 2-aminomethyl-5-methoxy-phenyl; 2-aminomethyl-6-fluoro-phenyl; 2-aminomethyl-phenyl; 2-amino-pyrid-4-yl; 2-aminosulfonyl-4-methoxy-phenyl; 2-aminosulfonyl-phenyl; 2-methylsulfonyl-phenyl; 3-(N,N-dimethylamino)-4-chloro-phenyl; 3-(N,N-dimethylamino)-phenyl; 3-(N-methylamino)-4-chloro-phenyl; 3-(N-methylamino)-phenyl; 3-amido-phenyl; 3-amino-4-chloro-phenyl; 3-aminomethyl-phenyl; 3-amino-phenyl; 3-chloro-phenyl; 4-(N,N-dimethylamino)-5-chloro-thien-2-yl; 4-(N-methylamino)-5-chloro-thien-2-yl; 4-amino-5-chloro-thien-2-yl; 4-chloro-phenyl; 4-methoxy-2-methylsulfonyl-phenyl; 4-methoxy-phenyl; 2-methoxy-pyrid-5-yl; 5-(N,N-dimethylamino)-4-chloro-thien-2-yl; 5-(N-methylamino)-4-chloro-thien-2-yl; 5-amino-4-chloro-thien-2-yl; 5-chloro-pyrid-2-yl; 5-chloro-thien-2-yl; 6-amino-5-chloro-pyrid-2-yl; 6-amino-pyrid-2-yl; 2-cyano-4-chloro-phenyl; 2-methoxy-4-chloro-phenyl; 2-fluoro-4-chloro-phenyl; phenyl; 4-ethyl-phenyl; 3-chloro-4-methyl-phenyl; 4-fluoro-phenyl; 3-fluoro-4-chloro-phenyl; 3-methyl-4-chloro-phenyl; 3-fluoro-4-methyl-phenyl; 3,4-dimethyl-phenyl; 3-chloro-4-fluoro-phenyl; 3-methyl-4-fluoro-phenyl; 4-methylsulfanyl-phenyl;

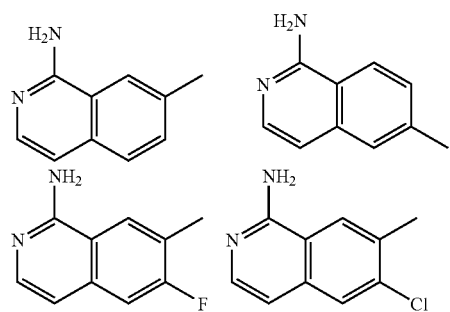

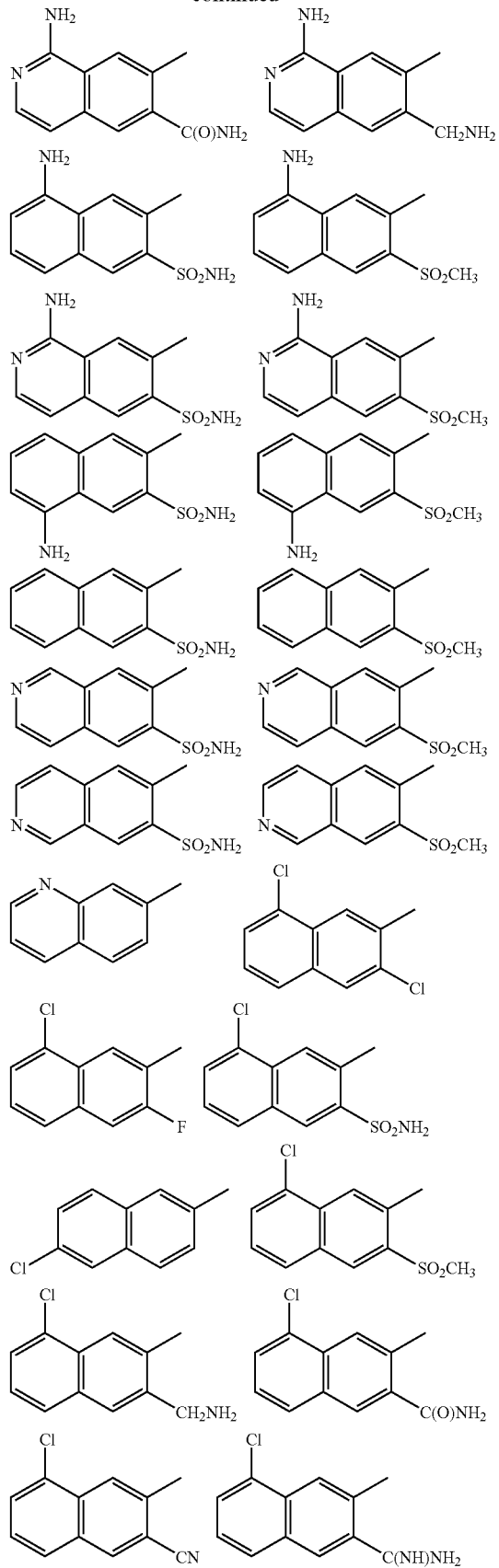

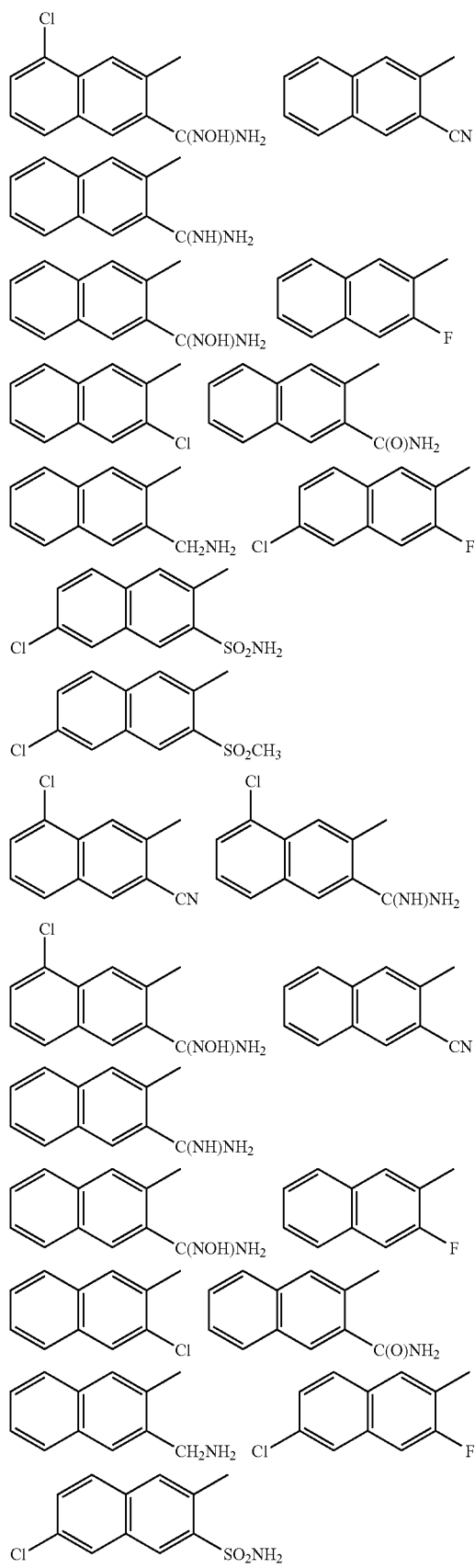
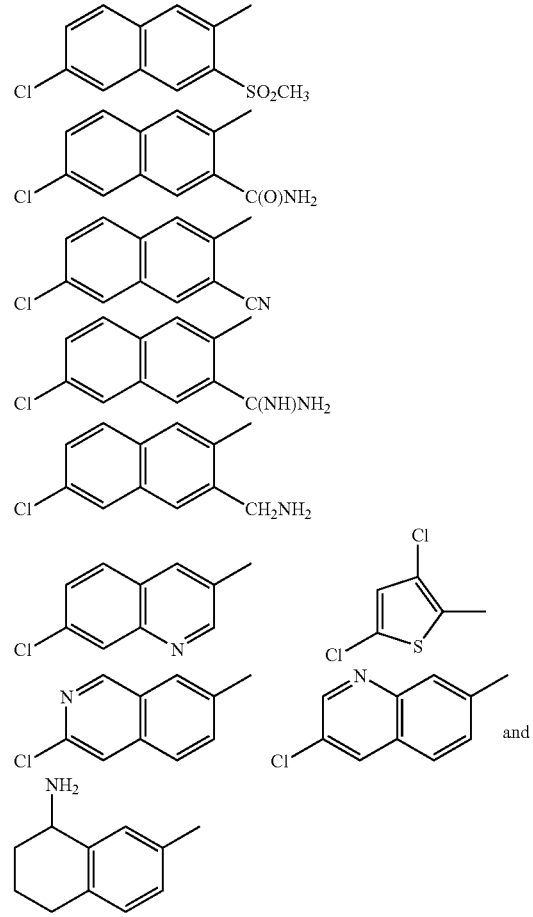

A is selected from one of the following carbocyclic groups which are substituted with 0–2 $R^4$; cyclohexyl and phenyl;

B is

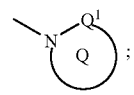

provided that Z and B are attached to different atoms on A;

$Q_1$ is selected from C=O and $SO_2$;

ring Q is a 6 membered monocyclic ring consisting of, in addition to the N—$Q_1$ group shown, carbon atoms, wherein: 0–2 double bonds are present within the ring and the ring is substituted with 0–2 $R^{4a}$;

$G_1$ is selected from $(CR^3R^{3a})_{1-3}$, $CR^3$=$CR^3$, $(CR^3R^{3a})_u$ $C(O)(CR^3R^{3a})_w$, $(CR^3R^{3a})_uO(CR^3R^{3a})_w$, $(CR^3R^{3a})_u$ $NR^{3b}(CR^3R^{3a})_w$, $(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^{3b}(CR^3R^{3a})_w$, $(CR^3R^{3a})_u$ $NR^{3b}S(O)_2(CR^3R^{3a})_w$, $(CR^3R^{3a})_uS(O)_2NR^{3b}(CR^3R^{3a})_w$, $(CR^3R^{3a})_uC(O)NR^{3b}S(O)_2(CR^3R^{3a})_w$, $(CR^3R^{3a})_uNR^{3b}C(O)(CR^3R^{3a})_uC(O)NR^{3b}(CR^3R^{3a})_w$, $(CR^3R^{3a})_uNR^{3b}(CR^3R^{3a})_uC(O)NR^{3b}(CR^3R^{3a})_w$, $(CR^3R^{3a})_uNR^{3b}C(O)(CR^3R^{3a})_uC(S)NR^{3b}$ $(CR^3R^{3a})_w$, and $(CR^3R^{3a})_uNR^{3b}C(S)(CR^3R^{3a})_uC(O)NR^{3b}(CR^3R^{3a})_w$, wherein u+w or u+u+w total 0, 1, or 2 and the right side of $G_1$ is attached to ring G, provided that $G_1$ does not form a N—S, $NCH_2N$, $NCH_2O$, or $NCH_2S$ bond with either group to which it is attached;

Z is selected from $(CR^3R^{3a})_{1-3}$, $(CR^3R^{3a})_uC(O)(CR^3R^{3a})_w$, $(CR^3R^{3a})_uO(CR^3R^{3a})_w$, $(CR^3R^{3a})_uNR^{3b}(CR^3R^{3a})_w$, $(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uNR^{3b}C(O)(CR^3R^{3a})_uC(O)NR^{3b}(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^{3b}(CR^3R^{3a})_w$, $(CR^3R^{3a})_uNR^{3b}S(O)_2(CR^3R^{3a})_w$, $(CR^3R^{3a})_uS(O)_2NR^{3b}(CR^3R^{3a})_w$, and $(CR^3R^{3a})_uC(O)NR^{3b}S(O)_2(CR^3R^{3a})_w$, wherein u+w or u+u+w total 0, 1, or 2 and the right side of Z is attached to A, provided that $G_1$ does not form a N—S, $NCH_2N$, $NCH_2O$, or $NCH_2S$ bond with either group to which it is attached;

$R^{1a}$ is selected from H, $-(CH_2)_r-R^{1b}$, $-(CH(CH_3))_r-R^{1b}$, $-(C(CH_3)_2)_r-R^{1b}$, $NHCH_2R^{1c}$, $OCH_2R^{1c}$, $SCH_2R^{1c}$, $NH(CH_2)_2(CH_2)_tR^{1b}$, and $O(CH_2)_2(CH_2)_tR^{1b}$, provided that $R^{1a}$ forms other than an N-halo, N—S, or N—CN bond;

$R^{1b}$ is selected from H, $CH_3$, $CH_2CH_3$, $CH_2CH_2CH_3$, $CH(CH_3)_2$, F, Cl, Br, I, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_pR^{2b}$, $NR^2(CH_2)_rOR^2$, $NR^2C(O)R^{2b}$, $NR^2C(O)NHR^2$, $NR^2C(O)_2R^{2a}$, $OC(O)NR^2R^{2a}$, $C(O)NR^2R^{2a}$, $C(O)NR^2R^{2b}$, $C(S)NR^2R^{2a}$, $C(O)NR^2(CH_2)_rOR^2$, $SO_2NR^2R^{2a}$, $NR^2SO_2R^2$, and $C_{3-6}$ carbocycle substituted with 0–2 $R^{4b}$, provided that $R^{1b}$ forms other than an O—O, N-halo, N—S, or N—CN bond;

$R^{1c}$ is selected from H, $CH(CH_2OR^2)_2$, $C(O)R^{2c}$, $C(O)NR^2R^{2a}$, $S(O)R^2$, $S(O)_2R^2$, and $SO_2NR^2R^{2a}$;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, and $C_{5-6}$ carbocycle substituted with 0–2 $R^{4b}$, a $-CH_2-C_{5-6}$ carbocyclic group substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, and $C_{3-6}$ carbocycle substituted with 0–2 $R^{4b}$;

$R^{2b}$, at each occurrence, is selected from $CF_3$, $C_{1-4}$ alkoxy, $C_{1-5}$ alkyl substituted with 0–3 $R^{4b}$, benzyl substituted with 0–2 $R^{4b}$, and $C_{3-6}$ carbocycle substituted with 0–2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, and $C_{5-6}$ carbocycle substituted with 0–2 $R^{4b}$;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and $C(=O)R^{3c}$;

$R^4$, at each occurrence, is selected from H, =O, $OR^2$, $CH_2OR^2$, $(CH_2)_2OR^2$, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $S(O)_pR^{5a}$, $CF_3$, $CF_2CF_3$, and 5–6 membered carbocycle substituted with 0–1 $R^5$;

$R^{4a}$, at each occurrence, is selected from H, =O, $OR^2$, $CH_2OR^2$, F, $CH_2F$, Br, $CH_2Br$, Cl, $CH_2Cl$, $C_{1-4}$ alkyl, —CN, —$CH_2CN$, $NO_2$, $CH_2NO_2$, $NR^2R^{2a}$, $CH_2NR^2R^{2a}$, $C(O)R^{2c}$, $CH_2C(O)R^{2c}$, $NR^2C(O)R^{2b}$, $(CH_2)_rC(O)NR^2R^{2a}$, $NR^2C(O)NR^2R^{2a}$, $(CH_2)_rSO_2NR^2R^{2a}$, $NR^2SO_2NR^2R^{2a}$, $NR^2SO_2-C_{1-4}$ alkyl, $NR^2SO_2R^5(CH_2)_rS(O)_pR^{5a}$, $CH_2CF_3$, $CF_3$, $CH_{2-5-6}$ membered carbocycle substituted with 0–1 $R^5$, and 5–6 membered carbocycle substituted with 0–1 $R^5$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $NR^3C(O)NR^3R^{3a}$, $CH_2NR^3C(O)NR^3R^{3a}$, $C(=NR^3)NR^3R^{3a}$, $CH_2C(=NR^3)NR^3R^{3a}$, $NR^3C(=NR^3)NR^3R^{3a}$, $CH_2NR^3C(=NR^3)NR^3R^{3a}$, $SO_2NR^3R^{3a}$, $CH_2SO_2NR^3R^{3a}$, $NR^3SO_2NR^3R^{3a}$, $CH_2NR^3SO_2NR^3R^{3a}$, $NR_3SO_2-C_{1-4}$ alkyl, $CH_2NR^3SO_2-C_{1-4}$ alkyl, $NR^3SO_2CF_3$, $CH_2NR^3SO_2CF_3$, $NR^3SO2$-phenyl, $CH_2NR^3SO_2$-phenyl, $S(O)_pCF_3$, $CH_2S(O)_pCF_3$, $S(O)_p-C_{1-4}$ alkyl, $CH_2S(O)_p-C_{1-4}$ alkyl, $S(O)_p$-phenyl, $CH_2S(O)_p$-phenyl, $CF_3$, and $CH_2CF_3$;

$R^{4c}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $CH_2OR^2$, $CH_2F$, $CH_2Br$, $CH_2Cl$, $CH_2CN$, $CH_2NO_2$, $CH_2NR^2R^{2a}$, $C(O)R^{2c}$, $CH_2C(O)R^{2c}$, $CH_2NR^2C(O)R^{2b}$, $C(O)NR^2R^{2a}$, $CH_2C(O)NR^2R^{2a}$, $CH_2NR^2C(O)NR^2R^{2a}$, $SO_2NR^2R^{2a}$, $CH_2SO_2NR^2R^{2a}$, $CH_2NR^2SO_2NR^2R^{2a}$, $CH_2NR^2SO_2-C_{1-4}$ alkyl, $C(O)NHSO_2-C_{1-4}$ alkyl, $CH_2C(O)NHSO_2-C_{14}$ alkyl, $CH_2NR^2SO_2R^5$, $S(O)_pR^{5a}$, $CH_2S(O)_pR^{5a}$, $CF_3$, $CH_2CF_3$, 5–6 membered carbocycle substituted with 0–1 $R^5$, and $CH_2$-5–6 membered carbocycle substituted with 0–1 $R^5$;

$R^5$, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR_3SO_2-C_{1-4}$ alkyl, $NR^3SO_2CF_3$, $NR^3SO_2$-phenyl, $S(O)_pCF_3$, $S(O)_p-C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$;

$R^{5a}$, at each occurrence, is selected from $C_{1-6}$ alkyl, $OR^3$, $CH_2OR^3$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $CF_3$, $CF_2CF_3$, phenyl substituted with 0–2 $R^6$, naphthyl substituted with 0–2 $R^6$, and benzyl substituted with 0–2 $R^6$, provided that $R^{5a}$ does not form a S—N or $S(O)_p-C(O)$ bond; and $R^6$, at each occurrence, is selected from H, OH, $OR^2$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $NR^2C(O)NR^2R^{2a}$, C(=NH)NH₂, NHC(=NH)NH₂, SO₂NR²R²ᵃ, NR²SO₂NR²R²ᵃ, and NR²SO₂C₁₋₄ alkyl.

3. A compound according to claim 2, wherein:

G is selected from: phenyl; 4-ethyl-phenyl; 2-aminomethyl-4-chloro-phenyl; 2-aminosulfonyl-4-chloro-phenyl; 2-amido-4-chloro-phenyl; 4-chloro-2-methylsulfonyl-phenyl; 2-aminosulfonyl-4-fluoro-phenyl; 2-amido-4-fluoro-phenyl; 4-fluoro-2-methylsulfonyl-phenyl; 2-aminomethyl-4-bromo-phenyl; 2-aminosulfonyl-4-bromo-phenyl; 2-amido-4-bromo-phenyl; 4-bromo-2-methylsulfonyl-phenyl; 2-aminomethyl-4-methyl-phenyl; 2-aminosulfonyl-4-methyl-phenyl; 2-amido-4-methyl-phenyl; 2-methylsulfonyl-4-methyl-phenyl; 4-fluoro-pyrid-2-yl; 4-bromo-pyrid-2-yl; 4-methyl-pyrid-2-yl; 5-fluoro-thien-2-yl; 5-bromo-thien-2-yl; 5-methyl-thien-2-yl; 2-amido-4-methoxy-phenyl; 2-amido-phenyl; 2-aminomethyl-3-fluoro-phenyl; 2-aminomethyl-4-fluoro-phenyl; 2-aminomethyl-5-fluoro-phenyl; 2-aminomethyl-6-fluoro-phenyl; 2-aminomethyl-phenyl; 2-amino-pyrid-4-yl; 2-aminosulfonyl-4-methoxy-phenyl; 2-aminosulfonyl-phenyl; 3-amido-phenyl; 3-amino-4-chloro-phenyl; 3-aminomethyl-phenyl; 3-chloro-phenyl; 4-chloro-phenyl; 4-methoxy-phenyl; 2-methoxy-pyrid-5-yl; 5-chloro-pyrid-2-yl; 5-chloro-thien-2-yl; 6-amino-5-chloro-pyrid-2-yl; 6-amino-pyrid-2-yl; 2-cyano-4-chloro-phenyl; 2-methoxy-4-chloro-phenyl; 2-fluoro-4-chloro-phenyl; 3-chloro-4-methyl-phenyl; 4-fluoro-phenyl; 3-fluoro-4-chloro-phenyl; 3-methyl-4-chloro-phenyl; 3-fluoro-4-methyl-phenyl; 3,4-dimethyl-phenyl; 3-chloro-4-fluoro-phenyl; 3-methyl-4-fluoro-phenyl; 4-methylsulfanyl-phenyl;

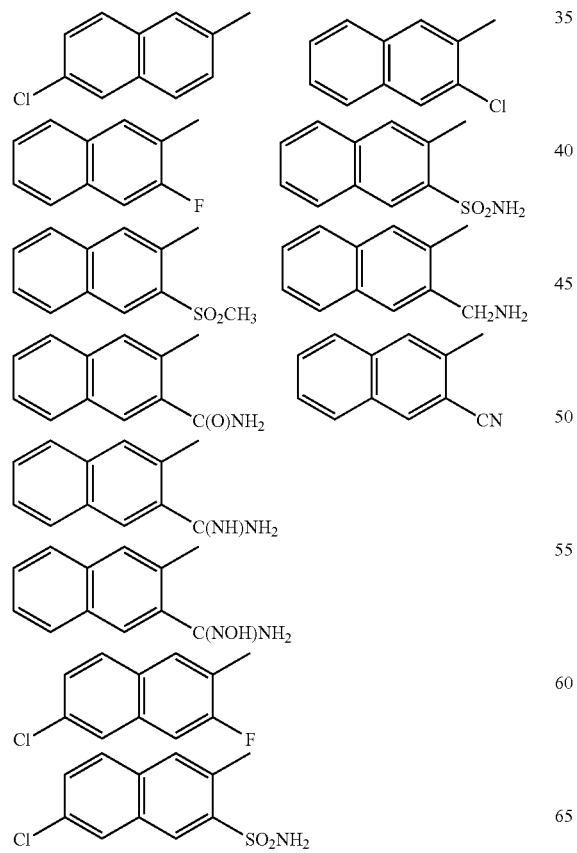

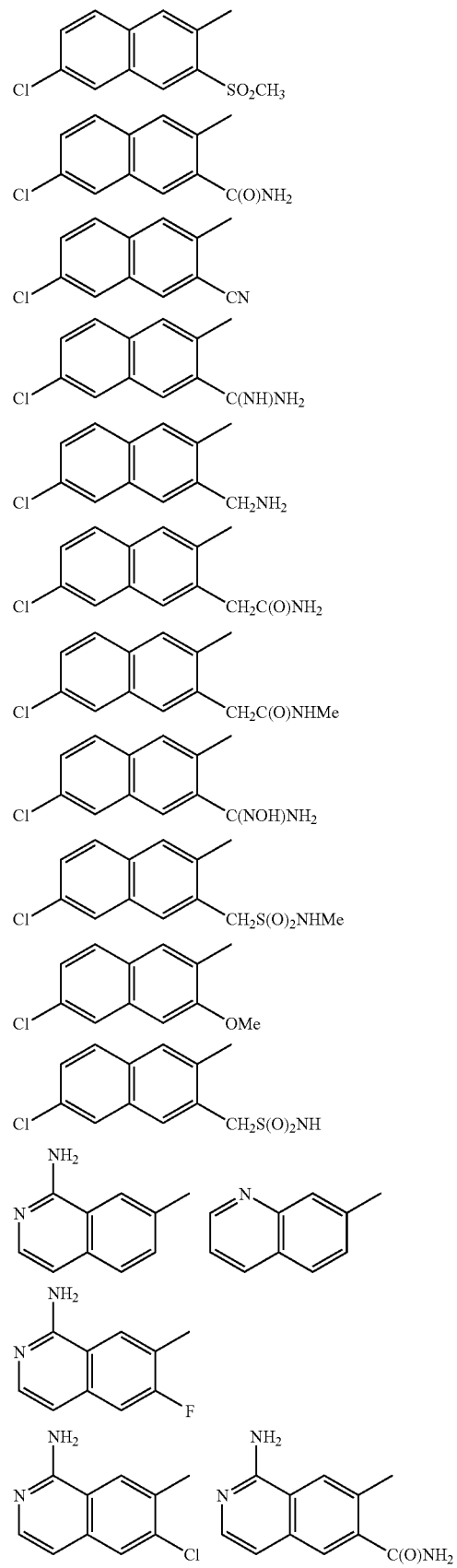

-continued

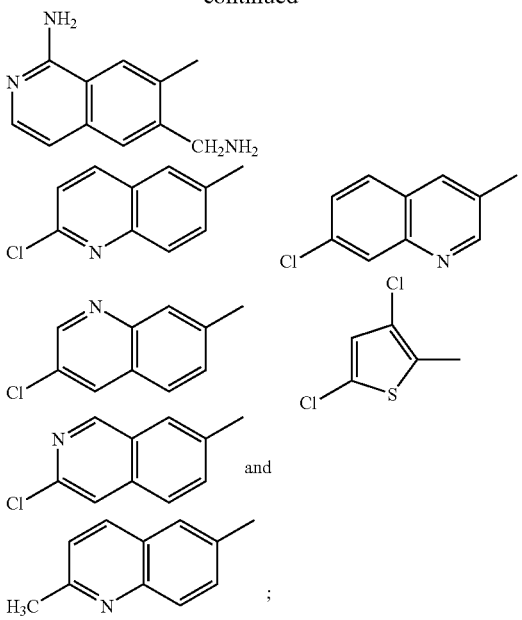

A is selected from the group: cyclohexyl, phenyl, 2-chloro-phenyl, 3-chloro-phenyl, 2-fluoro-phenyl, 3-fluoro-phenyl, 2-methylphenyl, 3-methylphenyl, 2-aminophenyl, 3-aminophenyl, 2-methoxyphenyl, and 3-methoxyphenyl;

B is attached to a different atom on A than M, is substituted with 0–2 $R^{4a}$, and is selected from the group:

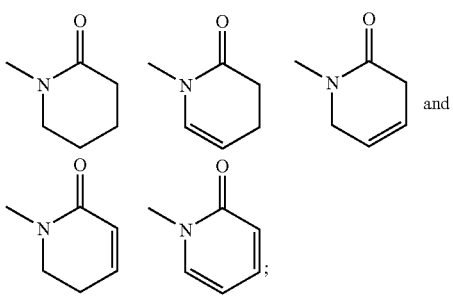

$G_1$ is selected from $CH_2$, $CH_2CH_2$, $CH=CH$, $CH_2O$, $OCH_2$, $C(O)$, $NH$, $CH_2NH$, $NHCH_2$, $CH_2C(O)$, $C(O)$ $CH_2$, $C(O)NH$, $NHC(O)$, $NHC(O)NH$, $NHC(O)CH_2C(O)NH$, $C(O)NHS(O)_2$, $CH_2S$, $SCH_2$, $CH_2S(O)$, $S(O)_2$, $CH_2S(O)_2$, $S(O)_2(CH_2)$, $SO_2NH$, $NHSO_2$, $NHCH_2C(O)NH$, $NHC(O)C(O)NH$, $NHC(O)C(S)NH$, and $NHC(S)C(O)NH$ and the right side of $G_1$ is attached to ring G, provided that Z does not form a N—S, $NCH_2N$, $NCH_2O$, or $NCH_2S$ bond with either group to which it is attached;

Z is selected from $CH_2$, $CH_2CH_2$, $CH_2O$, $OCH_2$, $C(O)$, $NH$, $CH_2NH$, $NHCH_2$, $CH_2C(O)$, $C(O)CH_2$, $C(O)NH$, $NHC(O)$, $NHC(O)NH$, $NHC(O)CH_2C(O)NH$, $C(O)NHS(O)_2$, $CH_2S$, $SCH_2$, $CH_2S(O)$, $S(O)_2$, $CH_2S(O)_2$, $S(O)_2(CH_2)$, $SO_2NH$, and $NHSO_2$ and the right side of Z is attached to A, provided that Z does not form a N—S, $NCH_2N$, $NCH_2O$, or $NCH_2S$ bond with either group to which it is attached;

$R^{1a}$ is selected from H, $R^{1b}$, $CH(CH_3)R^{1b}$, $C(CH_3)_2R^{1b}$, $CH_2R^{1b}$, and $CH_2CH_2R^{1b}$, provided that $R^{1a}$ forms other than an N-halo, N—S, or N—CN bond;

$R^{1b}$ is selected from H, $CH_3$, $CH_2CH_3$, F, Cl, Br, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_pR^{2b}$, $NR^2(CH_2)_rOR^2$, $NR^2C(O)R^{2b}$, $C(O)NR^2R^{2a}$, $C(O)NR^2R^{2b}$, $C(S)NR^2R^{2a}$, $SO_2NR^2R^{2a}$, $NR^2SO_2R^2$, $C_{3-5}$ cycloalkyl substituted with 0–2 $R^{4b}$, and phenyl substituted with 0–2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, phenyl substituted with 0–2 $R^{4b}$, and a benzyl substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, $C(CH_3)_3$, $C_{3-5}$ cycloalkyl substituted with 0–1 $R^{4b}$, benzyl substituted with 0–2 $R^{4b}$, and phenyl substituted with 0–2 $R^{4b}$;

$R^{2b}$, at each occurrence, is selected from $CF_3$, $C_{1-4}$ alkoxy, $C_{1-5}$ alkyl substituted with 0–3 $R^{4b}$, $C_{3-5}$ cycloalkyl substituted with 0–2 $R^{4b}$, benzyl substituted with 0–2 $R^{4b}$, and phenyl substituted with 0–2 $R^{4b}$;

$R^{2c}$, at each occurrence, is selected from $CF_3$, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl substituted with 0–2 $R^{4b}$, and phenyl substituted with 0–2 $R^{4b}$;

$R^{4a}$, at each occurrence, is selected from H, =O, $CH_2OR^2$, $OR^2$, F, Br, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $C(O)R^{2c}$, $NR^2C(O)R^{2b}$, $C(O)NR^2R^{2a}$, $NR^2C(O)NR^2R^{2a}$, $SO_2NR^2R^{2a}$, and —$CF_3$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $NR^3R^{3a}$, $SO_2NR^3R^{3a}$, $CH_2SO_2NR^3R^{3a}$, $NR^3SO_2$—$C_{1-4}$ alkyl, $CH_2NR^3SO_2$—$C_{1-4}$ alkyl, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, and $CF_3$;

$R^{4c}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $CH_2OR^2$, $CH_2F$, $CH_2Br$, $CH_2Cl$, $CH_2CN$, $CH_2NO_2$, $CH_2NR^2R^{2a}$, $C(O)R^{2c}$, $CH_2C(O)R^{2c}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $S(O)_pR^{5a}$, $CH_2S(O)_pR^{5a}$, $CF_3$, phenyl substituted with 0–1 $R^5$, and benzyl substituted with 0–1 $R^5$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$;

$R^{5a}$, at each occurrence, is selected from $CH_3$, $CH_2CH_3$, $CH_2CH_2CH_3$, $CH(CH_3)_2$, $OR^3$, $NR^3R^{3a}$, $C(O)R^3$, $NR^3C(O)R^{3a}$, $C(O)NR^3R^{3a}$, $CF_3$, phenyl substituted with 0–2 $R^6$, naphthyl substituted with 0–2 $R^6$, and benzyl substituted with 0–2 $R^6$, provided that $R^{5a}$ does not form a S—N or $S(O)_p$—C(O) bond; and $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $SO_2NR^2R^{2a}$, and $NR^2SO_2C_{1-4}$ alkyl.
4. A compound according to claim 3, wherein the compound is selected from:
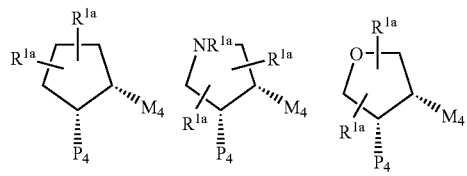
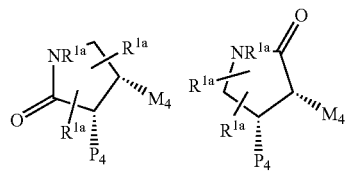
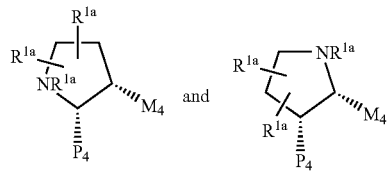
G is selected from:
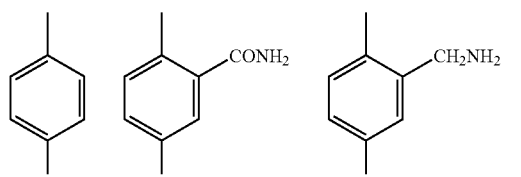
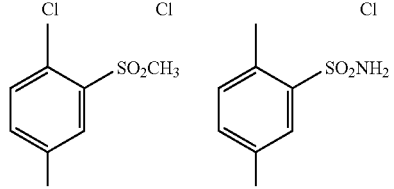
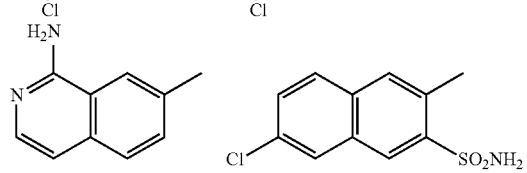
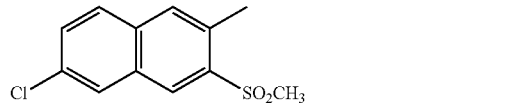
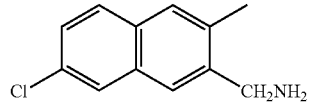
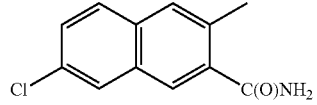
-continued
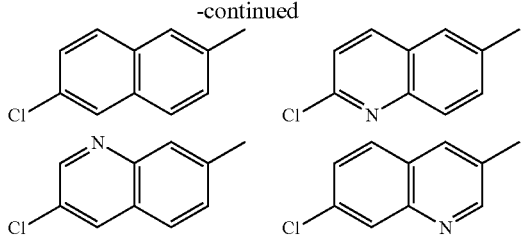
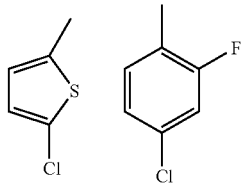
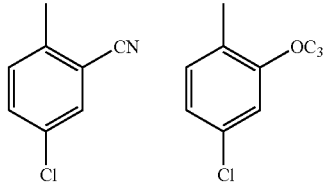
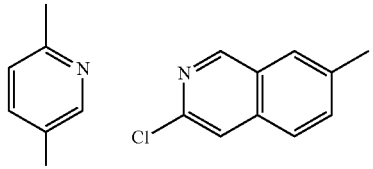
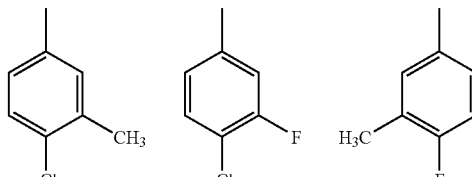
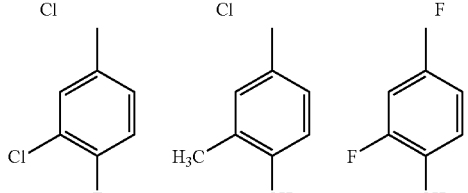
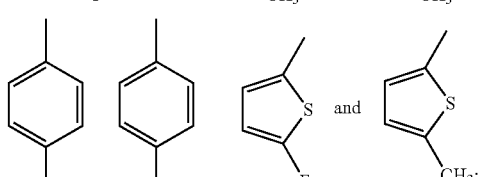
A-B is selected from:
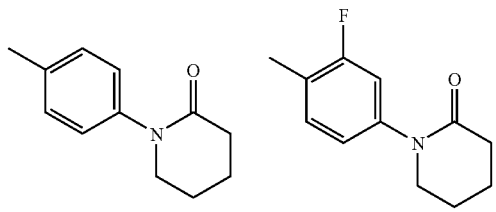

-continued

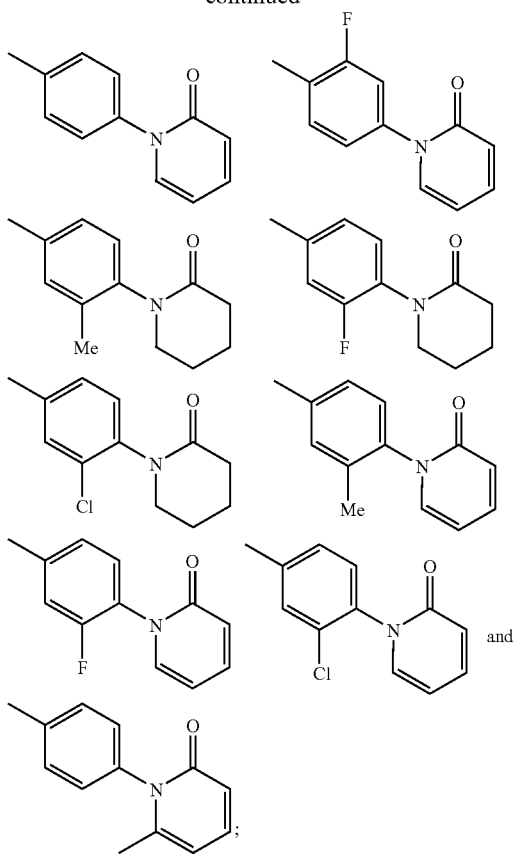

G$_1$ is selected from CH=CH, CH$_2$C(O), C(O)CH$_2$, NH, C(O)NH, NHC(O), CH$_2$S, SCH$_2$, CH$_2$S(O), CH$_2$SO$_2$, SO$_2$NH, NHSO$_2$NHCH$_2$C(O)NH, NHC(O)C(O)NH, NHC(O)C(S)NH, and NHC(S)C(O)NH and the right side of G$_1$ is attached to ring G, provided that Z does not form a N—S, NCH$_2$N, NCH$_2$O, or NCH$_2$S bond with either group to which it is attached;

Z is selected from CH$_2$C(O), C(O)CH$_2$, NH, C(O)NH, NHC(O), CH$_2$S, SCH$_2$, CH$_2$S(O), CH$_2$SO$_2$, SO$_2$NH, and NHSO$_2$ and the right side of Z is attached to A, provided that Z does not form a N—S, NCH$_2$N, NCH$_2$O, or NCH$_2$S bond with either group to which it is attached;

R$^{1a}$ is selected from H, R$^{1b}$, C(CH$_3$)$_2$R$^{1b}$, CH$_2$R$^{1b}$, and CH$_2$CH$_2$R$^{1b}$, provided that R$^{1a}$ forms other than an N-halo, N—S, or N—CN bond;

R$^{1b}$ is selected from CH$_3$, CH$_2$CH$_3$, F, Cl, Br, —CN, CF$_3$, OR$^2$, NR$^2$R$^{2a}$, C(O)R$^{2b}$, CO$_2$R$^{2b}$, CO$_2$R$^{2a}$, S(O)$_p$R$^{2b}$, C(O)NR$^2$R$^{2a}$, C(O)NR$^2$R$^{2b}$, C(S)NR$^2$R$^{2a}$, SO$_2$NR$^2$R$^{2a}$, NR$^2$SO$_2$R$^2$, and cyclopropyl substituted with 0–2 R$^{4b}$, provided that R$^{1b}$ forms other than an O—O, N-halo, N—S, or N—CN bond;

R$^2$, at each occurrence, is selected from H, CH$_3$, CH$_2$CH$_3$, CH$_2$CH$_2$CH$_3$, CH(CH$_3$)$_2$, phenyl substituted with 0–1 R$^{4b}$, and benzyl substituted with 0–1 R$^{4b}$;

R$^{2a}$, at each occurrence, is selected from H, CH$_3$, CH$_2$CH$_3$, CH$_2$CH$_2$CH$_3$, CH(CH$_3$)$_2$, C(CH$_3$)$_3$, cyclopropyl, benzyl substituted with 0–1 R$^{4b}$, and phenyl substituted with 0–1 R$^{4b}$;

R$^{2b}$, at each occurrence, is selected from CF$_3$, OH, OCH$_3$, OCH$_2$CH$_3$, OCH$_2$CH$_2$CH$_3$, OCH(CH$_3$)$_2$, C$_{1-5}$ alkyl substituted with 0–3 R$^{4b}$, C$_{3-5}$ cycloalkyl substituted with 0–1 R$^{4b}$, benzyl substituted with 0–1 R$^{4b}$, and phenyl substituted with 0–1 R$^{4b}$; and R$^{4b}$, at each occurrence, is selected from H, =O, OR$^3$, CH$_2$OR$^3$, F, Cl, CH$_3$, CH$_2$CH$_3$, CH$_2$CH$_2$CH$_3$, CH(CH$_3$)$_2$, —CN, NO$_2$, NR$^3$R$^{3a}$, CH$_2$NR$^3$R$^{3a}$, C(O)$^3$, C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl, NR$^3$SO$_2$-phenyl, S(O)$_p$—C$_{1-4}$ alkyl, S(O)$_p$-phenyl, and CF$_3$.

5. A compound according to claim 4, wherein the compound is selected from:

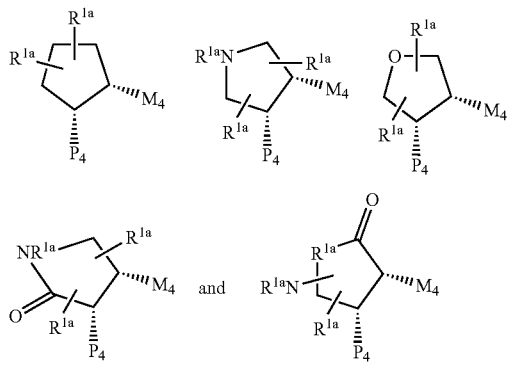

P$_4$ is G$_1$-G;
M$_4$ is Z-A-B;
G is selected from:

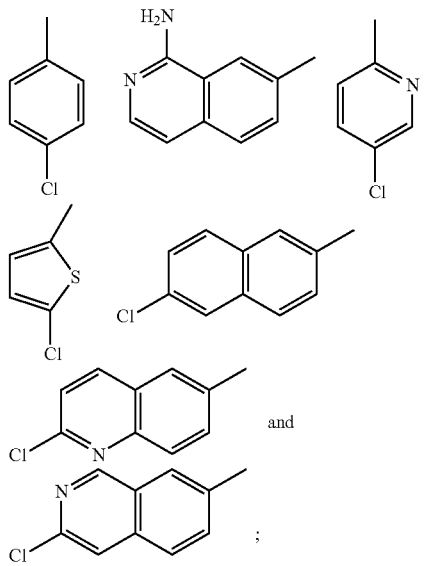

G$_1$ is NHCO or NHCOCONH;
alternatively, G-G$_1$- is selected from:

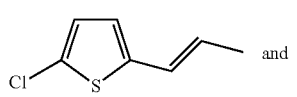 and

-continued
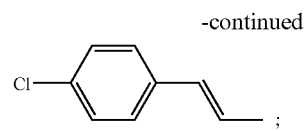
Z is NHCO or CONH;
A-B is selected from:
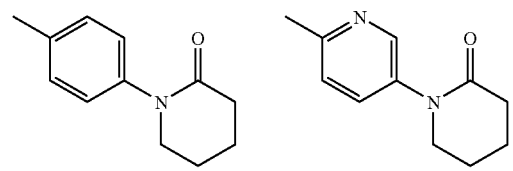
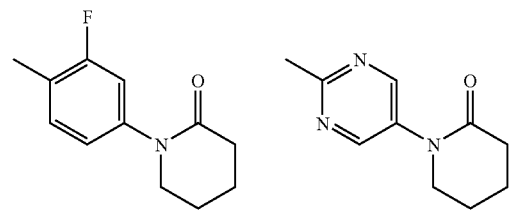
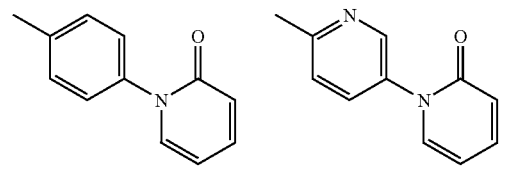
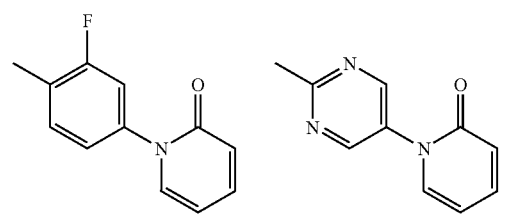
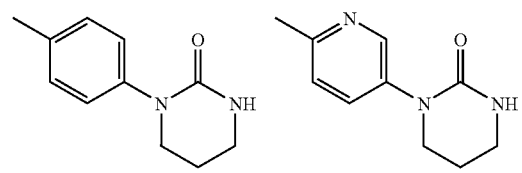
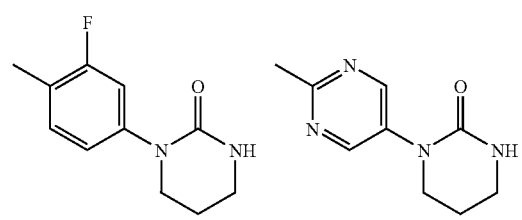
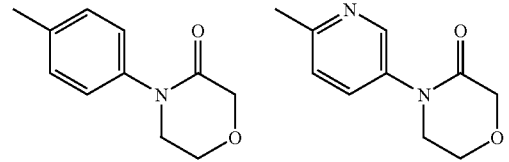
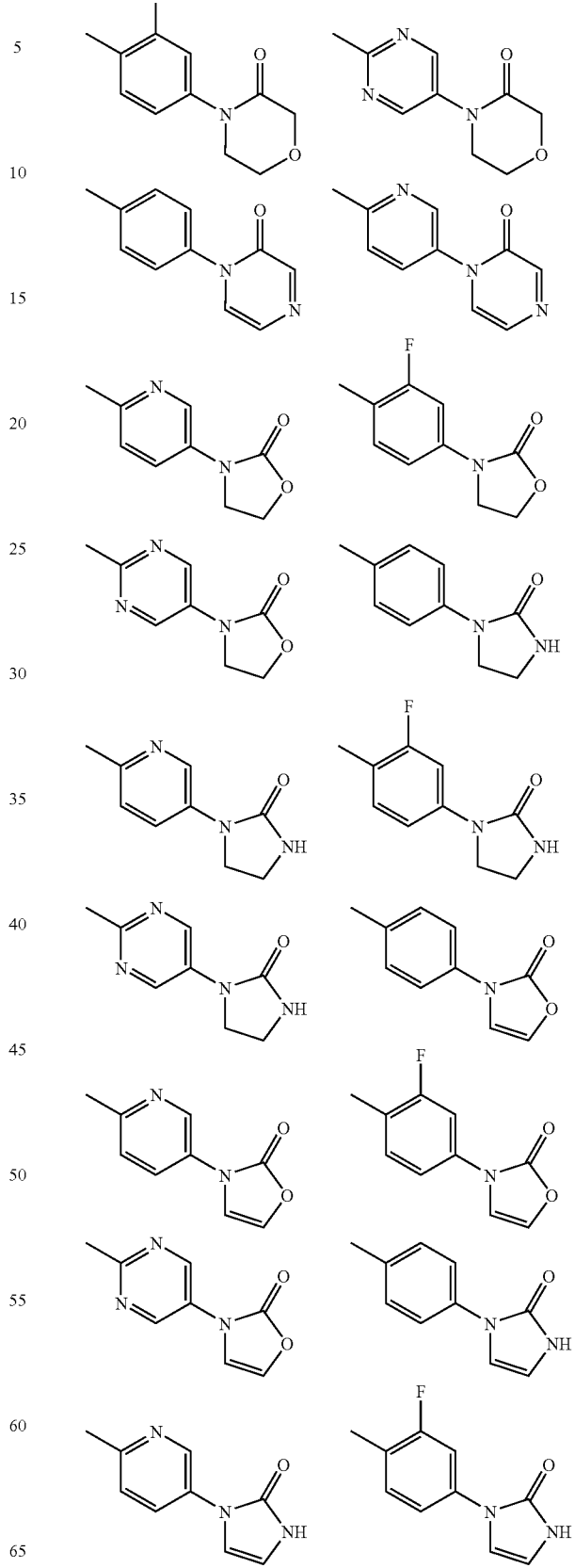

-continued

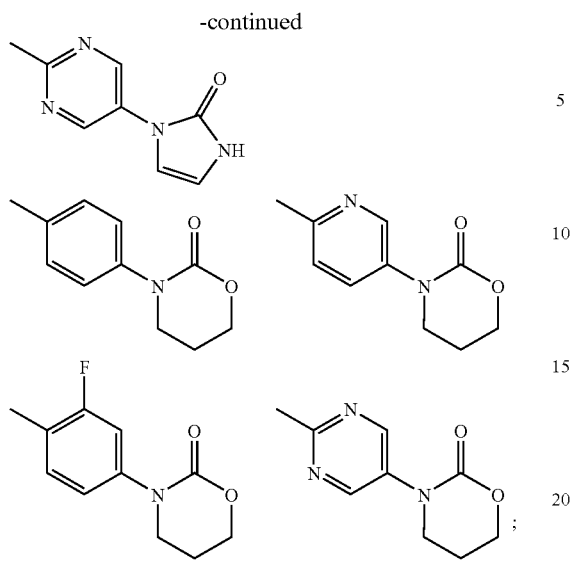

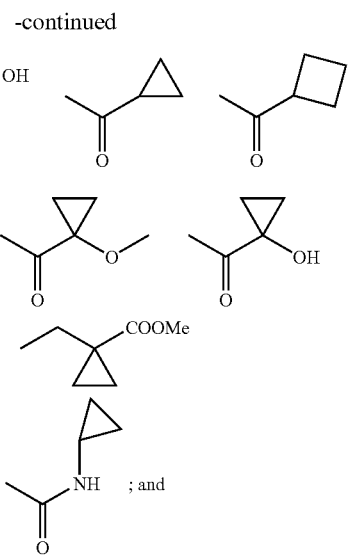

$R^{1a}$ is selected from H, $CH_3$, $CH_2CH_3$, $CH_2CH_2CH_3$, $OCH_3$, $CH_2OH$, $CH_2CH_2OH$, $C(CH_3)_2OH$, $CH_2OCH_3$, $CH_2CH_2OCH_3$, $NH_2$, $CH_2NH_2$, $NHCH_3$, $CH_2NHCH_3$, $N(CH_3)_2$, $CH_2N(CH_3)_2$, $CO_2H$, $CH_2CO_2H$, $CH_2CH_2CO_2H$, $CH_2CH_2CO_2CH_2CH_3$, $COCH_3$, $COCH_2C(CH_3)_3$, $COCF_3$, $CO_2CH_3$, $CO_2CH_2CH_3$, $CO_2CH(CH_3)_2$, $CO_2C(CH_3)_3$, $CH_2CO_2CH_3$, $CH_2CH_2CO_2CH_2CH_3$, $S(O)_2CH_3$, $CH_2S(O)_2CH_3$, $C(O)NH_2$, $CONH(CH_3)$, $CONH(CH_2CH_3)$, $CONHC(CH_3)_3$, $CON(CH_3)_2$, $CON(CH_3)(CH_2CH_3)$, $CON(CH_3)CH(CH_3)_2$, $CH_2C(O)NH_2$, $CH_2CON(CH_3)_2$, $CSN(CH_3)_2$, $SO_2NH_2$, $CH_2SO_2NH_2$, $NHSO_2CH_3$, $CH_2NHSO_2CH_3$, $SO_2CH_2CH_3$, $SO_2CH(CH_3)_2$, $SO_2CH_2CH_2CH_2$, $SO_2CH_2CH(CH_3)_2$, $SO_2CH_2CH_2OH$, $SO_2CH_2CH_2OCH_3$, $SO_2Ph$, $SO_2CH_2CF_2$, and $SO_2CF_2CF_3$;

alternatively, $R^{1a}$ is selected from:

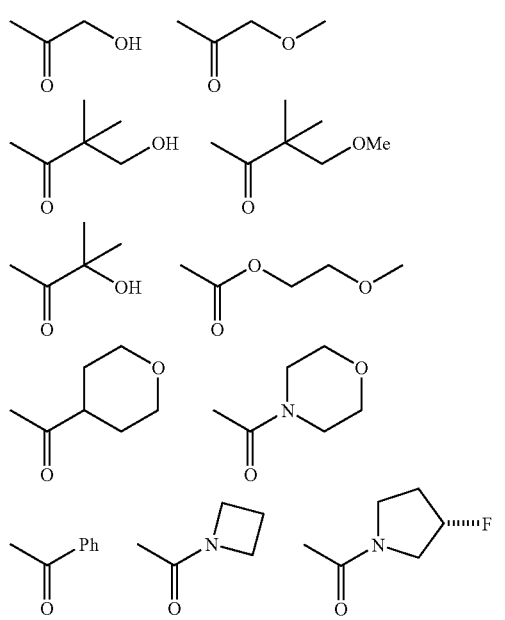

$R^{4b}$, at each occurrence, is selected from H, $=O$, $OR^3$, $CH_2OR^3$, F, Cl, $CH_3$, $CH_2CH_3$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$-phenyl, $S(O)_2CH_3$, $S(O)2$-phenyl, and $CF_3$.

6. A compound according to claim 5, wherein the compound is selected from:

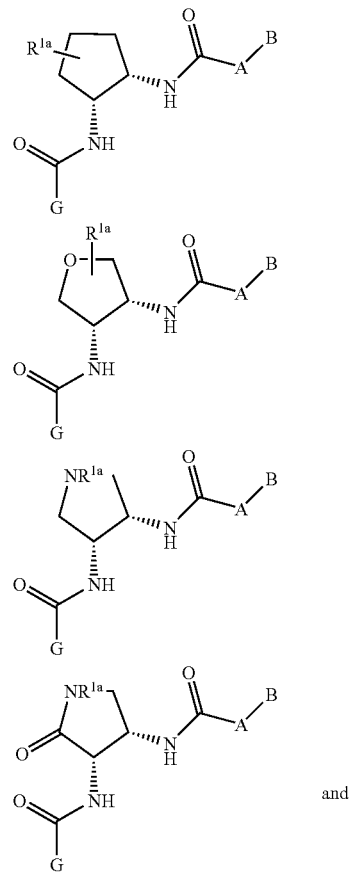

-continued

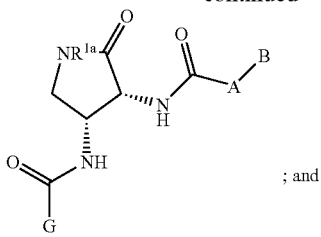

; and

A-B is selected from:

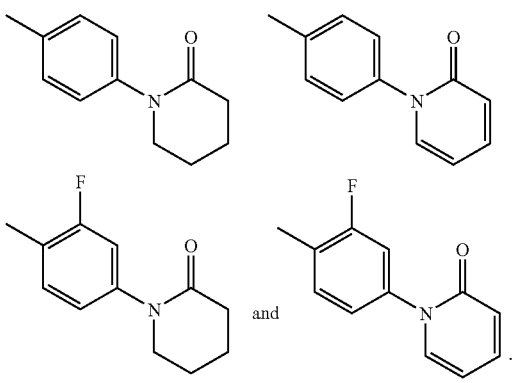

and

7. A compound according to claim 6, wherein the compound is selected from:

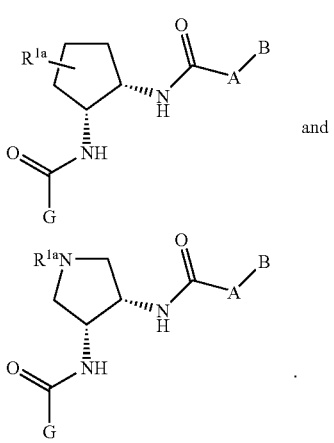

and

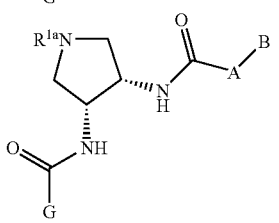

8. A compound according to claim 1, wherein the compound is selected from the group:

(1R,2S)-5-chloro-thiophene-2-carboxylic acid {2-[4-(2-oxo-2H-pyridin-1-yl)-benzoylamino]-cyclopentyl}-amide;

(1S,2R)-5-chloro-thiophene-2-carboxylic acid {2-[4-(2-oxo-2H-pyridin-1-yl)-benzoylamino]-cyclopentyl}-amide;

(1R,2S)-5-chloro-thiophene-2-carboxylic acid {2-[4-(2-oxo-piperidin-1-yl)-benzoylamino]-cyclopentyl}-amide;

(1S,2R)-4-methoxy-phenyl-carboxylic acid {2-[4-(2-oxo-2H-pyridin-1-yl)-benzoylamino]-cyclopentyl}-amide;

(1R,2S)-5-chloro-thiophene-2-carboxylic acid {2-[4-(2-oxo-2H-pyridin-1-yl)-benzoylamino]-cyclohexyl}-amide;

(1R,2S)-N-(5-chloro-pyridin-2-yl)-N'-{2-[4-(2-oxo-2H-pyridin-1-yl)-benzoylamino]-cyclopentyl}-oxalamide;

(1S,3R,4S)-3-[(5-chloro-thiophene-2-carbonyl)-amino]-4-[4-(2-oxo-2H-pyridin-1-yl)-benzoylamino]-cyclopentanecarboxylic acid methyl ester;

(1R,2S,4S)-5-chloro-thiophene-2-carboxylic acid {4-(2-methoxy-ethylcarbamoyl)-2-[4-(2-oxo-2H-pyridin-1-yl)-benzoylamino]-cyclopentyl}-amide;

(1R,2S)-4-chloro-phenylcarboxylic acid {2-[4-(2-oxo-2H-pyridin-1-yl)-benzoylamino]-cyclopentyl}-amide;

(1R,2S)-4-chloro-3-fluorophenylcarboxylic acid {2-[4-(2-oxo-2H-pyridin-1-yl)-benzoylamino]-cyclopentyl}-amide;

(1R,2S)-4-chloro-3-methylphenylcarboxylic acid {2-[4-(2-oxo-2H-pyridin-1-yl)-benzoylamino]-cyclopentyl}-amide;

(1R,2S)-4-chloro-3-methoxylphenylcarboxylic acid {2-[4-(2-oxo-2H-pyridin-1-yl)-benzoylamino]-cyclopentyl}-amide;

(1R,2S)-5-methyl-thiophene-2-carboxylic acid {2-[4-(2-oxo-2H-pyridin-1-yl)-benzoylamino]-cyclopentyl}-amide;

(1R,2S)-1H-indole-6-carboxylic acid {2-[4-(2-oxo-2H-pyridin-1-yl)-benzoylamino]-cyclopentyl}-amide;

(1R,2S)-6-chloro-naphthalene-2-carboxylic acid {2-[4-(2-oxo-2H-pyridin-1-yl)-benzoylamino]-cyclohexyl}-amide;

(1R,2S)-5-chloro-thiophene-2-carboxylic acid {2-[4-(2-oxo-2H-pyridin-1-yl)-benzylamino]-cyclopentyl}-amide;

(1R,2S)-N-{2-[(5-chloro-thiophen-2-ylmethyl)-amino]-cyclopentyl}-4-(2-oxo-2H-pyridin-1-yl)-benzamide;

(1R,2S)-5-chloro-thiophene-2-carboxylic acid {1-[4-(2-oxo-2H-pyrazin-1-yl)-benzoylamino]-indan-2-yl}-amide;

(1R,2S,4S)-5-chloro-thiophene-2-carboxylic acid {4-dimethylcarbamoyl-2-[4-(2-oxo-2H-pyridin-1-yl)-benzoylamino]-cyclopentyl}-amide;

(1R,2S,4S)-5-chloro-thiophene-2-carboxylic acid {4-cyclopropylcarbamoyl-2-[4-(2-oxo-2H-pyridin-1-yl)-benzoylamino]-cyclopentyl}-amide;

(1R,2S,4S)-5-chloro-thiophene-2-carboxylic acid {4-(morpholine-4-carbonyl)-2-[4-(2-oxo-2H-pyridin-1-yl)-benzoylamino]-cyclopentyl}-amide;

(1R,2S)-5-chloro-thiophene-2-carboxylic acid {2-[2-fluoro-4-(2-oxo-2H-pyridin-1-yl)-benzoylamino]-cyclopentyl}-amide;

(1R,2S)-5-chloro-thiophene-2-carboxylic acid {2-[4-(2-oxo-2H-pyrazin-1-yl)-benzoylamino]-cyclopentyl}-amide;

(1R,2S)-5-chloro-thiophene-2-carboxylic acid {2-[3-methyl-4-(2-oxo-2H-pyridin-1-yl)-benzoylamino]-cyclopentyl}-amide;

(3R,4S)-5-chloro-thiophene-2-carboxylic acid {4-[4-(2-oxo-2H-pyridin-1-yl)-benzoylamino]-pyrrolidin-3-yl}-amide;

(3R,4S)-5-chloro-thiophene-2-carboxylic acid {1-acetyl-4-[4-(2-oxo-2H-pyridin-1-yl)-benzoylamino]-pyrrolidin-3-yl}-amide;

(3R,4S)-5-chloro-thiophene-2-carboxylic acid {1-cyclopropanecarbonyl-4-[4-(2-oxo-2H-pyridin-1-yl)-benzoylamino]-pyrrolidin-3-yl}-amide;

(3R,4S)-5-chloro-thiophene-2-carboxylic acid {1-(2,2-dimethyl-propionyl)-4-[4-(2-oxo-2H-pyridin-1-yl)-benzoylamino]-pyrrolidin-3-yl}-amide;

(3R,4S)-5-chloro-thiophene-2-carboxylic acid {4-[4-(2-oxo-2H-pyridin-1-yl)-benzoylamino]-1-propionyl-pyrrolidin-3-yl}-amide;

(3R,4S)-5-chloro-thiophene-2-carboxylic acid {1-(2-methoxy-acetyl)-4-[4-(2-oxo-2H-pyridin-1-yl)-benzoylamino]-pyrrolidin-3-yl}-amide;

(3R,4S)-5-chloro-thiophene-2-carboxylic acid {1-isobutyryl-4-[4-(2-oxo-2H-pyridin-1-yl)-benzoylamino]-pyrrolidin-3-yl}-amide;

(3R,4S)-5-chloro-thiophene-2-carboxylic acid {1-benzoyl-4-[4-(2-oxo-2H-pyridin-1-yl)-benzoylamino]-pyrrolidin-3-yl}-amide;

(3R,4S)-5-chloro-thiophene-2-carboxylic acid {1-methanesulfonyl-4-[4-(2-oxo-2H-pyridin-1-yl)-benzoylamino]-pyrrolidin-3-yl}-amide;

(3R,4S)-5-chloro-thiophene-2-carboxylic acid {1-ethanesulfonyl-4-[4-(2-oxo-2H-pyridin-1-yl)-benzoylamino]-pyrrolidin-3-yl}-amide;

(3R,4S)-5-chloro-thiophene-2-carboxylic acid [4-[4-(2-oxo-2H-pyridin-1-yl)-benzoylamino]-1-(propane-2-sulfonyl)-pyrrolidin-3-yl]-amide;

(3R,4S)-5-chloro-thiophene-2-carboxylic acid [4-[4-(2-oxo-2H-pyridin-1-yl)-benzoylamino]-1-(pyrrolidine-1-carbonyl)-pyrrolidin-3-yl]-amide;

(3R,4S)-3-[(5-chloro-thiophene-2-carbonyl)-amino]-4-[4-(2-oxo-2H-pyridin-1-yl)-benzoylamino]-pyrrolidine-1-carboxylic acid methyl ester;

(3R,4S)-3-[(5-chloro-thiophene-2-carbonyl)-amino]-4-[4-(2-oxo-2H-pyridin-1-yl)-benzoylamino]-pyrrolidine-1-carboxylic acid ethyl ester;

(3R,4S)-3-[(5-chloro-thiophene-2-carbonyl)-amino]-4-[4-(2-oxo-2H-pyridin-1-yl)-benzoylamino]-pyrrolidine-1-carboxylic acid 2-methoxy-ethyl ester;

(1S,3R,4S)-3-[(5-chloro-thiophene-2-carbonyl)-amino]-4-[4-(2-oxo-2H-pyridin-1-yl)-benzoylamino]-cyclopentanecarboxylic acid;

(1R,2S,4S)-5-chloro-thiophene-2-carboxylic acid {4-hydroxymethyl-2-[4-(2-oxo-2H-pyridin-1-yl)-benzoylamino]-cyclopentyl}-amide;

(1S,2R)-5-chloro-thiophene-2-carboxylic acid {1-[4-(2-oxo-piperidin-1-yl)-benzoylamino]-indan-2-yl}-amide;

(3S,4R)-5-chloro-thiophene-2-carboxylic acid {4-[4-(2-oxo-2H-pyridin-1-yl)-benzoylamino]-tetrahydro-furan-3-yl}-amide;

(3S,R4)-3-chloro-1H-indole-6-carboxylic acid {4-[4-(2-oxo-2H-pyridin-1-yl)-benzoylamino]-tetrahydro-furan-3-yl}-amide;

(1R,2S)-6-chloro-naphthalene-2-carboxylic acid {2-[4-(2-oxo-2H-pyridin-1-yl)-benzoylamino]-cyclopentyl}-amide;

(1R,2S)-3-chloro-phenyl-carboxylic acid {2-[4-(2-oxo-2H-pyridin-1-yl)-benzoylamino]-cyclopentyl}-amide;

(1R,2S)-2-chloro-phenyl-carboxylic acid {2-[4-(2-oxo-2H-pyridin-1-yl)-benzoylamino]-cyclopentyl}-amide;

(1R,2S)-3,4-dichloro-phenyl-carboxylic acid {2-[4-(2-oxo-2H-pyridin-1-yl)-benzoylamino]-cyclopentyl}-amide;

(1R,2S)-4-chloro-2-fluoro-phenyl-carboxylic acid {2-[4-(2-oxo-2H-pyridin-1-yl)-benzoylamino]-cyclopentyl}-amide;

(1R,2S)-2,4-dichloro-phenyl-carboxylic acid {2-[4-(2-oxo-2H-pyridin-1-yl)-benzoylamino]-cyclopentyl}-amide;

(1R,2S)-4-chloro-2-methyl-phenyl-carboxylic acid {2-[4-(2-oxo-2H-pyridin-1-yl)-benzoylamino]-cyclopentyl}-amide;

(1R,2S)-4-methoxy-phenyl-carboxylic acid {2-[4-(2-oxo-2H-pyridin-1-yl)-benzoylamino]-cyclopentyl}-amide;

(1R,2S)-3-methoxy-phenyl-carboxylic acid {2-[4-(2-oxo-2H-pyridin-1-yl)-benzoylamino]-cyclopentyl}-amide;

(1R,2S)-N-{2-[3-(4-chloro-phenyl)-ureido]-cyclopentyl}-4-(2-oxo-2H-pyridin-1-yl)-benzamide;

cis-5-chloro-thiophene-2-carboxylic acid {1-cyclopropanecarbonyl-4-[4-(2-oxo-2H-pyridin-1-yl)-benzoylamino]-piperidin-3-yl}-amide;

cis-{1-cyclopropanecarbonyl-3-[4-(2-oxo-2H-pyridin-1-yl)-benzoylamino]-piperidin-4-yl}-carbamic acid benzyl ester;

(3R,4S)-3-(2-chlorothiophene-5-carboxamido)-N-methyl-4-(4-(2-oxopyridin-1(2H)-yl)benzamido)pyrrolidine-1-carboxamide; and (3R,4S)-3-(2-chlorothiophene-5-carboxamido)-N,N-dimethyl-4-(4-(2-oxopyridin-1(2H)-yl)benzamido)pyrrolidine-1-carboxamide;

or a pharmaceutically acceptable salt form thereof.

9. A compound according to claim 1, wherein the compound is selected from:

(1R,2S)-5-chloro-thiophene-2-carboxylic acid {2-[4-(2-oxo-pyrrolidin-1-yl)-benzoylamino]-cyclopentyl}-amide;

(1R,2S)-5-chloro-thiophene-2-carboxylic acid {2-[2-fluoro-4-(2-oxo-pyrrolidin-1-yl)-benzoylamino]-cyclopentyl}-amide;

5-chloro-N-((1R,2S4S)-2-(3-chloro-4-(2-oxopyridin-1(2H)-yl)benzamido)-4-(hydroxymethyl)cyclopentyl)thiophene-2-carboxamide;

5-chloro-N-((1R,2S,4S)-4-(hydroxymethyl)-2-(4-(2-oxopyrrolidin-1-yl)benzamido)cyclopentyl)thiophene-2-carboxamide;

5-chloro-N-((1R,2S,4S)-4-(hydroxymethyl)-2-(4-(2-oxopiperidin-1-yl)benzamido)cyclopentyl)thiophene-2-carboxamide;

(3R,4S)-5-chloro-thiophene-2-carboxylic acid {1-cyclopropanecarbonyl-4-[4-(2-oxo-piperidin-1-yl)-benzoylamino]-pyrrolidin-3-yl}-amide;

(3R,4S)-5-chloro-thiophene-2-carboxylic acid {1-cyclopropanecarbonyl-4-[2-fluoro-4-(2-oxo-2H-pyridin-1-yl)-benzoylamino]-pyrrolidin-3-yl}-amide;

5-chloro-N-((3R,4S)-1-(2-(methylamino)-2-oxoethyl)-4-(4-(2-oxopyridin-1(2H)-yl)benzamido)pyrrolidin-3-yl)thiophene-2-carboxamide;

(3R,4S)-5-chloro-thiophene-2-carboxylic acid {1-methyl-4-[4-(2-oxo-piperidin-1-yl)-benzoylamino]-pyrrolidin-3-yl}-amide;

(3R,4S)-5-chloro-thiophene-2-carboxylic acid {-methyl-4-[2-fluoro-4-(2-oxo-2H-pyridin-1-yl)-benzoylamino]-pyrrolidin-3-yl}-amide;

(3R,4S)-5-chloro-thiophene-2-carboxylic acid {1-methyl-4-[4-(2-oxo-2H-pyridin-1-yl)-benzoylamino]-pyrrolidin-3-yl}-amide;

(3R,4S)-5-chloro-thiophene-2-carboxylic acid {4-[4-(2-oxo-2H-pyridin-1-yl)-benzoylamino]-tetrahydro-furan-3-yl}-amide;

methyl2-((3R,4S)-3-(2-chlorothiophene-5-carboxamido)-4-(4-(2-oxopyridin-1(2H)-yl)benzamido)pyrrolidin-1-yl)acetate;

(3R,4S)-3-[(5-chloro-thiophene-2-carbonyl)-amino]-4-[4-(2-oxo-piperidin-1-yl)-benzoylamino]-pyrrolidine-1-carboxylic acid methyl ester;

N-((3R,4S)-1-(2-amino-2-oxoethyl)-4-(4-(2-oxopyridin-1(2H)-yl)benzamido)pyrrolidin-3-yl)-5-chlorothiophene-2-carboxamide;

(3R,4S)-5-chloro-thiophene-2-carboxylic acid {-acetyl-4-[4-(2-oxo-piperidin-1-yl)-benzoylamino]-pyrrolidin-3-yl}-amide;

(3R,4S)-5-chloro-thiophene-2-carboxylic acid {-methanesulfonyl-4-[4-(2-oxo-piperidin-1-yl)-benzoylamino]-pyrrolidin-3-yl}-amide;

(3R,4S)-3-[(5-chloro-thiophene-2-carbonyl)-amino]-4-[4-(2-oxo-2H-pyridin-1-yl)-benzoylamino]-pyrrolidine-1-carboxylic acid dimethylamide;

(3R,4S)-3-[(5-chloro-thiophene-2-carbonyl)-amino]-4-[4-(2-oxo-piperidin-1-yl)-benzoylamino]-pyrrolidine-1-carboxylic acid dimethylamide;

(3R,4S)-5-chloro-thiophene-2-carboxylic acid {4-[4-(2-oxo-piperidin-1-yl)-benzoylamino]-tetrahydro-furan-3-yl}-amide;

(3S,4S)-5-chloro-thiophene-2-carboxylic acid {1-methyl-2-oxo-4-[4-(2-oxo-2H-pyridin-1-yl)-benzoylamino]-pyrrolidin-3-yl}-amide;

(3S,4S)-5-chloro-thiophene-2-carboxylic acid {1-methyl-2-oxo-4-[4-(2-oxo-piperidin-1-yl)-benzoylamino]-pyrrolidin-3-yl}-amide;

(3S,4S)-5-chloro-thiophene-2-carboxylic acid {1-methyl-2-oxo-4-[4-(2-oxo-2H-pyridin-1-yl)-benzylamino]-pyrrolidin-3-yl}-amide;

(3S,4S)-5-chloro-thiophene-2-carboxylic acid {1-methyl-2-oxo-4-[4-(2-oxo-piperidin-1-yl)-benzylamino]-pyrrolidin-3-yl}-amide;

(3R,4R)-5-chloro-thiophene-2-carboxylic acid {1-methyl-5-oxo-4-[4-(2-oxo-2H-pyridin-1-yl)-benzoylamino]-pyrrolidin-3-yl}-amide;

(3R,4R)-5-chloro-thiophene-2-carboxylic acid {1-methyl-5-oxo-4-[4-(2-oxo-piperidin-1-yl)-benzoylamino]-pyrrolidin-3-yl}-amide;

(3R,4R)-5-chloro-thiophene-2-carboxylic acid {1-methyl-5-oxo-4-[4-(2-oxo-2H-pyridin-1-yl)-benzylamino]-pyrrolidin-3-yl}-amide;

(3R,4R)-5-chloro-thiophene-2-carboxylic acid {1-methyl-5-oxo-4-[4-(2-oxo-piperidin-1-yl)-benzylamino]-pyrrolidin-3-yl}-amide;

(3R,4S)-3-[(5-chloro-thiophene-2-carbonyl)-amino]-4-[4-(2-oxo-2H-pyridin-1-yl)-phenylcarbamoyl]-pyrrolidine-1-carboxylic acid methyl ester;

(3R,4S)-1-acetyl-4-[(5-chloro-thiophene-2-carbonyl)-amino]-pyrrolidine-3-carboxylic acid[4-(2-oxo-2H-pyridin-1-yl)-phenyl]-amide;

(3R,4S)-4-[(5-chloro-thiophene-2-carbonyl)-amino]-1-methanesulfonyl-pyrrolidine-3-carboxylic acid[4-(2-oxo-2H-pyridin-1-yl)-phenyl]-amide;

(3R,4S)-4-[(5-chloro-thiophene-2-carbonyl)-amino]-pyrrolidine-1,3-dicarboxylic acid 1-dimethylamide 3-{[4-(2-oxo-2H-pyridin-1-yl)-phenyl]-amide};

(3R,4S)-4-[(5-chloro-thiophene-2-carbonyl)-amino]-tetrahydro-furan-3-carboxylic acid [4-(2-oxo-2H-pyridin-1-yl)-phenyl]-amide;

N-{2-[2-(5-chloro-thiophen-2-yl)-2-oxo-ethyl]-cyclopentyl}-4-(2-oxo-2H-pyridin-1-yl)-benzamide;

5-chloro-thiophene-2-carboxylic acid (2-{2-oxo-2-[4-(2-oxo-2H-pyridin-1-yl)-phenyl]-ethyl}-cyclopentyl)-amide;

5-chloro-thiophene-2-carboxylic acid (1-methanesulfonyl-4-{2-oxo-2-[4-(2-oxo-2H-pyridin-1-yl)-phenyl]-ethyl}-pyrrolidin-3-yl)-amide;

N-{4-[2-(5-chloro-thiophen-2-yl)-2-oxo-ethyl]-1-methanesulfonyl-pyrrolidin-3-yl}-4-(2-oxo-2H-pyridin-1-yl)-benzamide;

5-chloro-N-((3R,4S)-4-(4-(2-oxopiperidin-1-yl)benzamido)-1-propionylpyrrolidin-3-yl)thiophene-2-carboxamide;

5-chloro-N-((3R,4S)-1-(3-methylbutanoyl)-4-(4-(2-oxopyridin-1(2H)-yl)benzamido)pyrrolidin-3-yl)thiophene-2-carboxamide;

5-chloro-N-((3R,4S)-1-(3-methylbutanoyl)-4-(4-(2-oxopiperidin-1-yl)benzamido)pyrrolidin-3-yl)thiophene-2-carboxamide;

5-chloro-N-((3R,4S)-1-(2-cyclopropylacetyl)-4-(4-(2-oxopyridin-1(2H)-yl)benzamido)pyrrolidin-3-yl)thiophene-2-carboxamide;

5-chloro-N-((3R,4S)-1-(2-cyclobutylacetyl)-4-(4-(2-oxopyridin-1(2H)-yl)benzamido)pyrrolidin-3-yl)thiophene-2-carboxamide;

5-chloro-N-((3R,4S)-1-(2-cyclopentylacetyl)-4-(4-(2-oxopyridin-1(2H)-yl)benzamido)pyrrolidin-3-yl)thiophene-2-carboxamide;

(3R,4S)-ethyl3-(2-chlorothiophene-5-carboxamido)-4-(4-(2-oxopiperidin-1-yl)benzamido)pyrrolidine-1-carboxylate;

5-chloro-N-((3R,4S)-1-isopropyl-4-(4-(2-oxopyridin-1(2H)-yl)benzamido)pyrrolidin-3-yl)thiophene-2-carboxamide;

5-chloro-N-((3R,4S)- 1-isopropyl-4-(4-(2-oxopiperidin-1-yl)benzamido)pyrrolidin-3-yl)thiophene-2-carboxamide;

5-chloro-N-((3R,4S)-1-(2-hydroxyethyl)-4-(4-(2-oxopyridin-1(2H)-yl)benzamido)pyrrolidin-3-yl)thiophene-2-carboxamide;

5-chloro-N-((3R,4S)-1-(2-methoxyethyl)-4-(4-(2-oxopyridin-1(2H)-yl)benzamido)pyrrolidin-3-yl)thiophene-2-carboxamide;

(3R,4S)-3-(2-chlorothiophene-5-carboxamido)-4-(4-(2-oxopyridin-1(2H)-yl)benzamido)pyrrolidine-1-carboxamide;

(3R,4S)-3-(2-chlorothiophene-5-carboxamido)-N-methyl-4-(4-(2-oxopyridin-1(2H)-yl)benzamido)pyrrolidine-1-carboxamide;

(3R,4S)-3-(2-chlorothiophene-5-carboxamido)-N-cyclopropyl-4-(4-(2-oxopyridin-1(2H)-yl)benzamido)pyrrolidine-1-carboxamide;

(3R,4S)-3-(2-chlorothiophene-5-carboxamido)-N-cyclopentyl-4-(4-(2-oxopyridin-1 (2H)-yl)benzamido)pyrrolidine-1-carboxamide;

(3R,4S)-3-(2-chlorothiophene-5-carboxamido)-N-cyclopropyl-4-(4-(2-oxopyridin-1(2H)-yl)benzamido)pyrrolidine-1-carboxamide;

(3R,4S)-isobutyl3-(2-chlorothiophene-5-carboxamido)-4-(4-(2-oxopyridin-1(2H)-yl)benzamido)pyrrolidine-1-carboxylate;

5-chloro-N-((3R,4S)-1-cyclopropyl-4-(4-(2-oxopyridin-1 (2H)-yl)benzamido)pyrrolidin-3-yl)thiophene-2-carboxamide;

5-chloro-N-((3R,4S)-1-(2-hydroxypropan-2-yl)-4-(4-(2-oxopyridin-1(2H)-yl)benzamido)pyrrolidin-3-yl)thiophene-2-carboxamide;

5-chloro-N-((3R,4S)-1-(1-(hydroxymethyl)cyclopropyl)-4-(4-(2-oxopyridin-1(2H)-yl)benzamido)pyrrolidin-3-yl)thiophene-2-carboxamide;

5-chloro-N-((3R,4S)-1-(methylsulfonyl)-4-(4-(2-oxopiperidin-1-yl)benzamido)pyrrolidin-3-yl)thiophene-2-carboxamide;

5-chloro-N-((3R,4S)-1-(ethylsulfonyl)-4-(4-(2-oxopiperidin-1-yl)benzamido)pyrrolidin-3-yl)thiophene-2-carboxamide;

5-chloro-N-((3R,4S)-1-(ethylsulfonyl)-4-(4-(2-oxopyridin-1(2H)-yl)benzamido)pyrrolidin-3-yl)thiophene-2-carboxamide;

5-chloro-N-((3R,4S)-4-(4-(2-oxopyridin-1(2H)-yl)benzamido)-1-(phenylsulfonyl)pyrrolidin-3-yl)thiophene-2-carboxamide;

5-chloro-N-((3R,4S)-1-(2-hydroxyethylsulfonyl)-4-(4-(2-oxopyridin-1(2H)-yl)benzamido)pyrrolidin-3-yl)thiophene-2-carboxamide;

5-chloro-N-((1R,2S,4S)-4-(methoxymethyl)-2-(4-(2-oxopyridin-1(2H)-yl)benzamido)cyclopentyl)thiophene-2-carboxamide;

5-chloro-N-((1R,2S,4S)-4-(ethoxymethyl)-2-(4-(2-oxopyridin-1(2H)-yl)benzamido)cyclopentyl)thiophene-2-carboxamide;

5-chloro-N-((1R,2S,4S)-4-hydroxy-2-(4-(2-oxopyridin-1(2H)-yl)benzamido)cyclopentyl)thiophene-2-carboxamide;

5-chloro-N-((1R,2S,4S)-4-methoxy-2-(4-(2-oxopyridin-1(2H)-yl)benzamido)cyclopentyl)thiophene-2-carboxamide;

5-chloro-N-((1R,2S,4S)-4-ethoxy-2-(4-(2-oxopyridin-1(2H)-yl)benzamido)cyclopentyl)thiophene-2-carboxamide; and 5-chloro-N-((1R,2S,4S)-4-((methylamino)methyl)-2-(4-(2-oxopyridin-1(2H)-yl)benzamido)cyclopentyl)thiophene-2-carboxamide;

or a pharmaceutically acceptable salt form thereof.

10. A pharmaceutical composition, comprising: a pharmaceutically acceptable carrier and a therapeutically effective amount of a compound of claim 1 or a pharmaceutically acceptable salt form thereof.

11. A method for treating a thromboembolic disorder, comprising: administering to a patient in need thereof a therapeutically effective amount of a compound of claim 1 or a pharmaceutically acceptable salt form thereof, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

12. A pharmaceutical composition, comprising: a pharmaceutically acceptable carrier and a therapeutically effective amount of a compound of claim 2 or a pharmaceutically acceptable salt form thereof.

13. A pharmaceutical composition, comprising: a pharmaceutically acceptable carrier and a therapeutically effective amount of a compound of claim 3 or a pharmaceutically acceptable salt form thereof.

14. A pharmaceutical composition, comprising: a pharmaceutically acceptable carrier and a therapeutically effective amount of a compound of claim 4 or a pharmaceutically acceptable salt form thereof.

15. A pharmaceutical composition, comprising: a pharmaceutically acceptable carrier and a therapeutically effective amount of a compound of claim 5 or a pharmaceutically acceptable salt form thereof.

16. A pharmaceutical composition, comprising: a pharmaceutically acceptable carrier and a therapeutically effective amount of a compound of claim 6 or a pharmaceutically acceptable salt form thereof.

17. A pharmaceutical composition, comprising: a pharmaceutically acceptable carrier and a therapeutically effective amount of a compound of claim 7 or a pharmaceutically acceptable salt form thereof.

18. A pharmaceutical composition, comprising: a pharmaceutically acceptable carrier and a therapeutically effective amount of a compound of claim 8 or a pharmaceutically acceptable salt form thereof.

19. A pharmaceutical composition, comprising: a pharmaceutically acceptable carrier and a therapeutically effective amount of a compound of claim 9 or a pharmaceutically acceptable salt form thereof.

* * * * *

UNITED STATES PATENT AND TRADEMARK OFFICE
CERTIFICATE OF CORRECTION

PATENT NO.        : 7,205,318 B2
APPLICATION NO. : 10/801469
DATED             : April 7, 2007
INVENTOR(S)       : Jennifer X. Qiao et al.

It is certified that error appears in the above-identified patent and that said Letters Patent is hereby corrected as shown below:

Title Page:
Section 54, Title should read: -- LACTAM-CONTAINING CYCLIC DIAMINES AND DERIVATIVES AS FACTOR XA INHIBITORS --

Column 202:

Line 60, insert -- 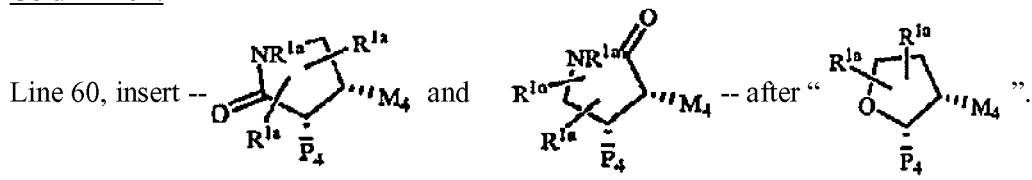.

Column 210:

Line 20, insert the following after " " "

-- 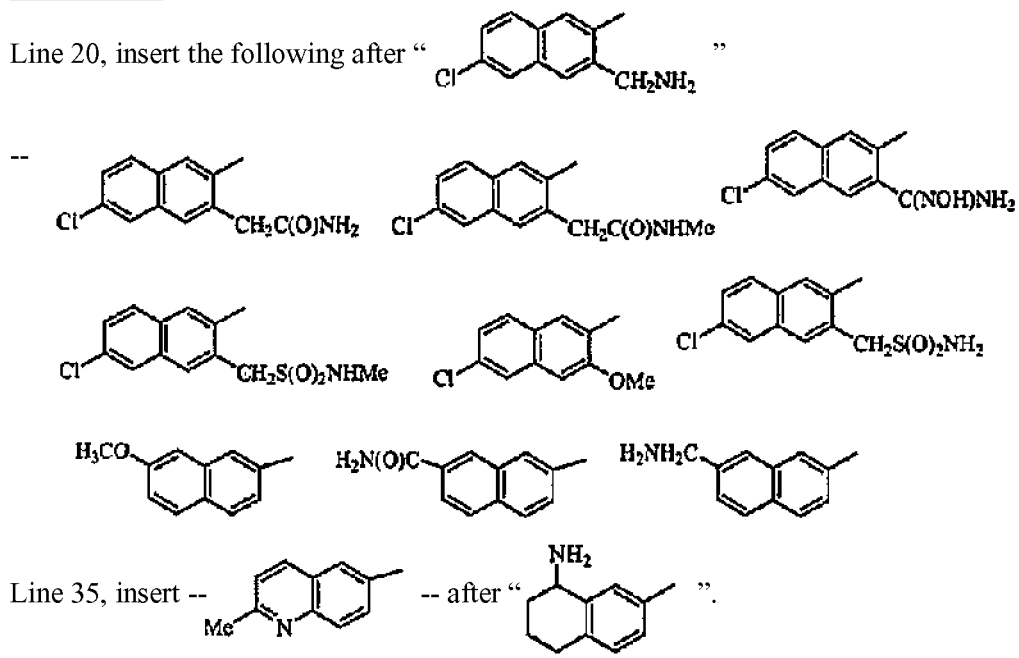 --.

Line 35, insert -- 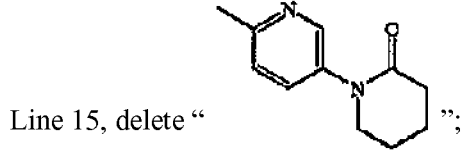 -- after " ".

Column 221:

Line 15, delete " ";

UNITED STATES PATENT AND TRADEMARK OFFICE
CERTIFICATE OF CORRECTION

PATENT NO. : 7,205,318 B2
APPLICATION NO. : 10/801469
DATED : April 7, 2007
INVENTOR(S) : Jennifer X. Qiao et al.

It is certified that error appears in the above-identified patent and that said Letters Patent is hereby corrected as shown below:

Column 221 (cont'd):

Line 25, delete " 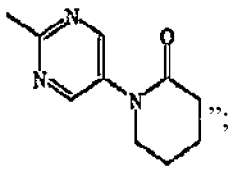 ";

Line 30, delete " 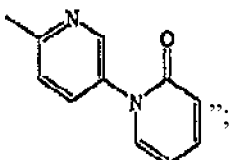 ";

Line 40, delete " 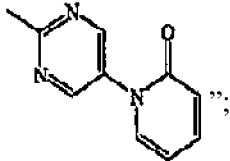 ";

Line 40, insert -- 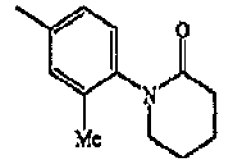 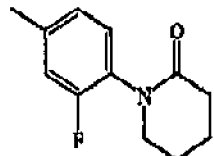 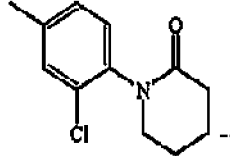 -- after " 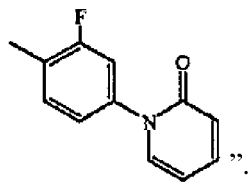 ".

Delete lines 45-65.

Column 222:
Delete lines 5-65.

Column 223:
Delete lines 5-20;

UNITED STATES PATENT AND TRADEMARK OFFICE
CERTIFICATE OF CORRECTION

PATENT NO. : 7,205,318 B2
APPLICATION NO. : 10/801469
DATED : April 7, 2007
INVENTOR(S) : Jennifer X. Qiao et al.

It is certified that error appears in the above-identified patent and that said Letters Patent is hereby corrected as shown below:

Column 223 (cont'd):

Line 60, delete " 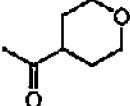 ";

Line 65, delete " 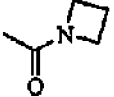 ".

Column 224:

Line 5, delete "  ";

Line 20, delete " 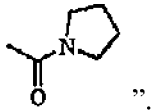 ".

Signed and Sealed this

Tenth Day of July, 2007

JON W. DUDAS
*Director of the United States Patent and Trademark Office*

UNITED STATES PATENT AND TRADEMARK OFFICE
CERTIFICATE OF CORRECTION

PATENT NO.       : 7,205,318 B2                                Page 1 of 3
APPLICATION NO.  : 10/801469
DATED            : April 17, 2007
INVENTOR(S)      : Jennifer X. Qiao et al.

It is certified that error appears in the above-identified patent and that said Letters Patent is hereby corrected as shown below:

Title Page:
Section 54, Title should read: -- LACTAM-CONTAINING CYCLIC DIAMINES AND DERIVATIVES AS FACTOR XA INHIBITORS --

Column 202:

Line 60, insert -- 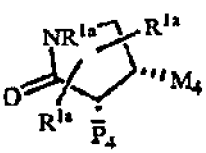 and 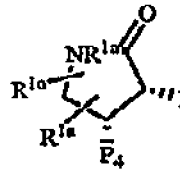 -- after " 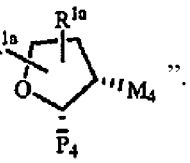 ".

Column 210:

Line 20, insert the following after " 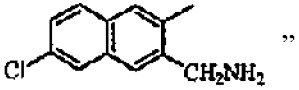 "

-- 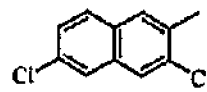 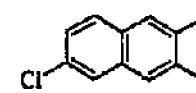 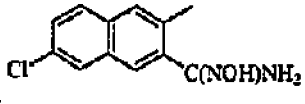

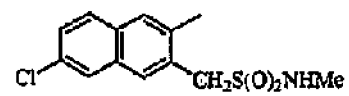 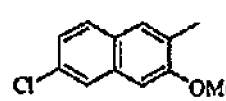 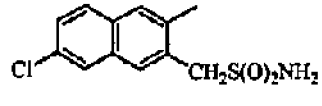

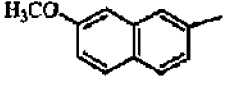 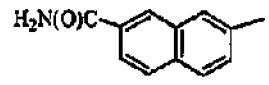 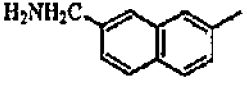 --.

Line 35, insert -- 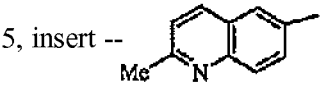 -- after " 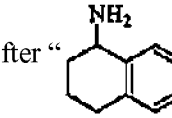 ".

Column 221:

Line 15, delete " 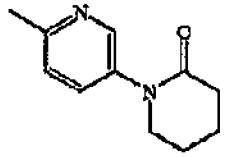 ";

UNITED STATES PATENT AND TRADEMARK OFFICE
CERTIFICATE OF CORRECTION

PATENT NO. : 7,205,318 B2
APPLICATION NO. : 10/801469
DATED : April 17, 2007
INVENTOR(S) : Jennifer X. Qiao et al.

It is certified that error appears in the above-identified patent and that said Letters Patent is hereby corrected as shown below:

Column 221 (cont'd):

Line 25, delete " 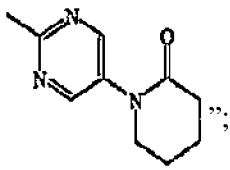 ";

Line 30, delete " 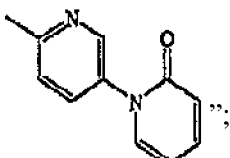 ";

Line 40, delete " 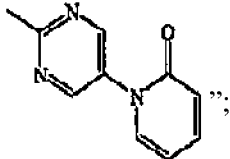 ";

Line 40, insert -- 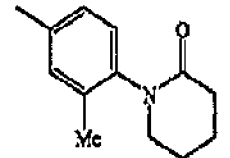 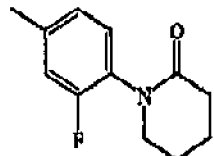 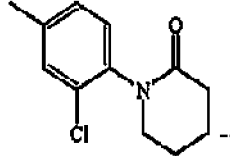 -- after " 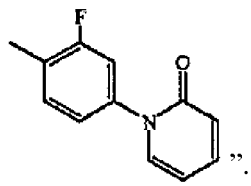 ".

Delete lines 45-65.

Column 222:
Delete lines 5-65.

Column 223:
Delete lines 5-20;

UNITED STATES PATENT AND TRADEMARK OFFICE
CERTIFICATE OF CORRECTION

PATENT NO. : 7,205,318 B2
APPLICATION NO. : 10/801469
DATED : April 17, 2007
INVENTOR(S) : Jennifer X. Qiao et al.

It is certified that error appears in the above-identified patent and that said Letters Patent is hereby corrected as shown below:

Column 223 (cont'd):

Line 60, delete " 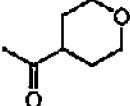 ";

Line 65, delete " 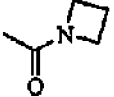 ".

Column 224:

Line 5, delete " 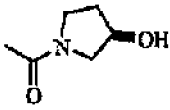 ";

Line 20, delete "  ".

This certificate supersedes Certificate of Correction issued July 10, 2007.

Signed and Sealed this

Thirty-first Day of July, 2007

JON W. DUDAS
*Director of the United States Patent and Trademark Office*